(12) United States Patent
Saatcioglu

(10) Patent No.: US 7,611,892 B2
(45) Date of Patent: Nov. 3, 2009

(54) PROSTATE-SPECIFIC OR TESTIS-SPECIFIC NUCLEIC ACID MOLECULES, POLYPEPTIDES, AND DIAGNOSTIC AND THERAPEUTIC METHODS

(75) Inventor: Fahri Saatcioglu, Oslo (NO)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/453,608

(22) Filed: Jun. 15, 2006

(65) Prior Publication Data

US 2007/0015246 A1   Jan. 18, 2007

Related U.S. Application Data

(63) Continuation-in-part of application No. 10/239,607, filed as application No. PCT/US01/09410 on Mar. 23, 2001, now Pat. No. 7,189,565, application No. 11/453,608, which is a continuation-in-part of application No. PCT/IB2005/001357, filed on Feb. 22, 2005.

(60) Provisional application No. 60/191,929, filed on Mar. 24, 2000, provisional application No. 60/545,822, filed on Feb. 19, 2004.

(51) Int. Cl.
  *C12N 15/63* (2006.01)
(52) U.S. Cl. .................. 435/320.1; 536/23.1; 536/24.3
(58) Field of Classification Search .............. 435/320.1; 536/23.1, 24.3
   See application file for complete search history.

(56) References Cited

U.S. PATENT DOCUMENTS

| | | | |
|---|---|---|---|
| 5,599,686 A | 2/1997 | DeFeo-Jones et al. | |
| 5,820,880 A | 10/1998 | Alving et al. | |
| 6,048,970 A | 4/2000 | Lal et al. | |
| 6,261,562 B1 | 7/2001 | Xu et al. | |
| 6,277,972 B1 | 8/2001 | Afar et al. | |
| 6,329,503 B1 | 12/2001 | Afar et al. | |
| 6,509,458 B1 | 1/2003 | Afar et al. | |
| 6,833,438 B1 * | 12/2004 | Afar et al. | 530/350 |
| 6,887,660 B2 | 5/2005 | Xu et al. | |
| 6,887,975 B2 | 5/2005 | Afar et al. | |
| 7,053,186 B2 | 5/2006 | Afar et al. | |
| 7,189,565 B2 | 3/2007 | Saatcioglu | |
| 2002/0187472 A1 | 12/2002 | Lal et al. | |
| 2003/0064397 A1 | 4/2003 | Spancake et al. | |
| 2004/0014087 A1 | 1/2004 | Hodgson et al. | |
| 2004/0137455 A1 | 7/2004 | Dong et al. | |
| 2005/0106643 A1 | 5/2005 | Saatcioglu | |

FOREIGN PATENT DOCUMENTS

| | | |
|---|---|---|
| EP | 0936270 A2 | 8/1999 |
| WO | WO 98/37418 A2 | 8/1998 |
| WO | WO 99/62941 A2 | 12/1999 |
| WO | WO 99/62941 A3 | 12/1999 |
| WO | WO 99/67384 A2 | 12/1999 |
| WO | WO 00/04149 A2 | 1/2000 |
| WO | WO 00/73509 A2 | 12/2000 |
| WO | WO 00/75298 A2 | 12/2000 |
| WO | WO 01/05970 A2 | 1/2001 |
| WO | WO 01/11032 A1 | 2/2001 |
| WO | WO 01/40276 A2 | 6/2001 |
| WO | WO 01/72962 A2 | 10/2001 |
| WO | WO 02/077243 A1 | 10/2002 |
| WO | WO 03/009814 A2 | 2/2003 |
| WO | WO 2005/114216 A2 | 12/2005 |

OTHER PUBLICATIONS

Boehringer Mannheim Biochemicals, 1994 Catalog, p. 93.
Bowie et al., "Deciphering the Message in Protein Sequences: Tolerance to Amino Acid Substitutions," *Science* 247:1306-1310 (1990).
Brennen et al., "Cytokine Production in Culture by Cells Isolated from the Synovial Membrane," *J. Autoimm.* 2 suppl.:177-186 (1989).
Burgess et al., "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *J. Cell Biol.* 111:2129-2138 (1990).
Conner et al., "Trk Receptor Alterations in Alzheimer's Disease," *Mol. Brain Res.* 42:1-17 (1996).
De Plaen et al., "Structure, Chromosomal Localization, and Expression of 12 Genes of the MAGE Family," *Immunogenetics* 40:360-369 (1994).
Deppenmeier et al., "Redox-Driven Proton Translocation in Methanogenic Archaea," *Cell. Mol. Life Sci.* 59:1513-1533 (2002).
Dias et al., "Shotgun Sequencing of the Human Transcriptome with ORF Expressed Sequence Tags," *Database EMBL Online*! Database Ascession No. AI908168 [XP002279053] (1999).
Diatchenko et al., "Suppression Subtractive Hybridization: A Method for Generating Differentially Regulated or Tissue-Specific cDNA Probes and Libraries," *Proc. Nat. Acad. Sci. U.S.A.* 93:6025-6030 (1996).
Eriksson et al., "Insulin Resistance in Type 2 (Non-Insulin-Dependent) Diabetic Patients and Their Relatives is not Associated with a Defect in the Expression of the Insulin-Responsive Glucose Transporter (GLUT-4) Gene in Human Skeletal Muscle," *Diabetologia* 35:143-147 (1992).

(Continued)

*Primary Examiner*—Larry R. Helms
*Assistant Examiner*—Minh-Tam Davis
(74) *Attorney, Agent, or Firm*—Kristina Bieker-Brady; Clark & Elbing LLP

(57) ABSTRACT

The invention provides novel STAMP2 nucleic acid molecules, polypeptides, antibodies, and modulatory compounds for use in methods of diagnosing, treating, and preventing diseases and conditions of the prostate and testis, such as cancer.

7 Claims, 51 Drawing Sheets
(4 of 51 Drawing Sheet(s) Filed in Color)

OTHER PUBLICATIONS

Gillies and Wesolowski, "Antigen Binding and Biological Activities of Engineered Mutant Chimeric Antibodies with Human Tumor Specificities," *Human Antibod. Hybrid.* 1:47-54 (1990).

Isogai et al., "*Homo sapiens* cDNA FLJ10829 fis, Clone NT2RP4001138," *Database EMBL Online*! Database Accession No. AK001691 [XP002241852] (2000).

Korkmaz et al., "An Efficient Procedure for Cloning Hormone-Responsive Genes from a Specific Tissue," *DNA Cell Biol.* 19:499-506 (2000).

Korkmaz et al. "Molecular Cloning and Characterization of STAMP1, a Highly Prostate-Specific Six Transmembrane Protein that is Overexpressed in Prostate Cancer," *J. Biol. Chem.* 277:36689-36696 (2002).

Lazar et al., "Transforming Growth Factor α: Mutation of Aspartic Acid 47 and Leucine 48 Results in Different Biological Activities," *Mol. Cell. Biol.* 8:1247-1252 (1988).

Mahairas et al., "Sequence-Tagged Connectors: A Sequence Approach to Mapping and Scanning the Human Genome," *Proc. Nat. Acad. Sci. U.S.A.* 96:9739-9744 (1999).

Moldes et al., "Tumor Necrosis Factor-α-Induced Adipose-Related Protein (TIARP), a Cell-Surface Protein that is Highly Induced by Tumor Necrosis Factor-α and Adipose Conversion," *J. Biol. Chem.* 276:33938-33946 (2001).

MPSRCH Search Report for U.S. Appl. No. 10/239,607 a-23.oligo-500.rni, pp. 1-2 (2005).

MPSRCH Search Report for U.S. Appl. No. 10/239,607 a-23-copy-1510-1647.rnpb, pp. 2-4(2004).

MPSRCH Search Report for U.S. Appl. No. 10/239,607 a-14-copy-445-490.rapb, pp. 1-4 (2004).

Nelson et al., "Molecular Cloning and Characterization of Prostase, an Androgen-Regulated Serine Protease with Prostate-Restricted Expression," *Proc. Nat. Acad. Sci. U.S.A.* 96:3114-3119 (1999).

Passer et al., "The p53-Inducible TSAP6 Gene Product Regulates Apoptosis and the Cell Cycle and Interacts with Nix and the Myt1 Kinase," *Proc. Nat. Acad. Sci. U.S.A.* 100:2284-2289 (2003).

Phang, "The Regulatory Functions of Proline and Pyrroline-5-Carboxylic Acid," *Curr. Top. Cell. Regul.* 25:91-132 (1985).

Schmid et al., "Expression of AMPA Receptor Subunit Flip/Flop Splice Variants in the Rat Auditory Brainstem and Inferior Colliculus," *J. Comp. Neurol.* 430:160-171 (2001).

Steiner et al., "Growth Inhibition of Prostate Cancer by an Adenovirus Expressing a Novel Tumor Suppressor Gene, pHyde," *Cancer Res.* 60:4419-4425 (2000).

Stephenson et al., "Localization of a New Prostate-Specific Antigen-Related Serine Protease Gene, KLK4, is Evidence for an Expanded Human Kallikrein Gene Family Cluster on Chromosome 19q13.3-13.4," *J. Biol. Chem.* 274:23210-23214 (1999).

Tao and Morrison, "Studies of Aglycosylated Chimeric Mouse-Human IgG. Role of Carbohydrate in the Structure and Effector Functions Mediated by the Human IgG Constant Region,:" *J. Immunol.* 143:2595-2601 (1989).

Ward, "Tumour Markers," in *Immunological Aspects of Cancer*, Hancock and Ward (Eds.), Martimus Nijhoff Publishers, Boston, pp. 91-106 (1985).

Warkentin et al., "Structures of $F_{420}H_2$:NADP$^+$ Oxidoreductase With and Without Its Substrates Bound," *EMBO J.* 20:6561-6569 (2001).

Watanabe et al., "Protein Kinase N (PKN) and PKN-Related Protein Rhophilin as Targets of Small GTPase Rho," *Science* 271:645-648 (1996).

Yousef et al., "Prostase/KLK-L1 is a New Member of the Human Kallikrein Gene Family, is Expressed in Prostate and Breast Tissues, and is Hormonally Regulated," *Cancer Res.* 59:4252-4256 (1999).

Zimmer, "Examination of the Calcium-Modulated Protein S100α and Its Target Proteins in Adult and Developing Skeletal Muscle," *Cell Motil. Cytoskeleton* 20:325-337 (1991).

International Preliminary Examination Report for PCT/US01/09410 dated Jul. 28, 2002.

International Search Report for PCT/US01/09410 dated Sep. 6, 2001.

International Search Report for PCT/IB05/001357 dated Jan. 10, 2006.

International Search Report for PCT/IB00/00673 dated Oct. 26, 2000.

Supplementary European Search Report for EP 01922630 dated May 5, 2004.

* cited by examiner

Multiple tissue northern blot. Lane 11: Prostate, 12:testis

| SEQ. ID NO. | SEQ. NAME | LENGTH | SEQUENCE |
|---|---|---|---|
| 1 | PSL 22 | 349 | ACTAATGTGAGGAAaCAAACATGTTCAGGCCTGAACATTTCCGGTGCTGACT CGGCcTTAAACGTTTGTGCCATAATGGAAAATATCTATCTATCTGTTCTCAA ATCCTGTTTTTCTCATAGTGTAAACTCACATTTGATGTGTTTTTATGAAGGAA AGTAACCAAGAAACCTCTAGGAATTAGGAAAAAAaGAACTTTTTTGAGGTG TGTTACTATACTGCTGTAAGTTATTTATTATATAAAGTATTGTAAATAGAAaT AGTGTTGAGATATGAAATATGGCTATTTTTAATGGTGACAATTATAGACTTT TAGgTCACTATTAAATTGGGGTTACCTATATCcAGT |
| 2 | PSL 229A | 251 | ACACATCCATCATTGTGAAATCTCTTTTCCAACAAACGTCCTCTTAATGAGC ACAATTCATTAAAaTCTTTGGGGACTAAGCTACGAACAAAGTTCAACTAAAC TACCTACTGACTTCAAAAGGAACATATACCCACCACGTGTGGTAGCTCATG ACTGTAATCCCAGCACTTTGGGAGGCTGAGGCAGGAGGATCACCTGAGCCC AGGAGTTCCAGACCAGCCTAAGCAACATGCCAAGACCCTGTATGT |
| 3 | PSL E15C | 51 | ACAAAGACACCCTTGTYCCCCGGGCAAGGTCCTCCAGCTACAAGGGGGCCA |
| 4 | PSL E156 | 149 | CCXYACATTGTCACAGAGAGGCTCCAGGCTTAAAGTTGACCTGCGTAGAAA GCAAGAATGAATTGTTGGAGGAAGTAAGGAGGGCGATTGAATAAAGACTTT TAGCAGCTGGGCCAGCTGAACCATCCCAACCCTTCAAATCCCCTTGT |
| 5 | PSL E157 | 261 | ACCCTAACTGAACCCATTTCAGCCACTCAGATTGATAGGGTGGAAAAGACA GGGCAGGTGGTAGCAGCTGTGAAGAAAAAGAGGAAAGCAGAAGGGTGGCCT ATAATCTACAGGCATGTAGAGAGGACTACATAGGCCTCTGTTCTTTGCCCTC AGGAGCCCCCTTCCTGTCCCTTGGACTCAGAATGGATCCTTCCAGCACACAT GGCCCAACACTGAGAGTGCAGGAAGCATGGGTAGGGGCCTCCTGCTGCTGG TATGT |
| 6 | PSL E391 | 121 | AGTNTGNGGGGANTTGAGGGCNGNTACGNNAAANGNTGGNCTACTNTAGA TGCTGCTCGAGCGGCCGCCAGTGTGATGGATACAAGCTTTCTTTTTTTTTTTT ATTTTCGNNTTTTTTTTC |
| 7 | PSL K31 | 93 | ACTCAGTAGGGACTGAGCACTAAATGCTTATTTTAAAAGAAATGTAAAGAG CAGAAAGCAATTCAGGCTACCCTGCCTTTTGTGCTGGCTAGT |
| 8 | PSL L28 | 169 | ACACTTAAAATAGTTAATGTGATACATTTTATGTTACATGTATTTTGCCCAC TGAAAAAATAAAAATATATAAACACACAGCAAATGATGACCAGGCCTTTGA AGAAAGCTTATAAAACAAAATTAAGAAGCCTGGCTACAGAGCGAGACTCTG TCTCAAAAAAAAAAAA |
| 9 | PSL L74 | 262 | ACTTTACAAGCATGAAGGATATTAGGGTAAGTGGCTAATTATAAATCTACT CTAGAGACATATAATCATACAGATTATTCATAAAATTTTTCAGTGCTGTCCT TCCACATTTAATTGCATTTTGCTCAAACTGTAGAATGCCCTACATTCCCCCC ACCCCAATTTGCTATTTCCTTATTAAAAATAGAAAATTATAGGCAAGATACAA TTATATGCGTTCCTCTTCCTGAAATTATAACATTTCTAAACTTACCCACGTAG GT |
| 10 | PSL SSH 20 | 175 | ACAGGTTGGCCCTTCACCTAGTTGACTCAGCCCTCGATAGTCTAGAGCCCAC CCCCTCCTCAGGAACTCAAGAGCTCAGCATTTATAATGAGCAGTTGGTAAT GAGTTGCCCTATGTGCTTGTCGCAAGCAGTCACAGAGATGAGCCCTATTACT TGATATTCAGGAACAAAGGT |
| 11 | PSL SSH 4 | 331 | ACATCCAAGCCTTCCTCTGCGTGAGAGCAAAGGCTTTGCTCATCAGCCAGCC AGTCTTGTTACTATCTGGCTACTTTTTAAGGTTAAAAAATAAAAGGCAGTTT CTTTGCTCTGCAGGCGGCAAGGCAGGAGGCGCAGGCCTCTTCATTGTTCAC ATGTCACAGGAGGAGGCTCTGAGCAAAGGCCACTGGCAAGTTAGGGCAAC ACCAAGAAGGCTCTGCGGAGAGACTCCCTGTGGGTTGGGGGsCTGGCAGGA ACGGTGCcTGTGGACTGTTTATGGTCTGTCCAGTTGAGGCTTGGTAAACCCA AGTAAAGTGTTAAAAAACCTCAGT |
| 12 | PSL SSH 9 | 170 | ACGACTCATCCACCTCCGGCTGAAGCTCCAGGAGCTGAAGGACCCCAATGA GGATGAGCCAAACATCCGAGTGCTCCTTGAGCACCGCTTTTACAAGGAGAA GAGCAAGAGCGTCAAGCAGACCTGTGACAAGTGTAACACCATCATCTGGGG GCTCATTCAGACCTGGT |

```
EXON_1    83bp
      1   ACGCGGGGGATCCAGCTTGGGTAGGCGGGGAAGCAGCTGGAGTGCGACCGCTACGGCAGC
     61   CACCCTGCAACCGCCAGTCGGAG

EXON_2    61bp
      1   AGCTAAGGGCAAGTCCTGAGGTTGGGCCCAGGAGAAAGAAGGCAAGGAGACATTGTCCCA
     61   G

EXON_3    525bp
      1   GATATTCTTGGTGATCTTGGAAGTGTCCGTATCATGGAATCAATCTCTATGATGGGAAGC
     61   CCTAAGAGCCTTAGTGAAACTTTTTTACCTAATGGCATAAATGGTATCAAAGATGCAAGG
    121   AAGGTCACTGTAGGTGTGATTGGAAGTGGAGATTTTGCCAAATCCTTGACCATTCGACTT
    181   ATTAGATGCGGCTATCATGTGGTCATAGGAAGTAGAAATCCTAAGTTTGCTTCTGAATTT
    241   TTTCCTCATGTGGTAGATGTCACTCATCATGAAGATGCTCTCACAAAAACAAATATAATA
    301   TTTGTTGCTATACACAGAGAACATTATACCTCCCTGTGGGACCTGAGACATCTGCTTGTG
    361   GGTAAAATCCTGATTGATGTGAGCAATAACATGAGGATAAACCAGTACCCAGAATCCAAT
    421   GCTGAATATTTGGCTTCATTATTCCCAGATTCTTTGATTGTCAAAGGATTTAATGTTGTC
    481   TCAGCTTGGGCACTTCAGTTAGGACCTAAGGATGCCAGCCGGCAG

EXON_4    528bp
      1   GTTTATATATGCAGCAACAATATTCAAGCGCGACAACAGGTTATTGAACTTGCCCGCCAG
     61   TTGAATTTCATTCCCATTGACTTGGGATCCTTATCATCAGCCAGAGAGATTGAAAATTTA
    121   CCCCTACGACTCTTTACTCTCTGGAGAGGGCCAGTGGTGGTAGCTATAAGCTTGGCCACA
    181   TTTTTTTTTCCTTTATTCCTTTGTCAGAGATGTGATTCATCCATATGCTAGAAACCAACAG
    241   AGTGACTTTTACAAAATTCCTATAGAGATTGTGAATAAAACCTTACCTATAGTTGCCATT
    301   ACTTTGCTCTCCCTAGTATACCTCGCAGGTCTTCTGCAGCCTGCTTATCAACTTTATTAC
    361   GGCACCAAGTATAGGAGATTTCCACCTTGGTTGGAAACCTGGTTACAGTGTAGAAAACAG
    421   CTTGGATTACTAAGTTTTTTCTTCGCTATGGTCCATGTTGCCTACAGCCTCTGCTTACCG
    481   ATGAGAAGGTCAGAGAGATATTTGTTTCTCAACATGGCTTATCAGCAG

EXON_5    165bp
      1   GTTCATGCAAATATTGAAAACTCTTGGAATGAGGAAGAAGTTTGGAGAATTGAAATGTAT
     61   ATCTCCTTTGGCATAATGAGCCTTGGCTTACTTTCCCTCCTGGCAGTCACTTCTATCCCT
    121   TCAGTGAGCAATGCTTTAAACTGGAGAGAATTCAGTTTTATTCAG

EXON_6    148bp
      1   TCTACACTTGGATATGTCGCTCTGCTCATAAGTACTTTCCATGTTTTAATTTATGGATGG
     61   AAACGAGCTTTTGAGGAAGAGTACTACAGATTTTATACACCACCAAACTTTGTTCTTGCT
    121   CTTGTTTTGCCCTCAATTGTAATTCTGG cont_6+UTR
      1   GTAAGATTATTTTATTCCTTCCATGTATAAGCCGAAAGCTAAAACGAATTAAAAAAGGCT
     61   GGGAAAAGAGCCAATTTCTGGAAGAAGGTATTGGAGGAACAATTCCTCATGTCTCCCCGG
    121   AGAGGGTCACAGTAATGTGATGATAAATGGTGTTCACAGCTGCCATATAAAGTTCTACTC
    181   ATGCCATTATTTTTATGACTTCTACGTTCAGTTACAAGTATGCTGTCAAATTATCGTGGG
    241   TTGAAACTTGTTAAATGAGATTTCAACTGACTTAGTGATAGAGTTTTCTTCAAGTTAATT
    301   TTCACAAATGTCATGTTTGCCAATATGAATTTTTCTAGTCAACATATTATTGTAATTTAG
    361   GTATGTTTTGTTTTGTTTTGCACAACTGTAACCCTGTTGTTACTTTATATTTCATAATCA
    421   GACAAAAATACTTACAGTTAATAATATAGATATAATGTTAAAAACAATTTGCAAACCAGC
    481   AGAATTTTAAGCTTTTAAAATAATTCAATGGATATACATTTTTTTCTGAAGATTAAGATT
    541   TTAATTATTCAACTTAAAAAGTAGAAATGCATTATTATACATTTTTTTAAGAAAGGACAC
    601   GTTATGTTAGCATCTAGGTAAGGCTGCATGATAGCATTCCTATATTTCTCTCATAAAATA
    661   GGATTTGAAGGATGAAATTAATTGTATGAAGCAATGTGATTATATGAAGAGACACAAATT
    721   AAAAAGACAAATTAAACCTGAAATTATATTTAAAATATATTTGAGACATGAAATACATAC
    781   TGATAATACATACCTCATGAAAGATTTTATTCTTTATTGTGTTACAGAGCAGTTTCATTT
    841   TCATATTAATATACTGATCAGGAAGAGGATTCAGTAACATTTGGCTTCCAAAACTGCTAT
    901   CTCTAATACGGTACCAATCCTAGGAACTGTATACTAGTTCCTACTTAGAACAAAAGTATC
```

FIGURE 4C

```
 961 AAGTTTGCACACAAGTAATCTGCCAGCTGACCTTTGTCGCACCTTAACCAGTCACCACTT
1021 GCTATGGTATAGGATTATACTGATGTTCTTTGAGGGATTCTGATGTGCTAGGCATGGTTC
1081 TAAGTACTTTACTTGTATTATCCCATTTAATACTTAGAACAACCCCGTGAGATAAGTAGT
1141 TATTATCCTCATTTTACACATGAGGGACCGAAGGATAGAAAAGTTATTTTTCAAAGGTCT
1201 TGCAGTTAATAAATGGCAGAGTGAGCATTCAAGTCCAGGTAGTCATATTCCAGAGGCCAC
1261 GGTTTTAACCACTAGGCTCTAGAGCTCCCGCCGCGCCCCTATGCATTATGTTCACAATGC
1321 CAATCTAGATGCTTCCTCTTTTGTATAAAGTCACTGACATTCTTTAGAGTGGGTTGGGTG
1381 CATCCAAAAATGTATAAAAATATTATTATAATAAACTTATTACTGCTTGTAGGGTAATTC
1441 ACAGTTACTTACCCTATTCTTGCTTGGAACATGAGCCTGGAGACCCATGGCAGTCCATAT
1501 GCCTCCCTATGCAGTGAAGGGCCCTAGCAGTGTTAACAAATTGCTGAGATCCCACGGAGT
1561 CTTTCAAAAATCTCTGTAGAGTTAGTCTTCTCCTTTTCTCTTCCTGAGAAGTTCTCCTGC
1621 CTGCATAACCATTCATTAGGGAGTACTTTACAAGCATGAAGGATATTAGGGTAAGTGGCT
1681 AATTATAAATCTACTCTAGAGACATATAATCATACAGATTATTCATAAAATTTTTCAGTG
1741 CTGTCCTTCCACATTTAATTGCATTTTGCTCAAACTGTAGAATGCCCTACATTCCCCCCA
1801 CCCCAATTTGCTATTTCCTTATTAAAATAGAAAATTATAGGCAAGATACAATTATATGCG
1861 TTCCTCTTCCTGAAATTATAACATTTCTAAACTTACCCACGTAGGGACTACTGAATCCAA
1921 CTGCCAACAATAAAAAGACTTTTATTTAGTAGAGGCTACCTTTCCCCCCAGTGACTCTTT
1981 TTCTACAACTGCCTTGTCAGTTTGGTAATTCACTTATGATTTTCTAATGTTCTCTTGGTG
2041 AATTTTATTATCTTGGACCCTCTTTTTTTTTTTTTTAAAGACAGAGTCTTGCTCTGTCA
2101 CCCATTGCTCTCGTTTGGGCAACAAGAGTGAAACTCTTGTCTCAAAAAAAAAAAAAAATG
2161 AGGTTTAAGACAGTTTTGTCATTACTGGTGGGATCTGGTCACACAAGATAGCATTAAACG
2221 TGACATGGCACATAAAATTGGTTAAAAAATTTTGTTTTTTAATTGCGTAATGTAAAAGCC
2281 CAACAAACACTTTATGCAAGATTGGAATGTATCTTCAAATTCAGATTTAATAAACATGTA
2341 AAGATCCTCTGTAAAAAAAAAAAAAAAAAAAAAAAAAAAAA
```

FIGURE 4C CONTINUED

```
   1 ACGCGGGGGATCCAGCTTGGGTAGGCGGGGAAGCAGCTGGAGTGCGACCGCTACGGCAGC
  61 CACCCTGCAACCGCCAGTCGGAGAGCTAAGGGCAAGTCCTGAGGTTGGGCCCAGGAGAAA
 121 GAAGGCAAGGAGACATTGTCCCAGGATATTCTTGGTGATCTTGGAAGTGTCCGTATCATG
 181 GAATCAATCTCTATGATGGGAAGCCCTAAGAGCCTTAGTGAAACTTGTTTACCTAATGGC
 241 ATAAATGGTATCAAAGATGCAAGGAAGGTCACTGTAGGTGTGATTGGAAGTGGAGATTTT
 301 GCCAAATCCTTGACCATTCGACTTATTAGATGCGGCTATCATGTGGTCATAGGAAGTAGA
 361 AATCCTAAGTTTGCTTCTGAATTTTTTCCTCATGTGGTAGATGTCACTCATCATGAAGAT
 421 GCTCTCACAAAAACAAATATAATATTTGTTGCTATACACAGAGAACATTATACCTCCCTG
 481 TGGGACCTGAGACATCTGCTTGTGGGTAAAATCCTGATTGATGTGAGCAATAACATGAGG
 541 ATAAACCAGTACCCAGAATCCAATGCTGAATATTTGGCTTCATTATTCCCAGATTCTTTG
 601 ATTGTCAAAGGATTTAATGTTGTCTCAGCTTGGGCACTTCAGTTAGGACCTAAGGATGCC
 661 AGCCGGCAGGTTTATATATGCAGCAACAATATTCAAGCGCGACAACAGGTTATTGAACTT
 721 GCCCGCCAGTTGAATTTCATTCCCATTGACTTGGGATCCTTATCATCAGCCAGAGAGATT
 781 GAAAATTTACCCCTACGACTCTTTACTTTCTGGAGAGGGCCAGTGGTGGTAGCTATAAGC
 841 TTGGCCACATTTTTTTTCCTTTATTCCTTTGTCAGAGATGTGATTCATCCATATGCTAGA
 901 AACCAACAGAGTGACTTTTACAAAATTCCTATAGAGATTGTGAATAAAACCTTACCTATA
 961 GTTGCCATTACTTTGCTCTCCCTAGTATACCTTGCAGGTCTTCTGGCAGCTGCTTATCAA
1021 CTTTATTACGGCACCAAGTATAGGAGATTTCCACCTTGGTTGGAAACCTGGTTACAGTGT
1081 AGAAAACAGCTTGGATTACTAAGTTTTTTCTTCGCTATGGTCCATGTTGCCTACAGCCTC
1141 TGCTTACCGATGAGAAGGTCAGAGAGATATTTGTTTCTCAACATGGCTTATCAGCAGGTT
1201 CATGCAAATATTGAAAACTCTTGGAATGAGGAAGAAGTTTGGAGAATTGAAATGTATATC
1261 TCCTTTGGCATAATGAGCCTTGGCTTACTTTCCCTCCTGGCAGTCACTTCTATCCCTTCA
1321 GTGAGCAATGCCTTAAACTGGAGAGAATTCAGTTTTATTCAGTCTACACTTGGATATGTC
1381 GCTCTGCTCATAAGTACTTTCCATGTTTAATTTATGGATGGAAACGAGCTTTTGAGGAA
1441 GAGTACTACAGATTTTATACACCACCAAACTTTGTTCTTGCTCTTGTTTTGCCCTCAATT
1501 GTAATTCTGGGTAAGATTATTTTATTCCTTCCATGTATAAGCCGAAAGCTAAAACGAATT
1561 AAAAAAGGCTGGGAAAGAGCCAATTTCTGGAAGAAGGTATTGGAGGAACAATTCCTCAT
1621 GTCTCCCCGGAGAGGGTCACAGTAATGTGATGATAAATGGTGTTCACAGCTGCCATATAA
1681 AGTTCTACTCATGCCATTATTTTTATGACTTCTACGTTCAGTTACAAGTATGCTGTCAAA
1741 TTATCGTGGGTTGAAACTTGTTAAATGAGATTTCAACTGACTTAGTGATAGAGTTTTCTT
1801 CAAGTTAATTTTCACAAATGTCATGTTTTGCTCAACATATTAATTTTTCTAGTCAACATATTAT
1861 TGTAATTTAGGTATGTTTTGTTTTGTTTTGCACAACTGTAACCCTGTTGTTACTTTATAT
1921 TTCATAATCAGACAAAAATACTTACAGTTAATAATATAGATATAATGTTAAAAACAATTT
1981 GCAAACCAGCAGAATTTTAAGCTTTTAAAATAATTCAATGGATATACATTTTTTTCTGAA
2041 GATTAAGATTTTAATTATTCAACTTAAAAAGTAGAAATGCATTATTATACATTTTTTTAA
2101 GAAAGGACACGTTATGTTAGCATCTAGGTAAGGCTGCATGATAGCATTCCTATATTTCTC
2161 TCATAAAATAGGATTTGAAGGATGAAATTAATTGTATGAAGCAATGTGATTATATGAAGA
2221 GACACAAATTAAAAAGACAAATTAAACCTGAAATTATATTTAAAATATATTTGAGACATG
2281 AAATACATACTGATAATACATACCTCATGAAAGATTTTATTCTTTATTGTGTTACAGAGC
2341 AGTTTCATTTTCATATTAATATACTGATCAGGAAGAGGATTCAGTAACATTTGGCTTCCA
2401 AAACTGCTATCTCTAATACGGTACCAATCCTAGGAACTGTATACTAGTTCCTACTTAGAA
2461 CAAAAGTATCAAGTTTGCACACAAGTAATCTGCCAGCTGACCTTTGTCGCACCTTAACCA
2521 GTCACCACTTGCTATGGTATAGGATTATACTGATGTTCTTTGAGGGATTCTGATGTGCTA
2581 GGCATGGTTCTAAGTACTTTACTTGTATTATCCCATTTAATACTTAGAACAACCCCGTGA
2641 GATAAGTAGTTATTATCCTCATTTTACACATGAGGGACCGAAGGATAGAAAAGTTATTTT
2701 TCAAAGGTCTTGCAGTTAATAAATGGCAGAGTGAGCATTCAAGTCCAGGTAGTCATATTC
2761 CAGAGGCCACGGTTTTAACCACTAGGCTCTAGAGGCTCCCGCCGCGCCCCTATGCATTATG
2821 TTCACAATGCCAATCTAGATGCTTCCTCTTTTGTATAAAGTCACTGACATTCTTTAGAGT
2881 GGGTTGGGTGCATCCAAAAATGTATAAAAATATTATTATAATAAACTTATTACTGCTTGT
2941 AGGGTAATTCACAGTTACTTACCCTATTCTTGCTTGGAACATGAGCCTGGAGACCCATGG
3001 CAGTCCATATGCCTCCCTATGCAGTGAAGGGCCCTAGCAGTGTTAACAAATTGCTGAGAT
3061 CCCACGGAGTCTTTCAAAAATCTCTGTAGAGTTAGTCTTCTCCTTTTCTCTTCCTGAGAA
3121 GTTCTCCTGCCTGCATAACCATTCATTAGGAGTACTTTACAAGCATGAAGGATATTAGG
3181 GTAAGTGGCTAATTATAAATCTACTCTAGAGACATATAATCATACAGATTATTCATAAAA
3241 TTTTTCAGTGCTGTCCTTCCACATTTAATTGCATTTTGCTCAAACTGTAGAATGCCCTAC
3301 ATTCCCCCCACCCCAATTTGCTATTTCCTTATTAAAAATGTATAAAAATATTATTATAAT
3361 AAACTTATTACTGCTTGTAGGGTAATTCACAGTTACTTACCCTATTCTTGCTTGGAACAT
```

FIGURE 4D

```
3421  GAGCCTGGAGACCCATGGCAGTCCATATGCCTCCCTATGCAGTGAAGGGCCCTAGCAGTG
3481  TTAACAAATTGCTGAGATCCCACGGAGTCTTTCAAAAATCTCTGTAGAGTTAGTCTTCTC
3541  CTTTTCTCTTCCTGAGAAGTTCTCCTGCCTGCATAACCATTCATTAGGGAGTACTTTACA
3601  AGCATGAAGGATATTAGGGTAAGTGGCTAATTATAAATCTACTCTAGAGACATATAATCA
3661  TACAGATTATTCATAAAATTTTTCAGTGCTGTCCTTCCACATTTAATTGCATTTTGCTCA
3721  AACTGTAGAATGCCCTACATTCCCCCACCCCAATTTGCTATTTCCTTATTAAAATAGAA
3781  AATTATAGGCAAGATACAATTATATGCGTTCCTCTTCCTGAAATTATAACATTTCTAAAC
3841  TTACCCACGTAGGGACTACTGAATCCAACTGCCAACAATAAAAAGACTTTTATTTAGTAG
3901  AGGCTACCTTTCCCCCCAGTGACTCTTTTTCTACAACTGCCTTGTCAGTTTGGTAATTCA
3961  CTTATGATTTTCTAATGTTCTCTTGGTGAATTTTATTATCTTGGACCCTCTTTTTTTTTT
4021  TTTTTAAAGACAGAGTCTTGCTCTGTCACCCATTGCTCTCGTTTGGGCAACAAGAGTGAA
4081  ACTCTTGTCTCAAAAAAAAAAAAAAAATGAGGTTTAAGACAGTTTTGTCATTACTGGTGGG
4141  ATCTGGTCACACAAGATAGCATTAAACGTGACATGGCACATAAAATTGGTTAAAAAATTT
4201  TGTTTTTTAATTGCGTAATGTAAAAGCCCAACAAACACTTTATGCAAGATTGGAATGTAT
4261  CTTCAAATTCAGATTTAATAAACATGTAAAGATCCTCTGTAAAAAAAAAAAAAAAAAAAA
4321  AAAAAAAAA
```

FIGURE 4D CONTINUED

```
  1 ACGCGGGGGATCCAGCTTGGGTAGGCGGGGAAGCAGCTGGAGTGCGACCGCTACGGCAGC
 61 CACCCTGCAACCGCCAGTCGGAGAGCTAAGGGCAAGTCCTGAGGTTGGGCCCAGGAGAAA

1                                                            M
121 GAAGGCAAGGAGACATTGTCCCAGGATATTCTTGGTGATCTTGGAAGTGTCCGTATCATG

2  E  S  I  S  M  M  G  S  P  K  S  L  S  E  T  C  L  P  N  G
181 GAATCAATCTCTATGATGGGAAGCCCTAAGAGCCTTAGTGAAACTTGTTTACCTAATGGC

22  I  N  G  I  K  D  A  R  K  V  T  V  G  V  I  G  S  G  D  F
241 ATAAATGGTATCAAAGATGCAAGGAAGGTCACTGTAGGTGTGATTGGAAGTGGAGATTTT

42  A  K  S  L  T  I  R  L  I  R  C  G  Y  H  V  V  I  G  S  R
301 GCCAAATCCTTGACCATTCGACTTATTAGATGCGGCTATCATGTGGTCATAGGAAGTAGA

62  N  P  K  F  A  S  E  F  F  P  H  V  V  D  V  T  H  H  E  D
361 AATCCTAAGTTTGCTTCTGAATTTTTTCCTCATGTGGTAGATGTCACTCATCATGAAGAT

82  A  L  T  K  T  N  I  I  F  V  A  I  H  R  E  H  Y  T  S  L
421 GCTCTCACAAAAACAAATATAATATTTGTTGCTATACACAGAGAACATTATACCTCCCTG

102  W  D  L  R  H  L  L  V  G  K  I  L  I  D  V  S  N  N  M  R
481 TGGGACCTGAGACATCTGCTTGTGGGTAAAATCCTGATTGATGTGAGCAATAACATGAGG

122  I  N  Q  Y  P  E  S  N  A  E  Y  L  A  S  L  F  P  D  S  L
541 ATAAACCAGTACCCAGAATCCAATGCTGAATATTTGGCTTCATTATTCCCAGATTCTTTG

142  I  V  K  G  F  N  V  V  S  A  W  A  L  Q  L  G  P  K  D  A
601 ATTGTCAAAGGATTTAATGTTGTCTCAGCTTGGGCACTTCAGTTAGGACCTAAGGATGCC

162  S  R  Q  V  Y  I  C  S  N  N  I  Q  A  R  Q  Q  V  I  E  L
661 AGCCGGCAGGTTTATATATGCAGCAACAATATTCAAGCGCGACAACAGGTTATTGAACTT

182  A  R  Q  L  N  F  I  P  I  D  L  G  S  L  S  S  A  R  E  I
721 GCCCGCCAGTTGAATTTCATTCCCATTGACTTGGGATCCTTATCATCAGCCAGAGAGATT

202  E  N  L  P  L  R  L  F  T  F  W  R  G  P  V  V  V  A  I  S
781 GAAAATTTACCCCTACGACTCTTTACTTTCTGGAGAGGGCCAGTGGTGGTAGCTATAAGC

222  L  A  T  F  F  F  L  Y  S  F  V  R  D  V  I  H  P  Y  A  R
841 TTGGCCACATTTTTTTTCCTTTATTCCTTTGTCAGAGATGTGATTCATCCATATGCTAGA

242  N  Q  Q  S  D  F  Y  K  I  P  I  E  I  V  N  K  T  L  P  I
901 AACCAACAGAGTGACTTTTACAAAATTCCTATAGAGATTGTGAATAAAACCTTACCTATA

262  V  A  I  T  L  L  S  L  V  Y  L  A  G  L  L  A  A  A  Y  Q
961 GTTGCCATTACTTTGCTCTCCCTAGTATACCTTGCAGGTCTTCTGGCAGCTGCTTATCAA

282  L  Y  Y  G  T  K  Y  R  R  F  P  P  W  L  E  T  W  L  Q  C
1021 CTTTATTACGGCACCAAGTATAGGAGATTTCCACCTTGGTTGGAAACCTGGTTACAGTGT

302  R  K  Q  L  G  L  L  S  F  F  F  A  M  V  H  V  A  Y  S  L
1081 AGAAAACAGCTTGGATTACTAAGTTTTTTCTTCGCTATGGTCCATGTTGCCTACAGCCTC

322  C  L  P  M  R  R  S  E  R  Y  L  F  L  N  M  A  Y  Q  Q  V
1141 TGCTTACCGATGAGAAGGTCAGAGAGATATTTGTTTCTCAACATGGCTTATCAGCAGGTT
```

FIGURE 4E

```
342   H  A  N  I  E  N  S  W  N  E  E  V  W  R  I  E  M  Y  I
1201  CATGCAAATATTGAAAACTCTTGGAATGAGGAAGAAGTTTGGAGAATTGAAATGTATATC

362   S  P  G  I  M  S  L  G  L  L  S  L  L  A  V  T  S  I  P  S
1261  TCCTTTGGCATAATGAGCCTTGGCTTACTTTCCCTCCTGGCAGTCACTTCTATCCCTTCA

382   V  S  N  A  L  N  W  R  E  F  S  F  I  Q  S  T  L  G  Y  V
1321  GTGAGCAATGCCTTAAACTGGAGAGAATTCAGTTTTATTCAGTCTACACTTGGATATGTC

402   A  L  L  I  S  T  F  H  V  L  I  Y  G  W  K  R  A  F  E  E
1381  GCTCTGCTCATAAGTACTTTCCATGTTTTAATTTATGGATGGAAACGAGCTTTTGAGGAA

422   E  Y  Y  R  F  Y  T  P  P  N  F  V  L  A  L  V  L  P  S  I
1441  GAGTACTACAGATTTTATACACCACCAAACTTTGTTCTTGCTCTTGTTTTGCCCTCAATT

442   V  I  L  G  K  I  I  L  F  L  P  C  I  S  R  K  L  K  R  I
1501  GTAATTCTGGGTAAGATTATTTTATTCCTTCCATGTATAAGCCGAAAGCTAAAACGAATT

462   K  K  G  W  E  K  S  Q  F  L  E  E  G  I  G  G  T  I  P  H
1561  AAAAAAGGCTGGGAAAAGAGCCAATTTCTGGAAGAAGGTATTGGAGGAACAATTCCTCAT

482   V  S  P  E  R  V  T  V  M  *
1621  GTCTCCCCGGAGAGGGTCACAGTAATGTGATGATAAATGGTGTTCACAGCTGCCATATAA
```

FIGURE 4E CONTINUED

```
EXON_1    75bp
      1   GATCCAGCTTGGGTAGGCGGGGAAGCAGCTGGAGTGCGACCGCCGCGGCAGCCACCCTGC
     61   AACCGCCAGTCGGAG

EXON_2    79bp
      1   AGAGCTAAGGGCAAGTCCTGAGGTTGGGCCCAGGAGAAAGAAGGCAAGGAGACATTGTCC
     61   CAGGTAGGATGTGTCCCAG

EXON_3    525bp
      1   GATATTCTTGGTGATCTTGGAAGTGTCCGTATCATGGAATCAATCTCTATGATGGGAAGC
     61   CCTAAGAGCCTTAGTGAAACTTTTTTACCTAATGGCATAAATGGTATCAAAGATGCAAGG
    121   AAGGTCACTGTAGGTGTGATTGGAAGTGGAGATTTTGCCAAATCCTTGACCATTCGACTT
    181   ATTAGATGCGGCTATCATGTGGTCATAGGAAGTAGAAATCCTAAGTTTGCTTCTGAATTT
    241   TTTCCTCATGTGGTAGATGTCACTCATCATGAAGATGCTCTCACAAAAACAAATATAATA
    301   TTTGTTGCTATACACAGAGAACATTATACCTCCCTGTGGGACCTGAGACATCTGCTTGTG
    361   GGTAAAATCCTGATTGATGTGAGCAATAACATGAGGATAAACCAGTACCCAGAATCCAAT
    421   GCTGAATATTTGGCTTCATTATTCCCAGATTCTTTGATTGTCAAAGGATTTAATGTTGTC
    481   TCAGCTTGGGCACTTCAGTTAGGACCTAAGGATGCCAGCCGGCAG

EXON_4    528bp
      1   GTTTATATATGCAGCAACAATATTCAAGCGCGACAACAGGTTATTGAACTTGCCCGCCAG
     61   TTGAATTTCATTCCCATTGACTTGGGATCCTTATCATCAGCCAGAGAGATTGAAAATTTA
    121   CCCCTACGACTCTTTACTCTCTGGAGAGGGCCAGTGGTGGTAGCTATAAGCTTGGCCACA
    181   TTTTTTTTCCTTTATTCCTTTGTCAGAGATGTGATTCATCCATATGCTAGAAACCAACAG
    241   AGTGACTTTTACAAAATTCCTATAGAGATTGTGAATAAAACCTTACCTATAGTTGCCATT
    301   ACTTTGCTCTCCCTAGTATACCTCGCAGGTCTTCTGGCAGCTGCTTATCAACTTTATTAC
    361   GGCACCAAGTATAGGAGATTTCCACCTTGGTTGGAAACCTGGTTACAGTGTAGAAAACAG
    421   CTTGGATTACTAAGTTTTTTCTTCGCTATGGTCCATGTTGCCTACAGCCTCTGCTTACCG
    481   ATGAGAAGGTCAGAGAGATATTTGTTTCTCAACATGGCTTATCAGCAG

EXON_5    165bp
      1   GTTCATGCAAATATTGAAAACTCTTGGAATGAGGAAGAAGTTTGGAGAATTGAAATGTAT
     61   ATCTCCTTTGGCATAATGAGCCTTGGCTTACTTTCCCTCCTGGCAGTCACTTCTATCCCT
    121   TCAGTGAGCAATGCTTTAAACTGGAGAGAATTCAGTTTTATTCAG

EXON_6    148bp
      1   TCTACACTTGGATATGTCGCTCTGCTCATAAGTACTTTCCATGTTTTAATTTATGGATGG
     61   AAACGAGCTTTTGAGGAAGAGTACTACAGATTTTATACACCACCAAACTTTGTTCTTGCT
    121   CTTGTTTTGCCCTCAATTGTAATTCTGG

EXON_7+UTR  718bp
      1   ATCTTTTGCAGCTTTGCAGATACCCAGACTGAGCTGGAACTGGAATTTGTCTTCCTATTG
     61   ACTCTACTTCTTTAAAAGCGGCTGCCCATTACATTCCTCAGCTGTCCTTGCAGTTAGGTG
    121   TACATGTGACTGAGTGTTGGCCAGTGAGATGAAGTCTCCTCAAAGGAAGGCAGCATGTGT
    181   CCTTTTTCATCCCTTCATCTTGCTGCTGGGATTGTGGATATAACAGGAGCCCTGGCAGCT
    241   GTCTCCAGAGGATCAAAGCCACACCCAAAGAGTAAGGCAGATTAGAGACCAGAAAGACCT
    301   TGACTACTTCCCTACTTCCACTGCTTTTTCCTGCATTTAAGCCATTGTAAATCTGGGTGT
    361   GTTACATGAAGTGAAAATTAATTCTTTCTGCCCTTCAGTTCTTTATCCTGATACCATTTA
    421   ACACTGTCTGAATTAACTAGACTGCAATAATTCTTTCTTTTGAAAGCTTTTAAAGGATAA
    481   TGTGCAATTCACATTAAAATTGATTTTCCATTGTCAATTAGTTATACTCATTTTCCTGCC
    541   TTGATCTTTCATTAGATATTTTGTATCTGCTTGGAATATATTATCTTCTTTTTAACTGTG
    601   TAATTGGTAATTACTAAAACTCTGTAATCTCCAAAATATTGCTATCAAATTACACACCAT
    661   GTTTTCTATCATTCTCATAGATCTGCCTTATAAACATTTAAATAAAAAGTACTATTTA
```

FIGURE 4F

```
   1 GATCCAGCTTGGGTAGGCGGGGAAGCAGCTGGAGTGCGACCGCCGCGGCAGCCACCCTGC
  61 AACCGCCAGTCGGAGAGAGCTAAGGGCAAGTCCTGAGGTTGGGCCCAGGAGAAAGAAGGC
 121 AAGGAGACATTGTCCCAGGTAGGATGTGTCCCAGGATATTCTTGGTGATCTTGGAAGTGT
 181 CCGTATCATGGAATCAATCTCTATGATGGGAAGCCCTAAGAGCCTTAGTGAAACTTTTTT
 241 ACCTAATGGCATAAATGGTATCAAAGATGCAAGGAAGGTCACTGTAGGTGTGATTGGAAG
 301 TGGAGATTTTGCCAAATCCTTGACCATTCGACTTATTAGATGCGGCTATCATGTGGTCAT
 361 AGGAAGTAGAAATCCTAAGTTTGCTTCTGAATTTTTTCCTCATGTGGTAGATGTCACTCA
 421 TCATGAAGATGCTCTCACAAAAACAAATATAATATTTGTTGCTATACACAGAGAACATTA
 481 TACCTCCCTGTGGGACCTGAGACATCTGCTTGTGGGTAAAATCCTGATTGATGTGAGCAA
 541 TAACATGAGGATAAACCAGTACCCAGAATCCAATGCTGAATATTTGGCTTCATTATTCCC
 601 AGATTCTTTGATTGTCAAAGGATTTAATGTTGTCTCAGCTTGGGCACTTCAGTTAGGACC
 661 TAAGGATGCCAGCCGGCAGGTTTATATATGCAGCAACAATATTCAAGCGCGACAACAGGT
 721 TATTGAACTTGCCCGCCAGTTGAATTTCATTCCCATTGACTTGGGATCCTTATCATCAGC
 781 CAGAGAGATTGAAAATTTACCCCTACGACTCTTTACTCTCTGGAGAGGGCCAGTGGTGGT
 841 AGCTATAAGCTTGGCCACATTTTTTTTCCTTTATTCCTTTGTCAGAGATGTGATTCATCC
 901 ATATGCTAGAAACCAACAGAGTGACTTTTACAAAATTCCTATAGAGATTGTGAATAAAAC
 961 CTTACCTATAGTTGCCATTACTTTGCTCTCCCTAGTATACCTCGCAGGTCTTCTGGCAGC
1021 TGCTTATCAACTTTATTACGGCACCAAGTATAGGAGATTTCCACCTTGGTTGGAAACCTG
1081 GTTACAGTGTAGAAAACAGCTTGGATTACTAAGTTTTTTCTTCGCTATGGTCCATGTTGC
1141 CTACAGCCTCTGCTTACCGATGAGAAGGTCAGAGAGATATTTGTTTCTCAACATGGCTTA
1201 TCAGCAGGTTCATGCAAATATTGAAAACTCTTGGAATGAGGAAGAAGTTTGGAGAATTGA
1261 AATGTATATCTCCTTTGGCATAATGAGCCTTGGCTTACTTTCCCTCCTGGCAGTCACTTC
1321 TATCCCTTCAGTGAGCAATGCTTTAAACTGGAGAGAATTCAGTTTTATTCAGTCTACACT
1381 TGGATATGTCGCTCTGCTCATAAGTACTTTCCATGTTTTAATTTATGGATGGAAACGAGC
1441 TTTTGAGGAAGAGTACTACAGATTTTATACACCACCAAACTTTGTTCTTGCTCTTGTTTT
1501 GCCCTCAATTGTAATTCTGGATCTTTTGCAGCTTTGCAGATACCCAGACTGAGCTGGAAC
1561 TGGAATTTGTCTTCCTATTGACTCTACTTCTTTAAAAGCGGCTGCCCATTACATTCCTCA
1621 GCTGTCCTTGCAGTTAGGTGTACATGTGACTGAGTGTTGGCCAGTGAGATGAAGTCTCCT
1681 CAAAGGAAGGCAGCATGTGTCCTTTTTCATCCCTTCATCTTGCTGCTGGGATTGTGGATA
1741 TAACAGGAGCCCTGGCAGCTGTCTCCAGAGGATCAAAGCCACACCCAAAGAGTAAGGCAG
1801 ATTAGAGACCAGAAAGACCTTGACTACTTCCCTACTTCCACTGCTTTTTCCTGCATTTAA
1861 GCCATTGTAAATCTGGGTGTGTTACATGAAGTGAAAATTAATTCTTTCTGCCCTTCAGTT
1921 CTTTATCCTGATACCATTTAACACTGTCTGAATTAACTAGACTGCAATAATTCTTTCTTT
1981 TGAAAGCTTTTAAAGGATAATGTGCAATTCACATTAAAATTGATTTTCCATTGTCAATTA
2041 GTTATACTCATTTTCCTGCCTTGATCTTTCATTAGATATTTTGTATCTGCTTGGAATATA
2101 TTATCTTCTTTTTAACTGTGTAATTGGTAATTACTAAAACTCTGTAATCTCCAAAATATT
2161 GCTATCAAATTACACACCATGTTTTCTATCATTCTCATAGATCTGCCTTATAAACATTTA
2221 AATAAAAAGTACTATTTA
```

FIGURE 4G

```
   1 GATCCAGCTTGGGTAGGCGGGGAAGCAGCTGGAGTGCGACCGCCGCGGCAGCCACCCTGCA

62 ACCGCCAGTCGGAGAGAGCTAAGGGCAAGTCCTGAGGTTGGGCCCAGGAGAAAGAAGGCA

122 AGGAGACATTGTCCCAGGTAGGATGTGTCCCAGGATATTCTTGGTGATCTTGGAAGTGTC

M   E   S   I   S   M   M   G   S   P   K   S   L   S   E   T   C   L
 182 CGTATCATGGAATCAATCTCTATGATGGGAAGCCCTAAGAGCCTTAGTGAAACTTGTTTA

19 P   N   G   I   N   G   I   K   D   A   R   K   V   T   V   G   V   I   G   S
 242 CCTAATGGCATAAATGGTATCAAAGATGCAAGGAAGGTCACTGTAGGTGTGATTGGAAGT

39 G   D   F   A   K   S   L   T   I   R   L   I   R   C   G   Y   H   V   V   I
 302 GGAGATTTTGCCAAATCCTTGACCATTCGACTTATTAGATGCGGCTATCATGTGGTCATA

59 G   S   R   N   P   K   F   A   S   E   F   F   P   H   V   V   D   V   T   H
 362 GGAAGTAGAAATCCTAAGTTTGCTTCTGAATTTTTTCCTCATGTGGTAGATGTCACTCAT

79 H   E   D   A   L   T   K   T   N   I   I   F   V   A   I   H   R   E   H   Y
 422 CATGAAGATGCTCTCACAAAAACAAATATAATATTTGTTGCTATACACAGAGAACATTAT

99 T   S   L   W   D   L   R   H   L   L   V   G   K   I   L   I   D   V   S   N
 482 ACCTCCCTGTGGGACCTGAGACATCTGCTTGTGGGTAAAATCCTGATTGATGTGAGCAAT

119 N   M   R   I   N   Q   Y   P   E   S   N   A   E   Y   L   A   S   L   F   P
 542 AACATGAGGATAAACCAGTACCCAGAATCCAATGCTGAATATTTGGCTTCATTATTCCCA

139 D   S   L   I   V   K   G   F   N   V   V   S   A   W   A   L   Q   L   G   P
 602 GATTCTTTGATTGTCAAAGGATTTAATGTTGTCTCAGCTTGGGCACTTCAGTTAGGACCT

159 K   D   A   S   R   Q   V   Y   I   C   S   N   N   I   Q   A   R   Q   Q   V
 662 AAGGATGCCAGCCGGCAGGTTTATATATGCAGCAACAATATTCAAGCGCGACAACAGGTT

179 I   E   L   A   R   Q   L   N   F   I   P   I   D   L   G   S   L   S   S   A
 722 ATTGAACTTGCCCGCCAGTTGAATTTCATTCCCATTGACTTGGGATCCTTATCATCAGCC

199 R   E   I   E   N   L   P   L   R   L   F   T   L   W   R   G   P   V   V   V
 782 AGAGAGATTGAAAATTTACCCCTACGACTCTTTACTCTCTGGAGAGGGCCAGTGGTGGTA

219 A   I   S   L   A   T   F   F   F   L   Y   S   F   V   R   D   V   I   H   P
 842 GCTATAAGCTTGGCCACATTTTTTTTCCTTTATTCCTTTGTCAGAGATGTGATTCATCCA

239 Y   A   R   N   Q   Q   S   D   F   Y   K   I   P   I   E   I   V   N   K   T
 902 TATGCTAGAAACCAACAGAGTGACTTTTACAAAATTCCTATAGAGATTGTGAATAAAACC

259 L   P   I   V   A   I   T   L   L   S   L   V   Y   L   A   G   L   L   A   A
 962 TTACCTATAGTTGCCATTACTTTGCTCTCCCTAGTATACCTCGCAGGTCTTCTGGCAGCT

279 A   Y   Q   L   Y   Y   G   T   K   Y   R   R   F   P   P   W   L   E   T   W
1022 GCTTATCAACTTTATTACGGCACCAAGTATAGGAGATTTCCACCTTGGTTGGAAACCTGG
```

FIGURE 4H

```
299  L   Q   C   R   K   Q   L   G   L   L   S   F   F   F   A   M   V   H   V   A
1082 TTACAGTGTAGAAAACAGCTTGGATTACTAAGTTTTTTCTTCGCTATGGTCCATGTTGCC

319  Y   S   L   C   L   P   M   R   R   S   E   R   Y   L   F   L   N   M   A   Y
1142 TACAGCCTCTGCTTACCGATGAGAAGGTCAGAGAGATATTTGTTTCTCAACATGGCTTAT

339  Q   Q   V   H   A   N   I   E   N   S   W   N   E   E   V   W   R   I   E
1202 CAGCAGGTTCATGCAAATATTGAAAACTCTTGGAATGAGGAAGAAGTTTGGAGAATTGAA

359  M   Y   I   S   F   G   I   M   S   L   G   L   L   S   L   L   A   V   T   S
1262 ATGTATATCTCCTTTGGCATAATGAGCCTTGGCTTACTTTCCCTCCTGGCAGTCACTTCT

379  I   P   S   V   S   N   A   L   N   W   R   E   F   S   F   I   Q   S   T   L
1322 ATCCCTTCAGTGAGCAATGCTTTAAACTGGAGAGAATTCAGTTTTATTCAGTCTACACTT

399  G   Y   V   A   L   L   I   S   T   F   H   V   L   I   Y   G   W   K   R   A
1382 GGATATGTCGCTCTGCTCATAAGTACTTTCCATGTTTTAATTTATGGATGGAAACGAGCT

419  F   E   E   E   Y   Y   R   F   Y   T   P   P   N   F   V   L   A   L   V   L
1442 TTTGAGGAAGAGTACTACAGATTTTATACACCACCAAACTTTGTTCTTGCTCTTGTTTTG

439  P   S   I   V   I   L   D   L   L   Q   L   C   R   Y   P   D   -
1502 CCCTCAATTGTAATTCTGGATCTTTTGCAGCTTTGCAGATACCCAGACTGAGCTGGAACT
```

FIGURE 4H CONTINUED

```
EXON_1   75bp
     1   GATCCAGCTTGGGTAGGCGGGGAAGCAGCTGGAGTGCGACCGCCGCGGCAGCCACCCTGC
    61   AACCGCCAGTCGGAG

EXON_2   79bp
     1   AGAGCTAAGGGCAAGTCCTGAGGTTGGGCCCAGGAGAAAGAAGGCAAGGAGACATTGTCC
    61   CAGGTAGGATGTGTCCCAG

EXON_3   525bp
     1   GATATTCTTGGTGATCTTGGAAGTGTCCGTATCATGGAATCAATCTCTATGATGGGAAGC
    61   CCTAAGAGCCTTAGTGAAACTTTTTTACCTAATGGCATAAATGGTATCAAAGATGCAAGG
   121   AAGGTCACTGTAGGTGTGATTGGAAGTGGAGATTTTGCCAAATCCTTGACCATTCGACTT
   181   ATTAGATGCGGCTATCATGTGGTCATAGGAAGTAGAAATCCTAAGTTTGCTTCTGAATTT
   241   TTTCCTCATGTGGTAGATGTCACTCATCATGAAGATGCTCTCACAAAAACAAATATAATA
   301   TTTGTTGCTATACACAGAGAACATTATACCTCCCTGTGGGACCTGAGACATCTGCTTGTG
   361   GGTAAAAATCCTGATTGATGTGAGCAATAACATGAGGATAAACCAGTACCCAGAATCCAAT
   421   GCTGAATATTTGGCTTCATTATTCCCAGATTCTTTGATTGTCAAAGGATTTAATGTTGTC
   481   TCAGCTTGGGCACTTCAGTTAGGACCTAAGGATGCCAGCCGGCAG

EXON_4   528bp
     1   GTTTATATATGCAGCAACAATATTCAAGCGCGACAACAGGTTATTGAACTTGCCCGCCAG
    61   TTGAATTTCATTCCCATTGACTTGGGATCCTTATCATCAGCCAGAGAGATTGAAAATTTA
   121   CCCCTACGACTCTTTACTCTCTGGAGAGGGCCAGTGGTGGTAGCTATAAGCTTGGCCACA
   181   TTTTTTTTCCTTTATTCCTTTGTCAGAGATGTGATTCATCCATATGCTAGAAACCAACAG
   241   AGTGACTTTTACAAAATTCCTATAGAGATTGTGAATAAAACCTTACCTATAGTTGCCATT
   301   ACTTTGCTCTCCCTAGTATACCTCGCAGGTCTTCTGGCAGCTGCTTATCAACTTTATTAC
   361   GGCACCAAGTATAGGAGATTTCCACCTTGGTTGGAAACCTGGTTACAGTGTAGAAAACAG
   421   CTTGGATTACTAAGTTTTTTCTTCGCTATGGTCCATGTTGCCTACAGCCTCTGCTTACCG
   481   ATGAGAAGGTCAGAGAGATATTTGTTTCTCAACATGGCTTATCAGCAG

EXON_5   165bp
     1   GTTCATGCAAATATTGAAAACTCTTGGAATGAGGAAGAAGTTTGGAGAATTGAAATGTAT
    61   ATCTCCTTTGGCATAATGAGCCTTGGCTTACTTTCCCTCCTGGCAGTCACTTCTATCCCT
   121   TCAGTGAGCAATGCTTTAAACTGGAGAGAATTCAGTTTTATTCAG

EXON_7 and 3'UTR   718bp
     1   ATCTTTTGCAGCTTTGCAGATACCCAGACTGAGCTGGAACTGGAATTTGTCTTCCTATTG
    61   ACTCTACTTCTTTAAAAGCGGCTGCCCATTACATTCCTCAGCTGTCCTTGCAGTTAGGTG
   121   TACATGTGACTGAGTGTTGGCCAGTGAGATGAAGTCTCCTCAAAGGAAGGCAGCATGTGT
   181   CCTTTTTCATCCCTTCATCTTGCTGCTGGATTGTGGATATAACAGGAGCCCTGGCAGCT
   241   GTCTCCAGAGGATCAAAGCCACACCCAAAGAGTAAGGCAGATTAGAGACCAGAAAGACCT
   301   TGACTACTTCCCTACTTCCACTGCTTTTTCCTGCATTTAAGCCATTGTAAATCTGGGTGT
   361   GTTACATGAAGTGAAAATTAATTCTTTCTGCCCTTCAGTTCTTTATCCTGATACCATTTA
   421   ACACTGTCTGAATTAACTAGACTGCAATAATTCTTTCTTTTGAAAGCTTTTAAAGGATAA
   481   TGTGCAATTCACATTAAAATTGATTTTCCATTGTCAATTAGTTATACTCATTTTCCTGCC
   541   TTGATCTTTCATTAGATATTTTGTATCTGCTTGGAATATATTATCTTCTTTTTAACTGTG
   601   TAATTGGTAATTACTAAAACTCTGTAATCTCCAAAATATTGCTATCAAATTACACACCAT
   661   GTTTTCTATCATTCTCATAGATCTGCCTTATAAACATTTAAATAAAAGTACTATTTA
```

FIGURE 4I

```
   1 GGATCCAGCTTGGGTAGGCGGGGAAGCAGCTGGAGTGCGACCGCTACGGCAGCCACCCTG
  61 CAACCGCCAGTCGGAGAGCTAAGGGCAAGTCCTGAGGTTGGGCCCAGGAGAAAGAAGGCA
 121 AGGAGACATTGTCCCAGGATATTCTTGGTGATCTTGGAAGTGTCCGTATCATGGAATCAA
 181 TCTCTATGATGGGAAGCCCTAAGAGCCTTAGTGAAACTTGTTTACCTAATGGCATAAATG
 241 GTATCAAAGATGCAAGGAAGGTCACTGTAGGTGTGATTGGAAGTGGAGATTTTGCCAAAT
 301 CCTTGACCATTCGACTTATTAGATGCGGCTATCATGTGGTCATAGGAAGTAGAAATCCTA
 361 AGTTTGCTTCTGAATTTTTTCCTCATGTGGTAGATGTCACTCATCATGAAGATGCTCTCA
 421 CAAAAACAAATATAATATTTGTTGCTATACACAGAGAACATTATACCTCCCTGTGGGACC
 481 TGAGACATCTGCTTGTGGGTAAAATCCTGATTGATGTGAGCAATAACATGAGGATAAACC
 541 AGTACCCAGAATCCAATGCTGAATATTTGGCTTCATTATTCCCAGATTCTTTGATTGTCA
 601 AAGGATTTAATGTTGTCTCAGCTTGGGCACTTCAGTTAGGACCTAAGGATGCCAGCCGGC
 661 AGGTTTATATATGCAGCAACAATATTCAAGCGCGACAACAGGTTATTGAACTTGCCCGCC
 721 AGTTGAATTTCATTCCCATTGACTTGGGATCCTTATCATCAGCCAGAGAGATTGAAAATT
 781 TACCCCTACGACTCTTTACTTTCTGGAGAGGGCCAGTGGTGGTAGCTATAAGCTTGGCCA
 841 CATTTTTTTTCCTTTATTCCTTTGTCAGAGATGTGATTCATCCATATGCTAGAAACCAAC
 901 AGAGTGACTTTTACAAAATTCCTATAGAGATTGTGAATAAAACCTTACCTATAGTTGCCA
 961 TTACTTTGCTCTCCCTAGTATACCTTGCAGGTCTTCTGGCAGCTGCTTATCAACTTTATT
1021 ACGGCACCAAGTATAGGAGATTTCCACCTTGGTTGGAAACCTGGTTACAGTGTAGAAAAC
1081 AGCTTGGATTACTAAGTTTTTTCTTCGCTATGGTCCATGTTGCCTACAGCCTCTGCTTAC
1141 CGATGAGAAGGTCAGAGAGATATTTGTTTCTCAACATGGCTTATCAGCAGGTTCATGCAA
1201 ATATTGAAAACTCTTGGAATGAGGAAGAAGTTTGGAGAATTGAAATGTATATCTCCTTTG
1261 GCATAATGAGCCTTGGCTTACTTTCCCTCCTGGCAGTCACTTCTATCCCTTCGGTGAGCA
1321 ATGCTTTAAACTGGAGAGAATTCAGTTTTATTCAGATCTTTTGCAGCTTTGCAGATACCC
1381 AGACTGAGCTGGAACTGGAATTTGTCTTCCTATTGACTCTACTTCTTTAAAAGCGGCTGC
1441 CCATTACATTCCTCAGCTGTCCTTGCAGTTAGGTGTACATGTGACTGAGTGTTGGCCAGT
1501 GAGATGAAGTCTCCTCAAAGGAAGGCAGCATGTGTCCTTTTTCATCCCTTCATCTTGCTG
1561 CTGGGATTGTGGATATAACAGGAGCCCTGGCAGCTGCTCCAGAGGATCAAAGCCACACCC
1621 AAAGAGTAAGGCAGATTAGAGACCAGAAAGACCTTGACTACTTCCCTACTTCCACTGCTT
1681 TTTCCTGCATTTAAGCCATTGTAAATCTGGGTGTGTTACATGAAGTGAAAATTAATTCTT
1741 TCTGCCCTTCAGTTCTTTATCCTGATACCATTTAACACTGTCTGAATTAACTAGACTGCA
1801 ATAATTCTTTCTTTTGAAAGCTTTTAAAGGATAATGTGCAATTCACATTAAAATTGATTT
1861 TCCATTGTCAATTAGTTATACTCATTTTCCTGCCTTGATCTTTCATTAGATATTTTGTAT
1921 CTGCTTGGAATATATTATCTTCTTTTTAACTGTGTAATTGGTAATTACTAAAACTCTGTA
1981 ATCTCCAAAATATTGCTATCAAATTACACACCATGTTTTCTATCATTCTCATAGATCTGC
2041 CTTATAAACATTTAAATAAAAGTACTATTTACCAAAAAAAAAAAAAAAAAAAAAAAAAAA
2101 AA
```

FIGURE 4J

```
  1 GGATCCAGCTTGGGTAGGCGGGGAAGCAGCTGGAGTGCGACCGCTACGGCAGCCACCCTGCA
 63 ACCGCCAGTCGGAGAGCTAAGGGCAAGTCCTGAGGTTGGGCCCAGGAGAAAGAAGGCAAG

1                                                    M  E  S  I
123 GAGACATTGTCCCAGGATATTCTTGGTGATCTTGGAAGTGTCCGTATCATGGAATCAATC

5  S  M  M  G  S  P  K  S  L  S  E  T  C  L  P  N  G  I  N  G
183 TCTATGATGGGAAGCCCTAAGAGCCTTAGTGAAACTTGTTTACCTAATGGCATAAATGGT

25  I  K  D  A  R  K  V  T  V  G  V  I  G  S  G  D  F  A  K  S
243 ATCAAAGATGCAAGGAAGGTCACTGTAGGTGTGATTGGAAGTGGAGATTTTGCCAAATCC

45  L  T  I  R  L  I  R  C  G  Y  H  V  V  I  G  S  R  N  P  K
303 TTGACCATTCGACTTATTAGATGCGGCTATCATGTGGTCATAGGAAGTAGAAATCCTAAG

65  F  A  S  E  F  P  P  H  V  V  D  V  T  H  H  E  D  A  L  T
363 TTTGCTTCTGAATTTTTTCCTCATGTGGTAGATGTCACTCATCATGAAGATGCTCTCACA

85  K  T  N  I  I  F  V  A  I  H  R  E  H  Y  T  S  L  W  D  L
423 AAAACAAATATAATATTTGTTGCTATACACAGAGAACATTATACCTCCCTGTGGGACCTG

105  R  H  L  L  V  G  K  I  L  I  D  V  S  N  N  M  R  I  N  Q
483 AGACATCTGCTTGTGGGTAAAATCCTGATTGATGTGAGCAATAACATGAGGATAAACCAG

125  Y  P  E  S  N  A  E  Y  L  A  S  L  P  P  D  S  L  I  V  K
543 TACCCAGAATCCAATGCTGAATATTTGGCTTCATTATTCCCAGATTCTTTGATTGTCAAA

145  G  F  N  V  V  S  A  W  A  L  Q  L  G  P  K  D  A  S  R  Q
603 GGATTTAATGTTGTCTCAGCTTGGGCACTTCAGTTAGGACCTAAGGATGCCAGCCGGCAG

165  V  Y  I  C  S  N  N  I  Q  A  R  Q  Q  V  I  E  L  A  R  Q
663 GTTTATATATGCAGCAACAATATTCAAGCGCGACAACAGGTTATTGAACTTGCCCGCCAG

185  L  N  F  I  P  I  D  L  G  S  L  S  S  A  R  E  I  E  N  L
723 TTGAATTTCATTCCCATTGACTTGGGATCCTTATCATCAGCCAGAGAGATTGAAAATTTA

205  P  L  R  L  F  T  F  W  R  G  P  V  V  V  A  I  S  L  A  T
783 CCCCTACGACTCTTTACTTTCTGGAGAGGGCCAGTGGTGGTAGCTATAAGCTTGGCCACA

225  F  F  P  L  Y  S  F  V  R  D  V  I  H  P  Y  A  R  N  Q  Q
843 TTTTTTTTCCTTTATTCCTTTGTCAGAGATGTGATTCATCCATATGCTAGAAACCAACAG

245  S  D  F  Y  K  I  P  I  E  I  V  N  K  T  L  P  I  V  A  I
903 AGTGACTTTTACAAAATTCCTATAGAGATTGTGAATAAAACCTTACCTATAGTTGCCATT

265  T  L  L  S  L  V  Y  L  A  G  L  L  A  A  A  Y  Q  L  Y  Y
963 ACTTTGCTCTCCCTAGTATACCTTGCAGGTCTTCTGGCAGCTGCTTATCAACTTTATTAC

285  G  T  K  Y  R  R  F  P  P  W  L  E  T  W  L  Q  C  R  K  Q
1023 GGCACCAAGTATAGGAGATTTCCACCTTGGTTGGAAACCTGGTTACAGTGTAGAAAACAG

305  L  G  L  L  S  F  F  P  A  M  V  H  V  A  Y  S  L  C  L  P
1083 CTTGGATTACTAAGTTTTTTCTTCGCTATGGTCCATGTTGCCTACAGCCTCTGCTTACCG

```
1143  ATGAGAAGGTCAGAGAGATATTTGTTTCTCAACATGGCTTATCAGCAGGTTCATGCAAAT

345   I  E  N  S  W  N  E  E  S  V  W  R  I  E  M  Y  I  S  P  G
1203  ATTGAAAACTCTTGGAATGAGGAAGAAGTTTGGAGAATTGAAATGTATATCTCCTTTGGC

365   I  M  S  L  G  L  L  S  L  L  A  V  T  S  I  P  S  V  S  N
1263  ATAATGAGCCTTGGCTTACTTTCCCTCCTGGCAGTCACTTCTATCCCTTCGGTGAGCAAT

385   A  L  N  W  R  E  F  S  F  I  Q  I  F  C  S  F  A  D  T  Q
1323  GCTTTAAAACTGGAGAGAATTCAGTTTTATTCAGATCTTTTGCAGCTTTGCAGATACCCAG

405   T  E  L  E  F  V  F  L  L  T  L  L  L  *
1383  ACTGAGCTGGAACTGGAATTTGTCTTCCTATTGACTCTACTTCTTTAAAAGCGGCTGCCC
1443  ATTACATTCCTCAGCTGTCCTTGCAGTTAGGTGTACATGTGACTGAGTGTTGGCCAGTGA
1503  GATGAAGTCTCCTCAAAGGAAGGCAGCATGTGTCCTTTTTCATCCCTTCATCTTGCTGCT
1563  GGGATTGTGGATATAACAGGAGCCCTGGCAGCTGCTCCAGAGGATCAAAGCCACACCCAA
1623  AGAGTAAGGCAGATTAGAGACCAGAAAGACCTTGACTACTTCCCTACTTCCACTGCTTTT
1683  TCCTGCATTTAAGCCATTGTAAATCTGGGTGTGTTACATGAAGTGAAAATTAATTCTTTC
1743  TGCCCTTCAGTTCTTTATCCTGATACCATTTAACACTGTCTGAATTAACTAGACTGCAAT
1803  AATTCTTTCTTTTGAAAGCTTTTAAAGGATAATGTGCAATTCACATTAAAATTGATTTTC
1863  CATTGTCAATTAGTTATACTCATTTTCCTGCCTTGATCTTTCATTAGATATTTTGTATCT
1923  GCTTGGAATATATTATCTTCTTTTTAACTGTGTAATTGGTAATTACTAAAACTCTGTAAT
1983  CTCCAAAATATTGCTATCAAATTACACACCATGTTTTCTATCATTCTCATAGATCTGCCT
2043  TATAAACATTTAAATAAAAAGTACTATTTACCAAAAAAAAAAAAAAAAAAAAAAAAAAAA
```

FIGURE 4K CONTINUED

```
  1  ACCCTTCGCCGCGGACCTTCAGCTGCCGCGGTCGCTCCGAGCGGCGGGCCGCAGAGGTTC
 61  AAGCGATTCTCCTGCTTCAGCCTCCGGAGTAGCTGGGATTACAGGCACGTGCCAACACAC

1              M   P   E   E   M   D   K   P   L   I   S   L   H   L   V   D
121  CCAGCCACCAAAATGCCAGAAGAGATGGACAAGCCACTGATCAGCCTCCACCTGGTGGAC

17   S   D   S   S   L   A   K   V   P   D   E   A   P   K   V   G   I   L   G   S
181  AGCGATAGTAGCCTTGCCAAGGTCCCCGATGAGGCCCCCAAAGTGGGCATCCTGGGTAGC

37   G   D   F   A   R   S   L   A   T   R   L   V   G   S   G   F   K   V   V   V
241  GGGGACTTTGCCCGCTCCCTGGCCACACGCCTGGTGGGCTCTGGCTTCAAAGTGGTGGTG

57   G   S   R   N   P   K   R   T   A   R   L   Y   P   S   A   A   Q   V   T   F
301  GGGAGCCGCAACCCCAAACGCACAGCCAGGCTGTATCCCTCAGCGGCCCAAGTGACTTTC

77   Q   E   E   A   V   S   S   P   E   V   I   F   V   A   V   F   R   E   H   Y
361  CAAGAGGAGGCAGTGAGCTCCCCGGAGGTCATCTTTGTGGCTGTGTTCCGGGAGCACTAC

97   S   S   L   C   S   L   S   D   Q   L   A   G   K   I   L   V   D   V   S   N
421  TCTTCACTGTGCAGTCTCAGTGACCAGCTGGCGGGCAAGATCCTGGTGGATGTGAGCAAC

117   P   T   E   Q   E   H   L   Q   H   R   E   S   N   A   E   Y   L   A   S   L
481  CCTACAGAGCAAGAGCACCTTCAGCATCGTGAGTCCAATGCTGAGTACCTGGCCTCCCTC

137   F   P   T   C   T   V   V   K   A   F   N   V   I   S   A   W   T   L   Q   A
541  TTCCCCACTTGCACAGTGGTCAAGGCCTTCAATGTCATCTCTGCCTGGACCCTGCAGGCT

157   G   P   R   D   G   N   R   Q   V   P   I   C   G   D   Q   P   E   A   K   R
601  GGCCCAAGGGATGGTAACAGGCAGGTGCCCATCTGCGGTGACCAGCCAGAAGCCAAGCGT

177   A   V   S   E   M   A   L   A   M   G   F   M   P   V   D   M   G   S   L   A
661  GCTGTCTCGGAGATGGCGCTCGCCATGGGCTTCATGCCCGTGGACATGGGATCCCTGGCG

197   S   A   W   E   V   E   A   M   P   L   R   L   L   P   A   W   K   V   P   T
721  TCAGCCTGGGAGGTGGAGGCCATGCCCCTGCGCCTCCTCCCGGCCTGGAAGGTGCCCACC

217   L   L   A   L   G   L   F   V   C   F   Y   A   Y   N   F   V   R   D   V   L
781  CTGCTGGCCCTGGGGCTCTTCGTCTGCTTCTATGCCTACAACTTCGTCCGGGACGTTCTG

237   Q   P   Y   V   Q   E   S   Q   N   K   F   F   K   L   P   V   S   V   V   N
841  CAGCCCTATGTGCAGGAAAGCCAGAACAAGTTCTTCAAGCTGCCCGTGTCCGTGGTCAAC

257   T   T   L   P   C   V   A   Y   V   L   L   S   L   V   Y   L   P   G   V   L
901  ACCACACTGCCGTGCGTGGCCTACGTGCTGCTGTCACTCGTGTACTTGCCCGGCGTGCTG

277   A   A   A   L   Q   L   R   R   G   T   K   Y   Q   R   F   P   D   W   L   D
961  GCGGCTGCCCTGCAGCTGCGGCGCGGCACCAAGTACCAGCGCTTCCCCGACTGGCTGGAC

297   H   W   L   Q   H   R   K   Q   I   G   L   L   S   F   C   A   A   L   H
1021 CACTGGCTACAGCACCGCAAGCAGATCGGGCTGCTCAGCTTCTTCTGCGCCGCCCTGCAC

317   A   L   Y   S   F   C   L   P   L   R   R   A   H   R   Y   D   L   V   N   L
1081 GCCCTCTACAGCTTCTGCTTGCCGCTGCGCCGCGCCCACCGCTACGACCTGGTCAACCTG

337   A   V   K   Q   V   L   A   N   K   S   H   L   W   V   E   E   E   V   W   R
1141 GCAGTCAAGCAGGTCTTGGCCAACAAGAGCCACCTCTGGGTGGAGGAGGAGGTCTGGCGG

357   M   E   I   Y   L   S   L   G   V   L   A   L   G   T   L   S   L   L   A   V
1201 ATGGAGATCTACCTCTCCCTGGGAGTGCTGGCCCTCGGCACGTTGTCCCTGCTGGCCGTG
```

Figure 4L

```
377  T  S  L  P  S  I  A  N  S  L  N  W  R  E  F  S  F  V  Q  S
1261 ACCTCACTGCCGTCCATTGCAAACTCGCTCAACTGGAGGGAGTTCAGCTTCGTTCAGTCC

397  S  L  G  F  V  A  L  V  L  S  T  L  H  T  L  T  Y  G  W  T
1321 TCACTGGGCTTTGTGGCCCTCGTGCTGAGCACACTGCACACGCTCACCTACGGCTGGACC

417  R  A  F  E  E  S  R  Y  K  F  Y  L  P  P  T  F  T  L  T  L
1381 CGCGCCTTCGAGGAGAGCCGCTACAAGTTCTACCTGCCTCCCACCTTCACGCTCACGCTG

437  L  V  P  C  V  V  I  L  A  K  A  L  F  L  L  P  C  I  S  R
1441 CTGGTGCCCTGCGTCGTCATCCTGGCCAAAGCCCTGTTTCTCCTGCCCTGCATCAGCCGC

457  R  L  A  R  I  R  R  G  W  E  R  E  S  T  I  K  F  T  L  P
1501 AGACTCGCCAGGATCCGGAGAGGCTGGGAGAGGGAGAGCACCATCAAGTTCACGCTGCCC

477  T  D  H  A  L  A  E  K  T  S  H  V  -
1561 ACAGACCACGCCCTGGCCGAGAAGACGAGCCACGTATGAGGTGCCTGCCCTGGGCTCTGG

1621 ACCCCGGGCACACGAGGGACGGTGCCCTGAGCCCGTTAGGTTTTCTTTTCTTGGTGGTGC
1681 AAAGTGGTATAACTGTGTGCAAATAGGAGGTTTGAGGTCCAAATTCCTGGGACTCAAATG
1741 TATGCAGTACTATTCAGAATGATATACACACATATGTGTATATGTATTTACATATATTCC
1801 ACATATATAACAGGATTTGCAATTATACATAGCTAGCTAAAAAGTTGGGTCTCTGAGATT
1861 TCAACTTGTAGATTTAAAAACAAGTGCCGTACGTTAAGAGAAGAGCAGATCATGCTATTG
1921 TGACATTTGCAGAGATATACACACACTTTTTGTACAGAAGAGGCTTGTGCTGTGGTGGGT
1981 TCGATTTATCCCTGCCCACCCCATCCCCACAACTTCCCTTTTGCTACTTCCCCAAGGCTC
2041 TTGCAGAGCTAGGGCTCTGAAGGGGAGGGAAGGCAACGGCTCTGCCCAGAGCCATCCCTG
2101 GAGCATGTGAGCAGCGGCTGGTCTCTTCCCTCCACCTGGGGCAGCAGCAGGAGGCCTGGG
2161 GGGGAGGAAAATCAGGCAGTCGGCCTGGAGTCTGTGCCTGGTCCTTTGCCCGGTGGTGGG
2221 AGGATGGAGGGATTGGGCTGAAGCTGCTCCACCTCATCCTTGCTGAGTGGGGGAGACATT
2281 TTCCCTGAAAGTCAGAAGTCACCATAGAGCCTGCAAATGGATCCTCCTGTGAGAGTGACG
2341 TCACCTCCTTTCCAGAGCCATTAGTGAGCCTGGCTTGGGAACAAGTGTAATTTCCTTCCC
2401 TCCTTTAACCTGGCGATGAGCGTCCTTTAAACCACTGTGCCTTCTCACCCTTTCCATCTT
2461 CAGTTTGAACGACTCCCAGGAAGGCCTAGAGCAGACCCTTTAGAAAATCAGCCCAAGGGGG
2521 AGAGCAAGAGAAAACACTCTAGGGAGTAAAGCTCCCGGGCGTCAGAGTTGAGCCCTGCC
2581 TGGGCTGAAGGACTGTCTTCACGAAGTCAGTCCTGAGGAAAAATATTGGGGACTCCAAAT
2641 GTCCTCTGGCAGAGGACCCAGAAAACCACACTGGCTCCAACTTCCTCCTCATGGGGCATT
2701 ACACTTCAAAACAGTGGGGAGCAACTTTTCCACCAAAGCTACAAACCTAAAATGCTGCTG
2761 CCCCAAAGCACAAGAGGGAAGAGCACCGCCGGGGCCACAGGACGTCTGTCCTCCAGTCAC
2821 AGGCCATCCTTGCTGCTCCCTACTGACTCTAGCTTACTTCCCTGTGAAGAAACAGGTGT
2881 TCTCGGCTGAGCCCCCAACCCTCTGCAGAACCAGGTTGATCTGCCACAGAAAAAGCATCT
2941 TTGAAGACAAAGAGGGTGAGGTCTTCATGAGTCTCCTGGGCCCAAAGCCATCTTCTGATG
3001 GAAGGAAGAGAGTAGGGCCAGTGAAGGCTGCCCAGAGGAATGTCACAGATGAGGCTGCC
3061 CCTGCCCCCTCCCCGCCAGGGAGGTTTCATGAGCTCATGTCTATGCAGCACATAAGGGTT
3121 CTTCAGTGAAAAGCAGGAGAAGAGCCCACTGCAAGGATAGCTCATTAGGCACATGACCGA
3181 TGCAGGGAAGGCCATGCCGGGGAAGCTCTTCCTGCAGGTATTTTCCATCTGCTGTGCCAA
3241 GGCTGAGCGGCAGAAACTTGTCTCATAAATTGGCACTGATGGAGCATCAGCTGTGGCCCA
3301 CAGAGAGCCTTGCTGAGAAGGGGGCAGGTAAAGCAGAGATTTTAGCATTGCCTTGGCATA
3361 ACAAGGGCCCATCGATTCCCTACTAATGAGAGGCAGGGAGAGCATGGGCAATGGAGACCC
3421 ACCAATGATCCCCAACCCCGGTGGGTACTGGCTGCCTGCCCTGGGCCAGGGAATGGCTCC
3481 TTATACCAAAGATGCTGGCACATAGCAGAACCCAGTGCACGTCCTCCCCTTCCCACCCAC
3541 CTCTGGCTGAAGGTGCTCAAGAGGGAAGCAATTATAAGGTGGGTGGCAGGAGGGAACAGG
3601 TGCCACCTGCTGGACAATCACACGAAAGGCAGGCGGGCTGTGTACTGGGCCCTGACTGTG
3661 CGTCCACTGCTGTCTTCCCTACCTCACCAGGCTACTGGCAGCAGCATCCCGAGAGCACAT
3721 CATCTCCACAGCCTGGTAAATTCCATGTGCCTCTGGGTACAAAAGTGCCTCAACGACATG
3781 CTCTGGAAATCCCAAATGCCACAGTCTGAGGTTGATATCTAAAATCTATGCCTTCAAAAG
3841 AGTCTCTGTTTTTTTTTTTTTAACCTGGTAGACGGTATAAAAGCAGTGCAAATAAACACCT
3901 AACCTTCTGC
```

```
   1 AGCGGCGGCTCCTGCAGCGGTGGTCGGCTGTTGGGTGTGGAGTTTCCCAGCGCCCCTCGGG
   1                                                         M  T
  62 TCCGACCCTTTGAGCGTTCTGCTCCGGCGCCAGCCTACCTCGCTCCTCGGCGCCATGACC

3  T  T  T  T  F  K  G  V  D  P  N  S  R  N  S  S  R  V  L  R
 122 ACAACCACCACCTTCAAGGGAGTCGACCCCAACAGCAGGAATAGCTCCCGAGTTTTGCGG

23  P  P  G  G  S  N  F  S  L  G  F  D  E  P  T  E  Q  P  V
 182 CCTCCAGGTGGTGGATCCAATTTTTCATTAGGTTTTGATGAACCAACAGAACAACCTGTG

43  R  K  N  K  M  A  S  N  I  F  G  T  P  E  E  N  Q  A  S  W
 242 AGGAAGAACAAAATGGCCTCTAATATCTTTGGGACACCTGAAGAAAATCAAGCTTCTTGG

63  A  K  S  A  G  A  K  S  S  G  G  R  E  D  L  E  S  S  G  L
 302 GCCAAGTCAGCAGGTGCCAAGTCTAGTGGTGGCAGGGAAGACTTGGAGTCATCTGGACTG

83  Q  R  R  N  S  S  E  A  S  S  G  D  F  L  D  L  K  G  E  G
 362 CAGAGAAGGAACTCCTCTGAAGCAAGCTCCGGAGACTTCTTAGATCTGAAGGGAGAAGGT

103  D  I  H  E  N  V  D  T  D  L  P  G  S  L  G  Q  S  E  E  K
 422 GATATTCATGAAAATGTGGACACAGACTTGCCAGGCAGCCTGGGGCAGAGTGAAGAGAAG

123  P  V  P  A  A  P  V  P  S  P  V  A  P  A  P  V  P  S  R  R
 482 CCCGTGCCTGCTGCGCCTGTGCCCAGCCCGGTGGCCCCGGCCCCAGTGCCATCCAGAAGA

143  N  P  P  G  G  K  S  S  L  V  L  G  *
 542 AATCCCCCTGGCGGCAAGTCCAGCCTCGTCTTGGGTTAGCTCTGACTGTCCTGAACGCTG

602 TCGTTCTGTCTGTTTCCTCCATGCTTGTGAACTGCACAACTTGAGCCTGACTGTACATCT
 662 CTTGGATTTGTTTCATTAAAAAGAAGCACTTTATGTACTGCTGTCTTTTTTTTTTTTCTT
 722 TTGAAGAACAGGTTTCTCTCTGTCCTTGACTCTTGGGTCTGTGGGCCATGGCATGAGTGT
 782 TTTCTAGTAGTAGATTGGAGGGAAAGCTTTGTGACACTTAGTACTGTGTTTTTAAGAAGA
 842 AATAATTTGGTTCCAGATGTGTTAGAGGATCTTTTGTACTGAGGTTTTTAACACTTTACT
 902 TGGGTTTACCAAGCCTCAACTGGACAGACCATAAACAGTCCACAGGCACCGTTCCTGCCA
 962 GGCCCCAACCCACAGGGAGTCTCTCCGCAGAGCCTTCTTGGTGTTGCCCTAACTTGCCAG
1022 TGGCCTTTGCTCAGAGCCTCCTCCTGTGACATGTGAACAATGAAGAGGCCTGCGCCTCCT
1082 GCCTTGCCGCCTGCAAAGCAAAGAAACTGCCTTTTATTTTTTAACCTTAAAAAGTAGCCA
1142 GATAGTAACAAGACTGGCTGGCTGATGAGCAAAGCCTTTGCTCTCACGCAGAGGAAGGCT
1202 TGGATGTACAATGAAACTGCCTGGAACTAAAAGCAGTGAAGCAAGGGAGGCAATCACACT
1262 GAAGCGGGTCTTCCTCCAGGAACGGGTCCCACAGGCGTGTTGTTTAAATAACCTGATG
1322 CTGTGTGCATGATGCTGGTGCTTGACCATGAAAGGAAAGTCTCATCCTTAAAATGTGTTG
1382 TACTTCACAATCCTGGACTGTTGCTTCAAGTAAACAATATCCACATTCTAAAAAAAAAAA
1442 AAAAAAAAAAAAAAAAAAAA
```

Predicted promoter tgaaaaccctataaaggcgtcgatcggccggacaggcggcAgcggcggct

SSH9 EXON-Intron boundaries;

EXON1  CATGACCACAACCaccaccttcaaggga...  INT1  ...tgccattatttgcagAGTTTTGCGGCCT

EXON2  AAATCAAGCTTCTtgggccaagtcagca...  INT2  ...tattttgattttttagGTGCCAAGTCTAG

EXON3  CTTAGATCTGAAGgtcagtgtgacagca...  INT4  ...tttttttcttttctagGGAGAAG

EXON4  GTGATATTCATGgtaagtacttctgaa...  INT5  ...tccctgttttcatagAAAATGTGGACAC

FIGURE 11C

```
   1 ATGACCGACGCGCTGTTGCCCGCGGCCCCCCAGCCGCTGGAGAAGGAGAACGACGGCTAC
  61 TTTCGGAAGGGCTGTAATCCCCTTGCACAAACCGGCCGGAGTAAATTGCAGAATCAAAGA
 121 GCTGCTTTGAATCAGCAGATCCTGAAAGCCGTGCGGATGAGGACCGGAGCGGAAAACCTT
 181 CTGAAAGTGGCCACAAACTCAAAGGTGCGGGAGCAAGTGCGGCTGGAGCTGAGCTTCGTC
 241 AACTCAGACCTGCAGATGCTCAAGGAAGAGCTGGAGGGGCTGAACATCTCGGTGGGCGTC
 301 TATCAGAACACAGAGGAGGCATTTACGATTCCCCTGATTCCTCTTGGCCTGAAGGAAACG
 361 AAAGACGTCGACTTTGCAGTCGTCCTCAAGGATTTTATCCTGGAACATTACAGTGAAGAT
 421 GGCTATTTATATGAAGATGAAATTGCAGATCTTATGGATCTGAGACAAGCTTGTCGGACG
 481 CCTAGCCGGGATGAGGCCGGGGTGGAACTGCTGATGACATACTTCATCCAGCTGGGCTTT
 541 GTCGAGAGTCGATTCTTCCCGCCCACACGGCAGATGGGACTCCTGTTCACCTGGTATGAC
 601 TCTCTCACTGGGGTTCCGGTCAGCCAGCAGAACCTGCTGCTGGAGAAGGCCAGTGTCCTG
 661 TTCAACACTGGGGCCCTCTACACCCAGATTGGGACCCGGTGCGATCGGCAGACGCAGGCT
 721 GGGCTGGAGAGTGCCATAGATGCCTTTCAGAGAGCCGCAGGGGTTTTAAATTACCTGAAA
 781 GACACATTTACCCATACTCCAAGTTACGACATGAGCCCTGCCATGCTCAGCGTGCTCGTC
 841 AAAATGATGCTTGCACAAGCCCAAGAAAGCGTGTTTGAGAAAATCAGCCTTCCTGGGATC
 901 CGGAATGAATTCTTCATGCTGGTGAAGGTGGCTCAGGAGGCTGCTAAGGTGGGAGAGGTC
 961 TACCAACAGCTACACGCAGCCATGAGCCAGGCGCCGGTGAAAGAGAACATCCCCTACTCC
1021 TGGGCCAGCTTAGCCTGCGTGAAGGCCCACCACTACGCGGCCCTGGCCCACTACTTCACT
1081 GCCATCCTCCTCATCGACCACCAGGTGAAGCCAGGCACGGATCTGGACCACCAGGAGAAG
1141 TGCCTGTCCCAGCTCTACGACCACATGCCAGAGGGGCTGACACCCTTGGCCACACTGAAG
1201 AATGATCAGCAGCGCCGACAGCTGGGGAAGTCCCACTTGCGCAGAGCCATGGCTCATCAC
1261 GAGGAGTCGGTGCGGGAGGCGAGCCTCTGCAAGAAGCTGCGGAGCATTGAGGTGCTACAG
1321 AAGGTGCTGTGTGCCGCACAGGAACGCTCCCGGCTCACGTACGCCCAGCACCAGGAGGAG
1381 GATGACCTGCTGAACCTGATCGACGCCCCAGTGTTGTTGCTAAAACTGAGCAAGAGGTT
1441 GACATTATATTGCCCCAGTTCTCCAAGCTGACAGTCACGGACTTCTTCCAGAAGCTGGGC
1501 CCCTTATCTGTGTTTTCGGCTAACAAGCGGTGGACGCCTCCTCGAAGCATCCGCTTCACT
1561 GCAGAAGAAGGGGACTTGGGGTTCACCTTGAGAGGGAACGCCCCCGTTCAGGTTCACTTC
1621 CTGGATCCTTACTGCTCTGCCTCGGTGGCAGGAGCCCGGGAAGGAGATTATATTGTCTCC
1681 ATTCAGCTTGTGGATTGTAAGTGGCTGACGCTGAGTGAGGTTATGAAGCTGCTGAAGAGC
1741 TTTGGCGAGGACGAGATCGAGATGAAAGTCGTGAGCCTCCTGGACTCCACATCATCCATG
1801 CATAATAAGAGTGCCACATACTCCGTGGGAATGCAGAAAACGTACTCCATGATCTGCTTA
1861 GCCATTGATGATGACGACAAAACTGATAAAACCAAGAAAATCTCCAAGAAGCTTTCCTTC
1921 CTGAGTTGGGGCACCAACAAGAACAGACAGAAGTCAGCCAGCACCTTGTGCCTCCCATCG
1981 GTCGGGGCTGCACGGCCTCAGGTCAAGAAGAAGCTGCCCTCCCCTTTCAGCCTTCTCAAC
2041 TCAGACAGTTCTTGGTACTAATGTGAGGAAACAAACATGTTCAGGCCCCGAACATTTCCG
2101 GTGCTGACTCGGCCTTAAACGTTTGTGCCATAATGGAAAATATCTATCTATCTGTTCTCA
2161 AATCCTGTTTTTCTCATAGTGTAAACTCACATTTGATGTGTTTTTATGAAGGAAAGTAAC
2221 CAAGAAACCTCTAGGAATTAGTGAAAAAAGAACTTTTTTGAGGTGTGTTACTATACTGCT
2281 GTAAGTTATTTATTATATAAAGTATTGTAAATAGAATAGTGTTGAAGATATGAAATATGG
2341 CTATTTTTAATGGTGACAATTATGACTTTTAGTCACTATTAAATTGGGGTTACCTATATC
2401 AGTACAATTTGTAGTTGTTTCCAGGTTTGGCTAATAATCATTCCTTAACCTAGAATTCAG
2461 ATGATCCTGGAATTAAGGCAGGTCAGAGGACTGTAATGATAGAATTAAATTAGTGTCACT
2521 AAAAACTGTCCCAAAGTGCTGCTTCCTAATAGGAATTCATTAACCTAAAACAAGATGTTA
2581 CTATTATATCGATAGACTATGAATGCTATTTCTAGAAAAAGTCTAGTGCCAAATTTGTCT
2641 TATTAAATAAAAACAATGTAGGAGCAGCTTTTCTTCTAGTTTGATGTCATTTAAGAATTA
2701 CTAACACAGTGGCAGTGTTAGATGAAGATGCTGTCTACAAGGTAGATAATATACTGTTTG
2761 ATACTCAAAACATTTTTCATTTGTTTAAAGTAGAAGTTACATAATTCTATATTTTAAGT
2821 CTTGGGTAAAAAGTAGTTTTACATTTTATAAAGTAAAGATGTAAATGATTCAGGTTTAA
2881 AGCTCTATTTGACTTCCTTTTTTTGTTTGAGATAGCGTCTTGCTGTGTTGCCCAGGCTGG
2941 AGTGCAGTGGTGTGATCTCAGCTCAGTGCAACCTCCGCCCCCTGGGATCAAGCGATTCTC
3001 CTACCTCAGCCTCCCAAATAGCTGGGACTACAAGGTGCCCTCCAGCATGCCTGGCTGATT
3061 TTTGTATTTTAGTTGAGGTGAGGTTTCACCATGTTGGCCAGGCGGGTTTCGAAATCCTG
3121 ACCTCAAATGATCCACCCACCTCAGCCTCCCAAAGTGCTGGGATTACAGGCATGAGCCAC
3181 CACAACCGTCCCACTATTTTACTTTTTAAAATGACATTCCTACTGATTGATTTTTATCTT
3241 GCTATAAGTTCGATGACACCGTGAATCTAATAAGGTTCACTGTTGACACAGTACAAGTTA
3301 CATAGCTAAAATACATAGCATTGAAGACTAATTTTAAGGATTGACAAGAGTTTATTTTCT
3361 ATTGTGCAATATCTTAAAGGAAGCAACCACCTTTGGGAAAGTGTATCTGCTGCTCCTAGG
3421 GCCATGCTTGTATACATATTTAAATAAACATATTCATTTACCCGAAAAAAAAAAAAAAAA
3481 AAAAAAAAAAAAAAAAAAAAAAAAAAAAAAAAAAAAAAAAAAAAAAAA
```

FIGURE 14A

```
  1   M   T   D   A   L   L   P   A   A   P   Q   P   L   E   K   E   N   D   G   Y
  1   ATGACCGACGCGCTGTTGCCCGCGGCCCCCCAGCCGCTGGAGAAGGAGAACGACGGCTAC

21   F   R   K   G   C   N   P   L   A   Q   T   G   R   S   K   L   Q   N   Q   R
 61   TTTCGGAAGGGCTGTAATCCCCTTGCACAAACCGGCCGGAGTAAATTGCAGAATCAAAGA

41   A   A   L   N   Q   Q   I   L   K   A   V   R   M   R   T   G   A   E   N   L
121   GCTGCTTTGAATCAGCAGATCCTGAAAGCCGTGCGGATGAGGACCGGAGCGGAAAACCTT

61   L   K   V   A   T   N   S   K   V   R   E   Q   V   R   L   E   L   S   F   V
181   CTGAAAGTGGCCACAAACTCAAAGGTGCGGGAGCAAGTGCGGCTGGAGCTGAGCTTCGTC

81   N   S   D   L   Q   M   L   K   E   E   L   E   G   L   N   I   S   V   G   V
241   AACTCAGACCTGCAGATGCTCAAGGAAGAGCTGGAGGGGCTGAACATCTCGGTGGGCGTC

101   Y   Q   N   T   E   E   A   F   T   I   P   L   I   P   L   G   L   K   E   T
301   TATCAGAACACAGAGGAGGCATTTACGATTCCCCTGATTCCTCTTGGCCTGAAGGAAACG

121   K   D   V   D   F   A   V   V   L   K   D   F   I   L   E   H   Y   S   E   D
361   AAAGACGTCGACTTTGCAGTCGTCCTCAAGGATTTTATCCTGGAACATTACAGTGAAGAT

141   G   Y   L   Y   E   D   E   I   A   D   L   M   D   L   R   Q   A   C   R   T
421   GGCTATTTATATGAAGATGAAATTGCAGATCTTATGGATCTGAGACAAGCTTGTCGGACG

161   P   S   R   D   E   A   G   V   E   L   L   M   T   Y   F   I   Q   L   G   F
481   CCTAGCCGGGATGAGGCCGGGGTGGAACTGCTGATGACATACTTCATCCAGCTGGGCTTT

181   V   E   S   R   F   F   P   P   T   R   Q   M   G   L   L   F   T   W   Y   D
541   GTCGAGAGTCGATTCTTCCCGCCCACACGGCAGATGGGACTCCTGTTCACCTGGTATGAC

201   S   L   T   G   V   P   V   S   Q   Q   N   L   L   L   E   K   A   S   V   L
601   TCTCTCACTGGGGTTCCGGTCAGCCAGCAGAACCTGCTGCTGGAGAAGGCCAGTGTCCTG

221   F   N   T   G   A   L   Y   T   Q   I   G   T   R   C   D   R   Q   T   Q   A
661   TTCAACACTGGGGCCCTCTACACCCAGATTGGGACCCGGTGCGATCGGCAGACGCAGGCT

241   G   L   E   S   A   I   D   A   F   Q   R   A   A   G   V   L   N   Y   L   K
721   GGGCTGGAGAGTGCCATAGATGCCTTTCAGAGAGCCGCAGGGGTTTTAAATTACCTGAAA

261   D   T   F   T   H   T   P   S   Y   D   M   S   P   A   M   L   S   V   L   V
781   GACACATTTACCCATACTCCAAGTTACGACATGAGCCCTGCCATGCTCAGCGTGCTCGTC

281   K   M   M   L   A   Q   A   Q   E   S   V   F   E   K   I   S   L   P   G   I
841   AAAATGATGCTTGCACAAGCCCAAGAAAGCGTGTTTGAGAAAATCAGCCTTCCTGGGATC

301   R   N   E   F   F   M   L   V   K   V   A   Q   E   A   A   K   V   G   E   V
901   CGGAATGAATTCTTCATGCTGGTGAAGGTGGCTCAGGAGGCTGCTAAGGTGGGAGAGGTC

321   Y   Q   Q   L   H   A   A   M   S   Q   A   P   V   K   E   N   I   P   Y   S
961   TACCAACAGCTACACGCAGCCATGAGCCAGGCGCCGGTGAAAGAGAACATCCCCTACTCC

341   W   A   S   L   A   C   V   K   A   H   H   Y   A   A   L   A   H   Y   F   T
1021  TGGGCCAGCTTAGCCTGCGTGAAGGCCCACCACTACGCGGCCCTGGCCCACTACTTCACT

361   A   I   L   L   I   D   H   Q   V   K   P   G   T   D   L   D   H   Q   E   K
1081  GCCATCCTCCTCATCGACCACCAGGTGAAGCCAGGCACGGATCTGGACCACCAGGAGAAG
```

FIGURE 14B

```
381  C  L  S  Q  L  Y  D  H  M  P  E  G  L  T  P  L  A  T  L  K
1141 TGCCTGTCCCAGCTCTACGACCACATGCCAGAGGGGCTGACACCCTTGGCCACACTGAAG

401  N  D  Q  Q  R  R  Q  L  G  K  S  H  L  R  R  A  M  A  H  H
1201 AATGATCAGCAGCGCCGACAGCTGGGGAAGTCCCACTTGCGCAGAGCCATGGCTCATCAC

421  E  E  S  V  R  E  A  S  L  C  K  K  L  R  S  I  E  V  L  Q
1261 GAGGAGTCGGTGCGGGAGGCGAGCCTCTGCAAGAAGCTGCGGAGCATTGAGGTGCTACAG

441  K  V  L  C  A  A  Q  E  R  S  R  L  T  Y  A  Q  H  Q  E  E
1321 AAGGTGCTGTGTGCCGCACAGGAACGCTCCCGGCTCACGTACGCCCAGCACCAGGAGGAG

461  D  D  L  N  L  I  D  A  P  S  V  V  A  K  T  E  Q  E  V
1381 GATGACCTGCTGAACCTGATCGACGCCCCCAGTGTTGTTGCTAAAACTGAGCAAGAGGTT

481  D  I  I  L  P  Q  F  S  K  L  T  V  T  D  F  F  Q  K  L  G
1441 GACATTATATTGCCCCAGTTCTCCAAGCTGACAGTCACGGACTTCTTCCAGAAGCTGGGC

501  P  L  S  V  F  S  A  N  K  R  W  T  P  P  R  S  I  R  P  T
1501 CCCTTATCTGTGTTTTCGGCTAACAAGCGGTGGACGCCTCCTCGAAGCATCCGCTTCACT

521  A  E  G  D  L  G  F  T  L  R  G  N  A  P  V  Q  V  H  F
1561 GCAGAAGAAGGGGACTTGGGGTTCACCTTGAGAGGGAACGCCCCCGTTCAGGTTCACTTC

541  L  D  P  Y  C  S  A  S  V  A  G  A  R  E  G  D  Y  I  V  S
1621 CTGGATCCTTACTGCTCTGCCTCGGTGGCAGGAGCCCGGGAAGGAGATTATATTGTCTCC

561  I  Q  L  V  D  C  K  W  L  T  L  S  E  V  M  K  L  L  K  S
1681 ATTCAGCTTGTGGATTGTAAGTGGCTGACGCTGAGTGAGGTTATGAAGCTGCTGAAGAGC

581  F  G  E  D  E  I  E  M  K  V  V  S  L  L  D  S  T  S  S  M
1741 TTTGGCGAGGACGAGATCGAGATGAAAGTCGTGAGCCTCCTGGACTCCACATCATCCATG

601  H  N  K  S  A  T  Y  S  V  G  M  Q  K  T  Y  S  M  I  C  L
1801 CATAATAAGAGTGCCACATACTCCGTGGGAATGCAGAAAACGTACTCCATGATCTGCTTA

621  A  I  D  D  D  K  T  D  K  T  K  K  I  S  K  K  L  S  F
1861 GCCATTGATGATGACGACAAAACTGATAAAACCAAGAAAATCTCCAAGAAGCTTTCCTTC

641  L  S  W  G  T  N  K  N  R  Q  K  S  A  S  T  L  C  L  P  S
1921 CTGAGTTGGGGCACCAACAAGAACAGACAGAAGTCAGCCAGCACCTTGTGCCTCCCATCG

661  V  G  A  A  R  P  Q  V  K  K  K  L  P  S  P  F  S  L  L  N
1981 GTCGGGGCTGCACGGCCTCAGGTCAAGAAGAAGCTGCCCTCCCCTTTCAGCCTTCTCAAC

681  S  D  S  S  W  Y
2041 TCAGACAGTTCTTGGTACTAATGTGAGGAAACAAACATGTTCAGGCCCCGAACATTTCCG
```

FIGURE 14B CONTINUED

TATA PROMOTER AND PUTATIVE TRANSCRIPTION START SITE
       AAAAAAAATAAATAAAAAGGCCGGGCGCGTTGGCCCGCGCcTGCAGCCCC

PSL 22_5'UTR
     1   TGCTACTTGGGAGGCTGAGGCTGGAGCATCGCTTGATCCTGGGAGGTCGAGGCTGCAAAG
    61   AGTCGAGATCGCAACACTGCTCTCCAGCCTGGGCGACAGAGCGAGGTCCCATCTCTTAAA
   121   AAAAAGAACTGTGCTCAAGGACATCTGCCGTGTCTGGGGCGCAAAACCCCTCCTGGTCCC
   181   CTCTCTCAGGGCAGTCCGCGAGCCCAGCGGATCCCACTCGTCTTTGCAGCGCGGACAGGG
   241   AATCGGCTGAGTTGATCCCATGCCAACAAGCCCGAGTAGTCCGGGCAAGGCGCTCGGCGG
   301   GGCAGTCAACGCTCCCTCCGCCATGGGCTCCCCTCTTGGGAAAAGCTTTTCCAAACCGCC
   361   GGGCCCAGGGCCCAGAGCTCCCGCCGCGCCCTCGACGTGGCGTCGAGTCTGGCCCCTTCC
   421   CCCGCGGCGCACGGGCTTCACCCAGGAGGGACGCGCCTGGATCCACGCCTTCCTCACTGA
   481   CTCCCCGGGCTCCAGGGCAGGGTGCAGGTCCACAGCCAGGGCTTCGCTGCGGCCCCTGAG
   541   ACCCCAGTGCCTTTCCTGCGCTCTCGCGGCACTCGCAAAGTTGAGTCAGCCACGACGCCC
   601   ACAGACAACCCCGAGGCGCCGCGCCCAGGGCGCAGCTCTCCGGGTGACGAGCGCCTCAAG
   661   GGGCGCGGGTTCGGGGCCCGCGACGGGGCGGGCGCGTCTCCAGGGCTCCAGTGCTCGGC
   721   CTCAGGCGGGCTAGAAGGGCCGCGGGACGGGGTGGGAGTGGAGGGGCGGGGAAGGGCGG
   781   GGACAGGGGCGGGGCCGCACGTCCTCTCGGGCCAGCCTCAGCCGCCGCGCCTCAGTCCGC
   841   CGTCCGCCCTCCGCGCCCGCGCCGCTAGC

EXON_1 69bp
     1   ATGACCGACGCGCTGTTGCCCGCGGCCCCCAGCCGCTGGAGAAGGAGAACGACGGCTAC
    61   TTTCGGAAG

EXON_2 117bp
     1   GGCTGTAATCCCCTTGCACAAACCGGCCGGAGTAAATTGCAGAATCAAAGAGCTGCTTTG
    61   AATCAGCAGATCCTGAAAGCCGTGCGGATGAGGACCGGAGCGGAAAACCTTCTGAAA

EXON_3 129bp
     1   GTGGCCACAAACTCAAAGGTGCGGGAGCAAGTGCGGCTGGAGCTGAGCTTCGTCAACTCA
    61   GACCTGCAGATGCTCAAGGAAGAGCTGGAGGGGCTGAACATCTCGGTGGGCGTCTATCAG
   121   AACACAGAG

EXON_4 75bp
     1   GAGGCATTTACGATTCCCCTGATTCCTCTTGGCCTGAAGGAAACGAAAGACGTCGACTTT
    61   GCAGTCGTCCTCAAG

EXON_5 79bp
     1   GATTTTATCCTGGAACATTACAGTGAAGATGGCTATTTATATGAAGATGAAATTGCAGAT
    61   CTTATGGATCTGAGACAAG

EXON_6 124bp
     1   CTTGTCGGACGCCTAGCCGGGATGAGGCCGGGGTGGAACTGCTGATGACATACTTCATCC
    61   AGCTGGGCTTTGTCGAGAGTCGATTCTTCCCGCCCACACGGCAGATGGGACTCCTGTTCA
   121   CCTG

EXON_7 167bp
     1   GTATGACTCTCTCACTGGGGTTCCGGTCAGCCAGCAGAACCTGCTGCTGGAGAAGGCCAG
    61   TGTCCTGTTCAACACTGGGGCCCTCTACACCCAGATTGGGACCCGGTGCGATCGGCAGAC
   121   GCAGGCTGGGCTGGAGAGTGCCATAGATGCCTTTCAGAGAGCCGCAG

EXON_8 188bp
     1   GGGTTTTAAATTACCTGAAAGACACATTTACCCATACTCCAAGTTACGACATGAGCCCTG
    61   CCATGCTCAGCGTGCTCGTCAAAATGATGCTTGCACAAGCCCAAGAAAGCGTGTTTGAGA
   121   AAATCAGCCTTCCTGGGATCCGGAATGAATTCTTCATGCTGGTGAAGGTGGCTCAGGAGG
   181   CTGCTAAG
EXON_9 156bp
     1   GTGGGAGAGGTCTACCAACAGCTACACGCAGCCATGAGCCAGGCGCCGGTGAAAGAGAAC

FIGURE 14C

```
     61 ATCCCCTACTCCTGGGCCAGCTTAGCCTGCGTGAAGGCCCACCACTACGCGGCCCTGGCC
    121 CACTACTTCACTGCCATCCTCCTCATCGACCACCAG

EXON_10 120bp
      1 GTGAAGCCAGGCACGGATCTGGACCACCAGGAGAAGTGCCTGTCCCAGCTCTACGACCAC
     61 ATGCCAGAGGGGCTGACACCCTTGGCCACACTGAAGAATGATCAGCAGCGCCGACAGCTG

EXON_11 196bp
      1 GGGAAGTCCCACTTGCGCAGAGCCATGGCTCATCACGAGGAGTCGGTGCGGGAGGCGAGC
     61 CTCTGCAAGAAGCTGCGGAGCATTGAGGTGCTACAGAAGGTGCTGTGTGCCGCACAGGAA
    121 CGCTCCCGGCTCACGTACGCCCAGCACCAGGAGGAGGATGACCTGCTGAACCTGATCGAC
    181 GCCCCCAGTGTTGTTG

EXON_12 77bp
      1 CTAAAACTGAGCAAGAGGTTGACATTATATTGCCCCAGTTCTCCAAGCTGACAGTCACGG
     61 ACTTCTTCCAGAAGCTG

EXON_13 147bp
      1 GGCCCCTTATCTGTGTTTTCGGCTAACAAGCGGTGGACGCCTCCTCGAAGCATCCGCTTC
     61 ACTGCAGAAGAAGGGGACTTGGGGTTCACCTTGAGAGGGAACGCCCCCGTTCAGGTTCAC
    121 TTCCTGGATCCTTACTGCTCTGCCTCG

EXON_14 156bp
      1 GTGGCAGGAGCCCGGGAAGGAGATTATATTGTCTCCATTCAGCTTGTGGATTGTAAGTGG
     61 CTGACGCTGAGTGAGGTTATGAAGCTGCTGAAGAGCTTTGGCGAGGACGAGATCGAGATG
    121 AAAGTCGTGAGCCTCCTGGACTCCACATCATCCATG

EXON_15 +3'UTR 1664bp+polyA tract
      1 CATAATAAGAGTGCCACATACTCCGTGGGAATGCAGAAAACGTACTCCATGATCTGCTTA
     61 GCCATTGATGATGACGACAAAACTGATAAAACCAAGAAAATCTCCAAGAAGCTTTCCTTC
    121 CTGAGTTGGGGCACCAACAAGAACAGACAGAAGTCAGCCAGCACCTTGTGCCTCCCATCG
    181 GTCGGGGCTGCACGGCCTCAGGTCAAGAAGAAGCTGCCCTCCCCTTTCAGCCTTCTCAAC
    241 TCAGACAGTTCTTGGTACTAATGTGAGGAAACAAACATGTTCAGGCCCCGAACATTTCCG
    301 GTGCTGACTCGGCCTTAAACGTTTGTGCCATAATGGAAAATATCTATCTATCTGTTCTCA
    361 AATCCTGTTTTTCTCATAGTGTAAACTCACATTTGATGTGTTTTTATGAAGGAAAGTAAC
    421 CAAGAAACCTCTAGGAATTAGTGAAAAAAGAACTTTTTTGAGGTGTGTTACTATACTGCT
    481 GTAAGTTATTTATTATATAAAGTATTGTAAATAGAATAGTGTTGAAGATATGAAATATGG
    541 CTATTTTTAATGGTGACAATTATGACTTTTAGTCACTATTAAATTGGGGTTACCTATATC
    601 AGTACAATTTGTAGTTGTTTCCAGGTTTGGCTAATAATCATTCCTTAACCTAGAATTCAG
    661 ATGATCCTGGAATTAAGGCAGGTCAGAGGACTGTAATGATAGAATTAAATTAGTGTCACT
    721 AAAAACTGTCCCAAAGTGCTGCTTCCTAATAGGAATTCATTAACCTAAAACAAGATGTTA
    781 CTATTATATCGATAGACTATGAATGCTATTTCTAGAAAAAGTCTAGTGCCAAATTTGTCT
    841 TATTAAATAAAAACAATGTAGGAGCAGCTTTTCTTCTAGTTTGATGTCATTTAAGAATTA
    901 CTAACACAGTGGCAGTGTTAGATGAAGATGCTGTCTACAAGGTAGATAATATACTGTTTG
    961 ATACTCAAAACATTTTTCATTTTGTTTAAAGTAGAAGTTACATAATTCTATATTTTAAGT
   1021 CTTGGGTAAAAAAGTAGTTTTACATTTTATAAAGTAAAGATGTAAATGATTCAGGTTTAA
   1081 AGCTCTATTTGACTTCCTTTTTTTGTTTGAGATAGCGTCTTGCTGTGTTGCCCAGGCTGG
   1141 AGTGCAGTGGTGTGATCTCAGCTCAGTGCAACCTCCGCCCCTGGGATCAAGCGATTCTC
   1201 CTACCTCAGCCTCCCAAATAGCTGGGACTACAAGGTGCCCTCCAGCATGCCTGGCTGATT
   1261 TTTGTATTTTTAGTTGAGGTGAGGTTTCACCATGTTGGCCAGGCGGGTTTCGAAATCCTG
   1321 ACCTCAAATGATCCACCCACCTCAGCCTCCCAAAGTGCTGGGATTACAGGCATGAGCCAC
   1381 CACAACCGTCCCACTATTTTACTTTTTAAAATGACATTCCTACTGATTGATTTTTATCTT
   1441 GCTATAAGTTCGATGACACCGTGAATCTAATAAGGTTCACTGTTGACACAGTACAAGTTA
   1501 CATAGCTAAAATACATAGCATTGAAGACTAATTTTAAGGATTGACAAGAGTTTATTTTCT
   1561 ATTGTGCAATATCTTAAAGGAAGCAACCACCTTTGGGAAAGTGTATCTGCTGCTCCTAGG
   1621 GCCATGCTTGTATACATATTTaaataaACATATTCATTTACCCGAAAAAAAAAAAAAAAA
   1681 AAAAAAAAAAAAAAAAAAAAAAAAAAAAAAAAAAAAAAAAAA
```

FIGURE 14C CONTINUED

```
   1 gCTGAGCTGCAGGCGCGGCGAAACTTCCCTCTACCCGCCCGGCCCGCGGCGCGCACCGTTG
   1                                                    M  E  K  T  C
  62 GCGCTGGACGCTTCCTCCTTGGAAGCGCCTCTCCCTCAGTCAGTTATGGAGAAAACTTGT
   6  I  D  A  L  P  L  T  M  N  S  S  E  K  Q  E  T  V  C  I  F
 122 ATAGATGCACTTCCTCTTACTATGAATTCTTCAGAAAAGCAAGAGACTGTATGTATTTTT
  26  G  T  G  D  F  G  R  S  L  G  L  K  M  L  Q  C  G  Y  S  V
 182 GGAACTGGTGATTTTGGAAGATCACTGGGATTGAAAATGCTCCAGTGTGGTTATTCTGTT
  46  V  F  G  S  R  N  P  Q  K  T  T  L  L  P  S  G  A  E  V  L
 242 GTTTTTGGAAGTCGAAACCCCCAGAAGACCACCCTACTGCCCAGTGGTGCAGAAGTCTTG
  66  S  Y  S  E  A  A  K  K  S  G  I  I  I  I  A  I  H  R  E  H
 302 AGCTATTCAGAAGCAGCCAAGAAGTCTGGCATCATAATCATAGCAATCCACAGAGAGCAT
  86  Y  D  F  L  T  E  L  T  E  V  L  N  G  K  I  L  V  D  I  S
 362 TATGATTTTCTCACAGAATTAACTGAGGTTCTCAATGGAAAAATATTGGTAGACATCAGC
 106  N  N  L  K  I  N  Q  Y  P  E  S  N  A  E  Y  L  A  H  L  V
 422 AACAACCTCAAAATCAATCAATATCCAGAATCTAATGCAGAGTACCTTGCTCATTTGGTG
 126  P  G  A  H  V  V  K  A  F  N  T  I  S  A  W  A  L  Q  S  G
 482 CCAGGAGCCCACGTGGTAAAAGCATTTAACACCATCTCAGCCTGGGCTCTCCAGTCAGGA
 146  A  L  D  A  S  R  Q  V  F  V  C  G  N  D  S  K  A  K  Q  R
 542 GCACTGGATGCAAGTCGGCAGGTGTTTGTGTGTGGAAATGACAGCAAAGCCAAGCAAAGA
 166  V  M  D  I  V  R  N  L  G  L  T  P  M  D  Q  G  S  L  M  A
 602 GTGATGGATATTGTTCGTAATCTTGGACTTACTCCAATGGATCAAGGATCACTCATGGCA
 186  A  K  E  I  E  K  Y  P  L  Q  L  P  P  M  W  R  F  P  F  Y
 662 GCCAAAGAAATTGAAAAGTACCCCCTGCAGCTATTTCCAATGTGGAGGTTCCCCTTCTAT
 206  L  S  A  V  L  C  V  F  L  F  F  Y  C  V  I  R  D  V  I  Y
 722 TTGTCTGCTGTGCTGTGTGTCTTCTTGTTTTTCTATTGTGTTATAAGAGACGTAATCTAC
 226  P  Y  V  Y  E  K  K  D  N  T  F  R  M  A  I  S  I  P  N  R
 782 CCTTATGTTTATGAAAAGAAAGATAATACATTTCGTATGGCTATTTCCATTCCAAATCGT
 246  I  F  P  I  T  A  L  T  L  L  A  L  V  Y  L  P  G  V  I  A
 842 ATCTTTCCAATAACAGCACTTACACTGCTTGCTTTGGTTTACCTCCCTGGTGTTATTGCT
 266  A  I  L  Q  L  Y  R  G  T  K  Y  R  R  F  P  D  W  L  D  H
 902 GCCATTCTACAACTGTACCGAGGCACAAAATACCGTCGATTCCCAGACTGGCTTGACCAC
 286  W  M  L  C  R  K  Q  L  G  L  V  A  L  G  F  A  F  L  H  V
 962 TGGATGCTTTGCCGAAAGCAGCTTGGCTTGGTAGCTCTGGGATTTGCCTTCCTTCATGTC
 306  L  Y  T  L  V  I  P  I  R  Y  Y  V  R  W  R  L  G  N  L  T
1022 CTCTACACACTTGTGATTCCTATTCGATATTATGTACGATGGAGATTGGGAAACTTAACC
 326  V  T  Q  A  I  L  K  K  E  N  P  F  S  T  S  S  A  W  L  S
1082 GTTACCCAGGCAATACTCAAGAAGGAGAATCCATTTAGCACCTCCTCAGCCTGGCTCAGT
 346  D  S  Y  V  A  L  G  I  L  G  F  F  L  F  V  L  L  G  I  T
1142 GATTCATATGTGGCTTTGGGAATACTTGGGTTTTTTCTGTTTGTACTCTTGGGAATCACT
 366  S  L  P  S  V  S  N  A  V  N  W  R  E  P  R  F  V  Q  S  K
1202 TCTTTGCCATCTGTTAGCAATGCAGTCAACTGGAGAGAGTTCCGATTTGTCCAGTCCAAA
 386  L  G  Y  L  T  L  I  L  C  T  A  H  T  L  V  Y  G  G  K  R
1262 CTGGGTTATTTGACCCTGATCTTGTGTACAGCCCACACCCTGGTGTACGGTGGAAGAGA
 406  F  L  S  P  S  N  L  R  W  Y  L  P  A  A  Y  V  L  G  L  I
1322 TTCCTCAGCCCTTCAAATCTCAGATGGTATCTTCCTGCAGCCTACGTGTTAGGGCTTATC
 426  I  P  C  T  V  L  V  I  K  F  V  L  I  M  P  C  V  D  N  T
1382 ATTCCTTGCACTGTGCTGGTGATCAAGTTTGTCCTAATCATGCCATGTGTAGACAACACC
 446  L  T  R  I  R  Q  G  W  E  R  N  S  K  H  -
1442 CTTACAAGGATCCGCCAGGGCTGGGAAAGGAACTCAAAACACTAG
```

PROSTATE-SPECIFIC OR TESTIS-SPECIFIC NUCLEIC ACID MOLECULES, POLYPEPTIDES, AND DIAGNOSTIC AND THERAPEUTIC METHODS

CROSS REFERENCE TO RELATED APPLICATIONS

This application is a continuation-in-part of U.S. application Ser. No. 10/239,607, filed Mar. 20, 2003, now patented, U.S. Pat. No. 7,189,565, which is the U.S. National Stage of International Application No. PCT/US01/09410, filed Mar. 23, 2001, and published in English, which claims the benefit of U.S. Provisional Application No. 60/191,929, filed Mar. 24, 2000. This application is also a continuation-in-part of International Application No. PCT/IB05/001357, filed Feb. 22, 2005, and published in English, which claims the benefit of U.S. Provisional Application No. 60/545,822, filed Feb. 19, 2004. Each of these applications is herein incorporated by reference.

FIELD OF THE INVENTION

The invention generally relates to the treatment of disorders associated with prostate dysfunction, testis dysfunction, and cell proliferation, and specifically relates to the identification and use of novel genes for diagnosis and treatment of such disorders.

BACKGROUND OF THE INVENTION

Genitourinary disorders are often difficult to diagnose and treat effectively because they are present non-specifically. Two causes of genitourinary disorders in men are disorders of the prostate gland and the testis.

The prostate is a variable sized gland located in the male pelvis, and is made up of several different cell types, including epithelial cells and stromal cells. Prostate-associated disorders include prostate cancer, benign prostatic hyperplasia, and prostatitis. The male hormone testosterone and other androgen related hormones have major roles in the growth and function of the prostate. The testis is also subject to many defects, including developmental anomalies, inflammation, and cancer.

In men, prostate cancer is the most commonly diagnosed cancer and the second leading cause of cancer mortality following skin cancer. In the initial stages, prostate cancer is dependent on androgens for growth, and this dependence is the basis for androgen ablation therapy. In most cases, however, prostate cancer progresses to an androgen-independent phenotype for which there is no effective therapy available at present.

Currently, there is limited information regarding the molecular details of prostate cancer progression. Several independent approaches resulted in the identification of a few highly prostate-enriched genes that may have unique roles in this process. The first such gene discovered was Prostate Specific Antigen (PSA), the detection of which is currently used as a diagnostic tool and also as a marker for the progression of prostate cancer, albeit with significant limitations. More recently, several additional prostate-enriched genes were identified including prostate-specific membrane antigen (PSMA), prostate carcinoma tumor antigen 1 (PCTA-1), NKX3.1, prostate stem cell antigen (PSCA), DD3, and PCGEM1.

It would be beneficial to provide reagents useful for the diagnosis and therapy of disorders associated with the prostate and the testis, as well as other tissues.

SUMMARY OF THE INVENTION

In general, the invention provides novel prostate-specific or testis-specific nucleic acid molecules, polypeptides, antibodies, and modulatory compounds for use in methods of diagnosing, treating, and preventing diseases and conditions of the prostate and testis, such as cancer.

STAMP2, a six-transmembrane protein, is one of the novel prostate-specific or testis-specific polypeptides that we have discovered. STAMP2 is expressed in prostate tissue and localizes primarily to the Golgi complex, the plasma membrane, and the early endosomes suggesting that STAMP2 may be involved in the secretory and endocytic pathways. Our findings also indicate that STAMP2 may be involved in the induction of cell proliferation and growth. We have also discovered that STAMP2 is an androgen responsive gene in androgen receptor positive prostate cancer cells, but not in androgen receptor negative cells. Similarly, STAMP2 is an androgen responsive polypeptide in androgen receptor positive prostate cancer cells, but not in androgen receptor negative cells. Furthermore, STAMP2 expression is increased in a subset of prostate cancers compared with matched normal prostate epithelial cells microdissected from the same radical prostatectomy specimens. The invention provides, in general, STAMP2 nucleic acids, polypeptides, antibodies, and modulatory compounds for use in methods of diagnosing, treating, and preventing diseases and conditions of the prostate and testis, such as cancer.

Accordingly, in a first aspect the invention features a substantially pure polynucleotide that includes a sequence at least 80%, preferably at least 86%, most preferably at least 90%, 95%, 96%, 97%, 98%, 99% or 100% identical to STAMP2 cDNA (SEQ ID NO: 33), the complementary sequence, or a fragment thereof. In preferred embodiments, the polynucleotide consists of the STAMP2 cDNA sequence set forth in SEQ ID NO: 33. Preferred fragments include nucleotides 107 to 167 and nucleotides 1306 to 1360 of STAMP2 cDNA (SEQ ID NO: 33). For example, the polynucleotide can be an antisense nucleobase oligomer that is identical to at least to at least 8 to 10, preferably 8 to 30, (including all integers in between), or more, consecutive nucleotides of nucleotides 107 to 167 or 1306 to 1360 of SEQ ID NO: 33. In another example, the polynucleotide can be double stranded RNA with at least one strand that is identical to or complementary to at least 8 to 10, preferably 8 to 25 (including all integers in between), consecutive nucleotides of nucleotides 107 to 167 or 1306 to 1360 of SEQ ID NO: 33.

The invention also features a substantially pure polynucleotide comprising a nucleic acid sequence encoding a protein at least 80%, preferably at least 86%, most preferably at least 90%, 95%, 96%, 97%, 98%, 99% or 100% identical to the STAMP2 polypeptide sequence set forth in SED ID NO: 34, or a fragment thereof. In preferred embodiments, the polynucleotide consists of the nucleic acid sequence encoding the STAMP2 polypeptide sequence set forth in SED ID NO: 34.

Desirably, the polynucleotide encodes or is complementary to a polynucleotide that encodes a polypeptide identical to amino acids 1 to 20, amino acids 70 to 82, amino acids 87 to 97, amino acids 330 to 347, amino acids 400 to 428, or amino acids 445 to 459 of the STAMP2 sequence set forth in SEQ ID NO: 34, or a fragment thereof. For example, the polynucleotide can be an antisense nucleobase oligomer that is identical to or complementary to at least 8 to 10, preferably 8 to 30, (including all integers in between), or more, consecutive nucleotides of a polynucleotide encoding amino acids 1 to 20, amino acids 70 to 82, amino acids 87 to 97, amino acids 330 to 347, amino acids 400 to 428, or amino acids 445 to 459 of the STAMP2 sequence set forth in SEQ ID NO: 34. In another example, the polynucleotide can be double stranded RNA with at least one strand that is identical to at least 8 to 10, preferably 8 to 25 (including all integers in between) consecutive nucleotides of a polynucleotide encoding amino acids 1 to 20, amino acids 70 to 82, amino acids 87 to 97, amino acids 330 to 347, amino acids 400 to 428, or amino acids 445 to 459 of the STAMP2 sequence set forth in SEQ ID NO: 34. The length of the antisense nucleobase oligomer or the double stranded RNA can vary but is preferably 8 to 30 nucleotides, at least 40, 60, 85, 120, or more nucleotides up to the length of the full length STAMP2 gene for antisense nucleobase oligomers and preferably greater than 10 nucleotides in length, and most preferably 15-25 nucleotides in length. The dsRNA can also be longer, e.g., 30, 40, 50 nucleotides in length up to the entire length of the full length STAMP2 gene for the dsRNA. A range of 18-25 nucleotides is the most preferred size for dsRNAs.

In another aspect, the invention features a substantially pure polynucleotide comprising a sequence that hybridizes at high stringency to the STAMP2 nucleic acid sequence set forth in SEQ ID NO: 33, or a fragment thereof. In a related aspect, the invention features a substantially pure polynucleotide comprising a sequence that hybridizes at high stringency to a nucleic acid sequence encoding the amino acid sequence set forth in SEQ ID NO: 34, or a fragment thereof.

For any of the above aspects, the polynucleotide can also have a nucleic acid sequence that is complementary to at least a portion of the STAMP2 nucleic acid sequence. Such complementary sequences can be used, for example, as a probe. In preferred embodiments of some of the above aspects, the invention provides a vector, wherein the polynucleotide is positioned for expression or operably linked to a promoter in the vector, a cell, a cell including the vector, and a non-human transgenic animal including any of the polynucleotides of the invention.

In another aspect, the invention features a substantially pure polypeptide comprising a sequence at least 80%, preferably 86%, and most preferably at least 90%, 95%, 96%, 97%, 98%, 99% or 100% identical to STAMP2 (SEQ ID NO: 34), or fragments thereof. In preferred embodiments, the polypeptide includes a sequence that is at least 80%, preferably at least 86%, 90%, 95%, 96%, 97%, 98%, 99% or 100% identical to amino acids 1 to 20, amino acids 70 to 82, amino acids 87 to 97, amino acids 330 to 347, amino acids 400 to 428, or amino acids 445 to 459 of the STAMP2 sequence set forth in SEQ ID NO: 34.

In additional aspects, the invention features an antibody that specifically binds to a STAMP2 polypeptide. Desirably, the antibody specifically binds to amino acids 1 to 20, amino acids 70 to 82, amino acids 87 to 97, amino acids 330 to 347, amino acids 400 to 428, or amino acids 445 to 459 of the STAMP2 sequence set forth in SEQ ID NO: 34.

In another aspect, the invention features a method of diagnosing a subject as having, or having a propensity to develop, a disorder of the prostate or testis that includes measuring the level of STAMP2 polypeptide in a sample from the subject. In additional preferred embodiments, the measuring of the STAMP2 polypeptide levels can be performed using an immunological assay such as an ELISA. In preferred embodiments, the method also includes comparing the level of STAMP2 polypeptide in a subject sample to a reference sample or level of STAMP2 polypeptide.

In another aspect, the invention features a method of diagnosing a subject as having, or having a propensity to develop, a disorder of the prostate or testis that includes measuring the level of a STAMP2 nucleic acid in a sample from the subject. In preferred embodiments, the method also includes comparing the level of a STAMP2 polynucleotide from a subject sample to a reference sample or level of a STAMP2 polynucleotide.

In preferred embodiments of any of the above methods of the invention, the measuring of the levels of STAMP2 polypeptide or polynucleotide is done on two or more occasions and an alteration (e.g., an increase of at least 10%, 25%, 50%, 75% or more) in the levels between measurements is a diagnostic indicator of a disorder, or a propensity to develop a disorder, of the prostate or testis.

In another aspect, the invention features a method of diagnosing a subject as having, or having a propensity to develop, a disorder of the prostate or testis, said method comprising determining the nucleic acid sequence of a STAMP2 gene in a sample from a subject and comparing it to a reference sequence. In this method, an alteration or polymorphism in the subject's nucleic acid sequence that changes the expression level or biological activity of the STAMP2 gene product in the subject diagnoses the subject with a disorder of the prostate, or a propensity to develop a disorder of the prostate or testis.

In preferred embodiments of the diagnostic aspects of the invention, the reference sample is a prior sample obtained from the same subject. In additional preferred embodiments, the reference standard or level is a level or number derived from such a sample. The reference standard or level can also be a value derived from a normal subject that is matched to the sample subject by at least one of the following criteria: sex, age, family history or prostate or testis disorders, and weight. In additional preferred embodiments, the reference sample is a normal control taken from a subject that does not have a disorder of the testis or prostate or a purified protein at known normal concentrations. If the reference sample or level is a normal reference, an increase (e.g., at least 10%, 25%, 50%, 75% or more) in the level of STAMP2 polypeptide or nucleic acid in the subject sample relative to the reference is a diagnostic indicator of a disorder of the prostate or testis, or a propensity to develop a disorder of the prostate or testis.

In preferred embodiments of any of the above aspects, the sample used for the diagnostic methods is blood, serum, urine, semen, cerebrospinal fluid, saliva, or a cell or tissue. In particularly preferred embodiments, the sample is a cell or tissue biopsy sample, for example a cell or tissue biopsy sample derived from a prostate or testis.

In yet another aspect, the invention features a kit for the diagnosis of a disorder of the prostate or testis in a subject, which includes a STAMP2 binding agent for detecting a STAMP2 polypeptide or any fragment thereof. In preferred embodiments, the STAMP2 binding agent is an antibody that specifically binds STAMP2. In additional preferred embodiments, the antibody specifically binds amino acids 1 to 20, amino acids 70 to 82, amino acids 87 to 97, amino acids 330 to 347, amino acids 400 to 428, or amino acids 445 to 459 of STAMP2 (SEQ ID NO: 34). Desirably, the kit also includes components for an immunological assay, an enzymatic assay, or a colorimetric assay.

In another related aspect, the invention features a kit for the analysis of a STAMP2 nucleic acid molecule, which includes a STAMP2 nucleic acid molecule (e.g., a probe or a primer) at least 80% identical, preferably at least 86%, most preferably at least 90% 90%, 95%, 96%, 97%, 98%, 99% or 100% identical to STAMP2 cDNA (SEQ ID NO: 33) or a fragment thereof, wherein the nucleic acid molecule specifically hybridizes under high stringecy conditions to the sequence set forth in SEQ ID NO: 33 or the complementary sequences thereof. In preferred embodiments, the probe includes a polynucleotide that is at least 80%, preferably 90%, 95%, 96%, 97%, 98%, 99% or 100% identical to nucleotides 107 to 167 or to nucleotides 1306-1360 of SEQ ID NO: 33 or to the nucleic acid sequence encoding amino acids 1 to 20, amino acids 70 to 82, amino acids 87 to 97, amino acids 330 to 347, amino acids 400 to 428, or amino acids 445 to 459 of STAMP2 (SEQ ID NO: 34).

In another aspect, the invention features a method of treating a subject having a disorder of the prostate or testis that includes administering a compound capable of decreasing the biological activity or the expression level of STAMP2 polynucleotide or polypeptide. In preferred embodiments, the compound is a nucleobase oligomer that is at least 90%, 91%, 92%, 93%, 94%, 96%, 96%, 97%, 98%, 99%, or 100% complementary to at least a portion of a STAMP2 nucleic acid sequence. The nucleobase oligomer can be an antisense nucleobase oligomer, preferably at least 90%, 91%, 92%, 93%, 94%, 96%, 96%, 97%, 98%, 99%, or 100% complementary to at least 8 to 10, preferably 8 to 30, (including all integers in between), or greater, consecutive nucleotides of the desired nucleic acid sequence. The nucleobase oligomer can also be a double stranded RNA (dsRNA), preferably a small interfering RNA (siRNA) that is preferably at least 90%, 91%, 92%, 93%, 94%, 96%, 96%, 97%, 98%, 99%, or 100% complementary to at least 8 to 10, preferably 8 to 25 (including all integers in between) consecutive nucleotides of the desired nucleic acid sequence (e.g., STAMP2 or fragments thereof).

In additional preferred embodiments of this aspect, the compound is an antibody or antigen-binding fragment, preferably a monoclonal antibody, that specifically binds STAMP2. In preferred embodiments, the antibody or antigen-binding fragment thereof is a human or humanized antibody. In additional preferred embodiments, the antibody specifically binds amino acids 1 to 20, amino acids 70 to 82, amino acids 87 to 97, amino acids 330 to 347, amino acids 400 to 428, or amino acids 445 to 459 of STAMP2 (SEQ ID NO: 34).

In yet another aspect, the invention features a pharmaceutical composition that includes at least one dose of a therapeutically effective amount of any of the compounds capable of decreasing the biological activity or the expression level of STAMP2 polynucleotide or polypeptide, as described above, in a pharmaceutically acceptable carrier.

In another aspect, the invention features a method of identifying a compound that ameliorates a disorder of the prostate or testis that includes contacting a cell that expresses a STAMP2 nucleic acid molecule with a candidate compound, and comparing the level of expression of the STAMP2 nucleic acid molecule in the cell contacted by the candidate compound with the level of expression in a control cell not contacted by the candidate compound. An alteration (e.g., a decrease of at least 10%, 25%, 50%, 75% or more) in expression of the STAMP2 nucleic acid molecule identifies the candidate compound as a compound that ameliorates a disorder of the prostate or testis.

In another aspect, the invention features a method of identifying a compound that ameliorates a disorder of the prostate or testis that includes contacting a cell that expresses a STAMP2 polypeptide with a candidate compound and comparing the level of expression of the STAMP2 polypeptide in the cell contacted by the candidate compound with the level of polypeptide expression in a control cell not contacted by the candidate compound. An alteration (e.g., a decrease of at least 10%, 25%, 50%, 75% or more) in the expression of the STAMP2 polypeptide identifies the candidate compound as a compound that ameliorates a disorder of the prostate or testis.

In preferred embodiments, the alteration in expression is assayed using an immunological assay, an enzymatic assay, or an immunoassay.

In another aspect, the invention features a method of identifying a compound that ameliorates a disorder of the prostate or testis, the method comprising contacting a cell that expresses a STAMP2 polypeptide with a candidate compound, and comparing the biological activity of the STAMP2 polypeptide in the cell contacted by the candidate compound with the level of biological activity in a control cell not contacted by the candidate compound, wherein an alteration in the biological activity of the STAMP2 polypeptide identifies the candidate compound as a compound that ameliorates a disorder of the prostate or testis.

By "alteration" is meant a change (increase or decrease) in the expression levels or biological activity of a gene or polypeptide as detected by standard art known methods such as those described above. As used herein, an increase or decrease includes a 10% change, preferably a 25% change, more preferably a 40% change, and most preferably a 50%, 75%, 95% or greater change in expression levels or biological activity of a prostate-specific or testis-specific nucleic acid molecule or polypeptide, preferably a STAMP2 polypeptide or nucleic acid molecule.

By "antisense" or "antisense nucleobase oligomer" as used herein in reference to a nucleic acid molecule or nucleobase oligomer, is meant a molecule having a nucleic acid sequence, regardless of length, that is complementary to at least part of the coding strand or mRNA. In one example, the antisense nucleobase oligomer is complementary to at least part of the coding strand or mRNA of a STAMP2 gene. The antisense nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to mRNA or DNA encoding a prostate-specific or testis-specific polypeptide (e.g., a STAMP2 protein), and may be as long as the full-length mRNA or gene. An antisense molecule may also include regulatory sequences such as transcription enhancers, hormone responsive elements, ribosomal- and RNA polymerase binding sites, etc., which may be located upstream or downstream of the coding region, and may have a distance of several ten base pairs to several ten thousand base pairs. An antisense nucleobase oligomer can be, for example, capable of preferentially lowering the production or expression of a prostate-specific or a testis-specific polypeptide (e.g., STAMP2) encoded by a prostate-specific or a testis-specific nucleic acid molecule.

By "cell proliferation" is meant the growth or reproduction of similar cells. By "inhibiting proliferation" is meant the decrease in the number of similar cells by at least 10%, more preferably by at least 20%, and most preferably by at least 50%. By "stimulating proliferation" is meant an increase in the number of similar cells by at least 10%, more preferably by at least 20%, and most preferably by at least 50%.

The reagents described herein, for example, vectors expressing antisense, antagonists, or inhibitors of prostate-specific or testis-specific polypeptides or nucleic acid molecules may be used, for example, to suppress the excessive proliferation of prostate or testicular cells.

By a "compound," "test compound," or "candidate compound" is meant a molecule, be it naturally-occurring or artificially-derived, and includes, for example, peptides, proteins, synthetic organic molecules, naturally-occurring organic molecules, nucleic acid molecules, and components thereof.

By "disorder of the prostate or testis" is meant a disturbance of function and/or structure of the prostate or testis in a living organism. Such a disorder can result from an external source, a genetic predisposition, a physical or chemical trauma, or a combination of the above. Exemplary disorders include prostate cancer, benign prostatic hyperplasia, acute prostatitis, testicular cancer, and developmental defects of the prostate or testis (such as cryptorchidism or undescended testis, and retractile, ascending, or vanished testis). Additional examples of disorders of the prostate or testis can be found in Campbell's Urology, Seventh Edition, W.B. Saunders Company, Philadelphia (1998). Such disorders include the proliferation of prostate or testicular cells.

By "expression" is meant the detection of a gene or polypeptide by standard art known methods. For example, polypeptide expression is often detected by immunological assays such as western blotting, immunohistochemistry, and ELISA; DNA expression is often detected by Southern blotting or polymerase chain reaction (PCR), and RNA expression is often detected by northern blotting, PCR, or RNAse protection assays.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1100, 1200, 1300, 1383, 1486 or more nucleotides. A fragment may contain 10, 20, 30, 40, 50, 60, 70, 80, 90, or 100, 200, 300, 400, 450, 459 or more amino acids. Exemplary fragments of STAMP2 polypeptide include any protein that includes amino acids 1 to 20, amino acids 70 to 82, amino acids 87 to 97, amino acids 330 to 347, amino acids 400 to 428, or amino acids 445 to 459 of STAMP2 (SEQ ID NO: 34).

Methods for generating such fragments are well known in the art (see, for example, Ausubel et al., *Current Protocols in Molecular Biology*, John Wiley & Sons, New York, N.Y., 1998), using the nucleotide sequences provided herein. For example, a STAMP2 polynucleotide fragment can be generated by PCR amplifying a desired STAMP2 nucleic acid molecule fragment using oligonucleotide primers designed based upon the STAMP2 nucleic acid sequences. Preferably, the oligonucleotide primers include unique restriction enzyme sites that facilitate insertion of the amplified fragment into the cloning site of an expression vector (e.g., a mammalian expression vector). This vector can then be introduced into a cell (e.g., a mammalian cell) using any of the various techniques known in the art such as those described herein, resulting in the production of a STAMP2 polypeptide fragment in the cell containing the expression vector.

By "homologous" is meant any gene or protein sequence that bears at least 30% homology, more preferably 40%, 50%, 60%, 70%, 80%, and most preferably 90%, 95%, 96%, 97%, 98%, 99% or 100% or more homology to a known gene or protein sequence over the length of the comparison sequence. A "homologous" protein can also have at least one biological activity of the comparison protein. For polypeptides, the length of comparison sequences will generally be at least 10 amino acids, preferably at least 15 amino acids, more preferably at least 20 amino acids, and most preferably 25 amino acids or more. For nucleic acids, the length of comparison sequences will generally be at least 15 nucleotides, preferably at least 30 nucleotides, more preferably at least 40 nucleotides, and most preferably at least 50 nucleotides. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

By "hybridize" is meant pair to form a double-stranded molecule between complementary polynucleotide sequences, or portions thereof, under various conditions of stringency. (See, e.g., Wahl and Berger (1987) *Methods Enzymol.* 152:399; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In another embodiment, hybridization will occur at 42° C. in 250 mM NaCl, 25 mM trisodium citrate, 1% SDS, 50% formamide, and 200 µg/ml ssDNA. Generally, by "high stringency conditions" is meant conditions that allow hybridization comparable with the hybridization that occurs using a DNA probe of at least 500 nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (these are typical conditions for high stringency Northern or Southern hybridizations). High stringency hybridization is also relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and may be found, for example, in Ausubel et al., *Current Protocols in Molecular Biology*, John Wiley & Sons, New York, N.Y., 1998, hereby incorporated by reference.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci.*, USA 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

The term "identity" is used herein to describe the relationship of the sequence of a particular nucleic acid molecule or polypeptide to the sequence of a reference molecule of the same type. For example, if a polypeptide or nucleic acid molecule has the same amino acid or nucleotide residue at a given position, compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment. The "identity" of two or more nucleic acid or polypeptide sequences can therefore be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part I, Griffin, A. M., and Griffin, H. G., eds., Humana Press, New Jersey, 1994; *Sequence Analysis in Molecular Biology*, von Heinje, Academic Press, 1987; and *Sequence Analysis Primer*, Gribskov, and Devereux, eds., M. Stockton Press, New York, 1991; and Carillo and Lipman, SIAM J. Applied Math. 48:1073, 1988.

Methods to determine identity are available in publicly available computer programs. Computer program methods to determine identity between two sequences include, but are not limited to, the GCG program package (Devereux et al., Nucleic Acids Research 12(1): 387, 1984), BLASTP, BLASTN, and FASTA (Altschul et al., J. Mol. Biol. 215: 403 (1990). The well known Smith Waterman algorithm may also be used to determine identity. The BLAST program is publicly available from NCBI and other sources (*BLAST Manual*, Altschul, et al., NCBI NLM NIH Bethesda, Md. 20894). Searches can be performed in URLs for any of the publicly available programs listed above, for example the URL for the BLAST 2 or BLAST searches are known to the skilled artisan. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A nucleic acid molecule or polypeptide is said to be "substantially identical" to a reference molecule if it exhibits, over its entire length, at least 50%, 60%, or 70%, preferably at least 80% or 90%, more preferably at least 95%, 96%, 97%, 98%, 99%, or 100% identity to the sequence of the reference molecule. For polypeptides, the length of comparison sequences is at least 10, 20, 30, 40, 50, 60, 70, 80, 90, or 100, 200, 300, 400, 450, 459 or more amino acids, up to the full length of the protein. For nucleic acid molecules, the length of comparison sequences is at least 10, 20, 30, 40, 50, 60, 70, 80, 90, or 100, 200, 300, 400, 500, 600, 700, 800, 900, 1000, 1100, 1200, 1300, 1383, 1486 or more nucleotides, up to the full length of the molecule. Alternatively, or additionally, two nucleic acid sequences are "substantially identical" if they hybridize under high stringency conditions. In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art.

By "isolated nucleic acid molecule," "substantially pure nucleic acid molecule," or "substantially pure and isolated nucleic acid molecule" is meant a nucleic acid molecule (for example, DNA) that is free of the genes that, in the naturally occurring genome of the organism from which the nucleic acid molecule of the invention is derived, flank the nucleic acid. The term includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

By "modulate" or "modulating" is meant changing, either by decrease or increase. In the present invention modulating can refer to changing the expression or biological activity of a prostate-specific or testis-specific nucleic acid molecule or polypeptide, as described herein. It will be appreciated that the degree of modulation provided by a modulating compound in a given assay will vary, but that one skilled in the art can determine the statistically significant change in the level of biological activity that identifies a compound that modulates a prostate-specific or testis-specific nucleic acid molecule or polypeptide.

By "nucleic acid," "nucleobase oligomer," or "polynucleotide" is meant a chain of at least eight nucleobases joined together by linkage groups. Included in this definition are natural and non-natural oligonucleotides, both modified and unmodified, as well as oligonucleotide mimetics such as Protein Nucleic Acids, locked nucleic acids, and arabinonucleic acids.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline solution. Other physiologically acceptable carriers and their formulations are known to one skilled in the art and described, for example, in *Remington: The Science and Practice of Pharmacy*, (19$^{th}$ edition), ed. A. Gennaro, 1995, Mack Publishing Company, Easton, Pa.

By "proliferative disease" is meant a disease that is caused by or results in inappropriately high levels of cell division, inappropriately low levels of apoptosis, or both. For example, cancers such as prostate cancer, testicular cancer, lymphoma, leukemia, melanoma, ovarian cancer, breast cancer, pancreatic cancer, liver cancer, and lung cancer are all examples of proliferative disease.

As used herein, by "polypeptide," "protein," or "polypeptide fragment" is meant a chain of two or more amino acids, regardless of any post-translational modification (e.g., glycosylation or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A protein can be made up of one or more polypeptides.

By "probe" or "primer" is meant a single-stranded DNA or RNA molecule of defined sequence that can base pair to a second DNA or RNA molecule that contains a complementary sequence ("target"). The stability of the resulting hybrid depends upon the extent of the base pairing that occurs. This stability is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are well known to those skilled in the art. Probes or primers specific for prostate-specific or a testis-specific nucleic acid molecules, for example STAMP2, preferably, have greater than 45% sequence identity, more preferably at least 55-75% sequence identity, still more preferably at least 75-85% sequence identity, yet more preferably at least 85-99% sequence identity, and most preferably 100% sequence identity to the nucleic acid sequences (e.g., SEQ ID NO: 33) encoding the amino acid sequences (e.g., SEQ ID NO: 34) described herein. Probes can be detectably-labeled, either radioactively or non-radioactively, by methods that are well-known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are well known to those skilled in the art.

A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably-labeling molecules are well known in the art and include, without limitation, radioactive labeling (e.g., with an isotope, such as $^{32}$P or $^{35}$S) and nonradioactive labeling (e.g., with a fluorescent label, such as fluorescein, or by generating a construct containing green fluorescent protein (GFP)).

By "prostate-specific" or "testis-specific" nucleic acid molecule is meant a nucleic acid molecule, such as a genomic DNA, cDNA, or RNA (e.g., mRNA) molecule, having at least 50, 60, or 75%, more preferably at least 80, 85, or 95%, and most preferably at least 99% amino acid identity to the nucleic acid molecules described herein, for example, in FIGS. 4A-4M, 11, 14, and 18. In addition, a nucleic acid molecule having at least 50, 60, or 75%, more preferably at least 80, 85, or 95%, and most preferably at least 99% nucleotide identity to a nucleotide sequence encoding amino acids 1-20, 70-82, 87-97, 330-347, 400-428, or amino acids 445 to 459 of STAMP2 (SEQ ID NO: 34), or the full length amino acid sequence of STAMP2 (SEQ ID NO: 34), can be considered a prostate-specific or testis-specific nucleic acid molecule. Specifically excluded from this definition are STEAP (AF186249) (Hubert, R. S. et al., *Proc Natl Acad Sci USA* 96, 14523-14528, 1999) and nucleic acid molecule sequences set forth in or encoding ESTs AF132025, AF177862, BAB23615, BAA91839, BAB15559, and NP_032190.

A preferred prostate-specific nucleic acid molecule may be preferentially expressed in prostate tissue at a level that is at least 5-fold higher, preferably at least 10-fold higher, more preferably at least 15-fold higher, and most preferably at least 20-fold higher than the level of the same nucleic acid molecule in at least one non-prostate tissue, preferably in all other non-prostate tissues. A prostate-specific nucleic acid molecule can also be expressed at high levels in a non-prostate tissue although, generally, the level of expression will be the highest in the prostate. Occasionally, as described herein, a prostate-specific nucleic acid molecule will be expressed at higher levels in non-prostate tissue (e.g., placenta, lung, or liver) than in the prostate.

A preferred testis-specific nucleic acid molecule may be preferentially expressed in testis tissue at a level that is at least 5-fold higher, preferably at least 10-fold higher, more preferably at least 15-fold higher, and most preferably at least 20-fold higher than the level of the same nucleic acid molecule in at least one non-testis tissue, preferably in all other non-testis tissues. A testis-specific nucleic acid molecule can also be expressed at high levels in a non-testis tissue although, generally, the level of expression will be the highest in the testis. Occasionally, as described herein, a testis-specific nucleic acid molecule will be expressed at higher levels in non-testis tissue (e.g., placenta, lung, or liver) than in the testis.

By "prostate-specific" or a "testis-specific" polypeptide or "prostate-specific" or a "testis-specific" protein is meant a polypeptide that is encoded by a prostate-specific or a testis-specific nucleic acid molecule. A prostate-specific or testis-specific polypeptide may also be defined as a polypeptide having at least 50, 60, or 75%, more preferably at least 80, 85, or 95%, and most preferably at least 99% amino acid identity to the polypeptides described herein, for example, in FIGS. 4A-M, 11, 14, and 18. Specifically excluded from this definition are STEAP (AF186249) (Hubert, R. S. et al., *Proc Natl Acad Sci U S A* 96, 14523-14528, 1999) and polypeptide sequences set forth in or encoded by ESTs AF132025, AF177862, BAB23615, BAA91839, BAB15559, and NP_032190. In addition, a polypeptide having at least 50, 60, or 75%, more preferably at least 80, 85, or 95%, and most preferably at least 99% amino acid identity to amino acids 1-20, 70-82, 87-97, 330-347, 400-428, or amino acids 445 to 459 of STAMP2 (SEQ ID NO: 34), or the full length amino acid sequence of STAMP2 (SEQ ID NO: 34), can be considered a prostate-specific or testis-specific polypeptide.

A preferred prostate-specific polypeptide is preferentially expressed in prostate tissue at a level that is at least 5-fold higher, preferably at least 10-fold higher, more preferably at least 15-fold higher, and most preferably at least 20-fold higher than the level of the same polypeptide in at least one non-prostate tissue, preferably in all other non-prostate tissues. A prostate-specific polypeptide can also be expressed at high levels in a non-prostate tissue although, generally, the level of expression will be the highest in the prostate. Occasionally, as described herein, a prostate-specific polypeptide will be expressed at higher levels in non-prostate (e.g., placenta, lung, liver) than in the prostate.

A preferred testis-specific polypeptide is preferentially expressed in testis tissue at a level that is at least 5-fold higher, preferably at least 10-fold higher, more preferably at least 15-fold higher, and most preferably at least 20-fold higher than the level of the same polypeptide in at least one non-testis tissue, preferably in all other non-testis tissues. A testis-specific polypeptide can also be expressed at high levels in a non-testis tissue although, generally, the level of expression will be the highest in the testis. Occasionally, as described herein, a testis-specific polypeptide will be expressed at higher levels in non-testis (e.g., placenta, lung, liver) than in the testis.

The term prostate-specific or testis-specific polypeptide includes homologs, analogs, fragments, and isoforms, e.g., alternatively spliced isoforms, of the sequences described herein. By "biologically active fragment" is meant a polypeptide fragment of a prostate-specific or testis-specific polypeptide that exhibits, for example, extracellular trafficking, cell signaling, cell proliferation, or other properties that are at least 30%, preferably at least 50%, more preferably at least 75%, and most preferably at least 100%, compared with the properties of a full length prostate-specific or testis-specific polypeptide. Examples of bioassays to test for biologically active homologs, analogs, fragments, and isoforms, are described in U.S. Patent Application No. 20030219761. By "analog" is meant any substitution, addition, or deletion in the amino acid sequence of a prostate-specific or testis-specific polypeptide that exhibits properties that are at least 30%, preferably at least 50%, more preferably at least 75%, and most preferably at least 100%, compared with the extracellular trafficking or cell signaling properties of the polypeptide from which it is derived. Fragments, homologs, and analogs can be generated using standard techniques, for example, solid phase peptide synthesis or polymerase chain reaction. For example, point mutations may arise at any position of the sequence from an apurinic, apyrimidinic, or otherwise structurally impaired site within the cDNA. Alternatively, point mutations may be introduced by random or site-directed mutagenesis procedures (e.g., oligonucleotide assisted or by error prone PCR). Likewise, deletions and/or insertions may be introduced into the sequences, and preferred insertions comprise 5'- and/or 3'-fusions with a polynucleotide that encodes a reporter moiety or an affinity moiety. Other preferred insertions comprise a nucleic acid that further includes functional elements such as a promoter, enhancer, hormone responsive element, origin of replication, transcription and translation initiation sites, etc. It should be appreciated that where insertions with one or more functional elements are present, the resulting nucleic acid may be linear or circular (e.g., transcription or expression cassettes, plasmids, etc.).

For use in the methods of the invention, the terms "prostate-specific" or "testis-specific" polypeptide further include the polypeptide sequences set forth in or encoded by ESTs AF132025, AF177862, BAB23615, BAA91839, BAB15559, and NP_032190, but does not include STEAP, and a prostate-specific or testis-specific nucleic acid molecule includes the nucleotide sequences set forth in or encoding ESTs AF132025, AF177862, BAB23615, BAA91839, BAB15559, and NP_032190, but does not include STEAP.

By "prostate-specific or a testis-specific gene or homolog or fragment thereof" is meant a gene, or homolog of a gene, that encodes a prostate-specific or testis-specific polypeptide.

By "sample" is meant a tissue biopsy, cells, blood, serum, urine, stool, or other specimen obtained from a patient or test subject.

A "reference sample" can include a sample taken from a different tissue or cell of the same subject, a different sample from the same subject known to be unaffected by any disorder of the prostate or testis, a sample previously taken from the same subject, or a sample taken from a different subject known to be unaffected by a disorder of the prostate or testis. A reference sample can also include a purified sample of a prostate-specific or a testis-specific gene or polypeptide (e.g., STAMP2) at a known normal level or a standard curve using a purified testis-specific gene or polypeptide (e.g., STAMP2). The reference sample can also be a value representing a known normal level of a testis-specific gene or polypeptide (e.g., STAMP2).

By "small interfering RNAs (siRNAs)" is meant an isolated dsRNA molecule comprised of both a sense and an anti-sense strand, preferably greater than 10 nucleotides in length, more preferably greater than 15 nucleotides in length, and most preferably 15-25 nucleotides in length. The dsRNA can also be longer, e.g., 30, 40, 50 nucleotides in length up to the entire length of the full length STAMP2 gene. A range of 18-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3'hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "specifically binds" is meant a compound (e.g., a polypeptide, polynucleotide, or an antibody) that recognizes and binds a polypeptide or polynucleotide, for example, a prostate-specific or a testis-specific polypeptide, and that when detectably labeled can be competed away for binding to that protein or polypeptide by an excess of compound that is not detectably labeled. A compound that non-specifically binds is not competed away by excess detectably labeled compound. A compound that specifically binds a polypeptide or polynucleotide of the invention does not substantially recognize and bind other molecules in a sample, for example a biological sample which naturally includes a polypeptide or polynucleotide of the invention.

By "STAMP2 polynucleotide" is meant a polynucleotide having a sequence that is at least 80%, preferably at least 86%, most preferably at least 90% 90%, 95%, 96%, 97%, 98%, 99% or 100% identical to the sequence set forth in SEQ ID NO: 33. Desirably the STAMP2 polynucleotide encodes a STAMP2 polypeptide. Included in this definition are fragments of STAMP2 polynucleotides that are at least 20 nucleotides in length, preferably 40 nucleotides, more preferably 50 nucleotides, and most preferably at least 60 nucleotides in length. Preferred fragments include the nucleotide sequences that encode the amino-terminal half of the STAMP2 polypeptide up to the sequences encoding the six transmembrane domains (i.e., amino acids 1 to 225); nucleotide sequences encoding the carboxy-terminal half of the polypeptide including the six transmembrane domains (i.e., amino acids 225 to 459); or nucleotide sequences that encode, for example, amino acids 1 to 20, amino acids 70 to 82, amino acids 87 to 97, amino acids 330 to 347, amino acids 400 to 428, or amino acids 445 to 459, or any portion thereof. Two additional preferred fragment include nucleotides 107-167 and 1306-1360 of SEQ ID NO: 33.

By "STAMP2 polypeptide" is meant a polypeptide having a sequence that is at least 80%, preferably at least 86%, most preferably at least 90% 90%, 95%, 96%, 97%, 98%, 99% or 100% identical to the sequence set forth in SEQ ID NO: 34. Preferably, the STAMP2 polypeptide has STAMP2 biological activity. Included in this definition are fragments of STAMP2 which are at least 10 amino acids in length, preferably 15 amino acids in length, and most preferably at least 25 amino acids in length. Preferred fragments of STAMP2 are the amino-terminal half of the polypeptide up to the sequences encoding the six transmembrane domains (i.e., amino acids 1 to 225), the carboxy-terminal half of the polypeptide including the six transmembrane domains (i.e., amino acids 225 to 459), or fragments including, for example, amino acids 1 to 20, amino acids 70 to 82, amino acids 87 to 97, amino acids 330 to 347, amino acids 400 to 428, or amino acids 445 to 459 or any portion thereof. All numbering is based on the numbering of the polynucleotide and polypeptide sequences set forth in SEQ ID NOS: 33 and 34.

By "STAMP2 biological activity" is meant exhibiting properties that contribute to extracellular trafficking pathways, secretory or endocytic pathways, or cell signaling pathways. SAMP2 biological activity also includes stimulation of cell proliferation or cell growth. Any of the above activities can be assayed using techniques known in the art or described herein. By "STAMP2 subcellular localization" is meant localization of STAMP2 protein to the Golgi, the plasma membrane, endoplasmic Reticulum, or the early endosome.

By "subject" is meant a mammal, including, but not limited to, a human or non-human mammal, such as a bovine, equine, canine, ovine, or feline.

By "substantially pure polypeptide" or "substantially pure and isolated polypeptide" is meant a polypeptide (or a fragment thereof) that has been separated from components that naturally accompany it. Typically, the polypeptide is substantially pure when it is at least 60%, by weight, free from the proteins and naturally occurring organic molecules with which it is naturally associated. Preferably, the polypeptide is a prostate-specific or a testis-specific polypeptide that is at least 75%, more preferably at least 90%, and most preferably at least 99%, by weight, pure. A substantially pure prostate-specific or a testis-specific polypeptide may be obtained by standard techniques, for example, by extraction from a natural source (e.g., prostate or testis tissue or cell lines), by expression of a recombinant nucleic acid encoding a prostate-specific or a testis-specific polypeptide, or by chemically synthesizing the polypeptide. Purity can be measured by any appropriate method, e.g., by column chromatography, polyacrylamide gel electrophoresis, or HPLC analysis.

A protein or polypeptide is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides not only include those derived from eukaryotic organisms but also those synthesized in *E. Coli* or other prokaryotes.

"Therapeutically effective amount" as used herein in reference to dosage of a medication, refers to the administration of a specific amount of a pharmacologically active agent (e.g., a prostate-specific or a testis-specific polypeptide, nucleic acid molecule, or modulatory compound) tailored to each individual patient manifesting symptoms characteristic of a specific disorder. For example, a patient receiving the treatment of the present invention might have prostate cancer. A person skilled in the art will recognize that the optimal dose of a pharmaceutical agent to be administered will vary from one individual to another. Dosage in individual patients should take into account the patients height, weight, rate of absorption and metabolism of the medication in question, the stage of the disorder to be treated, and what other pharmacological agents are administered concurrently.

By "transgenic" is meant any cell that includes a DNA sequence or transgene that is inserted by artifice into a cell and becomes part of the genome of the organism that develops from that cell. As used herein, the transgenic organisms are generally transgenic mammals (e.g., mice, rats, and goats) and the DNA (transgene) is inserted by artifice into the nuclear genome. By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism. By "knockout mutation" is meant an artificially induced alteration in the nucleic acid sequence (created via recombinant DNA technology or deliberate exposure to a mutagen) that reduces the biological activity of the polypeptide normally encoded therefrom by at least 80% relative to the unmutated gene. The mutation may, without limitation, be an insertion, deletion, frameshift mutation, or a missense mutation. The knockout mutation can be in a cell ex vivo (e.g., a tissue culture cell or a primary cell) or in vivo. A "knockout animal" is a mammal, preferably, a mouse, containing a knockout mutation as defined above.

By "treating" or "treatment" is meant the medical management of a patient with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The phrase "treatment" also includes symptomatic treatment, that is, treatment directed toward constitutional symptoms of the associated disease, pathological condition, or disorder. To "prevent disease" refers to prophylactic treatment of a subject who is not yet ill, but who is susceptible to, or otherwise at risk of, developing a particular disease. Thus, in the claims and embodiments, treating is the administration to a mammal either for therapeutic or prophylactic purposes.

The invention provides several advantages. For example, it provides methods and reagents that can be used in the diagnosis and treatment of prostate and testis associated diseases, as well as other disorders and conditions that are sensitive to the bioactivities of the reagents (e.g., polypeptides, nucleic acid molecules, antibodies) described herein. Since the prostate-specific or testis-specific polypeptides of the invention have been found to be highly expressed in the prostate and testis, these polypeptides can also be used in screens for therapeutics to treat disorders associated with the prostate and testis. These polypeptides are also expressed in other tissues, and can be used as therapeutics and diagnostics for cell proliferative disorders.

Other features and advantages of the invention will be apparent from the detailed description of the invention, the drawings, and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a table showing the nucleotide sequences of twelve clones (SEQ ID NOs: 1-12) isolated from prostate tissue and LNCaP cells.

FIG. 4B shows the nucleotide sequence, including the intron junction sequences (SEQ ID NO: 13), and predicted amino acid sequence (SEQ ID NO: 14) of STMP1.

FIG. 4C shows the nucleotide sequences of the exons and 3' UTR of STMP1 (SEQ ID NOs: 15-21).

FIG. 4D shows the nucleotide sequence of the ORF of STMP1 (SEQ ID NO: 22).

FIG. 4E shows the shows the cDNA sequence (SEQ ID NO: 23), and predicted amino acid sequence (SEQ ID NO: 14) of STMP1.

FIG. 4F shows the nucleotide sequences of the exons and 3' UTR of STMP1 ORF2 (SEQ ID NOs: 17-20 and 24-26).

FIG. 4G shows the nucleotide sequence of the ORF of STMP1 ORF2 (SEQ ID NO: 27).

FIG. 4H shows the cDNA sequence (SEQ ID NO: 28), and predicted amino acid sequence (SEQ ID NO: 29) of STMP1 ORF2.

FIG. 4I shows the nucleotide sequences of the exons and 3' UTR of STMP1 ORF3 (SEQ ID NOs: 17-19 and 24-26).

FIG. 4J shows the nucleotide sequence of the ORF of STMP1 ORF3 (SEQ ID NO: 30).

FIG. 4K shows the cDNA sequence (SEQ ID NO: 31), and predicted amino acid sequence (SEQ ID NO: 32) of STMP1 ORF3.

FIG. 4L shows the cDNA sequence (SEQ ID NO: 35), and predicted amino acid sequence (SEQ ID NO: 36) of STMP3.

FIG. 5 shows a sequence alignment of STMP1 (SEQ ID NO: 14), with STEAP (SEQ ID NO: 37, Accession No. AF186249), and two ESTs (Accession No. BAA91839 and Accession No. BAB15559; SEQ ID NOs: 38 and 39, respectively).

FIG. 11A shows the cDNA (SEQ ID NO: 40) and predicted amino acid sequence (SEQ ID NO: 41) for SSH9.

FIG. 11B shows the predicted promoter sequence for SSH9 (SEQ ID NO: 42).

FIG. 11C shows the predicted intron-exon boundaries for SSH9 (SEQ ID NOs: 43-50).

FIG. 14A shows the nucleotide sequence of the ORF of PSL22 (SEQ ID NO: 51).

FIG. 14B shows the cDNA sequence (SEQ ID NO: 52), and predicted amino acid sequence (SEQ ID NO: 53) of PSL22.

FIG. 14C shows the nucleotide sequences of the TATA promoter and transcription start site, exons, and 5' and 3' UTRs of PSL22 (SEQ ID NOs: 54-70).

FIG. 18 shows the cDNA sequence (SEQ ID NO: 33) and amino acid sequence (SEQ ID NO: 34) of STAMP2 and the locations of the predicted transmembrane domains are underlined. The N-terminal domain that has sequence similarity to dinucleotide binding motifs, oxidoreductases, or pyrroline 5-carboxylate reductase, is shown in bold.

FIG. 19 shows a sequence alignment of STAMP2 with TIARP (GenBank accession number NP473439), STAMP1 (GenBank accession number AAG32149), TSAP6 (GenBank accession number AAH42150), pHyde (GenBank accession number AAK00361.1), and STEAP (GenBank accession number AF186249) obtained by Clustal and GenDoc programs. Completely conserved residues are shaded in black;

residues that are conserved in four or five of the sequences are shaded light and dark gray, respectively.

Figure 20:
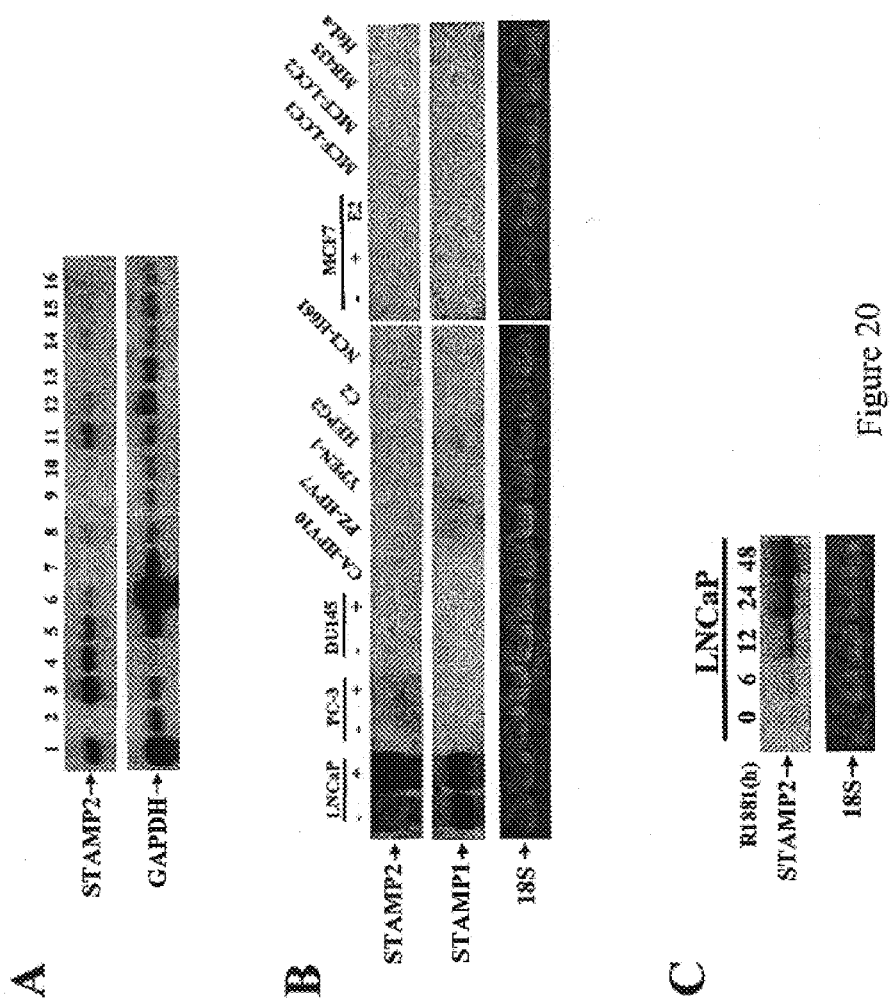

FIG. 20A is an autoradiogram showing the results of a multiple tissue Northern blot (Clontech) probed with STAMP2 or G3PDH cDNA. The lanes represent: 1. Heart, 2. Brain, 3. Placenta, 4. Lung, 5. Liver, 6. Skeletal Muscle, 7. Kidney, 8. Pancreas, 9. Spleen, 10. Thymus, 11. Prostate, 12. Testis, 13. Ovary, 14. Small Intestine, 15. Colon, 16. Peripheral blood leukocyte. The location of the full-length 4.0 kb mRNA is indicated by arrows to the left of the figure. The stronger hybridization that is observed with G3PDH in the heart and skeletal muscle samples is due to its higher expression in these tissues.

FIG. 20B is an autoradiogram showing the results of a Northern blot analysis of total RNA from LNCaP, PC3, or DU145 cells either left untreated or treated with the synthetic androgen R1881 ($10^{-8}$ M) for 24 hours as indicated, and probed with STAMP2. STAMP2 expression was also assessed in a number of prostate cancer cell lines not expressing the androgen receptor (PC-3, DU-145, CA-HPV10, PZ-HPV7, YPEN-1), in myotubes (C2), lung cancer cells (NCI-H661), breast cancer cells (MCF7, MCF7-LCC1, MCF7-LCC2, MB435), or cervical carcinoma cells (HeLa), as indicated. The same blot was also probed with a STAMP1 cDNA probe.

FIG. 20C is an autoradiogram showing the results of a Northern blot analysis of total RNA isolated from LNCaP cells either left untreated or treated with R1881 ($10^{-8}$ M) for the indicated time points.

Figure 21:
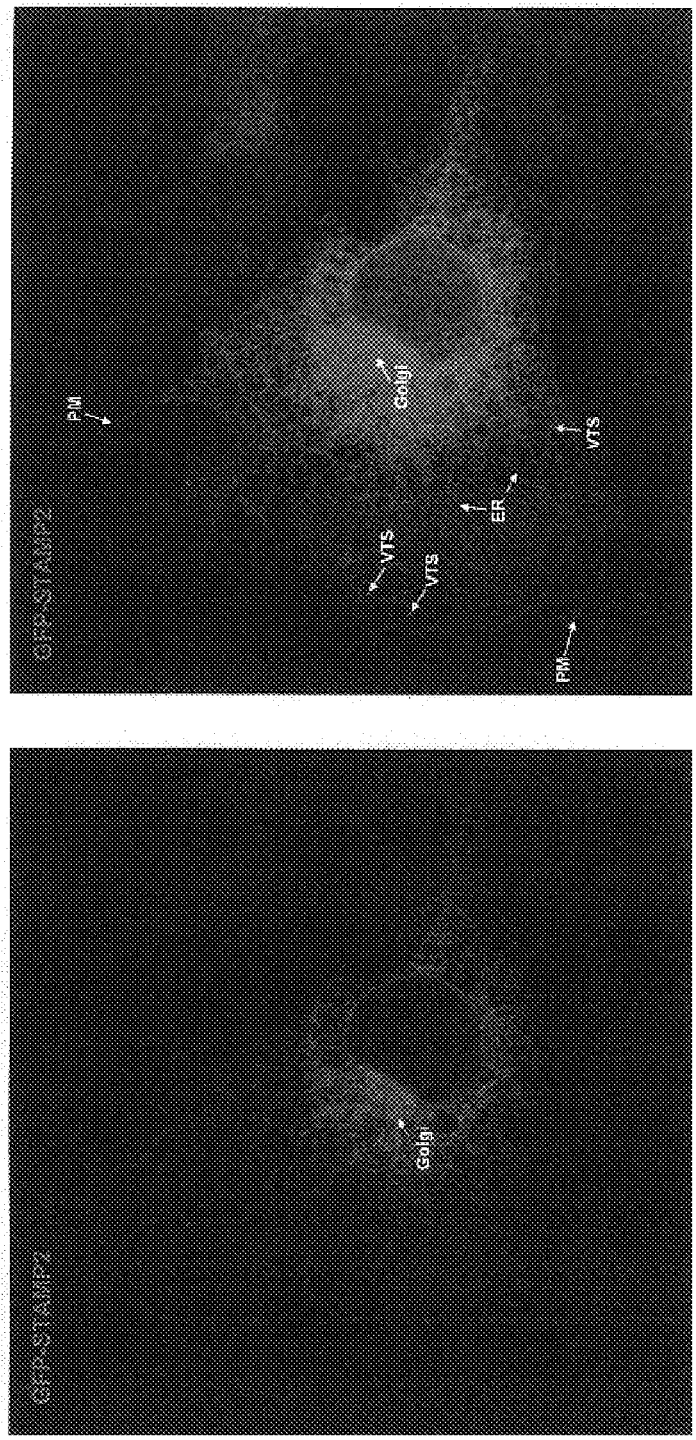

FIG. 21 is a series of images showing the intracellular localization of GFP-STAMP2. COS-1 cells were transiently transfected with GFP-STAMP2 and then fixed and processed for confocal microscopy as described below. A series of confocal sections were collected through a single cell along the z-axis at 100 nm intervals, one of which is shown in low and high exposure, to the left and the right, respectively. Areas of intracellular GFP-STAMP2 localization are indicated with arrows: Golgi; plasma membrane, PM; vesiculotubular structures, VTS; and endoplasmic reticulum (ER).

Figure 22:
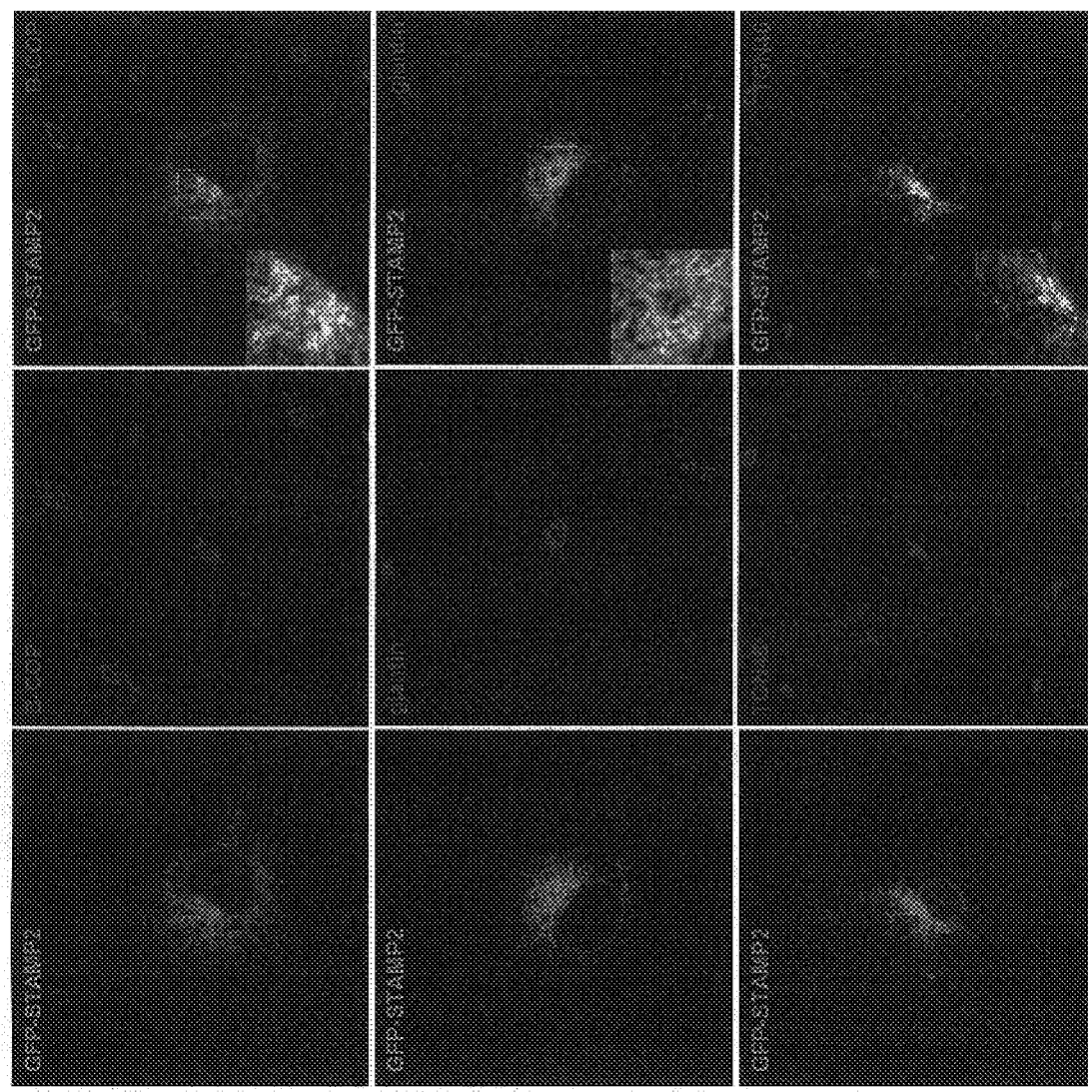

FIG. 22 is a series of images showing the colocalization of GFP-STAMP2 with Golgi and TGN markers. COS-1 cells transfected with GFP-STAMP2 were fixed and labeled with antibodies against well characterized Golgi and TGN markers: β-coat protein (β-COP), giantin, and TGN46. Green GFP-STAMP2 fluorescence and red (Texas Red-labeled secondary antisera) β-COP, giantin, and TGN46 fluorescence were detected by confocal laser microscopy. For each row, the image in the right column shows the overlay of the prior two images with yellow/orange staining indicating the regions of overlap. The areas marked by a rectangle are enlarged and shown as insets.

Figure 23:
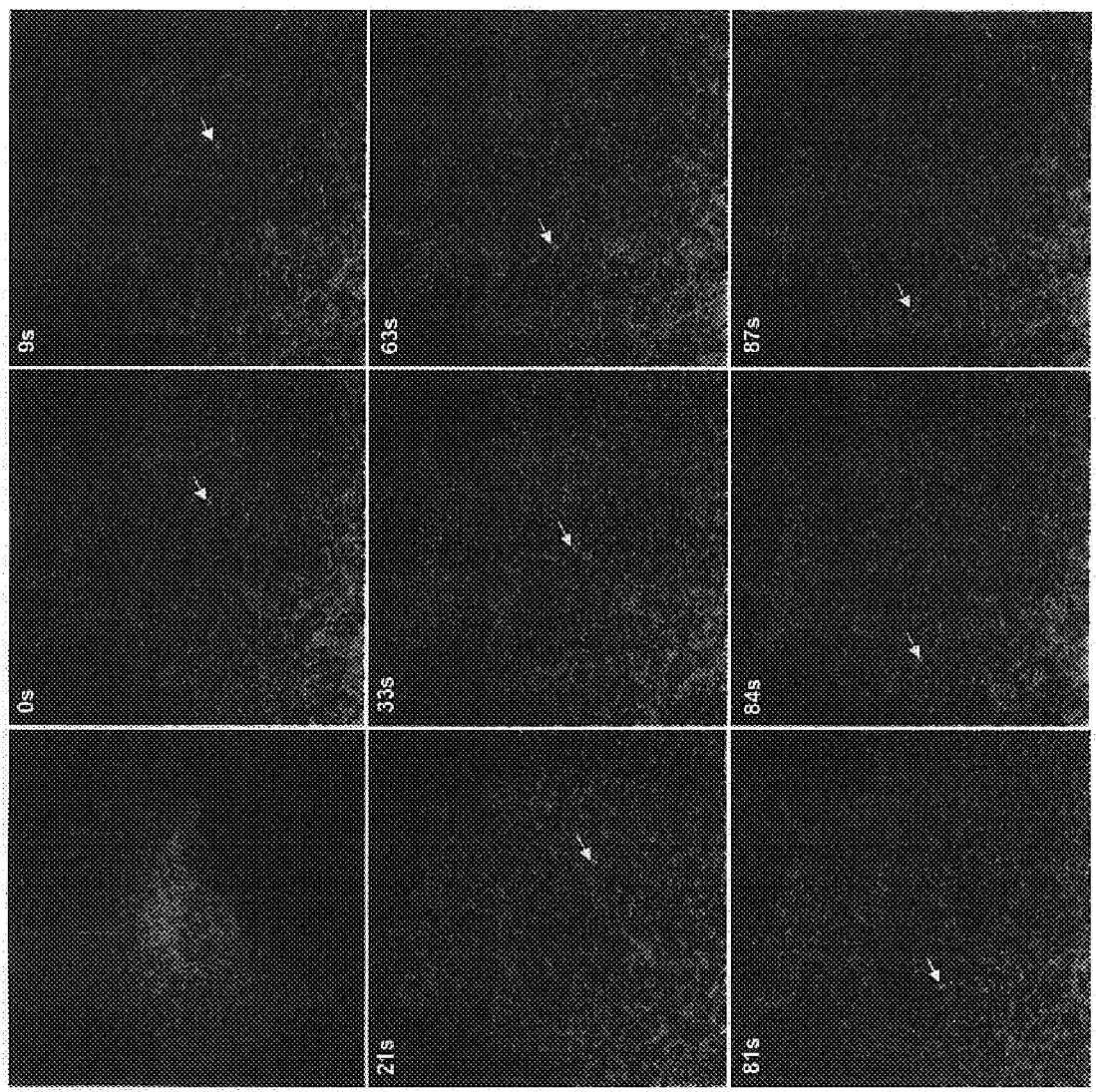

FIG. 23 is a series of images showing time-lapse microscopy of GFP-STAMP2 trafficking in living cells. A COS-1 cell transiently expressing GFP-STAMP2 was observed by live-cell confocal microscopy at 37° C. Eight consecutive images were taken at 3 second intervals. The movement of a particular vesicular structure from cytoplasm to plasma membrane is shown (white arrows) within the region of the cell that is magnified (white square). Note that the results shown are representative of multiple time-lapse analyses and the changes in the images are not due to movement from the plain of focus.

Figure 24:
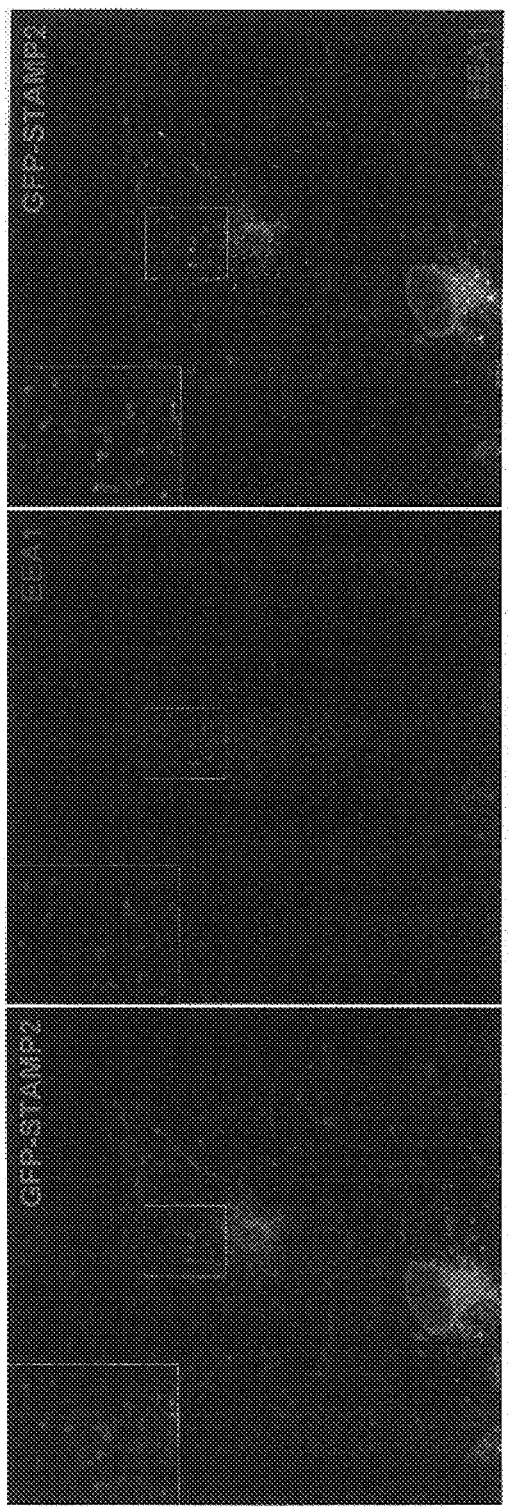

FIG. 24 is a series of images showing the colocalization of GFP-STAMP2 with the early endosomal marker EEA1 as detected by indirect immunofluorescence microscopy. COS-1 cells transfected with GFP-STAMP2 were fixed and labeled with antibodies against the well-characterized early endosomal marker EEA 1. Green GFP-STAMP2 fluorescence and red (Texas Red-labeled secondary antiserum) EEA1 fluorescence were detected by confocal laser microscopy. The right-hand panel shows the overlay images with yellow/orange staining indicating the regions of overlap. The areas marked by white rectangles are enlarged and shown as insets.

Figure 25:
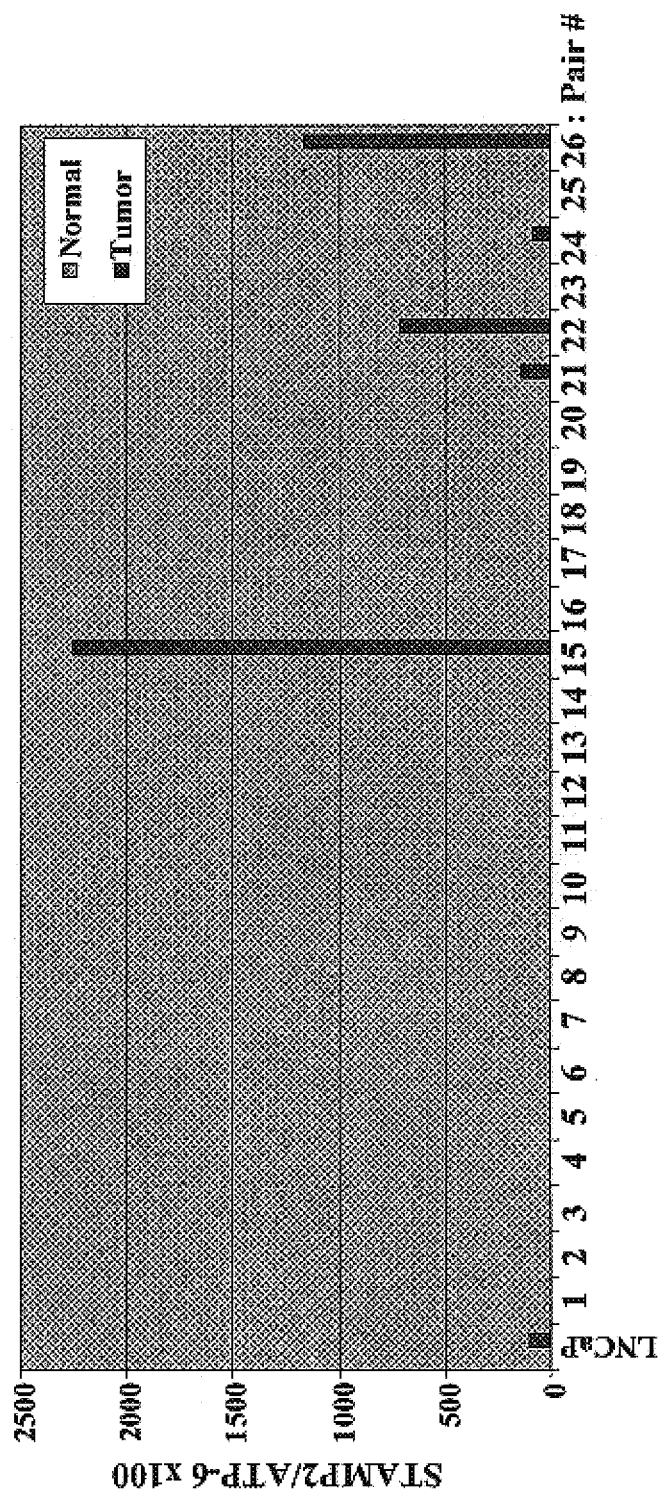

FIG. 25 is a graph showing the results of quantitative RT-PCR analysis of STAMP2 expression in microdissected, matched normal vs neoplastic prostate glands. Sections were obtained from radical prostatectomy specimens that were snap-frozen upon resection, and subjected to Laser Capture Microdissection (LCM). A pathologist procured normal and cancer glands from the same tissue (total of 26 matched pairs, from different patients). Total RNA was isolated, and used for cDNA synthesis and quantitative RT-PCR with STAMP2-specific primers. Note that no STAMP2 was detected in normal epithelial cells. The graph shows representative results obtained from two independent experiments.

Figure 26:
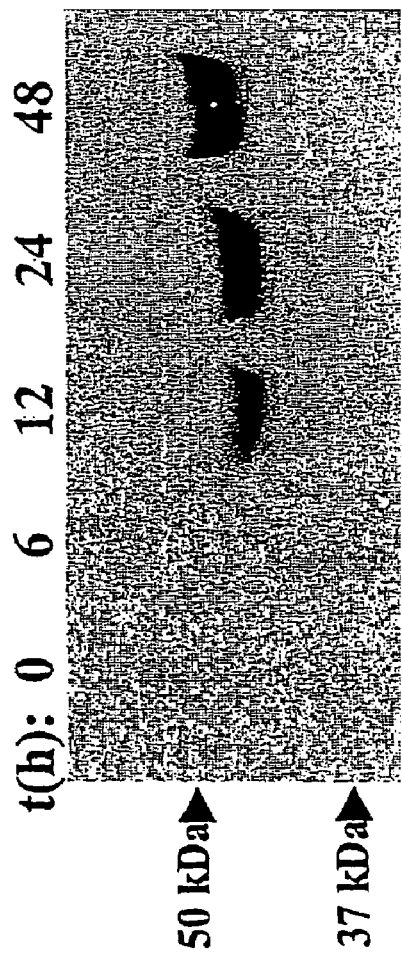

FIG. 26 is an autoradiogram showing the results of a western blot analysis of whole cell extracts isolated from LNCaP cells either left untreated or treated with R1881 ($10^{-8}$ M) for the indicated times. Extracts were separated by SDS-PAGE, transferred to a PVDF membrane and probed using an antiserum raised against a peptide corresponding to amino acids 445-459 of STAMP2.

Figure 27:
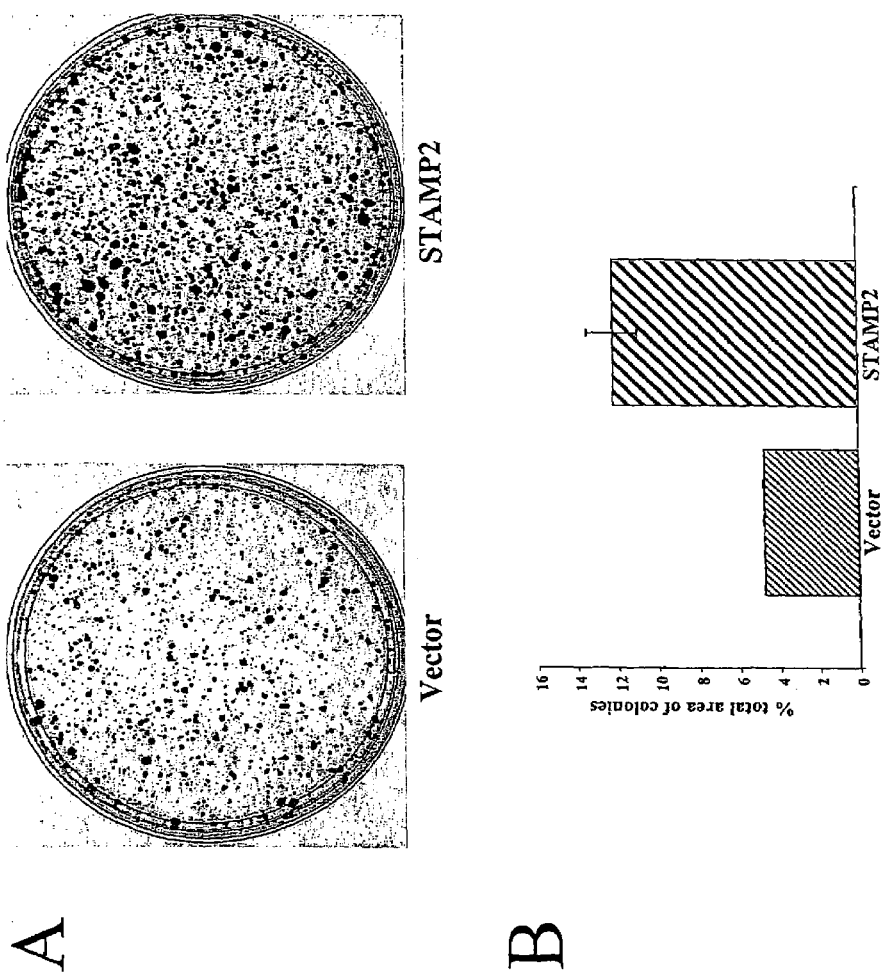

FIG. 27A is a photograph of two representative dishes of cell showing colony formation in the DU145 cells expressing vector alone and DU145 expressing STAMP2 cDNA. FIG. 27B is a graph showing the percent total area of the colonies for the DU145 cells expressing vector alone and DU145 cells expressing STAMP2. The results shown are from experiments done in triplicate repeated at least 3 times.

Figure 28:
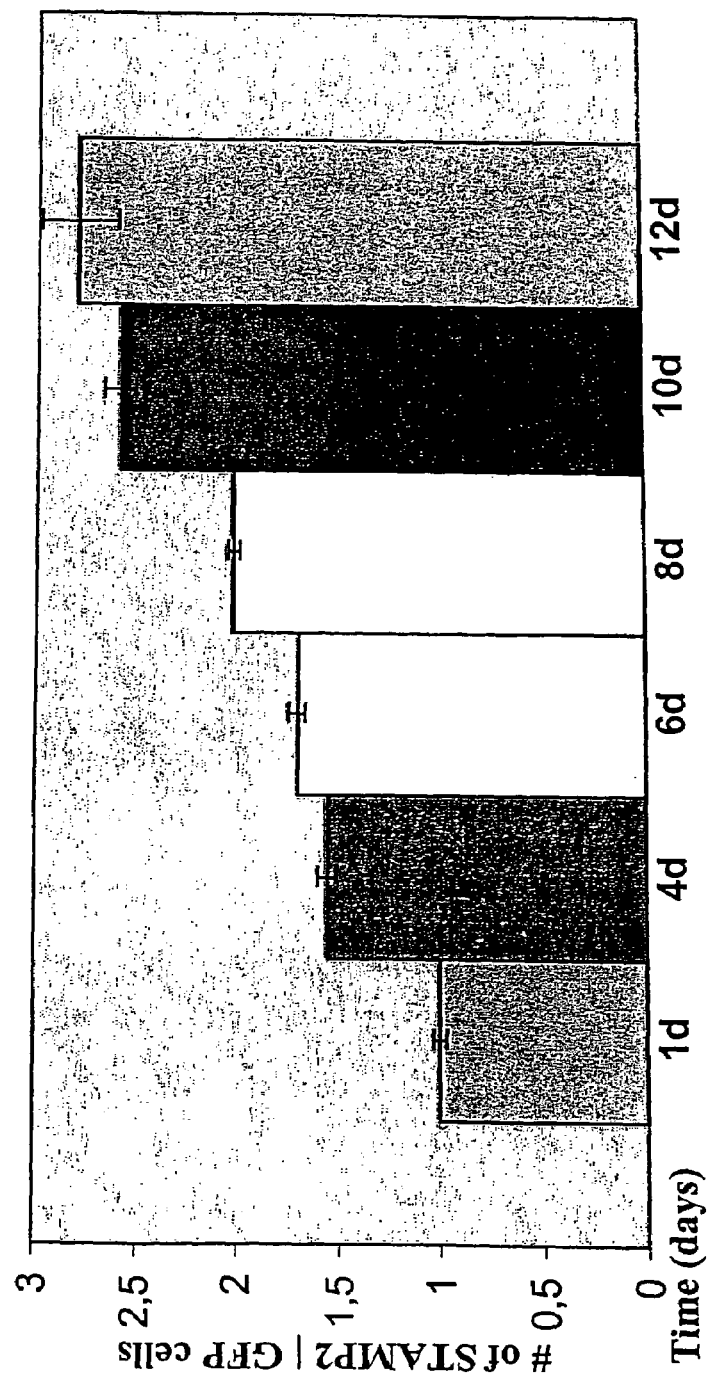

FIG. 28 is a graph showing the ratio of the number of COS7 cells expressing STAMP2 to COS7 cells expressing GFP over time. The results shown are from experiments done in triplicate repeated at least 3 times.

Figure 29:
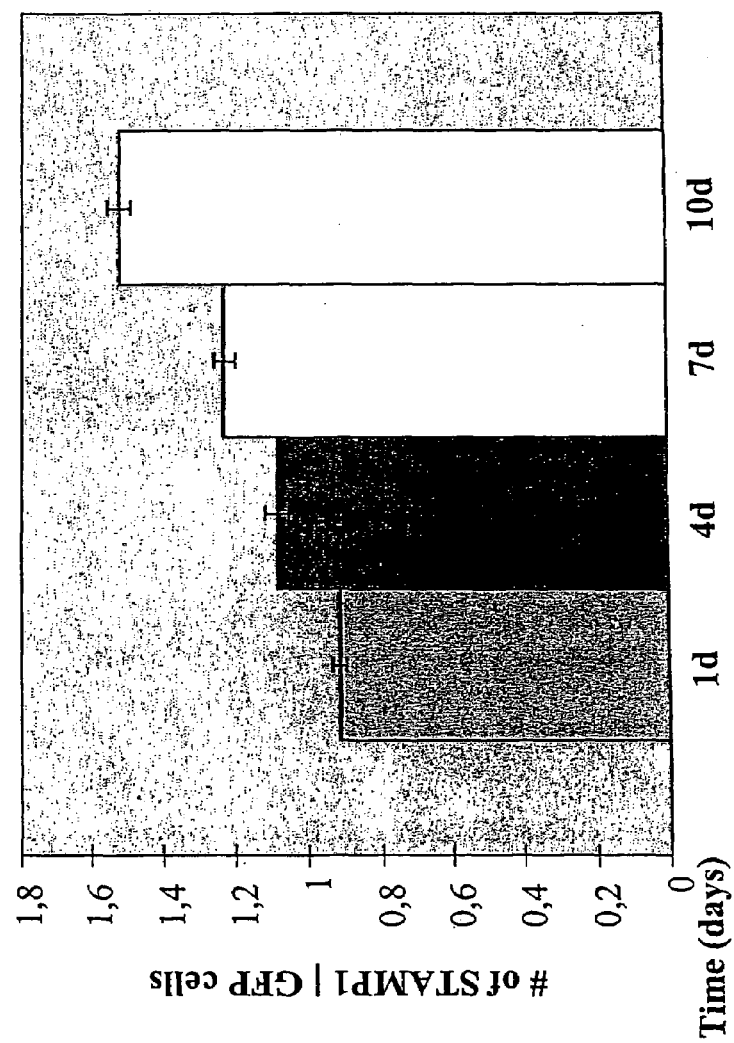

FIG. 29 is a graph showing the ratio of the number of DU145 cells expressing STAMP2 to the number of DU145 cells expressing GFP over time. The results shown are from experiments done in triplicate repeated at least 3 times.

DETAILED DESCRIPTION OF THE INVENTION

The basic biology of the normal prostate and testis, as well as prostate and testicular cancer initiation and progression is still poorly understood. It is therefore necessary to delineate the molecular events that are at the basis of these processes. To achieve this goal, we have identified, cloned, and characterized highly prostate- and testis-enriched genes whose gene products have important roles for both the normal physiology and the pathophysiology of the prostate and the testis. These gene products also have important roles in other disorders, for example, heart, brain, liver, pancreas, kidney, and colon, which are the tissues where variable low expression, and occasionally, very high expression of specific gene products, can be detected by Northern analysis.

The invention provides prostate-specific or testis-specific polypeptides and nucleic acid molecules, and diagnostic and therapeutic methods employing these polypeptides and nucleic acid molecules. The invention also provides methods for identifying compounds that modulate the biological activities of prostate-specific or testis-specific polypeptides and nucleic acid molecules, and therapeutic methods employing these compounds.

One of the prostate-specific or testis-specific polypeptides we have identified, cloned and characterized is STAMP2, a six transmembrane protein that is highly enriched in prostate tissues and cell lines. STAMP2 localizes to the Golgi, endosomes, and plasma membrane suggesting that STAMP2 may play a role in endocytic/secretory trafficking pathways. We have discovered that STAMP2 may play a role in cell proliferation and that STAMP2 is an androgen responsive gene which is specifically upregulated in androgen receptor positive prostate cancer cells.

While the description provided below refers specifically to STAMP2 polypeptides, nucleic acid molecules, and antibodies, it will be understood that the methods and compositions can apply to any of the prostate-specific or testis-specific polypeptides, nucleic acid molecules, and antibodies described herein.

STAMP2 Nucleic Acid Molecules and Polypeptides

We have discovered that STAMP2 is a six transmembrane protein that is androgen-regulated in prostate cancer cells expressing the androgen receptor, and is localized to the plasma membrane, the Golgi, and endosomes. We have also discovered that although STAMP2 shares homology with a distinct mouse protein, TIARP, and a rat protein pHyde, there are regions of STAMP2 that are unique and may be used to specifically target STAMP2 nucleic acids and polypeptides. The invention features methods and compositions that include STAMP2 polypeptides and polynucleotides, and fragments thereof, for example, for the treatment and diagnosis of disorders of the prostate or testis. The STAMP2 polypeptides and polynucleotides, and fragments thereof, can also be used for biochemical characterization of the STAMP2 fragments, substrates in the screening methods described herein, and as immunogens for the production of anti-STAMP2 antigens useful in the methods of the invention.

STAMP2 polypeptides include any polypeptide having a sequence that is at least 80%, preferably at least 86%, most preferably at least 90%, 95%, 96%, 97%, 98%, 99% or 100% identical to the sequence set forth in SEQ ID NO: 34. Fragments of STAMP2, particularly those that encompass regions that are unique to STAMP2 are also included. Preferred STAMP2 fragments include any polypeptide that includes the amino-terminal half of the protein which does not include the six transmembrane domains (i.e., amino acids 1 to 225), the carboxy-terminal half (i.e., amino acids 225 to 459), which includes the six transmembrane domains, amino acids 1-20, amino acids 70-82, amino acids 87-97, amino acids 330-347, amino acids 400-428, and amino acids 445 to 459. Polypeptides of the invention can include only these regions or can include these regions and additional sequences. Such STAMP2-containing polypeptides (e.g., chimeric fusion proteins) can be used, for example, to raise antibodies specific for various regions of STAMP2 polypeptides.

STAMP2 polynucleotides include any polynucleotide having a sequence that is at least 80%, preferably at least 86%, most preferably at least 90% 90%, 95%, 96%, 97%, 98%, 99% or 100% identical to the sequence set forth in SEQ ID NO: 33. Preferred polynucleotides include STAMP2 polynucleotides, or fragments thereof, or any nucleic acids that encode any of the above polypeptide fragments. One example of a preferred nucleic acid sequence includes nucleic acids 107 to 167 or 1306-1360. The STAMP2 polynucleotides, particularly the fragments, can be used, for example, to design antisense nucleobase oligomers or siRNAs for downregulation of STAMP2 gene expression, examples of which are described below. In one example, an antisense nucleobase oligomer to STAMP2 includes a nucleic acid sequence that is complementary to at least 8-10 nucleotides of nucleotides 107 or 167 or 1306 to 1360 of STAMP2. Full-length STAMP2 nucleic acids or fragments thereof can also be used as probes for the detection of STAMP2. Such probes are useful for example in the diagnostic methods described herein.

Synthesis of STAMP2 Proteins, Polypeptides, and Polypeptide Fragments

Those skilled in the art of molecular biology will understand that a wide variety of expression systems can be used to produce recombinant STAMP2 proteins. The precise host cell used is not critical to the invention. The STAMP2 proteins can be produced in a prokaryotic host (e.g., *E. coli*) or in a eukaryotic host (e.g., *S. cerevisiae*, insect cells such as Sf9 cells, or mammalian cells such as COS, NIH 3T3, CHO, or HeLa cells). These cells are commercially available from, for example, the American Type Culture Collection, Rockville, Md. (see also Ausubel et al., *Current Protocols in Molecular Biology*, John Wiley & Sons, New York, N.Y., 1998). The method of transformation and the choice of expression vehicle (e.g., expression vector) will depend on the host system selected. Transformation and transfection methods are described, (e.g., in Ausubel et al., *Current Protocols in Molecular Biology*, John Wiley & Sons, New York, N.Y., 1998, and expression vehicles can be chosen from those provided, e.g. in Pouwels et al., *Cloning Vectors: A Laboratory Manual*, 1985, Supp. 1987).

The characteristics of STAMP2 nucleic acid molecules are analyzed by introducing such genes into various cell types or using in vitro extracellular systems. The function of STAMP2 proteins produced by the STAMP2 nucleic acid molecule in such cells or systems are then examined under different physiological conditions. Also, cell lines can be produced that overexpress the STAMP2 gene product, allowing purification of STAMP2 proteins for biochemical characterization, large-scale production, antibody production, and patient therapy.

The polypeptides of the invention may be produced in vivo or in vitro, and may be chemically and/or enzymatically modified. Such modifications can be made to improve expression, stability, solubility, cellular uptake, or biological activity of the protein in the various expression systems. (See, for instance, Creighton, "Proteins: Structures and Molecular Properties," 2d Ed., W. H. Freeman and Co., N.Y., 1992; "Postranslational Covalent Modification of Proteins," Johnson, ed., Academic Press, New York, 1983; Seifter et al., *Meth. Enzymol.,* 182:626-646, 1990; Rattan et al., *Ann. NY Acad. Sci.,* 663:48-62, 1992). Additionally, the soluble endoglin polypeptide may contain one or more non-classical amino acids. The polypeptides can be isolated from prostate tissue or prostate cancer cells that may or may not be in a hormone dependent state. Alternatively, and especially where larger amounts (i.e., >10 mg) are desirable, recombinant production (e.g., in a bacterial, yeast, insect cell, or mammalian cell system) may advantageously be employed to generate significant quantities of STAMP2 polypeptides.

Recombinant production not only offers a more economical strategy to produce the polypeptides of the invention, but also allows specific modification in the amino acid sequence and composition to tailor particular biochemical, catalytic and physical properties. For example, where increased solubility of STAMP2 is desirable, one or more hydrophobic amino acids may be replaced with hydrophilic amino acids. Alternatively, where reduced or increased biological activity is required, one or more amino acids may be replaced or eliminated. A methionine may also be added to a truncated form to initiate translation.

In still another example, the polypeptides of the invention can be synthesized as fusion proteins including, for example, fusions with enzymatically active partners (e.g., for dye formation or substrate conversion) and fluorescent partners such as GFP, EGFP, and BFP and variants thereof.

With respect to chemical and enzymatic modifications of contemplated polypeptides, many modifications are appropriate, including addition of mono- and bifunctional linkers, coupling with protein- and non-protein macromolecules, and glycosylation. For example, mono- and bifunctional linkers are especially advantageous where polypeptides are immobilized to a solid support, or covalently coupled to a molecule that enhances immunogenicity of contemplated polypeptides (e.g., KLH, or BSA conjugation). Alternatively, the polypeptides may be coupled to antibodies or antibody fragments to allow rapid retrieval of the polypeptide from a mixture of molecules. Further couplings include covalent and non-covalent coupling of polypeptides with molecules that prolong the serum half-life and/or reduce immunogenicity such as cyclodextranes and polyethylene glycols see for example, U.S. Pat. No. 4,179,337).

Diagnostic Methods

Prostate-specific or testis-specific nucleic acid molecules, polypeptides, and antibodies are used in methods to diagnose or monitor a variety of diseases and conditions, including those involving mutations in, or inappropriate expression of, prostate-specific or testis-specific genes. Prostate-specific or testis-specific expression has been documented in a variety of tissues, as discussed above. Thus, detection of abnormalities in prostate-specific or testis-specific genes or their expression is used in methods to diagnose, or to monitor treatment or development of diseases of these tissues. Such methods are described in detail in U.S. Patent Application Publication No. 20030219761, herein incorporated by reference in its entirety. The diagnostic methods of the invention are used, for example, with subjects that have a disorder of the prostate or testis, for example, prostate or testicular cancer, in an effort to determine its etiology, and thus, to facilitate selection of an appropriate course of treatment. The diagnostic methods are also used with subjects that have not yet developed a disorder of the prostate or testis, but who may be at risk of developing such a disease (e.g., a patient with a family history of disorders of the prostate or testis), or with subjects that are at an early stage of developing such a disease. Many disorders of the prostate or testis occur during development, and thus, the diagnostic methods of the invention are also carried out on a fetus or embryo during development. Also, the diagnostic methods of the invention are used in prenatal genetic screening, for example, to identify parents who may be carriers of a mutation in a STAMP2 gene.

STAMP2 nucleic acid molecules, polypeptides, and antibodies are used in methods to diagnose or monitor a variety of diseases and conditions, including those involving mutations in, or inappropriate expression of STAMP2 polypeptides or nucleic acids.

Disorders of the prostate or tesis can be detected using the diagnostic methods of the invention include those characterized by, for example, (i) abnormal (e.g., increased levels or inappropriate localization) expression of STAMP2 polypeptides or nucleic acid molecules, (ii) mutations in a STAMP2 gene that result in the production of such polypeptides, (iii) mutations in a STAMP2 gene or polypeptide that result in production of abnormal amounts of STAMP2 nucleotides or polypeptides, and (iv) alterations in a STAMP2 gene or polypeptide that affect the biological activity or subcellular localization of STAMP2.

Levels of STAMP2 nucleic acid expression in a subject sample are determined by using any of a number of standard techniques that are well known in the art. In one embodiment, a subject having a disorder of the prostate or testis, or a propensity to develop such conditions, will show an increase (e.g., 10%, 20%, 30%, 40%, 50%, 60%, 70%, 80%, 90%, or more) in the level of STAMP2 nucleic acid or a nucleic acid encoding a STAMP2 polypeptide or fragments thereof (collectively referred to as STAMP2 nucleic acids). Preferred fragments include nucleic acids encoding amino acids 1 to 20, amino acids 70 to 82, amino acids 87 to 97, amino acids 330 to 347, amino acids 400 to 428, or amino acids 445 to 459 of STAMP2 (SEQ ID NO: 34), or nucleotides 107-167 or 1306-1360 of SEQ ID NO: 33.

Methods for detecting such alterations in nucleic acid levels are standard in the art and are described in Ausubel et al., supra. Desirably, STAMP2 expression in a biological sample (e.g., a blood, prostate or testis tissue or cell sample, urine or semen) from a patient is monitored by standard northern blot analysis, or by quantitative RT-PCR (see, e.g., Ausubel et al., *Current Protocols in Molecular Biology*, John Wiley & Sons, New York, N.Y., 1998; *PCR Technology: Principles and Applications for DNA Amplification*, H. A. Ehrlich, Ed., Stockton Press, NY; Yap et al. *Nucl. Acids. Res.* 19:4294, 1991). Additional examples include methods such as sequencing, single-strand conformational polymorphism (SSCP) analysis, or restriction fragment length polymorphism (RFLP) analysis of PCR products derived from a patient sample that may be used to detect a mutation in a gene encoding a prostate-specific or a testis-specific polypeptide (e.g., STAMP2); and PCR may be used to measure the level of nucleic acids encoding a prostate-specific or a testis-specific polypeptide (e.g., STAMP2). In another embodiment, nucleic acid probes that are capable of detecting a nucleic acid molecule encoding a polypeptide of the invention, including genomic sequences, or closely related molecules, may be used to hybridize to a STAMP2 nucleic acid sequence from a subject. Preferred nucleic acid probes are specific for STAMP2 nucleic acids or fragments thereof and hybridize to STAMP2 nucleic acid molecules to a greater extent than any other nucleic acid molecule in the sample. Probes that specifically bind to or hybridize to STAMP2 nucleic acid molecules, preferably, have greater than 45% sequence identity, more preferably at least 55-75% sequence identity, still more preferably at least 75-85% sequence identity, yet more preferably at least 85-95% sequence identity, and most preferably 96%, 97%, 98%, 99% or 100% sequence identity to the nucleic acid sequences encoding the amino acid sequences described herein.

The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques can be used for detection, prognosis, diagnosis, or monitoring of disorders of the prostate or testis. Hybridization techniques can also be used to identify mutations indicative of a disorder of the prostate or testis or a propensity to develop such a disorder or may be used to monitor expression levels of a STAMP2 nucleic acid (for example, by Northern analysis, Ausubel et al., supra).

In situ hybridization of RNA can be used to detect the expression of STAMP2 genes. RNA in situ hybridization techniques rely upon the hybridization of a specifically labeled nucleic acid probe to the cellular RNA in individual cells or tissues. Therefore, RNA in situ hybridization is a powerful approach for studying tissue- and temporal-specific gene expression. In this method, oligonucleotides, cloned DNA fragments, or antisense RNA transcripts of cloned DNA fragments corresponding to unique portions of STAMP2 genes are used to detect specific mRNA species, e.g., in the tissues of animals, such as mice, at various developmental stages, or to monitor tumor progression. Other gene expression detection techniques are known to those of skill in the art and can be employed for detection of STAMP2 gene expression.

A mutant STAMP2 gene or a polymorphism can also be identified using these sources as test samples, for example, by mismatch detection techniques. Preferably, the DNA sample is subjected to PCR amplification prior to analysis. A biological sample obtained from a patient can be analyzed for one or more mutations in STAMP2 nucleic acid molecules using a mismatch detection approach. Generally, this approach involves PCR amplification of nucleic acid molecules from a patient sample, followed by identification of a mutation (i.e., a mismatch) by detection of altered hybridization, aberrant electrophoretic gel migration, binding, or cleavage mediated by mismatch binding proteins, or by direct nucleic acid molecule sequencing. Any of these techniques can be used to facilitate detection of mutant prostate-specific or testis-specific genes, and each is well known in the art. Examples of these techniques are described, for example, by Orita et al. (*Proc. Natl. Acad. Sci. USA* 86:2766-2770, 1989) and Sheffield et al. (*Proc. Natl. Acad. Sci. USA* 86:232-236, 1989).

Mismatch detection assays also provide an opportunity to diagnose a STAMP2-mediated predisposition to a disease before the onset of symptoms. For example, a patient heterozygous for a STAMP2 mutation that suppresses normal prostate-specific or testis-specific biological activity or expression may show no clinical symptoms of a STAMP2 gene-related disease, and yet possess a higher than normal probability of developing a prostate or testicular disease. Given such a diagnosis, patients can take precautions to minimize their exposure to adverse environmental factors and to carefully monitor their medical condition (for example, through frequent physical examinations).

Measurement of STAMP2 polypeptide levels in a biological sample is also used in the diagnostic and monitoring methods of the invention. For example, STAMP2 binding agents (e.g., an anti-STAMP2 polyclonal or monoclonal antibody, such as those described herein), can be used in any of the assays described below to measure STAMP2 polypeptide levels. These levels are desirably compared to a normal reference value or sample and an increase (e.g., 10%, 20%, 30%, 40%, 50%, 60%, 70%, 80%, 90%, or more) in STAMP2 polypeptide levels as compared to the normal reference may be indicative of a disorder of the prostate or testis or a predisposition to such a condition.

There are a variety of assay formats known to those of ordinary skill in the art for measuring the level of a STAMP2 polypeptide in a sample, including, without limitation, immunoprecipitation followed by sodium dodecyl sulfate polyacrylamide gel electrophoresis, 2-dimensional gel electrophoresis, competitive and non-competitive assay systems using techniques such as Western blots, immunocytochemistry, immunohistochemistry, immunoassays, e.g., radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunoradiometric assays, fluorescent immunoassays and protein A immunoassays (See also, e.g., Harlow and Lane (1988) *Antibodies: A Laboratory Manual*, Cold Spring Harbor Laboratory). In general, a disorder of the prostate or testis in a subject may be determined by (a) contacting a biological sample obtained from a subject with an agent (e.g., an antibody) that specifically binds STAMP2; (b) detecting in the sample a level of STAMP2 polypeptide that binds to the agent; and (c) comparing the level of STAMP2 polypeptide with a reference value. Reference values may be determined by methods known in the art, such as by establishing ranges of expression that give degrees of confidence in distinguishing a sample indicative of a disorder of the prostate or testis from a normal sample. Desirably, the agent specifically binds a region unique to STAMP2, for example amino acids 1 to 20, amino acids 70 to 82, amino acids 87 to 97, amino acids 330 to 347, amino acids 400 to 428, or amino acids 445 to 459 of STAMP2 (SEQ ID NO: 34), or the nucleic acid sequence encoding these amino acid regions.

The detection process used in the diagnostic methods of the invention may include fluorescence detection, colorimetric detection, luminescence detection, scintigraphy, autoradiography, immunological assays, and formation of a dye. For example, for microscopic analysis of biopsy specimens, luciferase labeled probes are particularly advantageous in conjunction with a luminescence substrate (e.g., luciferin). Luminescence quantification may then be performed utilizing a CCD-camera and image analysis system. Similarly, radioactivity may be detected via autoradiographic or scintigraphic procedures on a tissue section, in a fluid or on a solid support. Where the probe is a natural or synthetic ligand of a STAMP2 polypeptide, the ligand may include molecules with a chemical modification that increases the affinity to the polypeptide and/or induce irreversible binding to the polypeptide. For example, transition state analogs or suicide inhibitors for a particular reaction catalyzed by the polypeptide are especially contemplated. Labeling of antibodies, antibody fragments, small molecules, and binding of the labeled entity is a technique that is well known in the art, and all known methods are generally suitable for use in conjunction with methods contemplated herein. Furthermore, the probe need not be limited to a fluorescein labeled antibody, and alternative probes include antibody fragments (e.g., Fab, Fab', scFab, etc.). General guidance regarding such techniques can be found in, e.g., Bancroft et al., *Theory and Practice of Histological Techniques*, Churchill Livingstone, 1982, and Ausubel et al., supra.

Still further contemplated variations include substitution of one or more atoms or chemical groups in the sequence with a radioactive atom or group. For example, where cDNAs are employed as a hybridization-specific probes, a fluorophor or enzyme (e.g., β-galactosidase for generation of a dye, or luciferase for generation of luminescence) may be coupled to the sequence to identify position and/or quantity of a complementary sequence. Alternatively, where contemplated cDNA molecules are utilized for affinity isolation procedures, the cDNA may be coupled to a molecule that is known to have a high-affinity (i.e., $K_d < 10^{-4}$ $mol^{-1}$) partner, such as biotin, or an oligo-histidyl tag. In another example, one or more phosphate groups may be exchanged for a radioactive phosphate group with a $^{32}P$ or $^{33}P$ isotope to assist in detection and quantification, where the radiolabeled cDNA is employed as a hybridization probe.

The diagnostic assays described above can be carried out using any biological sample (for example, a blood, serum, urine, semen, saliva, prostate or testis tissue or cell sample, or amniotic fluid) in which a STAMP2 polypeptide or nucleic acid molecule is normally expressed. In one example, the measurement of STAMP2 nucleic acids or polypeptides described herein preferably occurs on at least two different occasions and an alteration (e.g., increase) in the levels over time is used as an indicator of a disorder of the prostate or testis, or a propensity to develop such conditions. In another example, the measurement of any of the STAMP2 nucleic acids or polypeptides described herein is compared to a reference. If the reference is a normal reference, an increase is an indicator of a disorder of the prostate or testis, or a propensity to develop such conditions.

In a preferred example, a combined diagnostic method can be employed that includes an evaluation of STAMP2 protein expression (for example, by immunological techniques or the protein truncation test (Hogerrorst et al., *Nature Genetics* 10:208-212, 1995)), and a nucleic acid molecule-based detection technique designed to identify more subtle STAMP2 mutations (for example, point mutations). As described above, a number of mismatch detection assays are available to those skilled in the art, and any preferred technique can be used. Mutations in STAMP2 genes can be detected that either result in loss or gain of STAMP2 polypeptide or nucleic acid molecule expression or biological activity.

STAMP2 polypeptides or nucleic acid molecules can be used to correlate the course of prostate cancer to a marker other than PSA, to monitor the course of an anticancer therapy, or to detect a neoplastic cell in a system. For example, a predetermined level of STAMP2 RNA is correlated with the presence of a neoplastic cell, for example, from a biopsy. The total RNA is extracted from the biopsy specimen, and a real time quantitative RT-PCR employing individual reactions with primer pairs specific to STAMP2 sequences is performed in parallel with a biopsy specimen known to be free of cancer cells. Biopsy specimens are determined to have a cancer cell, where the detected STAMP2 mRNA level is at least 5 times higher than in the control specimen. In still other aspects of contemplated methods, the polypeptide level need not necessarily be limited to at least 5 times more than the control specimen in order to establish that the tissue has a cancer cell. For example, where the concentration of the polypeptide is hormone dependent, amounts between 3 to 8 fold and more may be appropriate. In contrast, where the concentration of cancer cells in the biopsy specimen is relatively low, levels of less than 5-fold, including 1.5 to 4.9-fold and less are contemplated.

In alternative aspects of the inventive subject matter, the method of detecting a neoplastic cell need not be limited to biopsy tissues from prostate or testis tissue, but may employ various alternative tissues, including lymphoma tumor cells, and various solid tumor cells, so long as the STAMP2 nucleic acid or polypeptide is detectable in such tumor cells. Likewise, the system need not be restricted to a subject, but may also include cell and tissue cultures grown in vitro. For example, tumor cell and tissue grown in vitro may advantageously be utilized to investigate drug action on such cells, and STAMP2 polynucleotides and polypeptides may conveniently be employed as a tumor marker. Alternatively, body fluids (e.g., serum, saliva, semen, blood, and urine) that may or may not contain tumor cells are also contemplated a suitable substrate for the method presented herein, so long as they contain a detectable level of STAMP2 nucleic acids or polypeptides.

The methods of detecting STAMP2 nucleotides and polypeptides can also be used to monitor specific treatment regimens in vivo. For example, since STAMP2 is an androgen-regulated gene, androgen withdrawal therapy can be monitored by detection of expression levels of STAMP2 nucleotides and polypeptides. In this example, a sample from a subject known to have a disorder of the prostate or testis, is tested for STAMP2 polynucleotide or polypeptide expression levels. During the course of androgen withdrawal therapy, samples from the subject are taken at specific intervals and monitored for STAMP2 polynucleotide or polypeptide expression levels. Androgen withdrawal therapy should result in a decrease in the levels of STAMP2 polynucleotide or polypeptide expression levels and this decrease can be used to monitor the effectiveness of the androgen withdrawal therapy.

Diagnostic Kits

The invention also provides for a diagnostic test kit. Although the specific example below provides reagents for STAMP2 polypeptides and nucleic acid molecules, it should be noted that the diagnostic test kits of the invention can include reagents for any prostate-specific or testis-specific polypeptide or nucleic acid molecule.

A diagnostic test kit for the detection of STAMP2 polypeptides can include binding agents, such as an antibody, to a STAMP2 polypeptide and components for detecting, and more preferably evaluating, binding between the binding agent and the STAMP2 polypeptide. For detection, either the binding agent or the STAMP2 polypeptide is labeled, and either the binding agent or the STAMP2 polypeptide is substrate-bound, such that STAMP2 polypeptide-binding agent interaction can be established by determining the amount of label attached to the substrate following binding between the binding agent and STAMP2 polypeptide. A conventional ELISA is a common, art-known method for detecting antibody-substrate interaction and can be provided with the kit of the invention. STAMP2 polypeptides can be detected in virtually any bodily fluid including, but not limited to urine, blood, semen, serum, plasma, saliva, amniotic fluid, or cerebrospinal fluid, or a cell or tissue sample from a biopsy.

The invention also provides for a diagnostic test kit that includes a STAMP2 nucleic acid probe or primer that can be used to detect and determine levels of STAMP2 nucleic acids or nucleic acids encoding a STAMP2 polypeptide. A kit that determines an alteration in the level of a STAMP2 polypeptide or STAMP2 nucleic acid relative to a reference, such as the level present in a normal control, is useful as a diagnostic kit in the methods of the invention. Probes or primers useful in the diagnostic test kits can specifically bind to or hybridize to STAMP2 nucleic acid molecules and, preferably, have greater than 45% sequence identity, more preferably at least 55-75% sequence identity, still more preferably at least 75-85% sequence identity, yet more preferably at least 85-95% sequence identity, and most preferably 96%, 97%, 98%, 99% or 100% sequence identity to a STAMP2 nucleic acid sequence, the complementary sequence, or a fragment thereof. Probes can be detectably-labeled, either radioactively or non-radioactively, by methods that are well-known to those skilled in the art. Probes can be 10, 20, 30, 40, 50, 60, 70, 80, 90, or 100, 200, 300, 400, 500, 600, 700, 800, 900, 1000, 1383, 1486 or more nucleotides in length up to the full length of the STAMP2 polynucleotide. Probes can bind within the coding region of the STAMP2 nucleic acid molecule or outside the coding region (e.g., in the introns, or 5' or 3' non coding regions).

A probe or primer can be "detectably-labeled" using methods well known in the art including, without limitation, radioactive labeling (e.g., with an isotope, such as $^{32}P$ or $^{35}S$) and nonradioactive labeling (e.g., with a fluorescent label, such as fluorescein, or by generating a construct containing green fluorescent protein (GFP)).

Desirably, the kit will contain instructions for the use of the kit. In one example, the kit contains instructions for the use of the kit for the diagnosis of a disorder of the prostate or testis, or the propensity to develop such a condition. In yet another example, the kit contains instructions for the use of the kit to monitor therapeutic treatment or dosage regimens.

For either the diagnostic or monitoring applications, an alteration of at least 20%, preferably 30%, more preferably at least 50%, and most preferably at least 60%, 70%, 80%, 90%, or more in the levels of a STAMP2 nucleic acid or polypeptide as compared to a reference sample (e.g., a normal reference for diagnostic applications or a positive reference sample or level from a subject having a known disorder for the monitoring applications) is considered a positive result and is interpreted by the clinician depending on the reference sample and the diagnostic or monitoring methods. Generally, in subjects having a disorder associated with an increase in STAMP2 nucleic acid or polypeptide levels, the desired result after therapy is a decrease in the level of STAMP2 nucleic acid or polypeptide expression.

Therapeutic Methods

The invention includes methods of treating or preventing prostate-specific or testis-specific diseases. Therapies are designed to circumvent or overcome a prostate-specific or testis-specific gene defect, or inadequate or excessive prostate-specific or testis-specific gene expression, and thus modulate and possibly alleviate conditions involving defects in prostate-specific or testis-specific genes or proteins. Such therapies are, preferably, targeted to the affected or potentially affected organs, for example, the prostate or the testis. Reagents that are used to modulate prostate-specific or testis-specific biological activity are described in detail in U.S. Patent Application Publication No. 20030219761. The methods of the present invention can be used to diagnose or treat the disorders described herein in any mammal, for example, humans, domestic pets, or livestock. Where a non-human mammal is treated or diagnosed, the prostate-specific or testis-specific polypeptide, nucleic acid molecule, or antibody employed is preferably specific for that species.

Reagents that are used to modulate STAMP2 expression or biological activity can include, without limitation, full length STAMP2 polypeptides or nucleic acids, which can be used, for example, to replace a mutant STAMP2 protein; mutants or fragments of STAMP2 polypeptides or nucleic acids; STAMP2 cDNA, mRNA, antisense RNA, or STAMP2 directed siRNA; STAMP2 antibodies; and any compound that modulates STAMP2 polypeptide or nucleic acid molecule biological activity, expression, or stability.

Therapeutic Nucleobase Oligomers that Inhibit STAMP2 Expression

Treatment or prevention of diseases resulting from a STAMP2 gene or polypeptide defect is accomplished, for example, by decreasing STAMP2 gene or protein levels or biological activity through the use of STAMP2 antisense nucleobase oligomer, RNAi, or antibodies, or any additional compounds that can reduce the levels of STAMP2.

The present invention also features compositions of nucleobase oligomers and the use of such compositions to downregulate expression of a STAMP2 nucleic acid or polypeptide. In one example, the nucleobase oligomer is an antisense nucleobase oligomer. By binding to the complementary nucleic acid sequence (the sense or coding strand), antisense nucleobase oligomers are able to inhibit protein expression presumably through the enzymatic cleavage of the RNA strand by RNAse H. Antisense-based strategies can be employed to explore STAMP2 gene function and as a basis for therapeutic drug design. These strategies are based on the principle that sequence-specific suppression of gene expression (via transcription or translation) can be achieved by intracellular hybridization between genomic DNA or mRNA and a complementary antisense nucleobase oligomer. The formation of a hybrid RNA duplex interferes with transcription of the target STAMP2-encoding genomic DNA molecule, or processing, transport, translation, or stability of the target STAMP2 mRNA molecule.

Preferably, the antisense nucleobase oligomer is capable of reducing expression of a STAMP2 polypeptide or nucleic acid in a cell that expresses increased levels of that protein. Preferably the decrease in protein expression is at least 10% relative to cells treated with a control nucleobase oligomer, more preferably 25%, and most preferably 50%, 60%, 70%, 80%, 90% or greater. Methods for selecting and preparing antisense nucleobase oligomers are well known in the art. The antisense STAMP2 mRNA can be produced and isolated by any standard technique, but is most readily produced by in vitro transcription using an antisense STAMP2 cDNA under the control of a high efficiency promoter (e.g., the T7 promoter).

Antisense nucleobase oligomers of the invention include any antisense nucleobase oligomer that is complementary to at least a part of the STAMP2 nucleic acid sequence. Examples of preferred antisense nucleobase oligomers of the invention include antisense nucleobase oligomers that are identical to or complementary to at least 8 to 10 consecutive nucleotides of the STAMP2 gene or a nucleic acid encoding a STAMP2 polypeptide. The antisense nucleobase oligomer can be any size, for example 8-30 nucleotides, 40, 60, 85, 120, up to the full-length mRNA or gene, and may be as long as the full-length mRNA or gene. Preferably the antisense nucleobase oligomer is from about 8 to 30 nucleotides in length. An antisense molecule may also include regulatory sequences or at least 8 to 10 consecutive nucleotides of the nucleic acid sequence that encodes the unique regions of STAMP2, for example, amino acids 1 to 20, 70 to 82, 87 to 97, 330 to 347, 400 to 428, or amino acids 445 to 459 of STAMP2 (SEQ ID NO: 34).

Antisense nucleobase oligomers can be delivered by a variety of approaches. For example, antisense nucleobase oligomers or antisense RNA can be directly administered (e.g., to the affected prostate or testis tissue or by intravenous injection) to a subject in a form that allows uptake into cells. Alternatively, viral or plasmid vectors that encode antisense RNA (or antisense RNA fragments) can be introduced into a cell in vivo or ex vivo. Antisense effects can be induced by control (sense) sequences; however, the extent of phenotypic changes are highly variable. Phenotypic effects induced by antisense effects are based on changes in criteria such as protein levels, protein activity measurement, and target mRNA levels. Administration of antisense STAMP2 mRNA to cells can be carried out by any of the methods for direct nucleic acid molecule administration described above.

The present invention also features double stranded RNA STAMP2 nucleobase oligomer compositions and the use of such compositions for RNA interference (RNAi) to inhibit expression of STAMP2. RNA interference (RNAi) is a post-transcriptional gene silencing (PTGS) mechanism in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene.

dsRNAs or siRNAs that are useful in the present invention are complementary to the mRNA sequence of STAMP2 mRNA, or any fragment thereof, and can reduce or inhibit expression of STAMP2. Preferably, the decrease in STAMP2 protein expression is at least 10% relative to untreated cells or cells treated with a control dsRNA or siRNA, more preferably 25%, and most preferably at least 50%, 60%, 70%, 80%, 90% or greater. Preferably, the dsRNA have at least one strand that is substantially identical to or substantially complementary to (e.g., at least 85%, 90%, 95%, 99%, or 100%) at least 8 to 10 consecutive nucleotides of a STAMP2 nucleic acid or a nucleic acid molecule encoding a STAMP2 polypeptide, or a fragment thereof. The length of the dsRNA can vary but is preferably greater than 10 nucleotides in length, and most preferably 15-25 nucleotides in length. The dsRNA can also be longer, e.g., 30, 40, 50 nucleotides in length up to the entire length of the full length STAMP2 gene for the dsRNA. A range of 18-25 nucleotides is the most preferred size for dsRNAs.

Examples of preferred dsRNAs of the invention include dsRNA molecules having at least one strand that is identical to or complementary to at least 18 consecutive nucleotides of the nucleic acid sequence encoding the unique regions of STAMP2, for example, amino acids 1 to 20, 70 to 82, 87 to 97, 330 to 347, 400 to 428, or amino acids 445 to 459 of STAMP2 (SEQ ID NO: 34).

The specific requirements and modifications of dsRNA are described in PCT Publication No. WO01/75164 (incorporated herein by reference). While dsRNA molecules can vary in length, it is most preferable to use siRNA molecules which are 21- to 23-nucleotide dsRNAs with characteristic 2- to 3-nucleotide 3' overhanging ends typically either (2'-deoxy) thymidine or uracil. The siRNAs typically comprise a 3' hydroxyl group. Single stranded siRNA as well as blunt ended forms of dsRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

Alternatively siRNA can be prepared using standard procedures for in vitro transcription of RNA and dsRNA annealing procedures as described in Elbashir et al. (Genes & Dev., 15:188-200, 2001). siRNAs are also obtained as described in Elbashir et al. by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the 21 to 23 nt RNAs.

In the RNAi reaction, both the sense and anti-sense strands of a dsRNA molecule are processed into small RNA fragments or segments ranging in length from 18 to 25 nucleotides, preferably 21 to 23 nucleotides (nt), and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

A variety of methods are available for transfection, or introduction, of dsRNA or oligonucleotides into mammalian cells. For example, there are several commercially available transfection reagents including but not limited to: TransIT-TKO™ (Mirus, Cat. # MIR 2150), Transmessenger™ (Qiagen, Cat. # 301525), and Oligofectamine™ (Invitrogen, Cat. # MIR 12252-011). Protocols for each transfection reagent are available from the manufacturer.

In the present invention, the nucleobase oligomers used include any modification that enhances the stability or function of the nucleic acid in any way. Examples include modifications to the phosphate backbone, the internucleotide linkage, or to the sugar moiety. Examples of modifications that may be used in the nucleobase oligomers of the invention, can be found in U.S. Patent Application Publication Nos. 20030114412, paragraphs [0030] to [0046] and 20030114407, paragraphs [0036] to [0055], and 20030190659, paragraphs [0083] to [0106].

Modes for Delivering Nucleic Acids

For any of the nucleic acid applications described herein, standard methods for administering nucleic acids can be used. For example, to simplify the manipulation and handling of the therapeutic nucleic acids, the STAMP2 nucleic acid is preferably inserted into a cassette where it is operably linked to a promoter. The promoter must be capable of driving expression of the nucleic acid in the desired target host cell. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., Hum. Gene Ther. 4:151-159, 1993) and mouse mammary tumor virus (MMTV) promoters may also be used. Certain proteins can be expressed using their native promoter. Other elements that can enhance expression can also be included (e.g., enhancers or a system that results in high levels of expression such as a tat gene and tar element). The enhancers used can include, without limitation, those that are characterized as tissue- or cell-specific enhancers. Alternatively, if a STAMP2 genomic clone is used as a therapeutic construct (such clones can be identified by hybridization with STAMP2 cDNA, described above), regulation can be mediated by the cognate regulatory sequences, or, if desired, by regulatory sequences derived from a heterologous source, including any of the promoters or regulatory elements described above.

The recombinant vector can be a plasmid vector such as pUC118, pBR322, or other known plasmid vectors, that includes, for example, an E. coli origin of replication (see, Sambrook, et al., Molecular Cloning: A Laboratory Manual, Cold Spring Harbor Laboratory press, 1989). The plasmid vector may also include a selectable marker such as the β lactamase gene for ampicillin resistance, provided that the marker polypeptide does not adversely affect the metabolism of the organism being treated. The cassette can also be bound to a nucleic acid binding moiety in a synthetic delivery system, such as the system disclosed in PCT Publication No. WO95/22618.

The nucleic acid can be introduced into the cells by any means appropriate for the vector employed. Many such methods are well known in the art (Sambrook et al., supra, and Watson et al., "Recombinant DNA", Chapter 12, 2d edition, Scientific American Books, 1992). Recombinant vectors can be transferred by methods such as calcium phosphate precipitation, calcium phosphate/DEAE dextran methods, electroporation, liposome-mediated transfection, gene gun, microinjection, viral capsid-mediated transfer, polybrene-mediated transfer, or protoplast fusion. For a review of the procedures for liposome preparation, targeting and delivery of contents, see Mannino and Gould-Fogerite, (*Bio Techniques,* 6:682-690, 1988), Felgner and Holm, (*Bethesda Res. Lab. Focus,* 11:21, 1989) and Maurer (*Bethesda Res. Lab. Focus,* 11:25, 1989).

Gene therapy can be performed in vivo or ex vivo by transfecting a cell line and then delivering the cells to the subject. Transducing retroviral, adenoviral, and adeno-associated viral vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., *Science* 272: 263-267, 1996; and Miyoshi et al., *Proc. Natl. Acad. Sci, USA* 94:10319-1032, 1997). For example, the full length STAMP2 gene, or a fragment thereof, can be cloned into a retroviral vector and expression can be driven from its endogenous promoter, from the retroviral long terminal repeat, or from a promoter specific for a target cell type of interest. Other viral vectors that can be used include, for example, vaccinia virus, bovine papilloma virus, or a herpes virus, such as Epstein-Barr Virus (also see, for example, the vectors of Miller, *Human Gene Therapy* 15-14, 1990; Friedman, *Science* 244: 1275-1281, 1989; Eglitis et al., *BioTechniques* 6:608-614, 1988; Tolstoshev et al., *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; or Miller et al., *Biotechnology* 7:980-990, 1989). Retroviral and lentiviral vectors are particularly well developed and have been used in clinical settings (Rosenberg et al., *N. Engl. J. Med* 323:370, 1990; Anderson et al., U.S. Pat. No. 5,399,346).

Transfer of the recombinant vector (either plasmid vector or viral vectors) can be accomplished through direct injection into the prostate or testis tissue or more generally via intravenous delivery. Transplantation of normal genes into the affected tissues of a patient can also be accomplished by transferring a normal STAMP2 gene into a cultivatable cell type ex vivo, after which the cell (or its descendants) is injected into a targeted tissue. Another strategy for inhibiting STAMP2 function using gene therapy involves intracellular expression of an anti-STAMP2 antibody or a portion of an anti-STAMP2 antibody. For example, the gene (or gene fragment) encoding a monoclonal antibody that specifically binds to STAMP2 polypeptide and inhibits its biological activity is placed under the transcriptional control of a tissue-specific gene regulatory sequence.

Non-viral approaches can also be employed for the introduction of therapeutic DNA into cells predicted to be subject to diseases involving a STAMP2 disorder. For example, a STAMP2 nucleic acid molecule or an antisense nucleic acid molecule can be introduced into a cell by lipofection (Felgner et al., *Proc. Natl. Acad. Sci. USA* 84:7413, 1987; Ono et al., *Neuroscience Letters* 17:259, 1990; Brigham et al, *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263: 14621, 1988; Wu et al, *Journal of Biological Chemistry* 264: 16985, 1989), or, less preferably, micro-injection under surgical conditions (Wolff et al., *Science* 247:1465, 1990).

Therapeutic Antibodies

Antibodies to prostate-specific or testis-specific proteins are used to detect prostate-specific or testis-specific proteins or to inhibit the biological activities of prostate-specific or testis-specific proteins. For example, a nucleic acid molecule encoding an antibody or portion of an antibody can be expressed within a cell to inhibit prostate-specific or testis-specific function. In addition, the antibodies can be coupled to compounds, such as radionuclides and liposomes for diagnostic or therapeutic uses. Antibodies that inhibit the activity of a prostate-specific or testis-specific polypeptide can also be useful in preventing or slowing the development of a disease caused by inappropriate expression of a wild type or mutant prostate-specific or testis-specific gene. For example, the antibodies of the invention may be utilized to localize and locally quantify disease-specific markers in prostate or testis tissue sections, e.g, in prostate or testicular cancer.

The present invention provides antibodies that bind specifically to a STAMP2 polypeptide. The antibodies are used to neutralize or inhibit the biological activity of STAMP2. Antibodies that inhibit the activity of a STAMP2 polypeptide can also be useful in preventing or slowing the development of a disease caused by inappropriate expression of a wild type or mutant STAMP2 gene. In one example, the antibodies of the invention may be utilized to localize and locally quantify disease-specific markers in prostate or testis tissue sections, e.g, in prostate or testicular cancer. Preferred antibodies of the invention specifically bind to amino acids 1 to 20, 70 to 82, 87 to 97, 330 to 347, 400 to 428, or 445 to 459 of STAMP2 (SEQ ID NO: 34), or a polypeptide comprising any one or more of these fragments.

Methods for the preparation and use of antibodies for therapeutic purposes are described in several patents including U.S. Pat. Nos. 6,054,297; 5,821,337; 6,365,157; and 6,165,464 and are incorporated herein by reference. Antibodies can be polyclonal or monoclonal; monoclonal antibodies are preferred.

Monoclonal antibodies, particularly those derived from rodents including mice, have been used for the treatment of various diseases; however, there are limitations to their use including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood,* 62:988-995 1983; Schroff et al., *Cancer Res.,* 45:879-885, 1985).

The art has attempted to overcome this problem by constructing "chimeric" antibodies in which an animal antigen-binding variable domain is coupled to a human constant domain (U.S. Pat. No. 4,816,567; Morrison et al., *Proc. Natl. Acad. Sci. USA,* 81:6851-6855, 1984; Boulianne et al., *Nature,* 312:643-646, 1984; Neuberger et al., *Nature,* 314: 268-270, 1985). The production and use of such chimeric antibodies are described below.

A cocktail of the monoclonal antibodies of the present invention can be used as an effective treatment for disorders of the prostate or testis. The cocktail may include as few as two, three, or four different antibodies or as many as six, eight, or ten different antibodies. In addition, the antibodies of the present invention can be combined with anti-cancer therapies that are known in the art (e.g., chemotherapy, radiotherapy).

Monoclonal antibodies that specifically bind to STAMP2, or fragments thereof, may be produced by methods known in the art. These methods include the immunological method described by Kohler and Milstein (*Nature*, 256: 495-497, 1975) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (Science, 246, 1275-1281, 1989). Additional methods are described in detail in PCT Publication No. WO 2005/114216.

Preparation of Immunogens

STAMP2 polypeptides, such as the STAMP2 sequence set forth in SEQ ID NO: 34 or fragments thereof may be used alone as an immunogen, or may be attached to a carrier protein or to other objects, such as sepharose beads. Preferred fragments are at least 80%, more preferably 85%, and most preferably 90%, 95%, 96%, 97%, 98%, 99%, or 100% identical to the sequence of amino acids 1 to 20, 70 to 82, 87 to 97, 330 to 347, 400 to 428, or 445 to 459 of STAMP2. STAMP2 polypeptides may be purified from cells known to express the endogenous protein such as prostate cells (e.g., LNCaP cells). Additionally, nucleic acid molecules that encode any of the polypeptides of the invention, or portions thereof, can be inserted into known vectors for expression in host cells using standard recombinant DNA techniques. Suitable host cells for protein expression include baculovirus cells (e.g., Sf9 cells), bacterial cells (e.g., *E. coli*), and mammalian cells (e.g., NIH3T3 cells).

In addition, peptides can be synthesized and used as immunogens. The methods for making antibody to peptides are well known in the art and generally require coupling the peptide to a suitable carrier molecule, such as serum albumin. Peptides can be any length, preferably 10 amino acids or greater, more preferably 25 amino acids or greater, and most preferably 40, 50, 60, 70, 80, or 100 amino acids or greater. The peptides can be commercially obtained or made using techniques well known in the art, such as, for example, the Merrifield solid-phase method (*Science,* 232:341-347, 1985). The procedure may use commercially available synthesizers such as a Biosearth 9500 automated peptide machine, with cleavage of the blocked amino acids being achieved with hydrogen fluoride, and the peptides purified by preparative HPLC using a Waters Delta Prep 3000 instrument, on a 15-20 μm Vydac C4 PrepPAK column.

Functional Equivalents of Antibodies

The invention also includes functional equivalents of the antibodies described in this specification. Functional equivalents include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies as well as fragments thereof. Methods of producing such functional equivalents are disclosed, for example, in PCT Publication No. WO93/21319; European Patent Application No. 239, 400; PCT Publication No. WO89/09622; European Patent Application No. 338,745; European Patent Application No. 332424; and U.S. Pat. No. 4,816,567; each of which is herein incorporated by reference. Methods for preparing functional equivalents of antibodies of the invention are described in detail in PCT Publication No. WO 2005/114216, herein incorporated by reference.

Antibody Screening and Selection

Monoclonal antibodies are isolated and purified using standard art-known methods. For example, antibodies can be screened using standard art-known methods such as ELISA or western blot analysis.

Therapeutic Uses of Antibodies

When used in vivo for the treatment or prevention of a disorder of the prostate or testis, the antibodies of the subject invention are administered to the subject in therapeutically effective amounts. Preferably, the antibodies are administered parenterally or intravenously by continuous infusion. The dose and dosage regimen depends upon the severity of the disease, and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies typically are formulated in such vehicles at concentrations of about 1 mg/ml to 10 mg/ml.

Combination Therapies

Optionally, a therapeutic of the invention may be administered in combination with any other standard anti-cancer therapy; such methods are known to the skilled artisan and include radiation therapy, chemotherapy, anti-cancer antibiotics, steroid hormones, or hormone antagonists, and therapeutic antibodies (e.g., Herceptin).

Therapeutic Formulations and Modes of Administration

The therapeutic compounds of the invention can be formulated and administered in a variety of ways, e.g., those routes known for specific indications, including, but not limited to, topically, orally, subcutaneously, intravenously, intracerebrally, intranasally, transdermally, intraperitoneally, intramuscularly, intrapulmonary, vaginally, rectally, intraarterially, intralesionally, parenterally, intraventricularly in the brain, or intraocularly. The therapeutic compound can be in the form of a pill, tablet, capsule, liquid, or sustained release tablet for oral administration; or a liquid for intravenous, subcutaneous or administration; or a polymer or other sustained release vehicle for local administration.

The STAMP2 polypeptide can be delivered systemically to the subject or directly to the prostate or testis cells, e.g., to a tumor or a tumor bed following surgical excision of the tumor. The dosage required depends on the choice of the route of administration; the nature of the formulation; the nature of the subject's illness; the subject's size, weight, surface area, and age; other drugs being administered; and the judgment of the attending physician.

Wide variations in the needed dosage are to be expected in view of the variety of polypeptides, nucleic acids, antibodies, compounds, and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 6-, 8-, 10-, 20-, 50-,100-, 150-, or more). Encapsulation of the polypeptide in a suitable delivery vehicle (e.g., polymeric microparticles or implantable devices) may increase the efficiency of delivery, particularly for oral delivery.

In subjects where a defect or mutation is detected in the STAMP2 gene or polypeptide, for example using the diagnostic methods described herein, treatment or prevention of disorders of the prostate or testis can be accomplished by replacing a mutant STAMP2 gene with a normal STAMP2 gene, modulating the biological activity of a mutant STAMP2 protein, or altering the levels of a mutant STAMP2 protein. It is also possible to correct a STAMP2 gene defect by modifying the physiological pathway (e.g., an intracellular trafficking or secretory pathway or cell proliferation pathway) in which the STAMP2 protein participates.

To replace a mutant or defective protein with normal protein, or to add protein to cells that do not express sufficient or normal STAMP2 protein, it may be necessary to obtain large amounts of pure STAMP2 protein from cultured cell systems in which the protein is expressed (see below). Delivery of the protein to the affected tissue can then be accomplished using appropriate packaging or administrating systems. For the therapeutic approaches that involve administration of recombinant STAMP2 polypeptide, STAMP2 can be administered either directly to the site of a potential or actual disease-affected tissue (for example, by injection) or systemically (for example, by any conventional recombinant protein administration technique). The dosage of STAMP2 depends on a number of factors, including the size and health of the individual patient, but, generally, between 0.001 mg/kg and 10 mg/kg, inclusive, are administered per day to an adult in any pharmaceutically acceptable formulation.

Methods that are well known in the art for making formulations are found, for example, in Remington's Pharmaceutical Sciences, (20$^{th}$ edition), ed. A. Gennaro, 2000, Lippincott, Williams & Wilkins, Philadelphia, Pa. Formulations for parenteral administration can, for example, contain excipients; sterile water; or saline; polyalkylene glycols, such as polyethylene glycol; oils of vegetable origin; or hydrogenated napthalenes. Sustained-release, biocompatible, biodegradable lactide polymer, lactide/glycolide copolymer, or polyoxyethylene-polyoxypropylene copolymers can be used to control the release of the compounds. Other potentially useful parenteral delivery systems for STAMP2 modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate, and deoxycholate, or can be oily solutions for administration in the form of nasal drops, or as a gel.

Alternatively, a polynucleotide containing a nucleic acid sequence encoding a soluble endoglin polypeptide can be delivered to the appropriate cells in the subject. Expression of the coding sequence can be directed to any cell in the body of the subject. In certain embodiments, expression of the coding sequence can be directed to the tumor or metastases themselves. This can be achieved by, for example, the use of polymeric, biodegradable microparticle or microcapsule delivery devices known in the art. Nucleic acid molecules encoding wild type STAMP2 proteins can be delivered to cells that lack sufficient, normal STAMP2 expression or biological activity (e.g., cells carrying mutations in STAMP2 genes). The nucleic acid molecules must be delivered to those cells in a form in which they can be taken up by the cells and so that levels of normal STAMP2 polypeptide, sufficient to provide effective STAMP2 function, can be produced. Alternatively, for some STAMP2 mutations, it may be possible to slow the progression of the resulting disease or to modulate STAMP2 activity by introducing another copy of a homologous gene bearing a second mutation in that gene, to alter the mutation, or to use another gene to block any negative effect.

For any of the above therapeutic methods, the therapies described herein can be administered before, during, or after the onset of the disease phenotype. In addition, compounds shown to modulate STAMP2 polypeptide or nucleic acid molecule expression or biological activity are administered to patients diagnosed with potential or actual diseases by any standard dosage and route of administration. In one example where a mutation in STAMP2 is detected prior to onset of disease, and known to be associated with disorders of the prostate or testis, gene therapy using a STAMP2 mRNA expression construct is undertaken to reverse or prevent the gene defect prior to the development of the full course of the disease.

The therapeutic methods of the invention are, in some cases, targeted to prenatal treatment. For example, a fetus found to have a STAMP2 mutation is administered a gene therapy vector including a normal STAMP2 gene, or administered a normal STAMP2 protein. Such treatment may be required only for a short period of time, or may, in some form, be required throughout such a patient's lifetime. Any continued need for treatment, however, is determined using, for example, the diagnostic methods described above. Also as discussed above, STAMP2 polypeptide or nucleic acid molecule abnormalities may be associated with diseases in adults, and thus, adults are subject to the therapeutic methods of the invention as well.

Additionally, STAMP2 polypeptides may be used to stimulate an immune system to assist in generating immunity against, for example, prostate cancer cells.

A STAMP2 polypeptide, nucleic acid molecule, or modulator is administered within a pharmaceutically-acceptable diluent, carrier, or excipient, in unit dosage form to patients or experimental animals. Also, conventional pharmaceutical practice is employed to provide suitable formulations or compositions in which to administer neutralizing STAMP2 antibodies or STAMP2-inhibiting compounds (e.g., a STAMP2 antisense molecule, STAMP2 dsRNA molecule, or a STAMP2 dominant negative mutant) to patients suffering from a STAMP2 disease, such as prostate cancer, testicular cancer, benign hyperplasia of the prostate, or developmental defects of the prostate or testis. Administration can begin before or after the patient is symptomatic.

Screening Assays

Isolation of prostate-specific or testis-specific cDNAs (as described herein) also facilitates the identification of molecules that increase or decrease prostate-specific or testis-specific polypeptide or nucleic acid molecule biological activity. Similarly, molecules whose activity is modulated by prostate-specific or testis-specific polypeptide or nucleic acid molecule biological activity can be identified. Such methods are described in U.S. Patent Application Publication No. 20030219761 and PCT Application Publication No. WO 2005/114216, herein incorporated by reference.

As discussed above, the expression of a STAMP2 nucleic acid or polypeptide is increased in a subject having a disorder of the prostate or the testis. Based on these discoveries, compositions of the invention are useful for the high-throughput low-cost screening of candidate compounds to identify those that modulate the expression of a STAMP2 nucleic acid or polypeptide whose expression is altered in a subject having a disorder of the prostate or the testis.

Any number of methods are available for carrying out screening assays to identify new candidate compounds that alter the expression of a STAMP2 nucleic acid or polypeptide. Examples of such screening assays and the test compounds and extracts are described in detail in U.S. Patent Application Publication No. 20030219761 and PCT Application Publication No. WO 2005/114216, herein incorporated by reference.

Prostate-Specific or Testis-Specific Fragments

Polypeptide fragments that include various portions of prostate-specific or testis-specific proteins are useful in identifying the domains important for their biological activities, such as protein-protein interactions and transcription. Methods for generating such fragments are well known in the art (see, for example, Ausubel et al., supra), using the nucleotide sequences provided herein. For example, a prostate-specific or testis-specific protein fragment can be generated by PCR amplifying a desired prostate-specific or testis-specific nucleic acid molecule fragment using oligonucleotide primers designed based upon the prostate-specific or testis-specific nucleic acid sequences. Preferably, the oligonucleotide primers include unique restriction enzyme sites that facilitate insertion of the amplified fragment into the cloning site of an expression vector (e.g., a mammalian expression vector, see above). This vector can then be introduced into a cell (e.g., a mammalian cell; see above) by artifice, using any of the various techniques known in the art such as those described herein, resulting in the production of a prostate-specific or testis-specific polypeptide fragment in the cell containing the expression vector.

Prostate-specific or testis-specific polypeptide fragments (e.g., chimeric fusion proteins) can also be used to raise antibodies specific for various regions of prostate-specific or testis-specific polypeptides. Preferred prostate-specific or testis-specific fragments include, without limitation, any of the STAMP2 fragments described herein, or fragments including the N-terminal domain of STMP1 (amino acids 1-200), the P5CR domain, and fragments thereof.

Synthesis of prostate-specific or testis-specific proteins, polypeptides, and polypeptide fragments are described in detail in U.S. Patent Application Publication No. 20030219761 and PCT Application Publication No. WO 2005/114216, herein incorporated by reference.

Identification of Additional Prostate-Specific or Testis-Specific Genes

Standard techniques, such as the polymerase chain reaction (PCR) and DNA hybridization, as well as the SSH and other techniques described herein, can be used to clone prostate-specific or testis-specific homologues in other species and other prostate-specific or testis-specific genes in humans. Prostate-specific or testis-specific genes and homologues can be readily identified using low-stringency DNA hybridization or low-stringency PCR with human prostate-specific or testis-specific probes or primers. Degenerate primers encoding human prostate-specific or testis-specific or human prostate-specific or testis-specific amino acid sequences can be used to clone additional prostate-specific or testis-specific genes and homologues by RT-PCR.

Additional prostate-specific or testis-specific genes include genes expressed during various growth and developmental phases of the diseased prostate or testis, e.g., those involved in prostate cancer, benign prostatic hyperplasia, or testicular cancer, and genes expressed as a result of a drug regimen.

Construction of Transgenic Animals and Knockout Animals

Characterization of prostate-specific or testis-specific genes provides information that allows prostate-specific or testis-specific knockout animal models to be developed by homologous recombination. Preferably, a prostate-specific or testis-specific knockout animal is a mammal, most preferably a mouse. Similarly, animal models of prostate-specific or testis-specific overproduction can be generated by integrating one or more prostate-specific or testis-specific sequences into the genome of an animal, according to standard transgenic techniques. Moreover, the effect of prostate-specific or testis-specific gene mutations (e.g., dominant gene mutations) can be studied using transgenic mice carrying mutated prostate-specific or testis-specific transgenes or by introducing such mutations into the endogenous prostate-specific or testis-specific gene, using standard homologous recombination techniques.

A replacement-type targeting vector, which can be used to create a knockout model, can be constructed using an isogenic genomic clone, for example, from a mouse strain such as 129/Sv (Stratagene Inc., LaJolla, Calif.). The targeting vector can be introduced into a suitably-derived line of embryonic stem (ES) cells by electroporation to generate ES cell lines that carry a profoundly truncated form of a prostate-specific or testis-specific gene. To generate chimeric founder mice, the targeted cell lines are injected into a mouse blastula-stage embryo. Heterozygous offspring can be interbred to homozygosity. Prostate-specific or testis-specific knockout mice (e.g., STAMP2 knock out mice) provide a tool for studying the role of prostate-specific or testis-specific polypeptides and nucleic acid molecules in embryonic development and in disease. Moreover, such mice provide the means, in vivo, for testing therapeutic compounds for amelioration of diseases or conditions involving a prostate-specific or testis-specific polypeptide or nucleic acid molecule-dependent or prostate-specific or testis-specific polypeptide or nucleic acid molecule-affected pathway.

Animal Models

The prostate-specific and testis-specific polypeptides, antisense compounds, etc., of the invention can also be used in conjunction with animal models of prostate or testis disorders, to test the therapeutic, diagnostic, and screening methods of the invention. An exemplary prostate cancer model in transgenic mice is called TRAMP, in which the SV40 large T antigen is targeted to the prostate (Greenberg et al., *Proc. Natl. Acad. Sci* 92, 3439-3443, 1995). Another test system is the CWR22 (androgen-dependent) and CWR22R (androgen-independent) xenografts, as known in the art and as described herein. Growth, PSA secretion, metastasis, etc. of these xenografts could be monitored in the presence and absence of the prostate-specific or testis-specific polypeptides, nucleic acid molecules, and other compounds of the invention. Other animal models, for example, animal models of other forms of cancer, or immunocompromised animals, e.g., nude mice, may also be used.

The following Examples will assist those skilled in the art to better understand the invention and its principles and advantages. It is intended that these Examples be illustrative of the invention and not limit the scope thereof.

EXAMPLE 1

Suppression Subtraction of Prostate- and Testes-Specific Genes and Subcloning Into pZero cDNA derived from poly(A)+ RNA of 10 different normal human tissues were subtracted against normal human prostate cDNA using suppression subtraction hybridization (SSH) (Diatchenko, L. et al., *Proc. Natl. Acad. Sci. USA* 93, 6025-6030, 1996) and the resulting cDNA fragments were cloned into an appropriate vector. SSH was performed as described (Clontech PCR-Select Cloning Kit) using prostate poly(A)+ RNA against a pool of poly(A)+ RNA obtained from ten normal human tissues (heart, brain, placenta, lung, liver, skeletal muscle, kidney, spleen, thymus, and ovary). Upon secondary PCR amplification (12 cycles), the reactions were extracted with phenol/chloroform, the DNA with ethanol, and the pellets washed once with 70% ethanol. After drying, the DNA pellet was dissolved in $0.2\times$ TE or MQ dH$_2$O and cut with RsaI in a 20 µl reaction for 2 hrs at 37° C. to excise adaptors. After digestion, the reactions were run on a 1.5% agarose gel, with molecular size markers on one side, at 5 V/cm, 40 min. Care was taken not to expose the gel to short wavelength UV light. The adapter bands were excised, and the gel was run at 5 V/cm for 15 min in a reversed electric field to concentrate the cDNA bands.

The gel was visualized (long wave UV light) and the amplified cDNAs, ranging in size between 100 bp-1 kB, were excised. The DNA was purified using the QAIEX gel DNA purification kit. The purified DNA was cloned into EcoRV-cut, dephosphorylated pZERO (Invitrogen). Ligation reactions were performed in 10 µl final volume in the presence of 5% PEG, 1× T4 Ligase buffer at 37° C. overnight and a 1/5 dilution of 1 µl of the ligation mix (PSL) was transformed into DH10B electrocompetent cells (>10$^{10}$ efficiency) or equivalent. Colonies were picked and the presence of cDNA inserts was confirmed. To that end, PCR was performed with T7 and SP6 primers directly from the colonies. 10% of the reactions were run on a 1.5% agarose gel to visualize amplified products. The colonies with inserts were grown and glycerol stocks (15%) were prepared and stored at −80° C.

EXAMPLE 2

Reverse Northern Blot and Sequence Analyses

To clone androgen-responsive genes represented in the PSL, the reverse northern technique was used (Hedrick, S. M. et al., *Nature* 308, 149-153, 1984; Sakaguchi, N. et al., *EMBO J* 5: 2139-2147, 1986). In this procedure, RNA made from two populations of cells that are to be compared is used to make cDNA probes that are then hybridized to two identical arrays of clones. To that end, PSL clones were amplified by PCR and spotted on nylon filters in 96-well format to generate two identical blots for each set of 92 clones (the remaining four spots were used for positive and negative controls). To make the probes, the androgen-responsive prostate cancer cell line LNCaP was used (Horoszewicz, J. S. et al., *Cancer Res.* 43, 1809-1818, 1983) and was either left untreated (the (−) probe) or treated with the synthetic androgen R1881 for 24 hours (the (+) probe). Poly(A)+ RNA was isolated from these cells and was used to make the $^{32}$P-labeled probes. After hybridization with the (−) and (+) probes, clones that showed differential hybridization were selected for further analysis, i.e., confirmation by a secondary reverse northern blot, and northern blotting.

Figure 1:
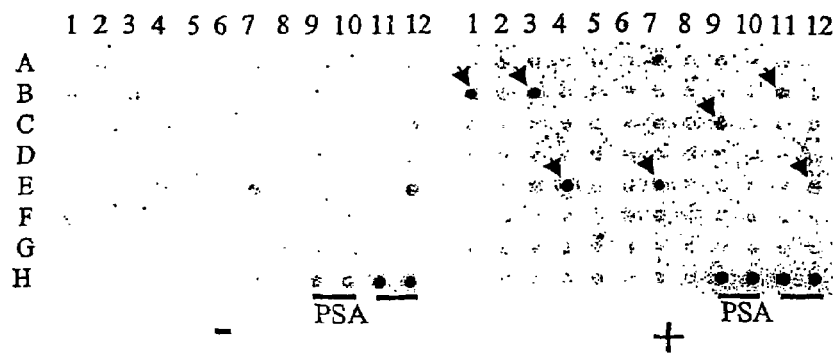
FIG. 1 shows an exemplary reverse northern analysis of several clones from a prostate specific cDNA library.

Reverse northern screening on the cDNA clones was done essentially as described previously (Hedrick, S. M. et al., supra; Sakaguchi, N. et al., supra) with some modifications. DNA (approximately 400 ng) from PCR amplification in step 6 was diluted in 200 µl of 0.4M NaOH, 10 mM EDTA and mixed well by pipetting. After incubation at 95° C. for 5-10 minutes, the tubes were chilled on ice. Denatured DNA was blotted on two separate pieces of Zeta Probe GT+ membrane (Bio-Rad) using a dot-blot apparatus (Bio-Rad). Positive (Prostate specific antigen (PSA) cDNA) and negative (glyceraldehyde 3-phosphate dehydrogenase (G3PDH) cDNA) controls were included on each blot (bottom right) in duplicate. The membranes were rinsed with 2×SSC, air dried, and then baked at 80° C. for 30 minutes. An exemplary reverse northern analysis is shown in FIG. 1. Note that there was a substantial increase in PSA hybridization in the (+) blot (probe prepared from cells that have been stimulated by androgens) compared with the (−) blot (probe prepared from unstimulated cells), whereas there was no significant change in hybridization of G3PDH between the two blots. Arrowheads indicate the positive clones identified in this experiment.

Figure 2:
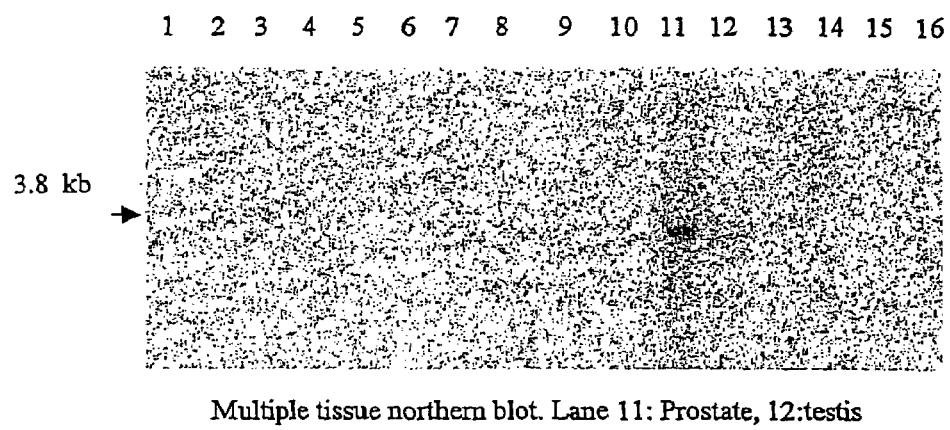
FIG. 2 shows an exemplary multiple tissue northern blot.

To verify the tissue-specific nature of the isolated sequences, positive clones were tested in a standard northern blot against RNA preparations of multiple non-prostate tissue samples. FIG. 2 shows a multiple tissue northern blot using NKX3A as a probe, to show an exemplary tissue expression pattern seen in the positive clones. Lanes 1-10, and 12-16 are RNA preparations from non-prostate tissues, lane 11 is a RNA preparation from prostate, lane 12 is a RNA preparation from testis.

Twelve clones with no significant homology to known sequences (by BLAST analysis) were isolated from prostate tissue and LNCaP cells. SEQ ID NOs: 1-9 were identified as androgen-responsive differentially-expressed genes in the prostate, while SEQ ID NOs: 10-12 were identified as androgen-responsive differentially-expressed genes in LNCaP cells.

EXAMPLE 3

Isolation and Characterization of The STMP1 Gene and mRNA

A normal prostate cDNA library was screened by 5'- and 3'-RACE analysis, and resulted in the full-length cDNA for L74. Since computer-aided secondary structure prediction of the deduced amino acid sequence of L74 suggested the presence of a six-transmembrane domain in its C-terminal half, L74 was renamed Six-Transmembrane Protein of Prostate 1 (STMP1).

Figure 4A:
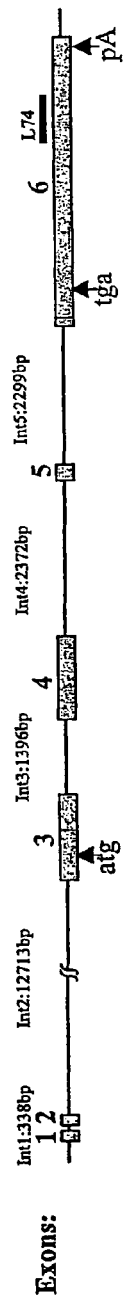
FIG. 4A is a schematic diagram showing the STMP1 gene structure.

When the full-length STMP1 cDNA was used in BLAST analysis, it was found to match a BAC clone (GenBank accession # AC002064) except for a 313 bp repetitive unit in the 3' UTR region, thereby identifying it as the STMP1 gene and localizing it to Chr7q21. The repetitive region is likely to be a cloning or sequencing artifact of the BAC clone. Computational exon/intron junction analysis and alignment of the full-length cDNA sequence with the BAC clone revealed that STMP1 gene is composed of six exons and five introns (FIG. 4A). The transcription start site, the location and size of the exons and introns, and the location of the partial cDNA clone L74 (black box) are indicated. The start (atg) and stop codons (tga), as well as the putative polyadenylation signal (pA) are also indicated. The first two exons are short, non-coding exons of 83 and 61 bp, whereas exons 3-6 encode the open reading frame (ORF) and are 525, 528, 165, and 3281 bp long, respectively (FIG. 4C). The STMP1 gene spans around 26 kb, which is in part due to the extremely large size of intron 2 (12713 bp). There are three different predicted promoters within 4 kb upstream of the STMP1 initiation codon, none of which has any significant TATA or CAAT box consensus sequences, suggesting that STMP1 is transcribed from a TATA-less promoter.

The STMP1 cDNA (GenBank accession # AY008445) has a predicted 5' untranslated region (5'UTR) of approximately 1 kb (deduced by RACE analysis) and an unusually long 3'UTR of approximately 4 kb that comprises ~77% of the total cDNA sequence. The ORF starts within the $3^{rd}$ exon and is predicted to encode a 490 amino-acid protein (FIG. 4B). A search for protein motifs identified six predicted transmembrane domains in the C-terminal half of STMP1 starting at F209 (FIGS. 4B and 4E). Only the cDNA sequence surrounding the ORF is indicated. The exon-intron junctions are indicated and the location of the predicted transmembrane domains are highlighted (TM 1-6) (FIG. 4B). The stop codon is indicated with an asterisk. STMP1 has two alternatively spliced forms, shown in FIGS. 4F-4K, which lead to two predicted isoforms of the protein.

EXAMPLE 4

STMP1 Belongs to a New Subfamily of Six-Transmembrane Domain Proteins

BLAST analysis of GenBank with the predicted STMP1 amino acid sequence identified two independent ESTs and STEAP, a recently discovered cell membrane protein enriched in prostate for expression. An alignment of these sequences, obtained by Clustal and GenDoc programs, is shown in FIG. 5. Completely conserved residues are shaded in black; residues that are conserved in two or three of the sequences are shaded light and dark gray, respectively. This alignment suggested that while the EST BAA91839 cDNA may be close to full-length, BAB15559 cDNA may represent a partial sequence.

The sequences of two proteins related to STMP1 were determined (FIGS. 18 and 4M, STMP2 and STMP3, respectively). The STMP2 and STMP3 sequences contain the EST sequences. The GFP-fusion of STMP2 gives similar localization as STMP1. Both STMP2 and STMP3 are more widely distributed and have higher levels in some tissues other than the prostate. For example, STMP2 has the highest expression in the placenta and the lung, and is also highly expressed in the heart, liver, prostate, and testis, while STMP3 has the highest expression in the liver, and is also highly expressed in the heart, placenta, lung, kidney, pancreas, prostate, testis, small intestine, and colon.

The sequence similarity between STMP1 and STEAP is limited and not significant before residue 210 of STMP1 where the predicted six-transmembrane coding domain starts. This suggests that the N-terminal region is structurally and functionally related among STMP proteins, forming a six-transmembrane protein subfamily that is distinct from STEAP.

EXAMPLE 5

STMP1 Expression is Highly Enriched in Prostate

Figure 6:
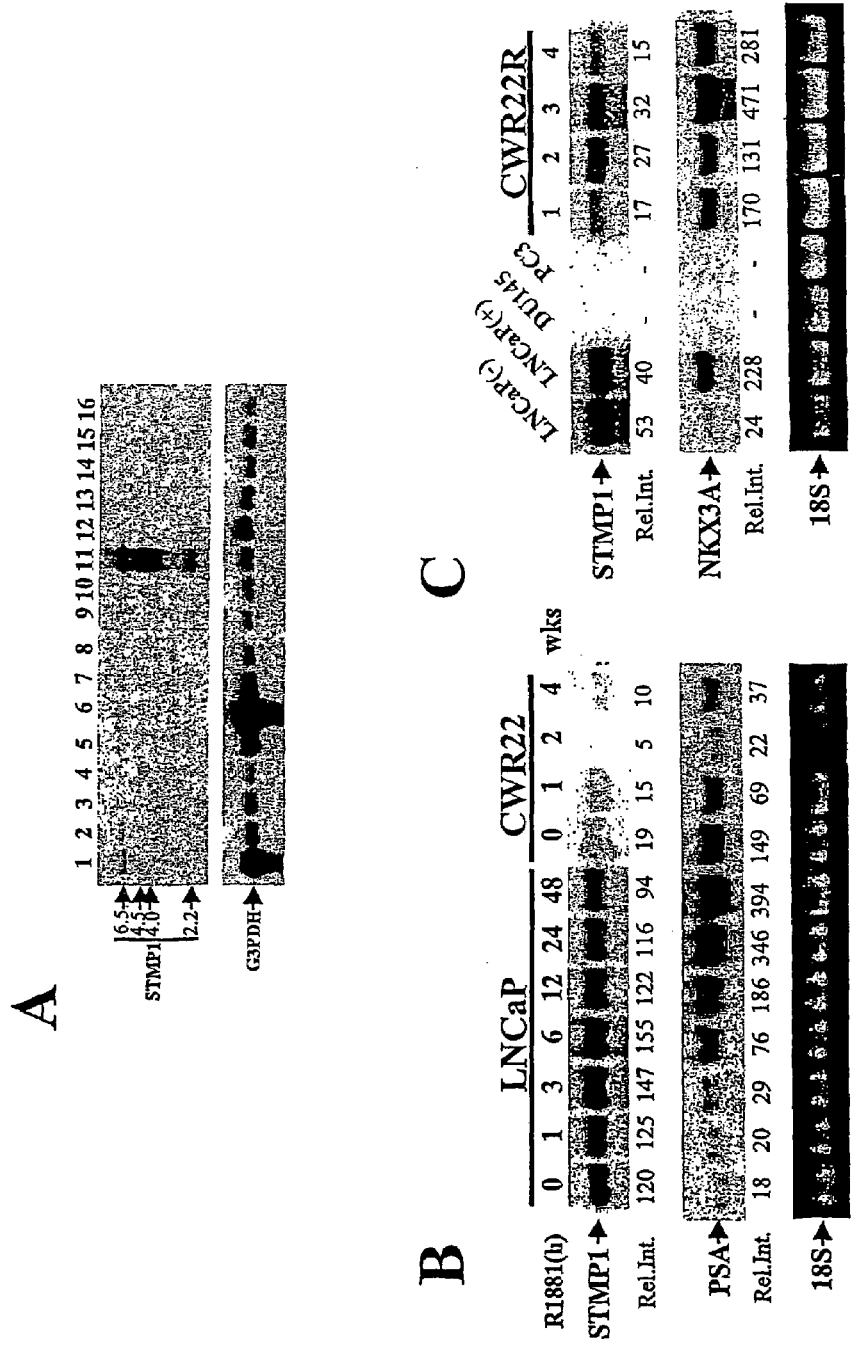
FIG. 6A shows a multiple tissue Northern blot probed with STMP1 or G3PDH cDNA.
FIG. 6B is a Northern blot probed with STMP1 and PSA in the androgen-responsive prostate cancer cell line LNCaP and in the CWR22 human prostate cancer xenograft model.
FIG. 6C is a Northern blot probed with STMP1 and NKX3A in LNCaP, PC-3, and DU-145 cell lines and in the CWR22R human prostate cancer xenograft model.

The expression profile of STMP1 was then determined in various human tissues by Northern analysis, in which a multiple tissue Northern blot was hybridized to the STMP1 probe (see Materials and Methods). As shown in FIG. 6A, STMP1 hybridized to a major mRNA species of 6.5 kb, and three minor mRNA species of 2.2, 4.0, and 4.5 kb in the prostate tissue. The stronger hybridization that is observed with G3PDH in the heart and skeletal muscle samples is due to its higher expression in these tissues. The lanes represent: 1.Heart, 2. Brain, 3. Placenta, 4. Lung, 5. Liver, 6. Skeletal Muscle, 7. Kidney, 8. Pancreas, 9. Spleen, 10. Thymus, 11. Prostate, 12. Testis, 13. Ovary, 14. Small Intestine, 15. Colon, 16. Peripheral blood leukocyte. The location of the full-length 6.5 kb mRNA, as well as the lower molecular weight STMP1 species are indicated by arrows to the left of the figure. There was 15-20-fold lower mRNA expression of the 6.5 kb band in the heart, brain, kidney, pancreas, and ovary, compared to prostate, and no detectable expression in other tissues. In contrast, the three lower molecular weight species, encoded by alternatively spliced forms of STMP1, were only detectable in the prostate. Hybridization with a glyceraldehyde 3-phosphate dehydrogenase (G3PDH) cDNA probe resulted in approximately similar signals in all lanes, except for the heart and skeletal muscle where G3PDH is known to be more abundant compared with other tissues. These data show that STMP1 expression is high in the prostate, although expression can be seen in other tissues, and that STMP1 has isoforms that are restricted to the prostate for expression.

EXAMPLE 6

Characterization of STMP1 Expression

Since androgen is a major hormonal stimulus for the normal prostate gland and for early stage prostate cancer, the possible androgen regulation of STMP1 was assessed by Northern analysis in the androgen-responsive prostate cancer cell line LNCaP. Cells were either left untreated or treated with the synthetic androgen R1881 ($10^{-8}$ M) with increasing amounts of time (hours) as indicated (FIG. 6B), harvested, and total RNA isolated and used in Northern analysis with STMP1 cDNA as probe. The same membrane was also probed for the androgen-dependent gene PSA. Relative induction of mRNA accumulation is indicated at the bottom of the lanes, as determined by phosphorimager analysis (Molecular Dynamics). The CWR22 xenograft was grown in nude mice and tumor samples were collected either before (t=0) or 1, 2, or 4 weeks after castration. Total RNA was isolated and was then used in Northern analysis with the same probes. Ethidium bromide-stained 18S RNA is shown as a control for RNA integrity and loading. At 6 hours, there was an approximately 25% increase in STMP1 expression, which was lost by 24 hours, with a final 20% decrease observed at 48 hours compared with basal levels. In contrast, the mRNA accumulation of the androgen-regulated gene PSA dramatically increased upon androgen stimulation in a time-dependent manner, as expected, reaching approximately 22-fold higher levels by 48 hours. Relative induction of STMP1 mRNA accumulation is indicated at the bottom of the lanes determined by phosphorimager analysis. As is shown in FIG. 6B, STMP1 displayed similar expression levels in untreated and R1881-treated LNCaP cells, indicating that STMP1 expression is not significantly regulated by androgens in LNCaP cells.

To determine the possible androgenic regulation of STMP1 expression in an in vivo setting, the androgen-dependent xenograft model CWR22, which is derived from a primary human prostate tumor, was used (Wainstein, M. A. et al., Cancer Res 54, 6049-6052, 1994). Since they are androgen-dependent for growth, the CWR22 tumors in nude mice display marked regression upon castration and may regress completely. CWR22 xenografts were grown in nude mice in the presence of a sustained release testosterone pellet. After the tumors had grown, the mice were castrated, the testosterone pellets were removed, and the regressing tumors were collected at 1, 2, or 4 weeks post-castration. Total RNA was prepared from these tumor samples and used in Northern analysis. As shown in FIG. 6B, similar to the observations in LNCaP cells, STMP1 mRNA accumulation in the CWR22 tumors showed no significant change upon castration and was not affected by the presence of androgens (note that there is underloading of RNA for CWR22 2 week sample). In contrast, the mRNA accumulation of the androgen-regulated gene PSA was dramatically decreased upon castration, dropping to approximately 16% of pre-castrate levels by two weeks post-castration. These results are consistent with the findings in LNCaP cells and suggest that STMP1 expression is not significantly regulated by androgens in prostate cancer cells. STMP1 expression was substantially lower in the CWR22 tumors compared with LNCaP cells.

The expression profile of STMP1 was also analyzed in the androgen-independent prostate cancer cell lines PC3 and DU145, as well as in four independent, relapsed derivatives of CWR22 tumors, named CWR22R (Nagabhushan, M. et al., *Cancer Res* 56, 3042-3046, 1996), representative of advanced prostate cancer (FIG. 6C). LNCaP (in the presence (+) or absence (−) of R1881 ($10^{-8}$ M)), PC-3, or DU-145 cells were grown and total RNA was isolated. Four independent lines of the androgen independent human prostate cancer xenograft CWR22R, were grown in nude mice, tumors were collected, and total RNA was isolated and used in Northern analysis with STMP1 or the androgen target gene NKX3.1 cDNAs as probes. Ethidium bromide-stained 18S RNA is shown as a control for RNA integrity and loading. The relative induction of STMP1 and NKX3.1 mRNA accumulation is indicated at the bottom of the lanes determined by phosphorimager analysis (Molecular Dynamics). As is shown in FIG. 6C, STMP1 expression was high in LNCaP cells and did not significantly change in response to R1881 treatment compared with a ~9-fold induction of the androgen target gene NKX3.1. There was no STMP1 expression in the androgen-independent prostate cancer cell lines PC-3 or DU-145, as was the case for NKX3.1. In contrast, there was significant STMP1 expression in tumors from all four independent CWR22R xenograft lines tested, ranging between ~30-60% of that observed in LNCaP cells. A similar overexpression pattern was also observed for NKX3.1 (FIG. 6C) consistent with previous findings (Korkmaz, K. S. et al., *Gene* 260, 25-36, 2000).

An interesting property of STMP1 expression profile is that even though it is expressed at low levels in the androgen dependent CWR22 xenograft, it is highly expressed in the relapsed CWR22R which is androgen receptor (AR) positive, but is not responsive to androgens. This indicates that STMP1 expression is deregulated once the prostate tumor progresses from an androgen-dependent to an androgen-independent phase. In addition, STMP1 is not expressed in the AR-negative prostate cancer cell lines PC-3 and DU-145, but is expressed at high levels in the AR-positive cell line LNCaP and the CWR22 and CWR22R xenografts. Thus, expression of STMP1 is correlated with the presence of a functional AR in the cell.

It has been known for over 50 years that androgens play a key role both in the development and maintenance of the normal prostate and the initiation and progression of prostate cancer. Androgen withdrawal results in involution of both the normal prostate gland as well as a prostate tumor in the early stages of the disease that is still androgen dependent. Consequently, androgen withdrawal is commonly used as treatment to reverse tumor growth. However, in the case of the prostate tumor, after a few months or years, the tumor recurs in almost all cases in an androgen-independent state. At this point there is no effective therapy and prognosis for survival is extremely poor. Since STMP1 is overexpressed during this later androgen-insensitive state, it will be a useful tool in diagnostic and therapeutic applications for prostate cancer.

These data indicate that STMP1 expression is deregulated once prostate cancer progresses from an androgen-dependent to an androgen-independent state.

EXAMPLE 7

Intracellular Localization of STMP1

To gain insight into the intracellular localization pattern of STMP1, a green fluorescent protein (GFP)-STMP1 fusion protein was generated. The use of such GFP chimeric proteins has recently become a standard method to assess intracellular localization and dynamics of proteins. COS-1 cells were transiently transfected with GFP-STMP1, fixed and processed for confocal microscopy as described in Materials and Methods.

Figure 7A:
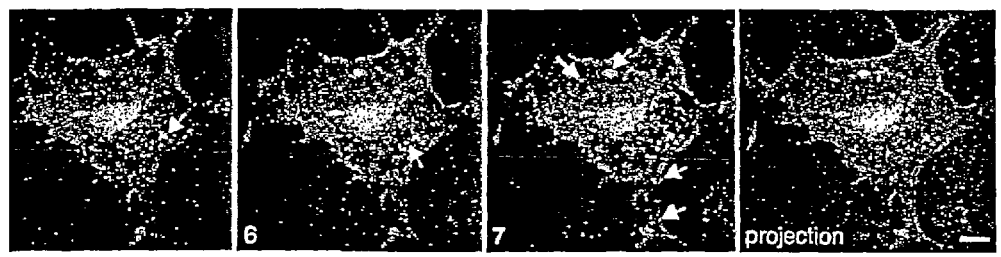
FIG. 7A shows fluorescence microscopy images of COS-1 cells transiently transfected with GFP-STMP1.

A series of 11 confocal sections along the z-axis were collected through a single cell at nominal 100 nm intervals. Three of the consecutive sections and the projection of all 11 sections are shown in FIG. 7A. Arrows indicate tubular-vesicular structures (VTS) in different sizes, shapes, and locations (Bar=5 μm). In all 11 z-plane sections, GFP-STMP1 showed bright juxtanuclear distribution pattern, characteristic of the Golgi complex. Additionally, GFP-STMP1 was dispersed in spots of variable size throughout the cytoplasm and at the cell periphery (z-7, projection). Some of these bright fluorescent spots were tubular (z-6, arrow and FIG. 8) or vesicular (z-5, arrow) in morphology.

Figure 7B:
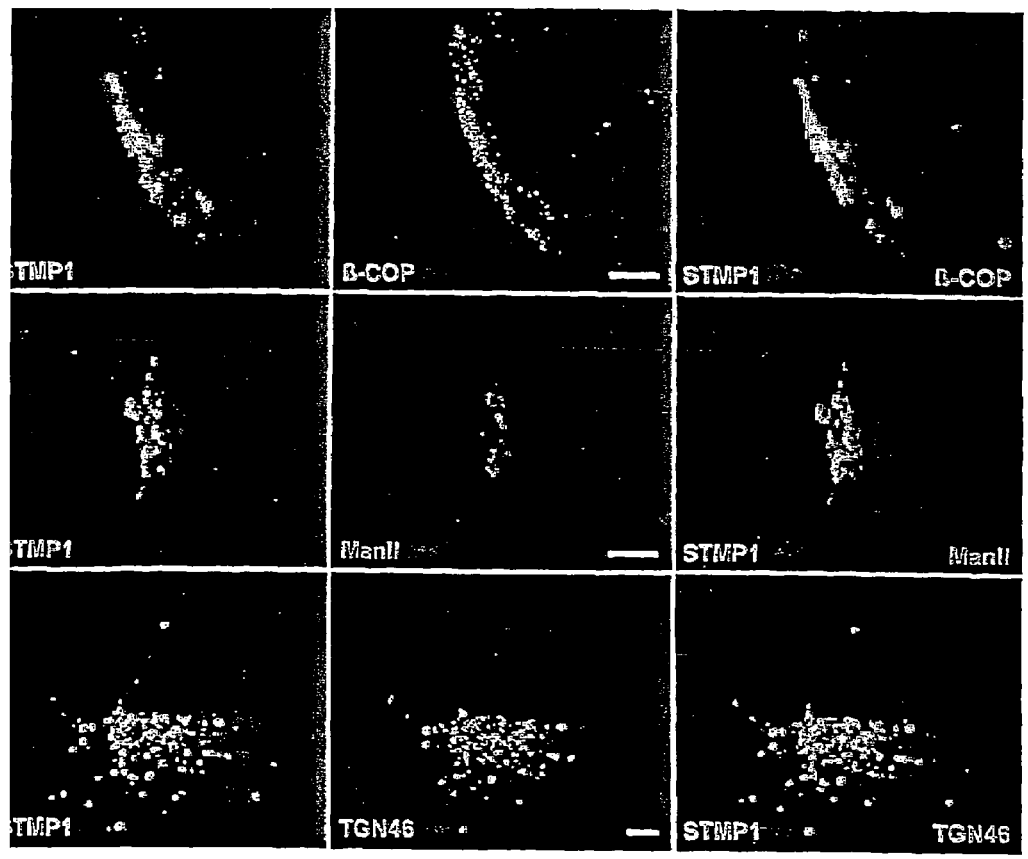
FIG. 7B shows fluorescence microscopy images of COS-1 cells transiently transfected with GFP-STMP1 and labeled with antibodies against Golgi markers.

To determine more directly whether GFP-STMP1 was localized to the Golgi complex, we compared its intracellular distribution with those of two well characterized Golgi markers, the medial Golgi enzyme mannosidase II (ManII) (Rabouille, C. et al., *J Cell Sci* 108, 1617-1627, 1995) and the coat protein β-COP (Pepperkok, R. et al., *Cell* 74, 71-82, 1993). COS-1 cells were transfected with GFP-STMP1, fixed, labeled with the appropriate primary and secondary antibodies and imaged by confocal laser scanning microscopy. Green GFP-STMP1 fluorescence and red (Texas Red-labeled secondary antisera) β-COP and ManII fluorescence were detected by confocal laser microscopy. Panels to the right show the overlay images with yellow/orange staining indicating the regions of colocalization. Bars=5 μm. As shown in FIG. 7B, the distribution of GFP-STMP1 extended throughout the Golgi complex, as evidenced by significant colocalization with both ManII and β-COP. However, some areas of non-overlap between the GFP-STMP1 and both Golgi markers were observed suggesting that STMP1, at least in part, is differentially localized within the Golgi complex compared with these two markers.

Since GFP-STMP1 was associated with VTS (FIG. 7A and FIG. 8), more specific localization of GFP-STMP1 to the trans-Golgi network (TGN), an important site for the sorting of proteins destined to the plasma membrane, secretory vesicles, or lysosomes (Farquhar, M. G. & Palade, G. E. *Trends Cell Biol* 8, 2-10, 1998; Mellman, I. & Warren, G., *Cell* 100, 99-112, 2000; Lemmon, S. K. & Traub, L. M., *Curr Opin Cell Biol* 12, 457-466, 2000) was assessed. An antibody against TGN46, a TGN resident protein that shuttles between the TGN and the plasma membrane (Prescott A R, et al., *Eur J Cell Biol* 72, 238-246, 1997; Ponnambalam, S. et al., *J Cell Sci.* 109, 675-685, 1996), was used in immunoflourescence microscopy experiments as above. As shown in FIG. 7B, GFP-STMP1 extensively colocalized with TGN46, greater than that observed with ManII and β-COP, suggesting that in the Golgi complex, STMP1 is primarily localized to the TGN. Note that the images with TGN46 were obtained with lower objective power.

EXAMPLE 8

Figure 8:
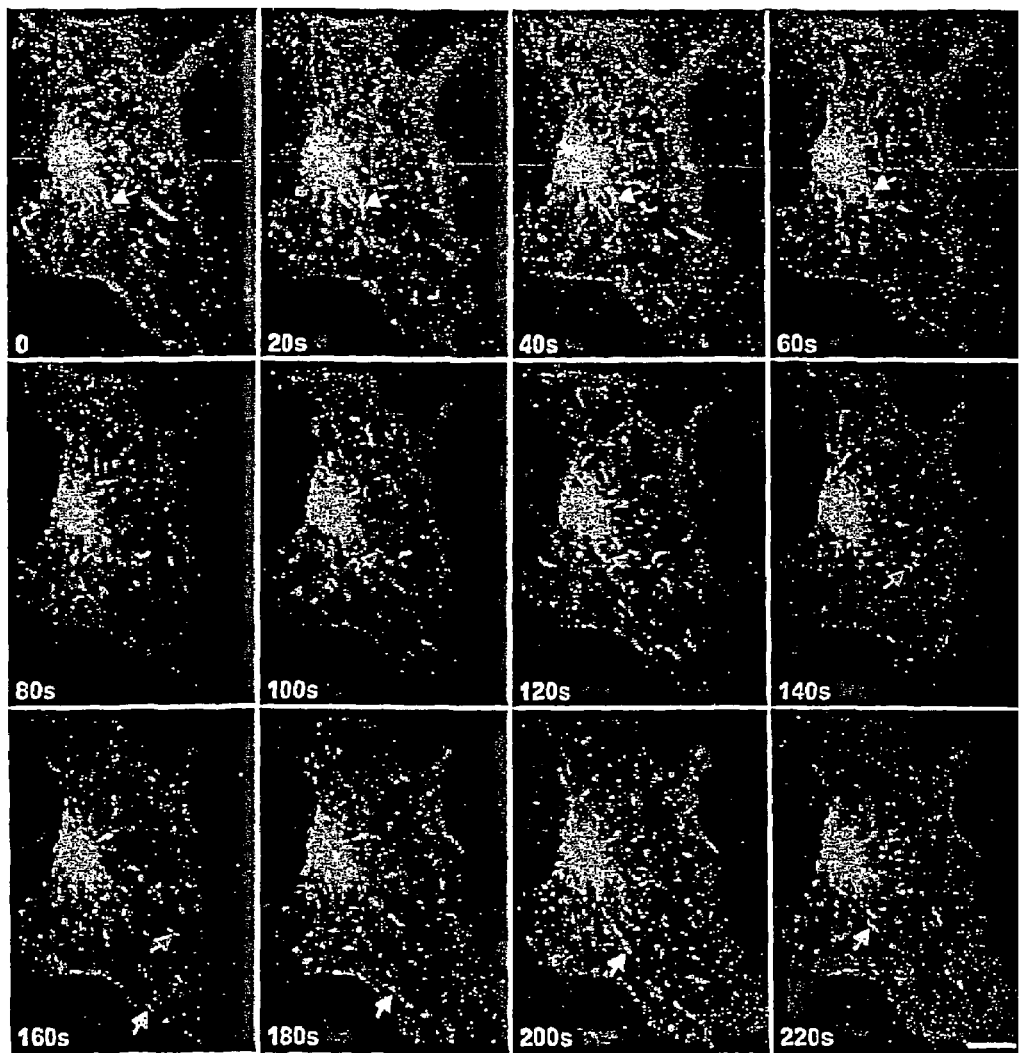
FIG. 8 shows fluorescence microscopy images of COS-1 cells transiently transfected with GFP-STMP1 and observed by live-cell confocal microscopy.

STMP1 Shuttles Between the Golgi and the Plasma Membrane and Colocalizes to the Early Endosomes The dynamic properties and intracellular trafficking of GFP-STMP1 were studied using confocal time-lapse imaging in living cells. COS-1 cells were transiently transfected with GFP-STMP1 and, 16 hours after transfection, 12 consecutive images were collected from live cells every 20 seconds at 37° C. by confocal laser scanning microscope (FIG. 8). The upper panel shows a VTS extending out and retracting back to the Golgi body (white arrows). In the middle panel and the first image in the lower panel (160 seconds), red arrows indicate the translocation of a VTS from the Golgi body to the cell periphery. In the lower panel, yellow arrows point to the movement of a VTS from the edge of the cell towards the Golgi body. Note that the results shown are representative of multiple time-lapse analyses and the changes in the images are not due to movement from the plain of focus. Bar=5 μm.

As shown in FIG. 8, some VTS were found to be detaching and some to be associating with the Golgi complex. The VTS were highly dynamic and pleiomorphic in size. Some of the VTS followed straight or curvilinear paths, some moved in a stop-and-go fashion, and some showed saltatory movements. The VTS indicated at the top panel (white arrows) extended away from and then retracted back to the Golgi. The VTS in the middle panel and the first image in the lower panel (red arrows) detached from the Golgi complex, paused, and then moved towards the cell periphery until it disappeared at the cell edge suggesting that STMP1 is associated with the secretory pathway. The VTS in the lower panel (yellow arrow) moved from the cell periphery towards the Golgi body suggesting that STMP1 is localized to the endocytic pathway.

EXAMPLE 9

Colocalization of GFP-STMP1 with the Early Endosomal Marker EEA1

Figure 9:
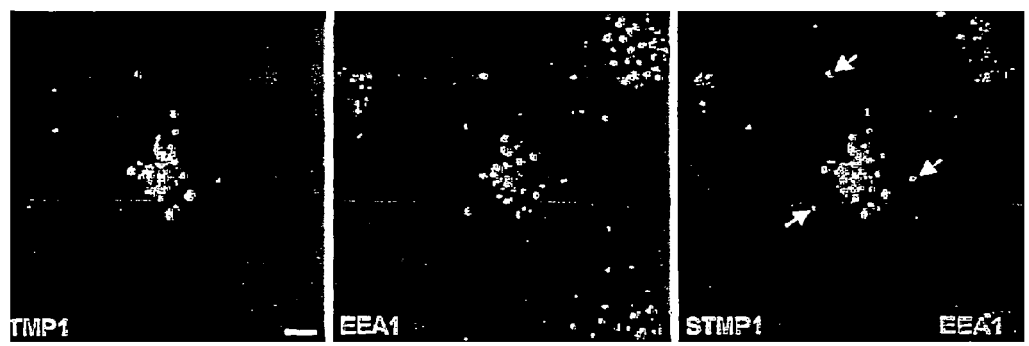
FIG. 9 shows fluorescence microscopy images of COS-1 cells transiently transfected with GFP-STMP1 and labeled with an antibody against an early endosomal marker.

To probe whether GFP-STMP1 was associated with the endocytic pathway, the intracellular distribution of GFP-STMP1 was compared with that of the early endosome protein EEA1 (Stenmark, H. et al., *J Biol Chem* 271, 204048-204054, 1996). COS-1 cells were transfected with GFP-STMP1, fixed, immunostained with EEA1 antibodies and observed by confocal laser scanning microscopy. Green GFP-STMP1 fluorescence and red (Texas Red-labeled secondary antiserum) EEA1 fluorescence were detected by confocal laser microscopy. The panel to the right shows the overlay images with yellow/orange staining indicating the regions of colocalization. Arrows indicate examples of the VTS in the cell periphery which contain both EEA1 and STMP1. Bar=5 μm. As shown in FIG. 9, EEA1 manifested a similar intracellular distribution in both transfected and untransfected cells. Furthermore, GFP-STMP1 significantly colocalized with EEA1 both in the cell periphery and also in the perinuclear area (FIG. 9, arrows) suggesting that STMP1 is associated with early endosomes and the endocytic pathway.

EXAMPLE 10

Isolation and Characterization of the SSH9 Gene and mRNA

Figure 10:
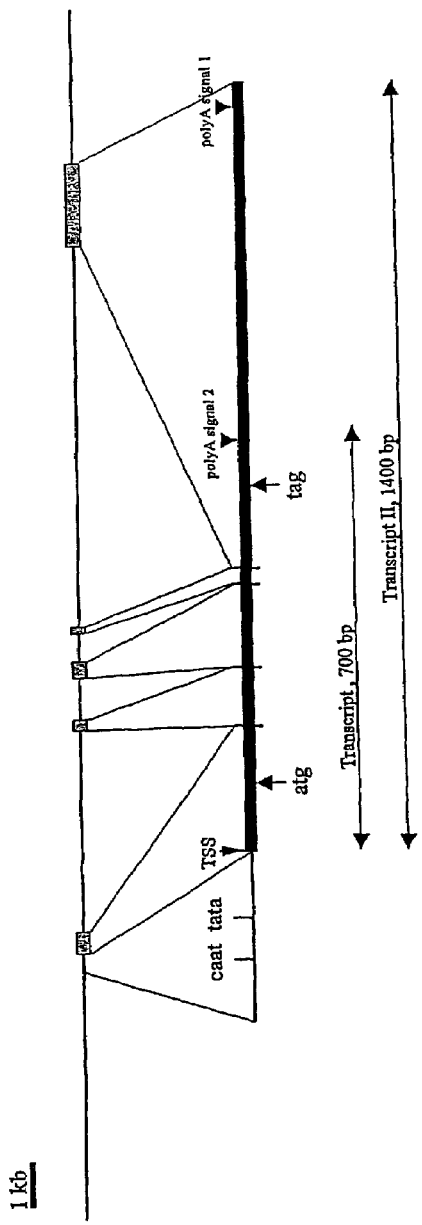
FIG. 10 is a schematic diagram showing the SSH9 gene structure and two mRNA species transcribed from the SSH9 gene.

The SSH9 gene was identified and mapped (FIG. 10). The predicted promoter site, the transcription start site, and the location and size of the exons and introns are indicated. The start and stop codons, as well as two polyadenylation signals, leading to two alternatively spliced transcripts, are also indicated. FIGS. 11A-C show the nucleotide and predicted amino acid sequence of SSH9, as well as the predicted promoter sequence and exon-intron boundaries.

The expression profile of SSH9, determined in various human tissues by Northern analysis (FIG. 12C), revealed that the 0.7 kb splice variant of SSH9 was highly testis-specific, while the 1.4 kb transcript was expressed in both prostate and testis.

Figure 12:
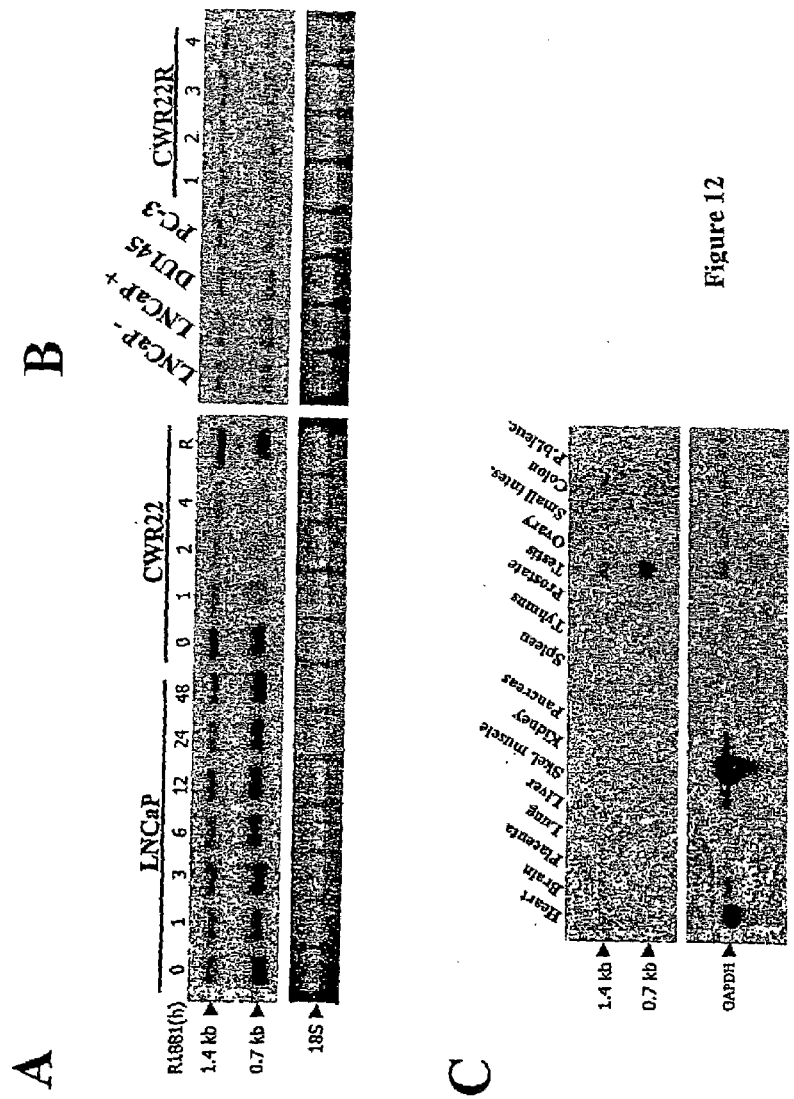
FIG. 12A is a Northern blot probed with SSH9 in the androgen-responsive prostate cancer cell line LNCaP cells and in the CWR22 human prostate cancer xenograft model.
FIG. 12B is a Northern blot probed with SSH9 in LNCaP, PC-3, and DU-145 cell lines, and CWR22R human prostate cancer xenograft model.
FIG. 12C is a multiple tissue Northern blot probed with SSH9 or GAPDH cDNA.

The androgen regulation of SSH9 was examined in LNCaP cells and in CWR22 xenografts (FIG. 12A) revealed that SSH9 is not regulated in LNCaP cells, but is regulated in CWR22 xenografts. The expression profile of SSH9 was also examined in the androgen-independent prostate cancer cell lines PC3 and DU145, and in CWR22R cells (FIG. 12B).

EXAMPLE 11

Isolation and Characterization of the PSL22 Gene and mRNA

Figure 13:
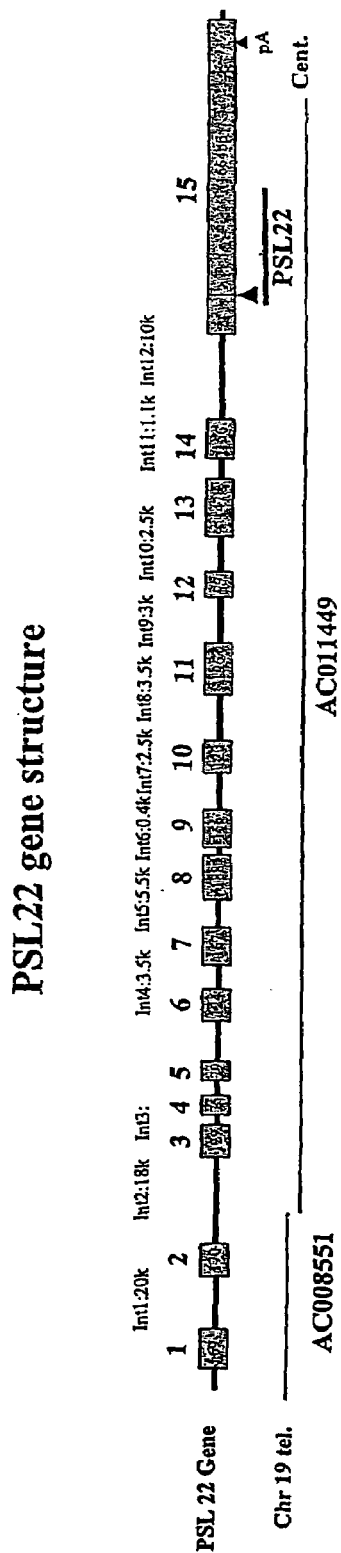
FIG. 13 is a schematic diagram showing the PSL22 gene structure.

The PSL22 gene was identified and mapped (FIG. 13). The location and size of the exons and introns, the location of the partial cDNA clone (black box), as well as the alignment of the full-length cDNA clone with GenBank Accession Nos. AC008551 and AC011449, are indicated. FIGS. 14A-C show the nucleotide sequence of the ORF, cDNA and predicted amino acid sequence, as well as the predicted promoter, exon, and UTR sequences of PSL22.

Figure 15:
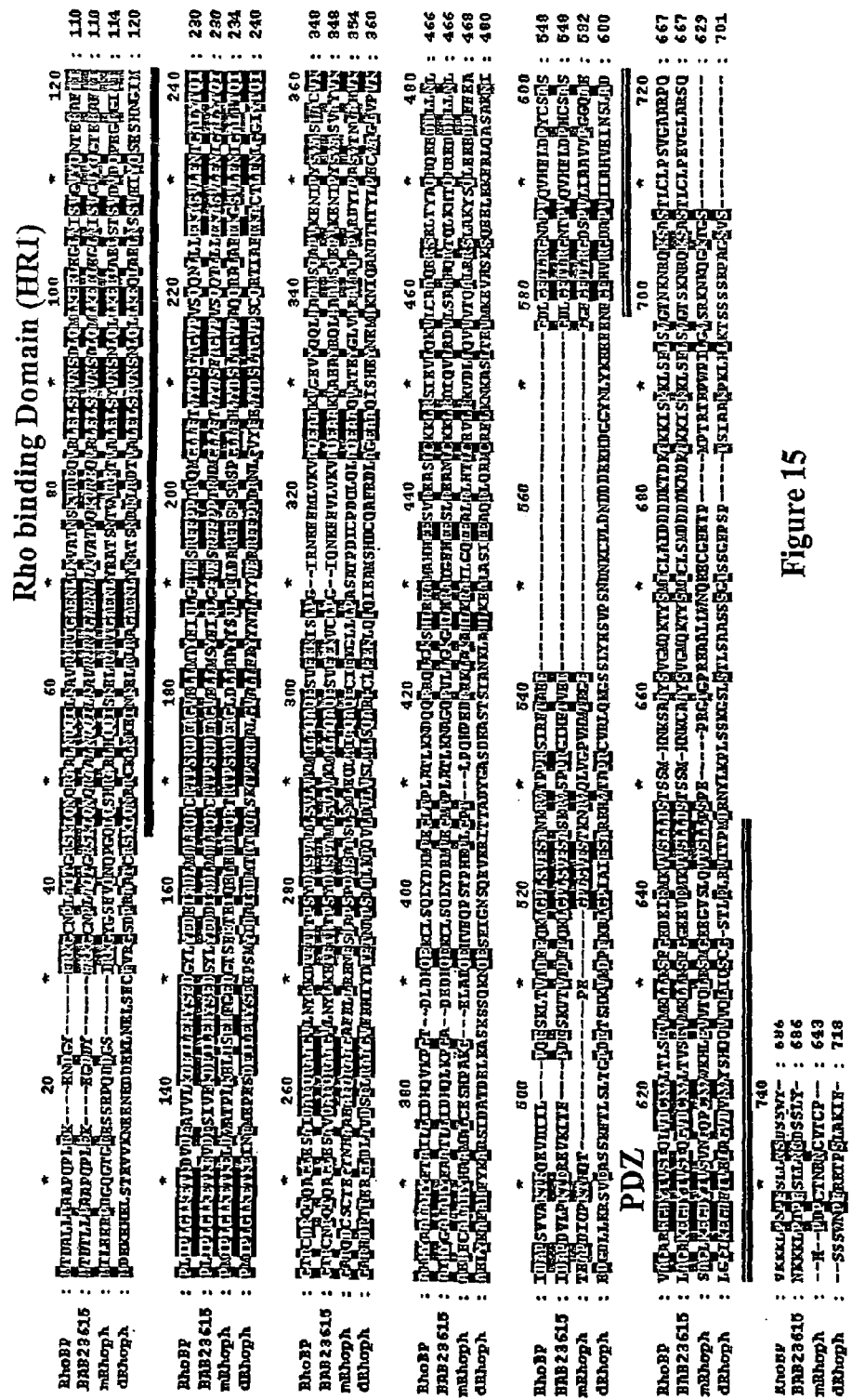
FIG. 15 shows a sequence alignment of PSL22 (RhoBP) (SEQ ID NO: 53), with ESTs NP032190 (mRhoph), AF132025 (dRhoph), and BAB23615 (SEQ ID Nos:71-73).

BLAST analysis of GenBank with the predicted PSL22 amino acid sequence identified PSL22 as a Rho binding protein. FIG. 15 shows a multiple sequence alignment of PSL22 with related proteins. Completely conserved residues are shown in black; residues found in three sequences are shaded.

The expression profile of PSL22, determined in various human tissues by Northern analysis (FIG. 16B), revealed that while the highest expression was seen in the prostate, high expression was seen in the kidney, pancreas, and colon.

Figure 16:
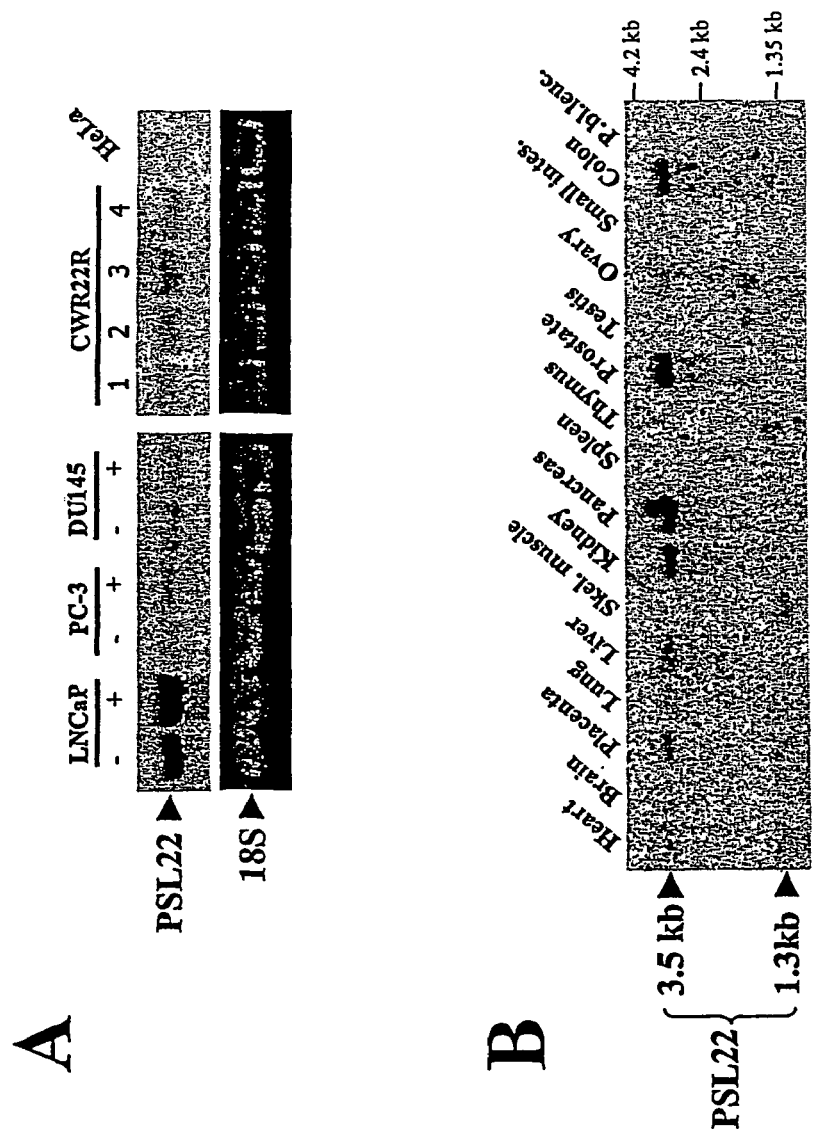
FIG. 16A is a Northern blot probed with PSL22 in LNCaP, PC-3, and DU-145 cell lines, and in the CWR22R human prostate cancer xenograft model.
FIG. 16B is a multiple tissue Northern blot probed with PSL22 cDNA.

The androgen regulation of PSL22 was examined in LNCaP cells, in the androgen-independent prostate cancer cell lines PC3 and DU145, and in CWR22R cells (FIG. 16A). The results showed that PSL22 is androgen regulated in LNCaP cells, where it is highly expressed, but is not androgen regulated in the PC3 and DU145 cells.

EXAMPLE 12

Isolation and Characterization of the STAMP2 gene and mRNA

Figure 17:
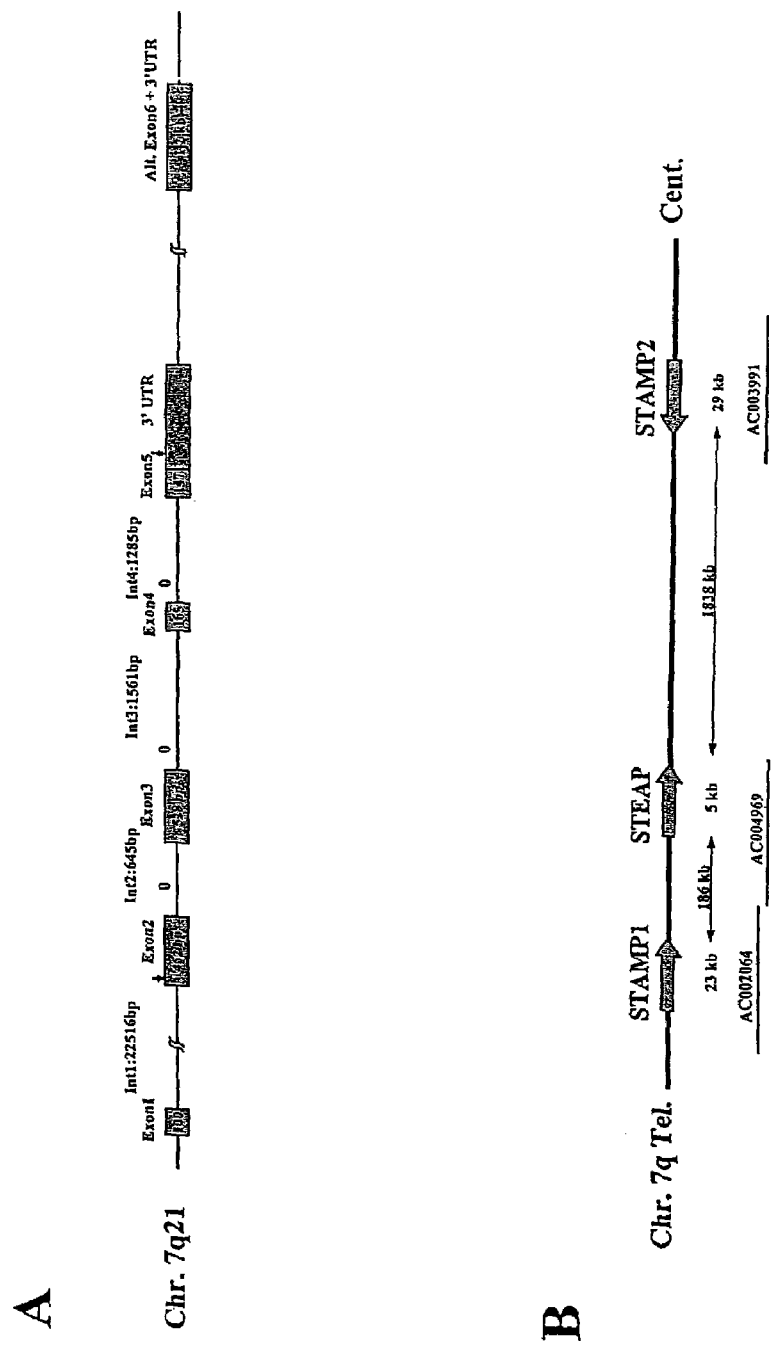
FIG. 17A shows the gene structure of the STAMP2 gene. Boxes denote exons. The sizes of the introns and exons are shown. The location of the predicted start and stop codons are indicated with black and grey arrows, respectively.
FIG. 17B shows the relative location of STAMP1, STAMP2, and STEAP genes on Chr7q. The telomeric (Tel) and centromeric (Centr) ends of the chromosome are indicated. The BAC clones encompassing the genes, as well as the distance between the genes, are indicated. The arrows indicate direction of transcription 5' to 3'.

In an attempt to identify genes that were similar to STAMP1 (Korkmaz et al., *DNA Cell Biol.* 19:499-506, 2000), we identified a BAC clone (GenBank accession # AC003991) on human Chr7q21 that showed significant sequence similarity to STAMP1 cDNA (FIG. 17A). Computational exon/intron junction analysis of this locus and alignment of the full-length cDNA sequence revealed that there is a gene at this locus that is composed of five exons and four introns (FIG. 17A). Given the similarity in both the gene structure, the predicted amino acid sequence (44% identity, 64% conservation), as well as the similarities in intracellular distribution to STAMP1 (see below), we named this gene STAMP2. The STAMP2 gene spans around 26 kb which is in part due to the extremely large size of intron 1 (22516 bp).

STAMP1 and STAMP2 both lie on Chr7q, but are transcribed in opposite directions (FIG. 17B). The STAMP1 related gene, Six Transmembrane Epithelial Antigen of Prostate (STEAP) (Hubert et al., *Proc. Natl. Acad. Sci.* 96:14523-14528, 1999) is also in this locus and is transcribed in the same direction as STAMP1. Thus, Chr7q contains a cluster of genes predicted to encode six transmembrane proteins.

We cloned the full-length cDNA for STAMP2 from an R1881-induced LNCaP cDNA library using PCR. The cDNA and predicted amino acid sequence are presented in FIG. 18. Because the STAMP2 mRNA runs as a 4.0 kb band in a northern blot analysis (see below) and the cDNA we cloned is runs as a 2.3 kb including the poly (A) tail, we predict that STAMP2 mRNA has approximately 1.7 kb of 5'-UTR sequences.

BLAST search of GenBank with the STAMP2 cDNA revealed some homology (78% identity on the predicted amino acid level) to the previously described Tumor Necrosis Factor α-induced Adipose-related Protein (TIARP; Moldes et al., *J. Biol. Chem.* 276:33938-33946, 2001), a mouse protein which may have a role in adipocyte differentiation (FIG. 19). In response to TNF-α stimulation, TIARP localizes to the plasma membrane suggesting that it may act as a channel or receptor on the mature adipocyte (Moldes et al., supra). In addition to TIARP and STAMP1, STAMP2 displays similarity to the rat protein pHyde (Steiner et al., *Cancer Res.* 60:4419-4425, 2000) (FIG. 19). When pHyde is overexpressed, it causes apoptosis in prostate cancer cells, and the human homolog of pHyde, TSAP6, regulates apoptosis and the cell cycle through interactions with Nix and Myt1 kinase (Passer et al., *Proc. Natl. Acad. Sci.* 100:2284-2289, 2003). These data suggest that STAMP1, STAMP2, and pHyde/TSAP6 may be structurally, and possibly also functionally, related proteins.

In addition to the six transmembrane domains in the C-terminal half of the predicted STAMP2 sequence (FIG. 18), a conserved domain search identified three motifs in the N-terminal domain of STAMP2. The first is a predicted dinucleotide-binding domain that is found in a number of bacterial proteins (Deppenmeier, *Cell Mol. Life Sci.* 59:1513-1533, 2002). Second is an NADP oxidoreductase motif that is coenzyme F420-dependent, such as F420H2:NADP+ oxidoreductase found in archeabacteria (Warkentin et al., *EMBO J.* 20:6561-6569, 2001). Third is a motif that resembles pyrroline 5-carboxylate reductase, an enzyme that is involved in amino acid transport and metabolism (Phang, *Curr. Top. Cell Regul.* 25:91-132, 1985).

EXAMPLE 13

STAMP2 Has a Restricted Tissue Distribution

We next determined the expression profile of STAMP2 in various human tissues by northern analysis in which a multiple tissue northern blot was hybridized to the STAMP2 cDNA probe. As shown in FIG. 20A, STAMP2 hybridized to a major mRNA species of 4.0 kb in placenta, lung, heart, and prostate, with substantially lower expression also seen in liver, skeletal muscle, pancreas, testis, and small intestine; there was no detectable expression in brain, kidney, spleen, colon or peripheral blood leukocytes. Hybridization with a glyceraldehyde 3-phosphate dehydrogenase (G3PDH) cDNA probe resulted in approximately similar signals in all lanes, except for the heart and skeletal muscle where G3PDH mRNA is known to be more abundant compared with other tissues.

EXAMPLE 14

Characterization of STAMP2 Expression in Cell Lines and its Androgen Regulation

Since one of the tissues in which STAMP2 is highly expressed is the prostate, where androgen is a major hormonal stimulus for growth and for early stage prostate cancer (Huggins et al., *Arch. Surg.* 43:209-223, 1941), we assessed the possible androgen regulation of STAMP2 by northern analysis in the androgen responsive prostate cancer cell line LNCaP (Horoszewicz et al., *Cancer Res.* 43:1809-1818, 1983). Cells were either left untreated or treated with the synthetic androgen R1881 for 24 hours and harvested. Total RNA was isolated and used in Northern analysis with STAMP2 cDNA as a probe. As shown in FIG. 20B, STAMP2 expression dramatically increased upon R1881 treatment of LNCaP cells. In contrast, there was no significant difference in the mRNA accumulation of STAMP1 in the same samples, consistent with previous findings (Korkmaz et al., supra). Similar to STAMP1, there was no detectable expression of STAMP2 in a number of prostate cancer cell lines that do not express the androgen receptor (PC-3, DU-145, CA-HPV10, PZ-HPV7, YPEN-1). In addition, STAMP2 was not expressed in myotubes (C2), lung cancer cells (NCI-H661), breast cancer cells (MCF7, MCF7-LCC1, MCF7-LCC2, MB435), or cervical carcinoma cells (HeLa) (FIG. 20B). Time course analysis of androgen treatment revealed that STAMP2 expression began around six hours and increased through 48 hours (FIG. 20C). Thus, expression of STAMP2 correlated with the presence of a functional androgen receptor in the cell. These data support the finding that STAMP2 is expressed in a tissue-restricted manner and that it is an androgen target gene in androgen responsive LNCaP cells.

EXAMPLE 15

Intracellular Localization of STAMP2

To gain insight into the cellular localization pattern of STAMP2, we labeled it with the Green Fluorescent Protein (GFP) to generate GFP-STAMP2. Such use of GFP fusion proteins is frequently used to assess intracellular localization and dynamics of proteins (Chalfie et al., Science, 263:802-805, 1994; for a review, see Tsien, *Annu. Rev. Biochem.* 67:509-544, 1998). COS-1 cells were transiently transfected with GFP-STAMP2, fixed and processed for confocal microscopy. A representative single optical section of a COS-1 cell is shown in FIG. 21. GFP-STAMP2 displays a strong juxtanuclear distribution that is typical of the Golgi complex. Additionally, significant GFP-STAMP2 distribution was observed in the cell periphery and in vesicular or tubular-shaped bright spots throughout the cytoplasm suggesting that STAMP2 localizes to plasma membrane (PM) and to vesiculotubular structures (VTS) in the cytosol (FIG. 21). At higher exposures, GFP-STAMP2 distribution can also be seen as a light reticular pattern in the cytosol, reminiscent of the endoplasmic reticulum (FIG. 21, right panel).

In order to directly assess whether GFP-STAMP2 is associated with the Golgi complex, we compared the intracellular distribution of GFP-STAMP2 with those of three well characterized Golgi markers, the coat protein β-COP (Pepperkok et al., *Cell* 74:71-82, 1993), mid-Golgi marker giantin (Linstedt et al., *Mol. Biol. Cell* 4:679-693, 1993), and trans-Golgi network (TGN) marker TGN-46 (Ponnambalam et al., *Curr. Biol.* 6:1076-1078, 1996). GFP-STAMP2 was transfected into COS-1 cells, which were then fixed, labeled with the appropriate primary and secondary antibodies, and then single optical sections were acquired by laser scanning confocal microscopy. As shown in FIG. 22, there was significant overlap of GFP-STAMP2 juxtanuclear distribution with Golgi and TGN markers, but there were also some differences. This suggests that STAMP2, at least in part, is differentially localized within the Golgi complex. Expression of STAMP2 in the Golgi suggests that six-transmembrane proteins may have unique functions in this organelle compared with the other Golgi resident proteins identified so far. Photobleaching experiments provided evidence that GFP-STAMP2 is rapidly exchanged between different parts of the Golgi with kinetics consitent with its role as a transmembrane protein.

EXAMPLE 16

GFP-STAMP2 is a Highly Mobile Protein and is Associated with Vesiculotubular Structures in the Cytosol To gain insight into the possible function of STAMP2, the kinetic properties of GFP-STAMP2 distribution and trafficking were studied in living cells by time-lapse confocal microscopy. COS-1 cells were transfected with GFP-STAMP2. 18 hours after transfection, images were obtained from live cells at 3 second intervals at 37° C.

There was rapid trafficking of GFP-STAMP2 in the cytosol in the form of predominantly vesiculotubular structures (VTS; FIG. 23). Some of the VTSs followed straight or curvilinear paths, some moved in a stop-and-go fashion, and some showed saltatory movements. The movement of one such VTS from cytoplasm to cell periphery is shown in consecutive images in FIG. 23. These data suggest that STAMP2 is associated with the secretory pathway.

To probe whether GFP-STAMP2 was associated with the endocytic pathway, we compared the intracellular distribution of GFP-STAMP2 with that of the early endosome protein EEA1 (Stenmark et al., *J. Biol. Chem.* 271, 24048-24054, 1996). GFP-STAMP2 was transfected into COS-1 cells, which were then fixed, immunostained with EEA1 antibodies, and observed by laser scanning confocal microscopy. As shown in FIG. 24, EEA1 had similar intracellular distribution in both transfected and untransfected cells. GFP-STAMP2 significantly colocalized with EEA1 both in the cell periphery and also in the perinuclear area (FIG. 24) suggesting that STAMP2 is associated with early endosomes and the endocytic pathway. The significant STAMP2 distribution in the plasma membrane and the movement of STAMP2 within transport vesicles to and from the plasma membrane in live cell imaging studies suggest that STAMP2 may be involved in the secretory and endocytic pathways.

In addition to the localization of GFP-STAMP2 in the Golgi, TGN, and the plasma membrane, a fraction of the GFP-STAMP2 protein can also be detected in the Endoplasmic Reticulum (ER). ER is the central organelle that is necessary for proper folding and delivery of proteins. Proteins destined for secretion, the plasma membrane or the cell surface, are translocated from the cytoplasm into the ER for further delivery of these proteins to their site of action. Since proteins are translocated into the ER in an unfolded state, it is the primary function of this organelle to modify and fold the translocated proteins to acquire their biologically active conformation (Haigh et al., Protein sorting at the membrane of the endoplasmic reticulum. In *Protein Targeting, Transport, and Translocation*, Dalbey R. E. and von Heine G. (eds.), Academic Press, London, UK, pp. 74-106, 2002). We do not know the significance of the presence of STAMP2 in the ER, or whether it has a functional role in this organelle. However, since the majority of STAMP2 expression is in the Golgi, TGN, early endosomes and the plasma membrane, it is possible that GFP-STAMP2 is unfolded in the ER and is kept there for further processing. Alternatively, there may be a functional role of STAMP2 in the ER.

EXAMPLE 17

Analysis of STAMP2 Expression in Normal vs. Adenocarcinoma of Prostate

Based on the expression of STAMP2 in prostate tissues and the androgen regulation of STAMP2 in androgen receptor positive prostate cancer cells, we studied its expression in normal prostate epithelial cells compared with adenocarcinoma of the prostate. To that end, Laser Capture Microdissection (LCM) (Bonner et al., *Science* 278:1481-1483, 1997) was used on human radical prostatectomy specimens that were snap frozen immediately upon resection. Normal epithelial cells and cancer cells from the same specimen were collected (matched normal/tumor pair). Total RNA was extracted and cDNA was made and used in a quantitative RT-PCR assay with STAMP2-specific primers. The results of this experiment representing normal/tumor pairs from 26 independent patient samples are presented in FIG. 25. LNCaP cells treated with R1881 for 24 hours were used as a positive control. The results of these experiments showed significant STAMP2 amplification in the control LNCaP cells treated with R1881. In contrast, none of the normal cell pools from prostatectomy specimens showed any STAMP2 expression. Interestingly, 5 of the 26 samples (#15, 21, 22, 24, 26) of cancer cell pools (~20%) in the prostate specimens showed very high STAMP2 mRNA expression reaching up to 30-fold higher than that observed in R1881-treated LNCaP cells. These data indicate that STAMP2 may have a role in the genesis of, and be a marker for, at least a subset of prostate cancers.

EXAMPLE 18

Androgen Regulation of STAMP2 Protein Expression

Since STAMP2 RNA was shown to be androgen-regulated (Example 14), we sought to determine if STAMP2 protein was also androgen-regulated. For these experiments LNCaP cells were either left untreated or treated with R1881 ($10^{-8}$ M) for the indicated times. The whole cell extracts (from a 10 cm dish) were prepared by resuspending the cells in 200 μl of lysis buffer (20 mM HEPES (pH 7.4), 300 mM NaCl, 1.5 mM $MgCl_2$, 0.2 mM EDTA, 0.1% Triton X-100, 0.5 mM DTT, 20 mM β-glycerophosphate, 0.1 mM $NaVO_3$, 0.5 mM PMSF, 1 mM leupeptin, 5 μg/ml aprotinin). The suspension was rotated at 4° C. for 2 hours, followed by centrifugation at 15,000×g for 30 minutes. The supernatant was collected and stored at −80° C. The protein concentrations were determined by the Bio-Rad Protein Assay. Protein extracts (100 μg) were electrophoresed on 10% SDS-PAGE gel. The proteins were then transferred to a PVDF membrane (BIO-RAD), which was blocked with 5% milk for 2 hours, followed by incubation with the primary antibody at 4° C. overnight. The ECL kit (Amersham Pharmacia) was used for detection according to the manufacturer's recommendations. 1/1000 dilution of the antiserum was used as the primary antibody. The results of this experiment demonstrate the androgen responsiveness of the STAMP2 protein (FIG. 26).

EXAMPLE 19

STAMP2 Expression Increases Cellular Proliferation and Colony Formation

The effects of ectopic expression of STAMP2 on cell growth were analyzed using DU145 cells. Colony formation assays were performed as described below in the Materials and Methods. Cells were either transfected with en empty expression plasmid pCDNA3 or one that encodes full length STAMP2 cDNA. 24 hours after transfection, cells were trypsinized, selected for plasmid integration in G418, and cultured for two weeks. Colony formation was detected by staining with crystal violet (0.1%) and measuring the area covered on each plate by the colonies using an imaging system (Syngene). The results shown in FIGS. 27A and 27B demonstrate that STAMP2 expression increases colony formation in DU145 cells. These results suggest a role for STAMP2 expression or overexpression in the induction of cell growth and proliferation. Results represent 3-5 experiments done at least in duplicate.

The effect of STAMP2 on cell growth and proliferation was also measured in DU145 cells and COS7 cells. For these experiments cells were either transfected with an empty expression plasmid plus a GFP expression vector (control), or the GFP expression vector together with an expression vector that encodes full length STAMP2 cDNA in a 1:5 ratio, to ensure that the great majority of the cells that have the STAMP2 cDNA also have GFP. At indicated time points, cells were trypsinized, fixed, and then counted for the GFP content by a FACS machine. The numbers of GFP positive cells were obtained and presented as the ratio between STAMP2 transfected compared with controls. The results shown in FIGS. 28 and 29 demonstrate that ectopic expression of STAMP2 increases cell proliferation in DU145 cells and COS7 cells. Results presented are from at least two experiments done in duplicate.

Materials And Methods

The following materials and methods were used in the examples described above. It is understood that these materials and methods are subject to modifications that do not change the nature of the invention, as will be understood by those of ordinary skill in the art.

Cell culture

All prostate cancer cell lines were routinely maintained and treated as previously described (Korkmaz et al., *DNA Cell Biol.* 19:499-506, 2000 and Korkmaz et al., *Gene* 260:25-36, 2000). Briefly, the cells were routinely maintained in RPMI 1640 medium (Gibco-BRL), supplemented with 10% fetal calf serum (FCS), penicillin/streptomycin (5 mg/ml), and L-glutamine (200 mM). For androgen induction and RNA preparation, cells were grown for 48 hours in RPMI 1640 containing 2% FCS that was charcoal-treated (CT) to remove steroids, followed by an additional 24 hours in RPMI 1640 containing 0.5% CT-FCS. The synthetic androgen R1881 ($10^{-8}$ M) (Dupont-NEN) was then added and cells were collected at indicated time points. Total RNA was prepared by the single step guanidine thiocyanate procedure and used in Northern analysis. All other cell lines were cultured in DMEM supplemented with 10% fetal calf serum (FCS), penicillin/streptomycin (5 mg/ml), and L-glutamine (200 mM).

Hybridization

Probes were generated by random priming as described in U.S. Patent Application Publication No.20030219761. Freshly prepared 25 ml Hybridization mix (7% SDS, 0.5 M NaHPO$_4$, 1 mM EDTA) was pre-warmed at 65° C. and 12.5 ml was used for prehybridization of each membrane, 5-10 minutes at 65° C. The probe was heat denatured at 95° C. for 3-5 minutes and transferred to the prehybridization mix at 65° C. Hybridization was carried out at 65° C. overnight. Wash solution I (2×SSC and 1% SDS) and II (0.1×SSC and 0.5% SDS) were prewarmed, and the membranes were washed once with Solution I and then with Solution II for 30 min at 65° C. The membranes were covered with plastic wrap and exposed to a phoshorimager screen. Clones that showed differences between the (−) and (+) blots were picked (usually 1-8 on each blot pair). A secondary round of reverse northern analysis for confirmation was performed, this time spotting each clone in duplicate on each blot. After phosphorimager analysis, the blots were stripped in 0.1×SSC and 0.5% SDS for 2×15 min at 95° C. and hybridized with a PSA probe (or depending on the hormone that is being used, with a probe for any abundant target genes in the tissue under study). For the clones that were confirmed to be different from PSA, for differential expression in the secondary reverse northern, northern analysis was performed using established protocols. A time course of R1881 induction of LNCaP cells, as well as the CWR22 xenograft model upon androgen ablation (Wainstein, M. A. et al., *Cancer Res.* 54, 6049-6052, 1994) and the androgen-independent CWR22R relapsed xenograft (Nagabhushan, M. et al., *Cancer Res.* 56, 3042-6, 1996), was used.

DNA Sequence Analysis

Sequence analysis was performed by the dideoxy chain termination methods using an ABI automated sequencer (as described in U.S. Patent Application Publication No.20030219761). The BigDye kit (Perkin Elmer), and automated dye termination system services of GATC, Germany, was also used for sequencing. The DNA sequences were analyzed by standard algorithms accessible at various web sites, including NCBI-BLAST, Clustal 1.8, and Gendoc 2.6.

Protein Sequence Analysis

Primary sequence analysis for STAMP2 was performed by BLAST at the NCBI website. Secondary protein structure predictions were performed by using the web tools SMART, at the EMBL website, SOSUI at the SOSUI proteome website, and PSORT at the PSORT prediction website.

Isolation of Prostate Cancer Related Genes from LNCaP Cells

The prostate cancer cell line LNCaP was cultured in two batches in culture conditions similar to those previously described (Horoszewicz J S et al., *Cancer Res.* 43: 1809-1818, 1983). The first batch was left untreated, while the second batch was treated with the synthetic androgen R1881 for 24 hrs. Cells from both batches were harvested and total RNA was then isolated from each batch. From the total RNA, polyA$^+$ RNA was obtained using standard procedures, and was used in the Suppression Subtraction Hybridization (SSH; Diatchenko et al., supra) procedure to identify hormone regulated genes. The tester in the SSH procedure was cDNA from untreated cells and the driver was cDNA from R1881-treated cells. The suppression subtraction protocol was performed according to the original description of the method (Diatchenko et al., supra).

Cloning and Plasmid Construction

A 262 bp cDNA fragment was originally obtained from a screen of a prostate specific library (Ausubel, F. M., et al. (1997) *Current Protocols in Molecular Biology* (John Wiley and Sons, New York) and termed L74. 5' Rapid Amplification of cDNA Ends (RACE) was performed (oligonucleotide sequences available upon request) using the Marathon-Ready cDNA that was prepared from normal prostate tissue (Clontech) and/or SMART-RACE LNCaP cDNA library (Clontech) that was generated according to the manufacturer's recommendations. RACE products were cloned into pCRII-TOPO (Invitrogen), positive clones were confirmed by Southern analysis, and sequenced. In parallel, a λgt10 cDNA library made from a pool of normal human prostates (Clontech) was screened by established procedures to obtain additional clones. Overlapping clones were used to deduce the full-length STMP1 cDNA sequence.

The full-length STMP1 ORF was amplified by using primers centered around the start and stop codons (sequences available upon request) and fused in frame to the C-terminus of green flourescent protein (GFP) using the vector pcDNA3.1-NT-GFP-TOPO (Invitrogen) to generate GFP-STMP1.

For STAMP2 cloning, several partial cDNA-clones as well as genomic clones were identified in a GenBank screen for sequences similar to STAMP1 (Korkmaz et al., *J. Biol. Chem.* 277:36689-36696, 2002). We termed this novel gene STAMP2. These STAMP2 clones were then used to computationally construct a full-length cDNA. Primers were designed on the basis of this sequence and used in PCR to amplify the full-length STAMP2 cDNA from an LNCaP SMART (Clontech) cDNA library. The amplified cDNA product was cloned into pCRII-TOPO, or pcDNA4-HisMax (Invitrogen, Calif.) and sequenced on both strands. In addition, the resulting cDNA sequence was aligned with the gene sequence (BAC AC003991) to determine gene structure and sequence accuracy.

The full-length STAMP2 ORF from pCRII-TOPO-STAMP2 was fused in frame to the C-terminus of green fluorescent protein (GFP) using the vector pEGFP-C1 (Clontech) to generate GFP-STAMP2.

Northern Analysis

Total RNA was prepared by the single step guanidine thiocyanate procedure and used in Northern analysis (Ausubel et al. Current Protocols in Molecular Biology, John Wiley and Sons, New York, 1997). 15 μg of total RNA was used per lane. Probes were generated by random priming and had a specific activity of >3×10$^8$ dpm/μg. For STMP1, a cDNA fragment of STMP1 spanning residues 145-2202 bp was used as probe. For STAMP2, a full-length cDNA (1-2263 bp) of STAMP2 (GenBank Accession number # AF423422) was used as probe. Bands were visualized and quantified by phosphorimager analysis (Molecular Dynamics).

Xenograft Studies

Transplantation, growth, and harvesting of tumors from mice bearing the CWR22 and CWR22R xenografts were as previously described (Wainstein, M. A., supra; Nagabhushan, M., supra).

Confocal Microscopy and Live Cell Imaging

For Examples 7 and 8, COS-1 cells were transiently transfected by electroporation using a BTX square-wave pulser at 150 V, 1 ms duration. Cells were grown either on cover slips placed in 6-well tissue culture plates for indirect immunofluorescence or on Lab-Tek Chambered Coverglass (Nalge Nunc International) for live-cell microscopy. Transiently transfected cells were observed 16 hours after transfection by Leica TCS-SP confocal microscope. All live-cell experiments were done at 37° C.

For Examples 15 and 16, COS-1 cells were transfected by Fugene (Roche). Cells were grown either on cover slips placed in 6-well tissue culture plates for indirect immunofluorescence microscopy or on Lab-Tek Chambered Coverglass (Nalgene Nunc International) for live-cell microscopy. For immunoflourescence, transiently transfected cells were observed 18 hours after transfection by Leica TCS-SP laser scanning confocal microscope using 488-nm Argon laser line. All live-cell experiments were done on a Zeiss 510 laser scanning confocal microscope using a 100×/1.3 N.A. oil immersion objective and 40 mW argon laser at 37° C. Imaging was carried out in the Fluorescence Imaging Facility, Laboratory of Receptor Biology and Gene Expression, National Cancer Institute.

Indirect Immunofluorescence

Indirect immunofluorescence was carried out as previously described (Misteli et al., *Mol. Cell* 3:697-705, 1999). The following antibodies were used: anti-β-coat protein (β-COP) (Affinity Bioreagents), anti-mannosidase II (kindly provided by T. Misteli), anti-giantin (Covance), anti-TGN46 (Serotec), and anti-EEA1 (BD Transduction Labs). Texas Red-conjugated secondary antibodies specific for mouse and rabbit were purchased from Jackson Immunoresearch Laboratories.

Prostate Tissue Preparation and Microdissection

Radical prostatectomy specimens were obtained at Aker University Hospital and snap frozen upon resection. Sections were obtained and microdissected by a pathologist using Laser Capture Microdissection (LCM) as previously described (Bonner et al., *Science* 278:1481-1483, 1997).

Quantitative RT-PCR

Total RNA was extracted from the LCM samples using Absolutely RNA™ Microprep Kit (Stratagene), including DNAse treatment. RNA was used for first strand cDNA synthesis with the Superscript II system (Invitrogen). STAMP2 expression level was determined using the Light Cycler Instrument (Roche, Mannheim, Germany), with the Light Cycler-FastStart DNA Master SYBR Green I Kit (Roche). The primers used were Forward: 5'-TGC AAG TCG GCA GGT GTT TG-3' (SEQ ID NO: 74), and Reverse: 5'-GCA AAG CAT CCA GTG GTC AA-3' (SEQ ID NO: 75). A standard curve made from serial dilutions of cDNA was used to calculate the relative amount of STAMP2 in each sample. These values were then normalized to the relative amount of the internal standard ATP6 Synthase (ATP-6) in the same samples, calculated from a standard curve established in the same way. Primers used for ATP-6 amplification were Forward: 5'-CAG TGA TTA TAG GCT TTC GCT CTA A-3' (SEQ ID NO: 76), and Reverse: 5'-CAG GGC TAT TGG TTG AAT GAG TA-3' (SEQ ID NO: 77). The experiment was repeated twice with similar results.

Colony Formation Assay

Cells were either transfected with en empty expression plasmid pCDNA3 or one that encodes full length STAMP2 cDNA. 24 hours after transfection, cells were trypsinized and seeded on new plates (10000 cells/100 mm$^2$ dish). Selection antibiotic (G418, Sigma) was added and cells were cultured for two weeks. Cells were then fixed with cold methanol at −20° C. for 30 minutes. The colonies formed were stained with crystal violet (0.1%) and the area covered on each plate by the colonies were measured using an imaging system (Syngene). Results represent 3-5 experiments done at least in duplicate.

Effect of STAMP2 on Cell Growth

Cells were either transfected with an empty expression plasmid plus a GFP expression vector (control), or the GFP expression vector together with an expression vector that encodes full length STAMP2 cDNA in 1 to 5 ratio, thus insuring that the great majority of the cells that have the STAMP2 cDNA also have GFP. At indicated time points, cells were trypsinized, fixed with cold methanol at −20° C. for 30 minutes, and then counted for the GFP content by a FACS machine. The numbers of GFP positive cells were obtained and presented as the ratio between STAMP2 transfected compared with controls. Results presented are from at least two experiments done in duplicate.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follow in the scope of the appended claims.

```

What is claimed is:

1. A substantially pure polynucleotide sequence that comprises the STAMP2 nucleic acid sequence as set forth in SEQ ID NO: 33, or the fully complementary sequence thereof.

2. The substantially pure polynucleotide of claim 1, wherein said polynucleotide consists of the nucleic acid sequence of SEQ ID NO: 33, or the fully complementary sequence thereof.

3. A substantially pure polynucleotide comprising a sequence encoding a polypeptide that comprises the amino acid sequence of SEQ ID NO: 34, or the fully complementary sequence of said polynucleotide.

4. The substantially pure polynucleotide of claim 3, comprising a sequence encoding a polypeptide that consists of the amino acid sequence of SEQ ID NO: 34, or the fully complementary sequence of said polynucleotide.

5. The substantially pure polynucleotide of claim 3, wherein said polynucleotide comprises a sequence identical or fully complementary to at least 8 consecutive nucleotides of nucleotides 107-167 or nucleotides 1306-1360 of SEQ ID NO: 33.

6. A vector comprising the polynucleotide of claim 1, wherein said polynucleotide is positioned for expression.

7. A vector comprising the polynucleotide of claim 3, wherein said polynucleotide is positioned for expression.

* * * * *

SEQUENCE LISTING

<160> NUMBER OF SEQ ID NOS: 77

<210> SEQ ID NO 1
<211> LENGTH: 349
<212> TYPE: DNA
<213> ORGANISM: Homo sapiens

<400> SEQUENCE: 1
actaatgtga ggaaacaaac atgttcaggc ctgaacattt ccggtgctga ctcggcctta      60
aacgtttgtg ccataatgga aaatatctat ctatctgttc tcaaatcctg tttttctcat     120
agtgtaaact cacatttgat gtgtttttat gaaggaaagt aaccaagaaa cctctaggaa     180
ttaggaaaaa aagaactttt ttgaggtgtg ttactatact gctgtaagtt atttattata     240
taaagtattg taaatagaaa tagtgttgag atatgaaata tggctatttt taatggtgac     300
aattatagac ttttaggtca ctattaaatt ggggttacct atatccagt                 349

<210> SEQ ID NO 2
<211> LENGTH: 251
<212> TYPE: DNA
<213> ORGANISM: Homo sapiens

<400> SEQUENCE: 2
acacatccat cattgtgaaa tctcttttcc aacaaacgtc ctcttaatga gcacaattca      60
ttaaaatctt tggggactaa gctacgaaca aagttcaact aaactaccta ctgacttcaa     120
aaggaacata tacccaccac gtgtggtagc tcatgactgt aatcccagca ctttgggagg     180
ctgaggcagg aggatcacct gagcccagga gttccagacc agcctaagca acatgccaag     240
accctgtatg t                                                          251

<210> SEQ ID NO 3
<211> LENGTH: 51
<212> TYPE: DNA
<213> ORGANISM: Homo sapiens

<400> SEQUENCE: 3
acaaagacac ccttgtyccc cgggcaaggt cctccagcta caaggggcc a                51
```

<210> SEQ ID NO 4
<211> LENGTH: 149
<212> TYPE: DNA
<213> ORGANISM: Homo sapiens
<220> FEATURE:
<221> NAME/KEY: misc_feature
<222> LOCATION: 3
<223> OTHER INFORMATION: n = A,T,C or G

<400> SEQUENCE: 4

```
ccnyacattg tcacagagag gctccaggct taaagttgac ctgcgtagaa agcaagaatg        60
aattgttgga ggaagtaagg agggcgattg aataaagact tttagcagct gggccagctg       120
aaccatccca acccttcaaa tccccttgt                                         149
```

<210> SEQ ID NO 5
<211> LENGTH: 261
<212> TYPE: DNA
<213> ORGANISM: Homo sapiens

<400> SEQUENCE: 5

```
accctaactg aacccatttc agccactcag attgataggg tggaaaagac agggcaggtg        60
gtagcagctg tgaagaaaag aggaaagcag aagggtggcc tataatctac aggcatgtag       120
agaggactac ataggcctct gttctttgcc ctcaggagcc cccttcctgt cccttggact       180
cagaatggat ccttccagca cacatggccc aacactgaga gtgcaggaag catgggtagg       240
ggcctcctgc tgctggtatg t                                                 261
```

<210> SEQ ID NO 6
<211> LENGTH: 121
<212> TYPE: DNA
<213> ORGANISM: Homo sapiens
<220> FEATURE:
<221> NAME/KEY: misc_feature
<222> LOCATION: 4, 7, 13, 22, 24, 29, 30, 34, 36, 40, 46, 111, 112
<223> OTHER INFORMATION: n = A,T,C or G

<400> SEQUENCE: 6

```
agtntgnggg ganttgaggg cngntacgnn aaangntggn ctactntaga tgctgctcga        60
gcggccgcca gtgtgatgga tacaagcttt cttttttttt tttattttcg nnttttttt       120 c                                                                       121
```

<210> SEQ ID NO 7
<211> LENGTH: 93
<212> TYPE: DNA
<213> ORGANISM: Homo sapiens

<400> SEQUENCE: 7

```
actcagtagg gactgagcac taaatgctta ttttaaaaga aatgtaaaga gcagaaagca        60
attcaggcta ccctgccttt tgtgctggct agt                                     93
```

<210> SEQ ID NO 8
<211> LENGTH: 169
<212> TYPE: DNA
<213> ORGANISM: Homo sapiens

<400> SEQUENCE: 8

```
acacttaaaa tagttaatgt gatacatttt atgttacatg tattttgccc actgaaaaaa        60
taaaaatata taaacacaca gcaaatgatg accaggcctt tgaagaaagc ttataaaaca       120
```

| | |
|---|---|
| aaattaagaa gcctggctac agagcgagac tctgtctcaa aaaaaaaa | 169 |

<210> SEQ ID NO 9
<211> LENGTH: 262
<212> TYPE: DNA
<213> ORGANISM: Homo sapiens

<400> SEQUENCE: 9

| | |
|---|---|
| actttacaag catgaaggat attagggtaa gtggctaatt ataaatctac tctagagaca | 60 |
| tataatcata cagattattc ataaaatttt tcagtgctgt ccttccacat ttaattgcat | 120 |
| tttgctcaaa ctgtagaatg ccctacattc cccccacccc aatttgctat ttccttatta | 180 |
| aaatagaaaa ttataggcaa gatacaatta tatgcgttcc tcttcctgaa attataacat | 240 |
| ttctaaactt acccacgtag gt | 262 |

<210> SEQ ID NO 10
<211> LENGTH: 175
<212> TYPE: DNA
<213> ORGANISM: Homo sapiens

<400> SEQUENCE: 10

| | |
|---|---|
| acaggttggc ccttcaccta gttgactcag ccctcgatag tctagagccc accccctcct | 60 |
| caggaactca agagctcagc atttataatg agcagttggt aatgagttgc cctatgtgct | 120 |
| tgtcgcaagc agtcacagag atgagcccta ttacttgata ttcaggaaca aaggt | 175 |

<210> SEQ ID NO 11
<211> LENGTH: 331
<212> TYPE: DNA
<213> ORGANISM: Homo sapiens

<400> SEQUENCE: 11

| | |
|---|---|
| acatccaagc cttcctctgc gtgagagcaa aggctttgct catcagccag ccagtcttgt | 60 |
| tactatctgg ctacttttta aggttaaaaa ataaaaggca gtttctttgc tctgcaggcg | 120 |
| gcaaggcagg aggcgcaggc ctcttcattg ttcacatgtc acaggaggag gctctgagca | 180 |
| aaggccactg gcaagttagg gcaacaccaa gaaggctctg cggagagact ccctgtgggt | 240 |
| tgggggsctg gcaggaacgg tgcctgtgga ctgtttatgg tctgtccagt tgaggcttgg | 300 |
| taaacccaag taaagtgtta aaaacctcag t | 331 |

<210> SEQ ID NO 12
<211> LENGTH: 170
<212> TYPE: DNA
<213> ORGANISM: Homo sapiens

<400> SEQUENCE: 12

| | |
|---|---|
| acgactcatc cacctccggc tgaagctcca ggagctgaag daccccaatg aggatgagcc | 60 |
| aaacatccga gtgctccttg agcaccgctt ttacaaggaa aagagcaaga gcgtcaagca | 120 |
| gacctgtgac aagtgtaaca ccatcatctg ggggctcatt cagacctggt | 170 |

<210> SEQ ID NO 13
<211> LENGTH: 1720
<212> TYPE: DNA
<213> ORGANISM: Homo sapiens

<400> SEQUENCE: 13

| | |
|---|---|
| acgcggggga tccagcttgg gtaggcgggg aagcagctgg agtgcgaccg ctacggcagc | 60 |
| caccctgcaa ccgccagtcg gaggtgcact agagctaagg gcaagtcctg aggttgggcc | 120 |

-continued

```
caggagaaag aaggcaagga gacattgtcc caggtaggat ctaggatatt cttggtgatc        180
ttggaagtgt ccgtatcatg aatcaatct ctatgatggg aagccctaag agccttagtg         240
aaacttgttt acctaatggc ataaatggta tcaaagatgc aaggaaggtc actgtaggtg        300
tgattggaag tggagatttt gccaaatcct tgaccattcg acttattaga tgcggctatc        360
atgtggtcat aggaagtaga atcctaagt ttgcttctga atttttcct catgtggtag          420 atgtcactca tcatgaagat gctctcacaa aaacaaatat aatatttgtt gctatacaca        480
gagaacatta tacctccctg tgggacctga cacatctgct tgtgggtaaa atcctgattg        540
atgtgagcaa taacatgagg ataaaccagt acccagaatc caatgctgaa tatttggctt       600
cattattccc agattctttg attgtcaaag gatttaatgt tgtctcagct tgggcacttc       660
agttaggacc taaggatgcc agccggcagg tatgacaggt ttatatatgc agcaacaata       720
ttcaagcgcg acaacaggtt attgaacttg cccgccagtt gaatttcatt cccattgact       780
tgggatcctt atcatcagcc agagagattg aaaatttacc cctacgactc tttactttct      840
ggagagggcc agtggtggta gctataagct tggccacatt ttttttcctt tattcctttg       900
tcagagatgt gattcatcca tatgctagaa accaacagag tgacttttac aaaattccta      960
tagagattgt gaataaaacc ttacctatag ttgccattac tttgctctcc ctagtatacc     1020
ttgcaggtct tctggcagct gcttatcaac tttattacgg caccaagtat aggagatttc     1080
caccttggtt ggaaacctgg ttacagtgta gaaaacagct tggattacta agttttttct     1140
tcgctatggt ccatgttgcc tacagcctct gcttaccgat gagaaggtca gagagatatt     1200
tgtttctcaa catggcttat cagcaggtac tttaggttca tgcaaatatt gaaaactctt     1260
ggaatgagga agaagtttgg agaattgaaa tgtatatctc ctttggcata atgagccttg     1320
gcttactttc cctcctggca gtcacttcta tcccttcagt gagcaatgcc ttaaactgga     1380
gagaattcag ttttattcag gtatgccaat ctacacttgg atatgtcgct ctgctcataa     1440
gtactttcca tgttttaatt tatggatgga acgagctttt gaggaagag tactacagat      1500 tttatacacc accaaacttt gttcttgctc ttgttttgcc ctcaattgta attctgggta     1560 agatttatttt attccttcca tgtataagcc gaaagctaaa acgaattaaa aaaggctggg    1620
aaaagagcca atttctggaa gaaggtattg gaggaacaat tcctcatgtc tccccggaga    1680
gggtcacagt aatgtgatga taaatggtgt tcacagctgc                          1720
```

<210> SEQ ID NO 14
<211> LENGTH: 490
<212> TYPE: PRT
<213> ORGANISM: Homo sapiens

<400> SEQUENCE: 14

```
Met Glu Ser Ile Ser Met Met Gly Ser Pro Lys Ser Leu Ser Glu Thr
 1               5                  10                  15

Cys Leu Pro Asn Gly Ile Asn Gly Ile Lys Asp Ala Arg Lys Val Thr
                20                  25                  30

Val Gly Val Ile Gly Ser Gly Asp Phe Ala Lys Ser Leu Thr Ile Arg
            35                  40                  45

Leu Ile Arg Cys Gly Tyr His Val Val Ile Gly Ser Arg Asn Pro Lys
        50                  55                  60

Phe Ala Ser Glu Phe Phe Pro His Val Asp Val Thr His His Glu
65                  70                  75                  80

Asp Ala Leu Thr Lys Thr Asn Ile Ile Phe Val Ala Ile His Arg Glu
```

-continued

```
                85                  90                  95
His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
            115                 120                 125

Asn Ala Glu Tyr Leu Ala Ser Leu Phe Pro Asp Ser Leu Ile Val Lys
            130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
            195                 200                 205

Phe Thr Phe Trp Arg Gly Pro Val Val Ala Ile Ser Leu Ala Thr
210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Tyr Gln Leu Tyr Tyr Gly Thr Lys Tyr
            275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
            355                 360                 365

Gly Leu Leu Ser Leu Leu Ala Val Thr Ser Ile Pro Ser Val Ser Asn
            370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Leu Gly Lys Ile Ile
            435                 440                 445

Leu Phe Leu Pro Cys Ile Ser Arg Lys Leu Lys Arg Ile Lys Lys Gly
            450                 455                 460

Trp Glu Lys Ser Gln Phe Leu Glu Glu Gly Ile Gly Gly Thr Ile Pro
465                 470                 475                 480

His Val Ser Pro Glu Arg Val Thr Val Met
                485                 490

<210> SEQ ID NO 15
```

```
<211> LENGTH: 83
<212> TYPE: DNA
<213> ORGANISM: Homo sapiens

<400> SEQUENCE: 15
acgcggggga tccagcttgg gtaggcgggg aagcagctgg agtgcgaccg ctacggcagc    60
caccctgcaa ccgccagtcg gag                                           83

<210> SEQ ID NO 16
<211> LENGTH: 61
<212> TYPE: DNA
<213> ORGANISM: Homo sapiens

<400> SEQUENCE: 16
agctaagggc aagtcctgag gttgggccca ggagaaagaa ggcaaggaga cattgtccca    60
g                                                                   61

<210> SEQ ID NO 17
<211> LENGTH: 525
<212> TYPE: DNA
<213> ORGANISM: Homo sapiens

<400> SEQUENCE: 17
gatattcttg gtgatcttgg aagtgtccgt atcatggaat caatctctat gatgggaagc    60
cctaagagcc ttagtgaaac ttttttacct aatggcataa atggtatcaa agatgcaagg   120
aaggtcactg taggtgtgat tggaagtgga gattttgcca atccttgac cattcgactt    180 attagatgcg gctatcatgt ggtcatagga agtagaaatc ctaagtttgc ttctgaattt   240
tttcctcatg tggtagatgt cactcatcat gaagatgctc tcacaaaaac aaatataata   300
tttgttgcta tacacagaga acattatacc tccctgtggg acctgagaca tctgcttgtg   360
ggtaaaatcc tgattgatgt gagcaataac atgaggataa accagtaccc agaatccaat   420
gctgaatatt tggcttcatt attcccagat tctttgattg tcaaaggatt taatgttgtc   480
tcagcttggg cacttcagtt aggacctaag gatgccagcc ggcag                   525

<210> SEQ ID NO 18
<211> LENGTH: 528
<212> TYPE: DNA
<213> ORGANISM: Homo sapiens

<400> SEQUENCE: 18
gtttatatat gcagcaacaa tattcaagcg cgacaacagg ttattgaact tgcccgccag    60
ttgaatttca ttcccattga cttgggatcc ttatcatcag ccagagagat tgaaaattta   120
cccctacgac tctttactct ctggagaggg ccagtggtgg tagctataag cttggccaca   180
ttttttttcc tttattcctt tgtcagagat gtgattcatc catatgctag aaaccaacag   240
agtgactttt acaaaattcc tatagagatt gtgaataaaa ccttacctat agttgccatt   300
actttgctct ccctagtata cctcgcaggt cttctggcag ctgcttatca actttattac   360
ggcaccaagt ataggagatt ccaccttggt tggaaacct ggttacagtg tagaaaacag    420
cttggattac taagtttttt cttcgctatg gtccatgttg cctacagcct ctgcttaccg   480
atgagaaggt cagagagata tttgtttctc aacatggctt atcagcag                528

<210> SEQ ID NO 19
<211> LENGTH: 165
<212> TYPE: DNA
<213> ORGANISM: Homo sapiens
```

<400> SEQUENCE: 19

```
gttcatgcaa atattgaaaa ctcttggaat gaggaagaag tttggagaat tgaaatgtat      60
atctcctttg gcataatgag ccttggctta ctttccctcc tggcagtcac ttctatccct     120
tcagtgagca atgctttaaa ctggagagaa ttcagttttta ttcag                    165
```

<210> SEQ ID NO 20
<211> LENGTH: 148
<212> TYPE: DNA
<213> ORGANISM: Homo sapiens

<400> SEQUENCE: 20

```
tctacacttg atatgtcgc tctgctcata agtactttcc atgttttaat ttatggatgg       60
aaacgagctt ttgaggaaga gtactacaga ttttatacac caccaaactt tgttcttgct    120
cttgttttgc cctcaattgt aattctgg                                        148
```

<210> SEQ ID NO 21
<211> LENGTH: 2381
<212> TYPE: DNA
<213> ORGANISM: Homo sapiens

<400> SEQUENCE: 21

```
gtaagattat tttattcctt ccatgtataa gccgaaagct aaaacgaatt aaaaaaggct      60
gggaaaagag ccaatttctg gaagaaggta ttggaggaac aattcctcat gtctccccgg    120
agagggtcac agtaatgtga tgataaatgg tgttcacagc tgccatataa agttctactc    180
atgccattat ttttatgact tctacgttca gttacaagta tgctgtcaaa ttatcgtggg    240
ttgaaacttg ttaaatgaga tttcaactga cttagtgata gagttttctt caagttaatt    300
ttcacaaatg tcatgtttgc caatatgaat ttttctagtc aacatattat tgtaatttag    360
gtatgttttg ttttgttttg cacaactgta accctgttgt tactttatat ttcataatca    420
gacaaaaata cttacagtta ataatataga tataatgtta aaaacaattt gcaaaccagc    480 agaatttttaa gctttttaaaa taattcaatg gatatacatt tttttctgaa gattaagatt    540
ttaattattc aacttaaaaa gtagaaatgc attattatac atttttttaa gaaaggacac    600
gttatgttag catctaggta aggctgcatg atagcattcc tatatttctc tcataaaata    660
ggatttgaag gatgaaatta attgtatgaa gcaatgtgat tatatgaaga gacacaaatt    720
aaaaagacaa attaaacctg aaattatatt taaaatatat ttgagacatg aaatacatac    780
tgataataca tacctcatga aagatttttat tctttattgt gttacagagc agtttcatttt    840 tcatattaat atactgatca ggaagaggat tcagtaacat ttggcttcca aaactgctat    900
ctctaatacg gtaccaatcc taggaactgt atactagttc ctacttagaa caaaagtatc    960
aagtttgcac acaagtaatc tgccagctga cctttgtcgc accttaacca gtcaccactt   1020
gctatggtat aggattatac tgatgttctt tgagggattc tgatgtgcta ggcatggttc   1080
taagtacttt acttgtatta tcccatttaa tacttagaac aacccgtga gataagtagt    1140 tattatcctc attttacaca tgagggaccg aaggatagaa aagttatttt tcaaaggtct   1200
tgcagttaat aaatggcaga gtgagcattc aagtccaggt agtcatattc cagaggccac   1260
ggttttaacc actaggctct agagctcccg ccgcgccccct atgcattatg ttcacaatgc   1320
caatctagat gcttcctctt ttgtataaag tcactgacat tctttagagt gggttgggtg   1380
catccaaaaa tgtataaaaa tattattata ataaactat tactgcttgt agggtaattc    1440
```

-continued

```
acagttactt accctattct tgcttggaac atgagcctgg agacccatgg cagtccatat      1500
gcctccctat gcagtgaagg gccctagcag tgttaacaaa ttgctgagat cccacggagt      1560
ctttcaaaaa tctctgtaga gttagtcttc tccttttctc ttcctgagaa gttctcctgc      1620
ctgcataacc attcattagg gagtacttta caagcatgaa ggatattagg gtaagtggct      1680
aattataaat ctactctaga gacatataat catacagatt attcataaaa tttttcagtg      1740
ctgtccttcc acatttaatt gcattttgct caaactgtag aatgccctac attcccccca      1800
ccccaatttg ctatttcctt attaaaatag aaaattatag gcaagataca attatatgcg      1860
ttcctcttcc tgaaattata acatttctaa acttacccac gtagggacta ctgaatccaa      1920
ctgccaacaa taaaaagact tttatttagt agaggctacc tttcccccca gtgactcttt      1980
ttctacaact gccttgtcag tttggtaatt cacttatgat tttctaatgt tctcttggtg      2040
aattttatta tcttggaccc tctttttttt tttttttaaa gacagagtct tgctctgtca      2100
cccattgctc tcgtttgggc aacaagagtg aaactcttgt ctcaaaaaaa aaaaaaaatg      2160
aggtttaaga cagttttgtc attactggtg ggatctggtc acacaagata gcattaaacg      2220
tgacatggca cataaaattg gttaaaaaat tttgtttttt aattgcgtaa tgtaaaagcc      2280
caacaaacac tttatgcaag attggaatgt atcttcaaat tcagatttaa taaacatgta      2340
aagatcctct gtaaaaaaaa aaaaaaaaaa aaaaaaaaa a                           2381
```

<210> SEQ ID NO 22
<211> LENGTH: 4329
<212> TYPE: DNA
<213> ORGANISM: Homo sapiens

<400> SEQUENCE: 22

```
acgcggggga tccagcttgg gtaggcgggg aagcagctgg agtgcgaccg ctacggcagc       60
caccctgcaa ccgccagtcg gagagctaag ggcaagtcct gaggttgggc ccaggagaaa      120
gaaggcaagg agacattgtc ccaggatatt cttggtgatc ttggaagtgt ccgtatcatg      180
gaatcaatct ctatgatggg aagccctaag agccttagtg aaacttgttt acctaatggc      240
ataaatggta tcaaagatgc aaggaaggtc actgtaggtg tgattggaag tggagatttt      300
gccaaatcct tgaccattcg acttattaga tgcggctatc atgtggtcat aggaagtaga      360
aatcctaagt ttgcttctga attttttcct catgtggtag atgtcactca tcatgaagat      420
gctctcacaa aaacaaatat aatatttgtt gctatacaca gagaacatta tacctccctg      480
tgggacctga gacatctgct tgtgggtaaa atcctgattg atgtgagcaa taacatgagg      540
ataaaccagt acccagaatc caatgctgaa tatttggctt cattattccc agattctttg      600
attgtcaaag gatttaatgt tgtctcagct tgggcacttc agttaggacc taaggatgcc      660
agccggcagg tttatatatg cagcaacaat attcaagcgc gacaacaggt tattgaactt      720
gcccgccagt tgaatttcat tcccattgac ttgggatcct tatcatcagc cagagagatt      780
gaaaatttac ccctacgact ctttactttc tggagagggc cagtggtggt agctataagc      840
ttggccacat tttttttcct ttattccttt gtcagagatg tgattcatcc atatgctaga      900
aaccaacaga gtgacttta caaaattcct atagagattg tgaataaaac cttacctata      960
gttgccatta ctttgctctc cctagtatac cttgcaggtc ttctggcagc tgcttatcaa     1020
ctttattacg gcaccaagta taggagattt ccaccttggt tggaaacctg gttacagtgt     1080
agaaaacagc ttggattact aagttttttc ttcgctatgg tccatgttgc ctacagcctc     1140
tgcttaccga tgagaaggtc agagagatat ttgtttctca acatggctta tcagcaggtt     1200
```

```
catgcaaata ttgaaaactc ttggaatgag gaagaagttt ggagaattga aatgtatatc    1260
tcctttggca taatgagcct tggcttactt tccctcctgg cagtcacttc tatcccttca    1320
gtgagcaatg ccttaaactg gagagaattc agttttattc agtctacact tggatatgtc    1380
gctctgctca taagtacttt ccatgtttta atttatggat ggaaacgagc ttttgaggaa    1440
gagtactaca gattttatac accaccaaac tttgttcttg ctcttgtttt gccctcaatt    1500
gtaattctgg gtaagattat tttattcctt ccatgtataa gccgaaagct aaaacgaatt    1560
aaaaaaggct gggaaaagag ccaatttctg gaagaaggta ttggaggaac aattcctcat    1620
gtctccccgg agagggtcac agtaatgtga tgataaatgg tgttcacagc tgccatataa    1680
agttctactc atgccattat ttttatgact tctacgttca gttacaagta tgctgtcaaa    1740
ttatcgtggg ttgaaacttg ttaaatgaga tttcaactga cttagtgata gagttttctt    1800
caagttaatt ttcacaaatg tcatgtttgc caatatgaat ttttctagtc aacatattat    1860
tgtaatttag gtatgttttg ttttgttttg cacaactgta accctgttgt tactttatat    1920
ttcataatca gacaaaaata cttacagtta ataatataga tataatgtta aaaacaattt    1980
gcaaaccagc agaattttaa gcttttaaaa taattcaatg gatatacatt tttttctgaa    2040
gattaagatt ttaattattc aacttaaaaa gtagaaatgc attattatac attttttttaa    2100 gaaaggacac gttatgttag catctaggta aggctgcatg atagcattcc tatatttctc    2160
tcataaaata ggatttgaag gatgaaatta attgtatgaa gcaatgtgat tatatgaaga    2220
gacacaaatt aaaaagacaa attaaacctg aaattatatt taaatatat ttgagacatg    2280 aaatacatac tgataataca tacctcatga aagatttat tctttattgt gttacagagc    2340
agtttcattt tcatattaat atactgatca ggaagaggat tcagtaacat ttggcttcca    2400
aaactgctat ctctaatacg gtaccaatcc taggaactgt atactagttc ctacttagaa    2460
caaaagtatc aagtttgcac acaagtaatc tgccagctga cctttgtcgc accttaacca    2520
gtcaccactt gctatggtat aggattatac tgatgttctt tgagggattc tgatgtgcta    2580
ggcatggttc taagtacttt acttgtatta tcccatttaa tacttagaac aaccccgtga    2640
gataagtagt tattatcctc attttacaca tgagggaccg aaggatagaa aagttatttt    2700
tcaaaggtct tgcagttaat aaatggcaga gtgagcattc aagtccaggt agtcatattc    2760
cagaggccac ggttttaacc actaggctct agagctcccg ccgcgcccct atgcattatg    2820
ttcacaatgc caatctagat gcttcctctt ttgtataaag tcactgacat tctttagagt    2880
gggttgggtg catccaaaaa tgtataaaaa tattattata ataaacttat tactgcttgt    2940
agggtaattc acagttactt accctattct tgcttggaac atgagcctgg agacccatgg    3000
cagtccatat gcctccctat gcagtgaagg gccctagcag tgttaacaaa ttgctgagat    3060
cccacggagt ctttcaaaaa tctctgtaga gttagtcttc tccttttctc ttcctgagaa    3120
gttctcctgc ctgcataacc attcattagg gagtacttta caagcatgaa ggatattagg    3180
gtaagtggct aattataaat ctactctaga gacatataat catacagatt attcataaaa    3240 ttttttcagtg ctgtccttcc acatttaatt gcattttgct caaactgtag aatgccctac    3300 attccccccca ccccaatttg ctatttcctt attaaaaatg tataaaaata ttattataat    3360
aaacttatta ctgcttgtag ggtaattcac agttacttac cctattcttg cttggaacat    3420
gagcctggag acccatggca gtccatatgc ctccctatgc agtgaagggc cctagcagtg    3480
ttaacaaatt gctgagatcc cacggagtct ttcaaaaatc tctgtagagt tagtcttctc    3540
```

-continued

```
cttttctctt cctgagaagt tctcctgcct gcataaccat tcattaggga gtactttaca      3600
agcatgaagg atattagggt aagtggctaa ttataaatct actctagaga catataatca      3660
tacagattat tcataaaatt tttcagtgct gtccttccac atttaattgc attttgctca      3720
aactgtagaa tgccctacat tccccccacc ccaatttgct atttccttat taaaatagaa      3780
aattataggc aagatacaat tatatgcgtt cctcttcctg aaattataac atttctaaac      3840
ttacccacgt agggactact gaatccaact gccaacaata aaaagacttt tatttagtag      3900
aggctacctt tcccccagt gactcttttt ctacaactgc cttgtcagtt tggtaattca       3960
cttatgattt tctaatgttc tcttggtgaa ttttattatc ttggaccctc ttttttttt       4020 tttttaaaga cagagtcttg ctctgtcacc cattgctctc gtttgggcaa caagagtgaa      4080
actcttgtct caaaaaaaaa aaaaaatgag gtttaagaca gttttgtcat tactggtggg      4140
atctggtcac acaagatagc attaaacgtg acatggcaca taaaattggt taaaaaattt     4200 tgtttttttaa ttgcgtaatg taaaagccca acaaacactt tatgcaagat tggaatgtat    4260
cttcaaattc agatttaata aacatgtaaa gatcctctgt aaaaaaaaaa aaaaaaaaa      4320 aaaaaaaaa                                                              4329

<210> SEQ ID NO 23
<211> LENGTH: 1680
<212> TYPE: DNA
<213> ORGANISM: Homo sapiens

<400> SEQUENCE: 23
acgcggggga tccagcttgg gtaggcgggg aagcagctgg agtgcgaccg ctacggcagc        60
caccctgcaa ccgccagtcg gagagctaag ggcaagtcct gaggttgggc ccaggagaaa       120
gaaggcaagg agacattgtc ccaggatatt cttggtgatc ttggaagtgt ccgtatcatg       180
gaatcaatct ctatgatggg aagccctaag agccttagtg aaacttgttt acctaatggc       240
ataaatggta tcaaagatgc aaggaaggtc actgtaggtg tgattggaag tggagatttt       300
gccaaatcct tgaccattcg acttattaga tgcggctatc atgtggtcat aggaagtaga       360
aatcctaagt ttgcttctga attttttcct catgtggtag atgtcactca tcatgaagat       420
gctctcacaa aaacaaatat aatatttgtt gctatacaca gagaacatta tacctccctg      480
tgggacctga gacatctgct tgtgggtaaa atcctgattg atgtgagcaa taacatgagg      540
ataaaccagt acccagaatc caatgctgaa tatttggctt cattattccc agattctttg      600
attgtcaaag gatttaatgt tgtctcagct tgggcacttc agttaggacc taaggatgcc      660
agccggcagg tttatatatg cagcaacaat attcaagcgc gacaacaggt tattgaactt      720
gcccgccagt tgaatttcat tcccattgac ttgggatcct tatcatcagc cagagagatt      780
gaaaatttac ccctacgact ctttactttc tggagagggc cagtggtggt agctataagc      840
ttggccacat ttttttcct ttattccttt gtcagagatg tgattcatcc atatgctaga       900
aaccaacaga gtgactttta caaaattcct atagagattg tgaataaaac cttacctata       960
gttgccatta ctttgctctc cctagtatac cttgcaggtc ttctggcagc tgcttatcaa      1020
ctttattacg gcaccaagta taggagattt ccaccttggt tggaaacctg gttacagtgt     1080
agaaaacagc ttggattact aagttttttc ttcgctatgg tccatgttgc ctacagcctc     1140
tgcttaccga tgagaaggtc agagagatat ttgtttctca acatggctta tcagcaggtt     1200
catgcaaata ttgaaaactc ttggaatgag gaagaagttt ggagaattga aatgtatatc    1260
tcctttggca taatgagcct tggcttactt tccctcctgg cagtcacttc tatcccttca     1320
```

```
gtgagcaatg ccttaaactg gagagaattc agttttattc agtctacact tggatatgtc    1380
gctctgctca taagtacttt ccatgtttta atttatggat ggaaacgagc ttttgaggaa    1440
gagtactaca gattttatac accaccaaac tttgttcttg ctcttgtttt gccctcaatt    1500
gtaattctgg gtaagattat tttattcctt ccatgtataa gccgaaagct aaaacgaatt    1560
aaaaaaggct gggaaaagag ccaatttctg gaagaaggta ttggaggaac aattcctcat    1620
gtctccccgg agagggtcac agtaatgtga tgataaatgg tgttcacagc tgccatataa    1680
```

<210> SEQ ID NO 24
<211> LENGTH: 75
<212> TYPE: DNA
<213> ORGANISM: Homo sapiens

<400> SEQUENCE: 24

```
gatccagctt gggtaggcgg ggaagcagct ggagtgcgac cgccgcggca gccaccctgc     60
aaccgccagt cggag                                                      75
```

<210> SEQ ID NO 25
<211> LENGTH: 79
<212> TYPE: DNA
<213> ORGANISM: Homo sapiens

<400> SEQUENCE: 25

```
agagctaagg gcaagtcctg aggttgggcc caggagaaag aaggcaagga gacattgtcc     60
caggtaggat gtgtcccag                                                  79
```

<210> SEQ ID NO 26
<211> LENGTH: 718
<212> TYPE: DNA
<213> ORGANISM: Homo sapiens

<400> SEQUENCE: 26

```
atcttttgca gctttgcaga tacccagact gagctggaac tggaatttgt cttcctattg     60
actctacttc tttaaaagcg gctgcccatt acattcctca gctgtccttg cagttaggtg    120
tacatgtgac tgagtgttgg ccagtgagat gaagtctcct caaaggaagg cagcatgtgt    180 ccttttcat ccccttcatct tgctgctggg attgtggata taacaggagc cctggcagct    240
gtctccagag gatcaaagcc acacccaaag agtaaggcag attagagacc agaaagacct    300
tgactacttc cctacttcca ctgctttttc ctgcatttaa gccattgtaa atctgggtgt    360
gttacatgaa gtgaaaatta attctttctg cccttcagtt ctttatcctg ataccattta    420
acactgtctg aattaactag actgcaataa ttctttcttt tgaaagcttt taaggataa    480 tgtgcaattc acattaaaat tgattttcca ttgtcaatta gttatactca ttttcctgcc    540
ttgatctttc attagatatt ttgtatctgc ttggaatata ttatcttctt tttaactgtg    600
taattggtaa ttactaaaac tctgtaatct ccaaaatatt gctatcaaat tacacaccat    660
gttttctatc attctcatag atctgcctta taaacatta aataaaaagt actattta      718
```

<210> SEQ ID NO 27
<211> LENGTH: 2238
<212> TYPE: DNA
<213> ORGANISM: Homo sapiens

<400> SEQUENCE: 27

```
gatccagctt gggtaggcgg ggaagcagct ggagtgcgac cgccgcggca gccaccctgc     60
```
aaccgccagt cggagagagc taagggcaag tcctgaggtt gggccaagga gaaagaaggc     120
aaggagacat tgtcccaggt aggatgtgtc ccaggatatt cttggtgatc ttggaagtgt     180
ccgtatcatg gaatcaatct ctatgatggg aagccctaag agccttagtg aaacttttt     240 acctaatggc ataaatggta tcaaagatgc aaggaaggtc actgtaggtg tgattggaag     300
tggagatttt gccaaatcct tgaccattcg acttattaga tgcggctatc atgtggtcat     360
aggaagtaga atcctaagt ttgcttctga atttttcct catgtggtag atgtcactca       420
tcatgaagat gctctcacaa aaacaaatat aatatttgtt gctatacaca gagaacatta     480
tacctccctg tgggacctga gacatctgct tgtgggtaaa atcctgattg atgtgagcaa     540
taacatgagg ataaaccagt acccagaatc caatgctgaa tatttggctt cattattccc     600
agattctttg attgtcaaag gatttaatgt tgtctcagct tgggcacttc agttaggacc     660
taaggatgcc agccggcagg tttatatatg cagcaacaat attcaagcgc gacaacaggt     720
tattgaactt gcccgccagt tgaatttcat tcccattgac ttgggatcct tatcatcagc     780
cagagagatt gaaaatttac ccctacgact ctttactctc tggagagggc cagtggtggt     840
agctataagc ttggccacat tttttttcct ttattccttt gtcagagatg tgattcatcc     900
atatgctaga aaccaacaga gtgacttta caaaattcct atagagattg tgaataaaac      960
cttacctata gttgccatta cttcgtctc cctagtatac ctcgcaggtc ttctggcagc     1020
tgcttatcaa ctttattacg gcaccaagta taggagattt ccaccttggt tggaaacctg    1080
gttacagtgt agaaaacagc ttggattact aagttttttc ttcgctatgg tccatgttgc    1140
ctacagcctc tgcttaccga tgagaaggtc agagagatat ttgtttctca acatggctta    1200
tcagcaggtt catgcaaata ttgaaaactc ttggaatgag gaagaagttt ggagaattga    1260
aatgtatatc tcctttggca taatgagcct tggcttactt tccctcctgg cagtcacttc    1320
tatcccttca gtgagcaatg ctttaaactg gagagaattc agttttattc agtctacact    1380
tggatatgtc gctctgctca aagtacttt ccatgtttta atttatggat ggaaacgagc     1440
ttttgaggaa gagtactaca gatttttatac accaccaaac tttgttcttg ctcttgttt    1500 gccctcaatt gtaattctgg atcttttgca gctttgcaga tacccagact gagctggaac    1560
tggaatttgt cttcctattg actctacttc tttaaaagcg gctgcccatt acattcctca    1620
gctgtccttg cagttaggtg tacatgtgac tgagtgttgg ccagtgagat gaagtctcct    1680
caaaggaagg cagcatgtgt ccttttttcat cccttcatct tgctgctggg attgtggata    1740
taacaggagc cctggcagct gtctccagag gatcaaagcc acacccaaag agtaaggcag    1800
attagagacc agaaagacct tgactacttc cctacttcca ctgcttttc ctgcatttaa     1860 gccattgtaa atctgggtgt gttacatgaa gtgaaaatta attctttctg cccttcagtt    1920
ctttatcctg ataccatta acactgtctg aattaactag actgcaataa ttctttcttt     1980
tgaaagcttt taaaggataa tgtgcaattc acattaaaat tgattttcca ttgtcaatta    2040
gttatactca ttttcctgcc ttgatctttc attagatatt ttgtatctgc ttggaatata    2100
ttatcttctt tttaactgtg taattggtaa ttactaaaac tctgtaatct ccaaaatatt    2160
gctatcaaat tacacaccat gttttctatc attctcatag atctgcctta taaacattta    2220
aataaaaagt actattta                                                  2238

<210> SEQ ID NO 28
<211> LENGTH: 1561
<212> TYPE: DNA
<213> ORGANISM: Homo sapiens

<400> SEQUENCE: 28

```
gatccagctt gggtaggcgg ggaagcagct ggagtgcgac cgccgcggca gccaccctgc      60
aaccgccagt cggagagagc taagggcaag tcctgaggtt gggcccagga gaaagaaggc     120
aaggagacat tgtcccaggt aggatgtgtc ccaggatatt cttggtgatc ttggaagtgt     180
ccgtatcatg gaatcaatct ctatgatggg aagccctaag agccttagtg aaacttgttt     240
acctaatggc ataaatggta tcaaagatgc aaggaaggtc actgtaggtg tgattggaag     300
tggagatttt gccaaatcct tgaccattcg acttattaga tgcggctatc atgtggtcat     360
aggaagtaga atcctaagt ttgcttctga atttttttcct catgtggtag atgtcactca      420
tcatgaagat gctctcacaa aaacaaatat aatatttgtt gctatacaca gagaacatta     480
tacctccctg tgggacctga cacatctgct tgtgggtaaa atcctgattg atgtgagcaa     540
taacatgagg ataaaccagt acccagaatc caatgctgaa tatttggctt cattattccc     600
agattctttg attgtcaaag gatttaatgt tgtctcagct gggcacttc agttaggacc      660
taaggatgcc agccggcagg tttatatatg cagcaacaat attcaagcgc gacaacaggt     720
tattgaactt gcccgccagt tgaatttcat tcccattgac ttgggatcct tatcatcagc     780
cagagagatt gaaaatttac ccctacgact ctttactctc tggagagggc cagtggtggt     840
agctataagc ttggccacat ttttttttcct ttattccttt gtcagagatg tgattcatcc     900
atatgctaga aaccaacaga gtgacttta caaaattcct atagagattg tgaataaaac      960
cttacctata gttgccatta ctttgctctc cctagtatac ctcgcaggtc ttctggcagc    1020
tgcttatcaa cttaattacg gcaccaagta taggagattt ccaccttggt tggaaacctg    1080
gttacagtgt agaaaacagc ttggattact aagttttttc ttcgctatgg tccatgttgc    1140
ctacagcctc tgcttaccga tgagaaggtc agagagatat ttgtttctca acatggctta    1200
tcagcaggtt catgcaaata ttgaaaactc ttggaatgag gaagaagttt ggagaattga    1260
aatgtatatc tcctttggca aatgagcct tggcttactt tccctcctgg cagtcacttc     1320
tatcccttca gtgagcaatg ctttaaactg gagagaattc agtttattc agtctacact    1380
tggatatgtc gctctgctca aagtacttt ccatgtttta atttatggat ggaaacgagc      1440
tttttgaggaa gagtactaca gattttatac accaccaaac tttgttcttg ctcttgtttt    1500
gccctcaatt gtaattctgg atcttttgca gctttgcaga tacccagact gagctggaac    1560
t                                                                   1561
```

<210> SEQ ID NO 29
<211> LENGTH: 454
<212> TYPE: PRT
<213> ORGANISM: Homo sapiens

<400> SEQUENCE: 29

```
Met Glu Ser Ile Ser Met Met Gly Ser Pro Lys Ser Leu Ser Glu Thr
 1               5                  10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80
```

```
Asp Ala Leu Thr Lys Thr Asn Ile Ile Phe Val Ala Ile His Arg Glu
                 85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
                290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Asp Leu Leu Gln
        435                 440                 445

Leu Cys Arg Tyr Pro Asp
450
```

<210> SEQ ID NO 30
<211> LENGTH: 2102
<212> TYPE: DNA
<213> ORGANISM: Homo sapiens

<400> SEQUENCE: 30

```
ggatccagct tgggtaggcg gggaagcagc tggagtgcga ccgctacggc agccaccctg      60
caaccgccag tcggagagct aagggcaagt cctgaggttg ggcccaggag aaagaaggca     120
aggagacatt gtcccaggat attcttggtg atcttggaag tgtccgtatc atggaatcaa     180
tctctatgat gggaagccct aagagcctta gtgaaacttg tttacctaat ggcataaatg     240
gtatcaaaga tgcaaggaag gtcactgtag gtgtgattgg aagtggagat tttgccaaat     300
ccttgaccat tcgacttatt agatgcggct atcatgtggt cataggaagt agaaatccta     360
agtttgcttc tgaattttt cctcatgtgg tagatgtcac tcatcatgaa gatgctctca     420
caaaaacaaa tataatattt gttgctatac acagagaaca ttatacctcc ctgtgggacc     480
tgagacatct gcttgtgggt aaaatcctga ttgatgtgag caataacatg aggataaacc     540
agtacccaga atccaatgct gaatatttgg cttcattatt cccagattct tgattgtca      600
aaggatttaa tgttgtctca gcttgggcac ttcagttagg acctaaggat gccagccggc     660
aggtttatat atgcagcaac aatattcaag cgcgacaaca ggttattgaa cttgcccgcc     720
agttgaattt cattcccatt gacttgggat cctatcatc agccagagag attgaaaatt      780
taccctacg actctttact ttctggagag ggccagtggt ggtagctata agcttggcca      840
catttttttt cctttattcc tttgtcagag atgtgattca tccatatgct agaaaccaac     900
agagtgactt ttacaaaatt cctatagaga ttgtgaataa aaccttacct atagttgcca     960
ttactttgct ctccctagta taccttgcag gtcttctggc agctgcttat caactttatt    1020
acggcaccaa gtataggaga tttccaccct tggttggaaac ctggttacag tgtagaaaac    1080
agcttggatt actaagtttt ttcttcgcta tggtccatgt tgcctacagc ctctgcttac    1140
cgatgagaag gtcagagaga tatttgtttc tcaacatggc ttatcagcag gttcatgcaa    1200
atattgaaaa ctcttggaat gaggaagaag tttggagaat tgaaatgtat atctcctttg    1260
gcataatgag ccttggctta cttccctcc tggcagtcac ttctatccct tcggtgagca     1320
atgctttaaa ctggagagaa ttcagtttta ttcagatctt ttgcagcttt gcagataccc    1380
agactgagct ggaactggaa tttgtcttcc tattgactct acttctttaa aagcggctgc    1440
ccattacatt cctcagctgt ccttgcagtt aggtgtacat gtgactgagt gttggccagt    1500
gagatgaagt ctcctcaaag gaaggcagca tgtgtccttt ttcatccctt catcttgctg    1560
ctgggattgt ggatataaca ggagccctgg cagctgctcc agaggatcaa agccacaccc    1620
aaagagtaag gcagattaga gaccagaaag accttgacta cttccctact tccactgctt    1680
tttcctgcat ttaagccatt gtaaatctgg gtgtgttaca tgaagtgaaa attaattctt    1740
tctgcccttc agttctttat cctgatacca tttaacactg tctgaattaa ctagactgca    1800
ataattcttt cttttgaaag cttttaaagg ataatgtgca attcacatta aaattgattt    1860
tccattgtca attagttata ctcatttttcc tgccttgatc tttcattaga tattttgtat    1920
ctgcttggaa tatattatct tcttttttaac tgtgtaattg gtaattacta aaactctgta    1980
atctccaaaa tattgctatc aaattacaca ccatgttttc tatcattctc atagatctgc    2040
cttataaaca tttaaataaa aagtactatt taccaaaaaa aaaaaaaaaa aaaaaaaaa     2100
aa                                                                   2102
```

<210> SEQ ID NO 31
<211> LENGTH: 2102
<212> TYPE: DNA
<213> ORGANISM: Homo sapiens

<400> SEQUENCE: 31

```
ggatccagct tgggtaggcg gggaagcagc tggagtgcga ccgctacggc agccaccctg      60
caaccgccag tcggagagct aagggcaagt cctgaggttg ggcccaggag aaagaaggca     120
aggagacatt gtcccaggat attcttggtg atcttggaag tgtccgtatc atggaatcaa     180
tctctatgat gggaagccct aagagcctta gtgaaacttg tttacctaat ggcataaatg     240
gtatcaaaga tgcaaggaag gtcactgtag gtgtgattgg aagtggagat tttgccaaat     300
ccttgaccat tcgacttatt agatgcggct atcatgtggt cataggaagt agaaatccta     360
agtttgcttc tgaattttt cctcatgtgg tagatgtcac tcatcatgaa gatgctctca     420
caaaaacaaa tataatattt gttgctatac acagagaaca ttatacctcc ctgtgggacc     480
tgagacatct gcttgtgggt aaaatcctga ttgatgtgag caataacatg aggataaacc     540
agtacccaga atccaatgct gaatatttgg cttcattatt cccagattct ttgattgtca     600
aaggatttaa tgttgtctca gcttgggcac ttcagttagg acctaaggat gccagccggc     660
aggtttatat atgcagcaac aatattcaag cgcgacaaca ggttattgaa cttgcccgcc     720
agttgaattt cattcccatt gacttgggat ccttatcatc agccagagag attgaaaatt     780
taccctacg actctttact ttctggagag ggccagtggt ggtagctata agcttggcca     840
catttttttt cctttattcc tttgtcagag atgtgattca tccatatgct agaaaccaac     900
agagtgactt ttacaaaatt cctatagaga ttgtgaataa aaccttacct atagttgcca     960
ttactttgct ctccctagta taccttgcag gtcttctggc agctgcttat caactttatt    1020
acggcaccaa gtataggaga tttccacctt ggttggaaac ctggttacag tgtagaaaac    1080
agcttggatt actaagtttt ttcttcgcta tggtccatgt tgcctacagc ctctgcttac    1140
cgatgagaag gtcagagaga tatttgtttc tcaacatggc ttatcagcag gttcatgcaa    1200
atattgaaaa ctcttggaat gaggaagaag tttggagaat tgaaatgtat atctcctttg    1260
gcataatgag ccttggctta ctttccctcc tggcagtcac ttctatccct tcggtgagca    1320
atgctttaaa ctggagagaa ttcagtttta ttcagatctt ttgcagcttt gcagataccc    1380
agactgagct ggaactggaa tttgtcttcc tattgactct acttctttaa aagcggctgc    1440
ccattacatt cctcagctgt ccttgcagtt aggtgtacat gtgactgagt gttggccagt    1500
gagatgaagt ctcctcaaag gaaggcagca tgtgtccttt ttcatcccct tcatcttgctg    1560
ctgggattgt ggatataaca ggagccctgg cagctgctcc agaggatcaa agccacaccc    1620
aaagagtaag gcagattaga gaccagaaag accttgacta cttccctact tccactgctt    1680
tttcctgcat ttaagccatt gtaaatctgg gtgtgttaca tgaagtgaaa attaattctt    1740
tctgccctcc agttctttat cctgatacca tttaacactg tctgaattaa ctagactgca    1800
ataattcttt cttttgaaag cttttaaagg ataatgtgca attcacatta aaattgattt    1860
tccattgtca attagttata ctcatttcc tgccttgatc tttcattaga tatttgtat     1920
ctgcttggaa tatattatct tcttttaac tgtgtaattg gtaattacta aaactctgta    1980
atctccaaaa tattgctatc aaattacaca ccatgtttc tatcattctc atagatctgc    2040
cttataaaca tttaaataaa aagtactatt taccaaaaaa aaaaaaaaaa aaaaaaaaaa    2100
aa                                                                  2102
```

<210> SEQ ID NO 32
<211> LENGTH: 419
<212> TYPE: PRT

<213> ORGANISM: Homo sapiens

<400> SEQUENCE: 32

```
Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Phe Trp Arg Gly Pro Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ile Phe Cys Ser Phe
385                 390                 395                 400
```

```
Ala Asp Thr Gln Thr Glu Leu Glu Leu Glu Phe Val Phe Leu Leu Thr
            405                 410                 415

Leu Leu Leu

<210> SEQ ID NO 33
<211> LENGTH: 1396
<212> TYPE: DNA
<213> ORGANISM: Homo sapiens

<400> SEQUENCE: 33
acagatctat ggagaaaact tgtatagatg cacttcctct tactatgaat tcttcagaaa      60
agcaagagac tgtatgtatt tttggaactg gtgattttgg aagatcactg ggattgaaaa     120
tgctccagtg tggttattct gttgtttttg gaagtcgaaa cccccagaag accaccctac     180
tgcccagtgg tgcagaagtc ttgagctatt cagaagcagc caagaagtct gacatcataa     240
tcatagcaat ccacagagag cattatgatt ttctcacaga attaactgag gttctcaatg     300
gaaaaatatt ggtagacatc agcaacaacc tcaaaatcaa tcaatatcca gaatctaatg     360
cagagtacct tgctcatttg gtgccaggag cccacgtggt aaaagcattt aacaccatct     420
cagcctgggc tctccagtca ggagcactgg atgcaagtcg gcaggtgttt gtgtgtggaa     480
atgacagcaa agccaagcaa agagtgatgg atattgttcg taatcttgga cttactccaa     540
tggatcaagg atcactcatg gcagccaaag aaattgaaaa gtaccccctg cagctatttc     600
caatgtggag gttccccttc tatttgtctg ctgtgctgtg tgtcttcttg ttttctatt      660 gtgttataag agacgtaatc taccttatg tttatgaaaa gaaagataat acatttcgta     720
tggctatttc cattccaaat cgtatctttc caataacagc acttacactg cttgctttgg     780
tttacctccc tggtgttatt gctgccattc tacaactgta ccgaggcaca aaataccgtc     840
gattcccaga ctggcttgac cactggatgc tttgccgaaa gcagcttggc ttggtagctc     900
tgggatttgc cttccttcat gtcctctaca cacttgtgat tcctattcga tattatgtac     960
gatggagatt gggaaactta accgttaccc aggcaatacc caagaaggag aatccattta    1020
gcacctcctc agcctggctc agtgattcat atgtggcttt gggaatactt gggttttttc    1080
tgtttgtact cttgggaatc acttctttgc catctgttag caatgcagtc aactggagag    1140
agttccgatt tgtccagtcc aaactgggtt atttgaccct gatcttgtgt acagcccaca    1200
ccctggtgta cggtgggaag agattcctca gcccttcaaa tctcagatgg tatcttcctg    1260
cagcctacgt gttagggctt atcattcctt gcactgtgct ggtgatcaag tttgtcctaa    1320
tcatgccatg tgtagacaac accccttacaa ggatccgcca gggctgggaa aggaactcaa    1380
aacactagct cgaggt                                                    1396

<210> SEQ ID NO 34
<211> LENGTH: 459
<212> TYPE: PRT
<213> ORGANISM: Homo sapiens
<220> FEATURE:
<221> NAME/KEY: VARIANT
<222> LOCATION: 122
<223> OTHER INFORMATION: Xaa = Ala or Thr
<220> FEATURE:
<221> NAME/KEY: VARIANT
<222> LOCATION: 331
<223> OTHER INFORMATION: Xaa = Pro or Leu

<400> SEQUENCE: 34

Met Glu Lys Thr Cys Ile Asp Ala Leu Pro Leu Thr Met Asn Ser Ser
  1               5                  10                  15
```

-continued

```
Glu Lys Gln Glu Thr Val Cys Ile Phe Gly Thr Gly Asp Phe Gly Arg
             20                  25                  30
Ser Leu Gly Leu Lys Met Leu Gln Cys Gly Tyr Ser Val Val Phe Gly
             35                  40                  45
Ser Arg Asn Pro Gln Lys Thr Thr Leu Leu Pro Ser Gly Ala Glu Val
 50                  55                  60
Leu Ser Tyr Ser Glu Ala Ala Lys Lys Ser Asp Ile Ile Ile Ala
 65                  70                  75                  80
Ile His Arg Glu His Tyr Asp Phe Leu Thr Glu Leu Thr Glu Val Leu
                 85                  90                  95
Asn Gly Lys Ile Leu Val Asp Ile Ser Asn Asn Leu Lys Ile Asn Gln
             100                 105                 110
Tyr Pro Glu Ser Asn Ala Glu Tyr Leu Xaa His Leu Val Pro Gly Ala
             115                 120                 125
His Val Val Lys Ala Phe Asn Thr Ile Ser Ala Trp Ala Leu Gln Ser
 130                 135                 140
Gly Ala Leu Asp Ala Ser Arg Gln Val Phe Val Cys Gly Asn Asp Ser
145                 150                 155                 160
Lys Ala Lys Gln Arg Val Met Asp Ile Val Arg Asn Leu Gly Leu Thr
                 165                 170                 175
Pro Met Asp Gln Gly Ser Leu Met Ala Ala Lys Glu Ile Glu Lys Tyr
             180                 185                 190
Pro Leu Gln Leu Phe Pro Met Trp Arg Phe Pro Phe Tyr Leu Ser Ala
             195                 200                 205
Val Leu Cys Val Phe Leu Phe Tyr Cys Val Ile Arg Asp Val Ile
 210                 215                 220
Tyr Pro Tyr Val Tyr Glu Lys Lys Asp Asn Thr Phe Arg Met Ala Ile
225                 230                 235                 240
Ser Ile Pro Asn Arg Ile Phe Pro Ile Thr Ala Leu Thr Leu Leu Ala
                 245                 250                 255
Leu Val Tyr Leu Pro Gly Val Ile Ala Ala Ile Leu Gln Leu Tyr Arg
             260                 265                 270
Gly Thr Lys Tyr Arg Arg Phe Pro Asp Trp Leu Asp His Trp Met Leu
             275                 280                 285
Cys Arg Lys Gln Leu Gly Leu Val Ala Leu Gly Phe Ala Phe Leu His
 290                 295                 300
Val Leu Tyr Thr Leu Val Ile Pro Ile Arg Tyr Tyr Val Arg Trp Arg
305                 310                 315                 320
Leu Gly Asn Leu Thr Val Thr Gln Ala Ile Xaa Lys Lys Glu Asn Pro
                 325                 330                 335
Phe Ser Thr Ser Ser Ala Trp Leu Ser Asp Ser Tyr Val Ala Leu Gly
             340                 345                 350
Ile Leu Gly Phe Phe Leu Phe Val Leu Leu Gly Ile Thr Ser Leu Pro
             355                 360                 365
Ser Val Ser Asn Ala Val Asn Trp Arg Glu Phe Arg Phe Val Gln Ser
 370                 375                 380
Lys Leu Gly Tyr Leu Thr Leu Ile Leu Cys Thr Ala His Thr Leu Val
385                 390                 395                 400
Tyr Gly Gly Lys Arg Phe Leu Ser Pro Ser Asn Leu Arg Trp Tyr Leu
                 405                 410                 415
Pro Ala Ala Tyr Val Leu Gly Leu Ile Ile Pro Cys Thr Val Leu Val
             420                 425                 430
```

Ile Lys Phe Val Leu Ile Met Pro Cys Val Asp Asn Thr Leu Thr Arg
        435                 440                 445

Ile Arg Gln Gly Trp Glu Arg Asn Ser Lys His
        450                 455

<210> SEQ ID NO 35
<211> LENGTH: 3910
<212> TYPE: DNA
<213> ORGANISM: Homo sapiens

<400> SEQUENCE: 35

| | | | | | |
|---|---|---|---|---|---|
| acccttcgcc | gcggaccttc | agctgccgcg | gtcgctccga | gcggcgggcc | gcagaggttc | 60 |
| aagcgattct | cctgcttcag | cctccggagt | agctgggatt | acaggcacgt | gccaacacac | 120 |
| ccagccacca | aaatgccaga | agagatggac | aagccactga | tcagcctcca | cctggtggac | 180 |
| agcgatagta | gccttgccaa | ggtccccgat | gaggccccca | agtgggcat | cctgggtagc | 240 |
| ggggactttg | cccgctccct | ggccacacgc | ctggtgggct | ctggcttcaa | agtggtggtg | 300 |
| gggagccgca | accccaaacg | cacagccagg | ctgtatccct | cagcggccca | agtgactttc | 360 |
| caagaggagg | cagtgagctc | cccggaggtc | atctttgtgg | ctgtgttccg | ggagcactac | 420 |
| tcttcactgt | gcagtctcag | tgaccagctg | gcgggcaaga | tcctggtgga | tgtgagcaac | 480 |
| cctacagagc | aagagcacct | tcagcatcgt | gagtccaatg | ctgagtacct | ggcctccctc | 540 |
| ttccccactt | gcacagtggt | caaggccttc | aatgtcatct | ctgcctggac | cctgcaggct | 600 |
| ggcccaaggg | atggtaacag | gcaggtgccc | atctgcggtg | accagccaga | agccaagcgt | 660 |
| gctgtctcgg | agatggcgct | cgccatgggc | ttcatgcccg | tggacatggg | atccctggcg | 720 |
| tcagcctggg | aggtggaggc | catgcccctg | cgcctcctcc | cggcctggaa | ggtgcccacc | 780 |
| ctgctggccc | tggggctctt | cgtctgcttc | tatgcctaca | acttcgtccg | ggacgttctg | 840 |
| cagcccctatg | tgcaggaaag | ccagaacaag | ttcttcaagc | tgcccgtgtc | cgtggtcaac | 900 |
| accacactgc | cgtgcgtggc | ctacgtgctg | ctgtcactcg | tgtacttgcc | cggcgtgctg | 960 |
| gcggctgccc | tgcagctgcg | gcgcggcacc | aagtaccagc | gcttccccga | ctggctggac | 1020 |
| cactggctac | agcaccgcaa | gcagatcggg | ctgctcagct | tcttctgcgc | cgccctgcac | 1080 |
| gccctctaca | gcttctgctt | gccgctgcgc | cgcgcccacc | gctacgacct | ggtcaacctg | 1140 |
| gcagtcaagc | aggtcttggc | caacaagagc | caccctctggg | tggaggagga | ggtctggcgg | 1200 |
| atggagatct | acctctcccct | gggagtgctg | gccctcggca | cgttgtccct | gctggccgtg | 1260 |
| acctcactgc | cgtccattgc | aaactcgctc | aactggaggg | agttcagctt | cgttcagtcc | 1320 |
| tcactgggct | ttgtggccct | cgtgctgagc | acactgcaca | cgctcaccta | cggctggacc | 1380 |
| cgcgccttcg | aggagagccg | ctacaagttc | tacctgcctc | ccaccttcac | gctcacgctg | 1440 |
| ctggtgccct | cgtcgtcat | cctggccaaa | gccctgtttc | tcctgccctg | catcagccgc | 1500 |
| agactcgcca | ggatccggag | aggctgggag | agggagagca | ccatcaagtt | cacgctgccc | 1560 |
| acagaccacg | ccctggccga | aagacgagc | cacgtatgag | gtgcctgccc | tgggctctgg | 1620 |
| accccgggca | cacgagggac | ggtgcccctga | gcccgttagg | ttttcttttc | ttggtggtgc | 1680 |
| aaagtggtat | aactgtgtgc | aaataggagg | tttgaggtcc | aaattcctgg | gactcaaatg | 1740 |
| tatgcagtac | tattcagaat | gatatacaca | catatgtgta | tatgtattta | catatattcc | 1800 |
| acatatataa | caggatttgc | aattatacat | agctagctaa | aaagttgggt | ctctgagatt | 1860 |
| tcaacttgta | gatttaaaaa | caagtgccgt | acgttaagag | aagagcagat | catgctattg | 1920 |
| tgacatttgc | agagatatac | acacactttt | tgtacagaag | aggcttgtgc | tgtggtgggt | 1980 |

```
tcgatttatc cctgcccacc ccatcccacc aacttcccct ttgctacttc cccaaggctc    2040
ttgcagagct agggctctga aggggaggga aggcaacggc tctgcccaga gccatccctg    2100
gagcatgtga gcagcggctg gtctcttccc tccacctggg gcagcagcag gaggcctggg    2160
ggggaggaaa atcaggcagt cggcctggag tctgtgcctg gtcctttgcc cggtggtggg    2220
aggatggagg gattgggctg aagctgctcc acctcatcct tgctgagtgg gggagacatt    2280
ttccctgaaa gtcagaagtc accatagagc ctgcaaatgg atcctcctgt gagagtgacg    2340
tcacctcctt tccagagcca ttagtgagcc tggcttggga acaagtgtaa tttccttccc    2400
tcctttaacc tggcgatgag cgtcctttaa accactgtgc cttctcaccc tttccatctt    2460
cagtttgaac gactcccagg aaggcctaga gcagacccct tagaaatcag cccaaggggg    2520
agagcaagag aaaacactct agggagtaaa gctccccggg cgtcagagtt gagccctgcc    2580
tgggctgaag gactgtcttc acgaagtcag tcctgaggaa aaatattggg gactccaaat    2640
gtcctctggc agaggaccca gaaaaccaca ctggctccaa cttcctcctc atggggcatt    2700
acacttcaaa acagtgggga gcaacttttc caccaaagct acaaacctaa aatgctgctg    2760
ccccaaagca caagagggaa gagcaccgcc ggggccacag gacgtctgtc ctccagtcac    2820
aggccatcct tgctgctccc tactgactct agcttacttc ccctgtgaag aaacaggtgt    2880
tctcggctga gcccccaacc ctctgcagaa ccaggttgat ctgccacaga aaaagcatct    2940
ttgaagacaa agagggtgag gtcttcatga gtctcctggg cccaaagcca tcttctgatg    3000
gaaggaagag agtagggcca gtgaaggctg cccagagaga atgtcacaga tgaggctgcc    3060
cctgccccct ccccgccagg gaggtttcat gagctcatgt ctatgcagca cataagggtt    3120
cttcagtgaa aagcaggaga agagcccact gcaaggatag ctcattaggc acatgaccga    3180
tgcagggaag gccatgccgg ggaagctctt cctgcaggta ttttccatct gctgtgccaa    3240
ggctgagcgg cagaaacttg tctcataaat tggcactgat ggagcatcag ctgtggccca    3300
cagagagcct tgctgagaag ggggcaggta aagcagagat tttagcattg ccttggcata    3360
acaagggccc atcgattccc tactaatgag aggcaggag agcatgggca atggagaccc    3420
accaatgatc cccaaccccg gtgggtactg gctgcctgcc ctgggccagg gaatggctcc    3480
ttataccaaa gatgctggca catagcagaa cccagtgcac gtcctcccct tcccacccac    3540
ctctggctga aggtgctcaa gagggaagca attataaggt gggtggcagg agggaacagg    3600
tgccacctgc tggacaatca cacgaaaggc aggcgggctg tgtactgggc cctgactgtg    3660
cgtccactgc tgtcttccct acctcaccag gctactggca gcagcatccc gagagcacat    3720
catctccaca gcctggtaaa ttccatgtgc ctctgggtac aaaagtgcct caacgacatg    3780
ctctggaaat cccaaatgcc acagtctgag gttgatatct aaaatctatg ccttcaaaag    3840
agtctctgtt ttttttttt aacctggtag acggtataaa agcagtgcaa ataaacacct    3900
aaccttctgc                                                          3910
```

<210> SEQ ID NO 36
<211> LENGTH: 488
<212> TYPE: PRT
<213> ORGANISM: Homo sapiens

<400> SEQUENCE: 36

```
Met Pro Glu Glu Met Asp Lys Pro Leu Ile Ser Leu His Leu Val Asp
 1               5                  10                  15

Ser Asp Ser Ser Leu Ala Lys Val Pro Asp Glu Ala Pro Lys Val Gly
```

```
                    20                  25                  30
Ile Leu Gly Ser Gly Asp Phe Ala Arg Ser Leu Ala Thr Arg Leu Val
            35                  40                  45
Gly Ser Gly Phe Lys Val Val Gly Ser Arg Asn Pro Lys Arg Thr
        50                  55                  60
Ala Arg Leu Tyr Pro Ser Ala Ala Gln Val Thr Phe Gln Glu Glu Ala
65                  70                  75                  80
Val Ser Ser Pro Glu Val Ile Phe Val Ala Val Phe Arg Glu His Tyr
                85                  90                  95
Ser Ser Leu Cys Ser Leu Ser Asp Gln Leu Ala Gly Lys Ile Leu Val
            100                 105                 110
Asp Val Ser Asn Pro Thr Glu Gln Glu His Leu Gln His Arg Glu Ser
            115                 120                 125
Asn Ala Glu Tyr Leu Ala Ser Leu Phe Pro Thr Cys Thr Val Val Lys
            130                 135                 140
Ala Phe Asn Val Ile Ser Ala Trp Thr Leu Gln Ala Gly Pro Arg Asp
145                 150                 155                 160
Gly Asn Arg Gln Val Pro Ile Cys Gly Asp Gln Pro Glu Ala Lys Arg
                165                 170                 175
Ala Val Ser Glu Met Ala Leu Ala Met Gly Phe Met Pro Val Asp Met
            180                 185                 190
Gly Ser Leu Ala Ser Ala Trp Glu Val Glu Ala Met Pro Leu Arg Leu
        195                 200                 205
Leu Pro Ala Trp Lys Val Pro Thr Leu Leu Ala Leu Gly Leu Phe Val
    210                 215                 220
Cys Phe Tyr Ala Tyr Asn Phe Val Arg Asp Val Leu Gln Pro Tyr Val
225                 230                 235                 240
Gln Glu Ser Gln Asn Lys Phe Lys Leu Pro Val Ser Val Asn
                245                 250                 255
Thr Thr Leu Pro Cys Val Ala Tyr Val Leu Leu Ser Leu Val Tyr Leu
            260                 265                 270
Pro Gly Val Leu Ala Ala Leu Gln Leu Arg Arg Gly Thr Lys Tyr
            275                 280                 285
Gln Arg Phe Pro Asp Trp Leu Asp His Trp Leu Gln His Arg Lys Gln
    290                 295                 300
Ile Gly Leu Leu Ser Phe Cys Ala Ala Leu His Ala Leu Tyr Ser
305                 310                 315                 320
Phe Cys Leu Pro Leu Arg Arg Ala His Arg Tyr Asp Leu Val Asn Leu
            325                 330                 335
Ala Val Lys Gln Val Leu Ala Asn Lys Ser His Leu Trp Val Glu Glu
            340                 345                 350
Glu Val Trp Arg Met Glu Ile Tyr Leu Ser Leu Gly Val Leu Ala Leu
        355                 360                 365
Gly Thr Leu Ser Leu Leu Ala Val Thr Ser Leu Pro Ser Ile Ala Asn
    370                 375                 380
Ser Leu Asn Trp Arg Glu Phe Ser Phe Val Gln Ser Ser Leu Gly Phe
385                 390                 395                 400
Val Ala Leu Val Leu Ser Thr Leu His Thr Leu Thr Tyr Gly Trp Thr
                405                 410                 415
Arg Ala Phe Glu Glu Ser Arg Tyr Lys Phe Tyr Leu Pro Pro Thr Phe
            420                 425                 430
Thr Leu Thr Leu Leu Val Pro Cys Val Val Ile Leu Ala Lys Ala Leu
            435                 440                 445
```

```
Phe Leu Leu Pro Cys Ile Ser Arg Arg Leu Ala Arg Ile Arg Arg Gly
    450                 455                 460
Trp Glu Arg Glu Ser Thr Ile Lys Phe Thr Leu Pro Thr Asp His Ala
465                 470                 475                 480
Leu Ala Glu Lys Thr Ser His Val
                485

<210> SEQ ID NO 37
<211> LENGTH: 339
<212> TYPE: PRT
<213> ORGANISM: Homo sapiens

<400> SEQUENCE: 37

Met Glu Ser Arg Lys Asp Ile Thr Asn Gln Glu Leu Trp Lys Met
  1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                 85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Leu Ile Phe
    290                 295                 300

Lys Ser Ile Leu Phe Leu Pro Cys Leu Arg Lys Ile Leu Lys Ile
305                 310                 315                 320

Arg His Gly Trp Glu Asp Val Thr Lys Ile Asn Lys Thr Glu Ile Cys
```

Ser Gln Leu
            325         330         335

<210> SEQ ID NO 38
<211> LENGTH: 488
<212> TYPE: PRT
<213> ORGANISM: Homo sapiens

<400> SEQUENCE: 38

Met Pro Glu Glu Met Asp Lys Pro Leu Ile Ser Leu His Leu Val Asp
  1               5                  10                  15

Ser Asp Ser Ser Leu Ala Lys Val Pro Asp Glu Ala Pro Lys Val Gly
             20                  25                  30

Ile Leu Gly Ser Gly Asp Phe Ala Arg Ser Leu Ala Thr Arg Leu Val
         35                  40                  45

Gly Ser Gly Phe Lys Val Val Val Gly Ser Arg Asn Pro Lys Arg Thr
     50                  55                  60

Ala Arg Leu Tyr Pro Ser Ala Ala Gln Val Thr Phe Gln Glu Glu Ala
 65                  70                  75                  80

Val Ser Ser Pro Glu Val Ile Phe Val Ala Val Phe Arg Glu His Tyr
                 85                  90                  95

Ser Ser Leu Cys Ser Leu Ser Asp Gln Leu Ala Gly Lys Ile Leu Val
            100                 105                 110

Asp Val Ser Asn Pro Thr Glu Gln Glu His Leu Gln His Arg Glu Ser
        115                 120                 125

Asn Ala Glu Tyr Leu Ala Ser Leu Phe Pro Thr Cys Thr Val Val Lys
    130                 135                 140

Ala Phe Asn Val Ile Ser Ala Trp Thr Leu Gln Ala Gly Pro Arg Asp
145                 150                 155                 160

Gly Asn Arg Gln Val Pro Ile Cys Gly Asp Gln Pro Glu Ala Lys Arg
                165                 170                 175

Ala Val Ser Glu Met Ala Leu Ala Met Gly Phe Met Pro Val Asp Met
            180                 185                 190

Gly Ser Leu Ala Ser Ala Trp Glu Val Glu Ala Met Pro Leu Arg Leu
        195                 200                 205

Leu Pro Ala Trp Lys Val Pro Thr Leu Leu Ala Leu Gly Leu Phe Val
    210                 215                 220

Cys Phe Tyr Ala Tyr Asn Phe Val Arg Asp Val Leu Gln Pro Tyr Val
225                 230                 235                 240

Gln Glu Ser Gln Asn Lys Phe Phe Lys Leu Pro Val Ser Val Val Asn
                245                 250                 255

Thr Thr Leu Pro Cys Val Ala Tyr Val Leu Leu Ser Leu Val Tyr Leu
            260                 265                 270

Pro Gly Val Leu Ala Ala Ala Leu Gln Leu Arg Arg Gly Thr Lys Tyr
        275                 280                 285

Gln Arg Phe Pro Asp Trp Leu Asp His Trp Leu Gln His Arg Lys Gln
    290                 295                 300

Ile Gly Leu Leu Ser Phe Phe Cys Ala Ala Leu His Ala Leu Tyr Ser
305                 310                 315                 320

Phe Cys Leu Pro Leu Arg Arg Ala His Arg Tyr Asp Leu Val Asn Leu
                325                 330                 335

Ala Val Lys Gln Val Leu Ala Asn Lys Ser His Leu Trp Val Glu Glu
            340                 345                 350

Glu Val Trp Arg Met Glu Ile Tyr Leu Ser Leu Gly Val Leu Ala Leu

-continued

```
                355                 360                 365
Gly Thr Leu Ser Leu Leu Ala Val Thr Ser Leu Pro Ser Ile Ala Asn
        370                 375                 380

Ser Leu Asn Trp Arg Glu Phe Ser Phe Val Gln Ser Ser Leu Gly Phe
385                 390                 395                 400

Val Ala Leu Val Leu Ser Thr Leu His Thr Leu Thr Tyr Gly Trp Thr
                405                 410                 415

Arg Ala Phe Glu Glu Ser Arg Tyr Lys Phe Tyr Leu Pro Pro Thr Phe
            420                 425                 430

Thr Leu Thr Leu Leu Val Pro Cys Val Val Ile Leu Ala Lys Ala Leu
        435                 440                 445

Phe Leu Leu Pro Cys Ile Ser Arg Arg Leu Ala Arg Ile Arg Arg Gly
    450                 455                 460

Trp Glu Arg Glu Ser Thr Ile Lys Phe Thr Leu Pro Thr Asp His Ala
465                 470                 475                 480

Leu Ala Glu Lys Thr Ser His Val
                485
```

<210> SEQ ID NO 39
<211> LENGTH: 283
<212> TYPE: PRT
<213> ORGANISM: Homo sapiens

<400> SEQUENCE: 39

```
Met Glu Lys Thr Cys Ile Asp Ala Leu Pro Leu Thr Met Asn Ser Ser
1               5                   10                  15

Glu Lys Gln Glu Thr Val Cys Ile Phe Gly Thr Gly Asp Phe Gly Arg
            20                  25                  30

Ser Leu Gly Leu Lys Met Leu Gln Cys Gly Tyr Ser Val Val Phe Gly
        35                  40                  45

Ser Arg Asn Pro Gln Lys Thr Thr Leu Leu Pro Ser Gly Ala Glu Val
    50                  55                  60

Leu Ser Tyr Ser Glu Ala Ala Lys Lys Ser Asp Ile Ile Ile Ile Ala
65                  70                  75                  80

Ile His Arg Glu His Tyr Asp Phe Leu Thr Glu Leu Thr Glu Val Leu
                85                  90                  95

Asn Gly Lys Ile Leu Val Asp Ile Ser Asn Asn Leu Lys Ile Asn Gln
            100                 105                 110

Tyr Pro Glu Ser Asn Ala Glu Tyr Leu Ala His Leu Val Pro Gly Ala
        115                 120                 125

His Val Val Lys Ala Phe Asn Thr Ile Ser Ala Trp Ala Leu Gln Ser
    130                 135                 140

Gly Ala Leu Asp Ala Ser Arg Gln Val Phe Val Cys Gly Asn Asp Ser
145                 150                 155                 160

Lys Ala Lys Gln Arg Val Met Asp Ile Val Arg Asn Leu Gly Leu Thr
                165                 170                 175

Pro Met Asp Gln Gly Ser Leu Met Ala Ala Lys Glu Ile Glu Lys Tyr
            180                 185                 190

Pro Leu Gln Leu Phe Pro Met Trp Arg Phe Pro Phe Tyr Leu Ser Ala
        195                 200                 205

Val Leu Cys Val Phe Leu Phe Phe Tyr Cys Val Ile Arg Asp Val Ile
    210                 215                 220

Tyr Pro Tyr Val Tyr Glu Lys Lys Asp Asn Thr Phe Arg Met Ala Ile
225                 230                 235                 240
```

Ser Ile Pro Asn Arg Ile Phe Pro Ile Thr Ala Pro Tyr Thr Ala Cys
                245                 250                 255

Phe Gly Leu Pro Pro Trp Cys Tyr Cys Cys His Ser Thr Thr Val Pro
            260                 265                 270

Arg His Lys Ile Pro Ser Ile Pro Arg Leu Ala
        275                 280

<210> SEQ ID NO 40
<211> LENGTH: 1461
<212> TYPE: DNA
<213> ORGANISM: Homo sapiens

<400> SEQUENCE: 40

| | | | | | |
|---|---|---|---|---|---|
| agcggcggct | cctgcagcgg | tggtcggctg | ttgggtgtgg | agtttcccag | cgcccctcgg | 60 |
| gtccgaccct | ttgagcgttc | tgctccggcg | ccagcctacc | tcgctcctcg | gcgccatgac | 120 |
| cacaaccacc | accttcaagg | gagtcgaccc | caacagcagg | aatagctccc | gagttttgcg | 180 |
| gcctccaggt | ggtggatcca | attttttcatt | aggttttgat | gaaccaacag | aacaacctgt | 240 |
| gaggaagaac | aaaatggcct | ctaatatctt | tgggacacct | gaagaaaatc | aagcttcttg | 300 |
| ggccaagtca | gcaggtgcca | gtctagtgg | tggcagggaa | gacttggagt | catctggact | 360 |
| gcagagaagg | aactcctctg | aagcaagctc | cggagacttc | ttagatctga | agggagaagg | 420 |
| tgatattcat | gaaaatgtgg | acacagactt | gccaggcagc | ctggggcaga | gtgaagagaa | 480 |
| gcccgtgcct | gctgcgcctg | tgcccagccc | ggtggccccg | gcccagtgc | catccagaag | 540 |
| aaatccccct | ggcggcaagt | ccagcctcgt | cttgggttag | ctctgactgt | cctgaacgct | 600 |
| gtcgttctgt | ctgtttcctc | catgcttgtg | aactgcacaa | cttgagcctg | actgtacatc | 660 |
| tcttggattt | gtttcattaa | aaagaagcac | tttatgtact | gctgtctttt | ttttttttct | 720 |
| tttgaagaac | aggtttctct | ctgtccttga | ctcttgggtc | tgtgggccat | ggcatgagtg | 780 |
| ttttctagta | gtagattgga | gggaaagctt | tgtgacactt | agtactgtgt | ttttaagaag | 840 |
| aaataatttg | gttccagatg | tgttagagga | tcttttgtac | tgaggttttt | aacactttac | 900 |
| ttgggtttac | caagcctcaa | ctggacagac | cataaacagt | ccacaggcac | cgttcctgcc | 960 |
| aggccccaac | ccacagggag | tctctccgca | gagccttctt | ggtgttgccc | taacttgcca | 1020 |
| gtggcctttg | ctcagagcct | cctcctgtga | catgtgaaca | atgaagaggc | ctgcgcctcc | 1080 |
| tgccttgccg | cctgcaaagc | aaagaaactg | ccttttattt | tttaacctta | aaagtagcc | 1140 |
| agatagtaac | aagactggct | ggctgatgag | caaagccttt | gctctcacgc | agaggaaggc | 1200 |
| ttggatgtac | aatgaaactg | cctggaacta | aaagcagtga | agcaagggag | gcaatcacac | 1260 |
| tgaagcgggt | cttcctccag | gaacggggtc | ccacaggcgt | gttgttttaa | ataacctgat | 1320 |
| gctgtgtgca | tgatgctggt | gcttgaccat | gaaaggaaag | tctcatcctt | aaaatgtgtt | 1380 |
| gtacttcaca | atcctggact | gttgcttcaa | gtaaacaata | tccacattct | aaaaaaaaaa | 1440 |
| aaaaaaaaaa | aaaaaaaaa | a | | | | 1461 |

<210> SEQ ID NO 41
<211> LENGTH: 154
<212> TYPE: PRT
<213> ORGANISM: Homo sapiens

<400> SEQUENCE: 41

Met Thr Thr Thr Thr Thr Phe Lys Gly Val Asp Pro Asn Ser Arg Asn
1               5                   10                  15

Ser Ser Arg Val Leu Arg Pro Pro Gly Gly Gly Ser Asn Phe Ser Leu

```
                     20                  25                  30
Gly Phe Asp Glu Pro Thr Glu Gln Pro Val Arg Lys Asn Lys Met Ala
             35                  40                  45

Ser Asn Ile Phe Gly Thr Pro Glu Glu Asn Gln Ala Ser Trp Ala Lys
 50                  55                  60

Ser Ala Gly Ala Lys Ser Ser Gly Arg Glu Asp Leu Glu Ser Ser
 65                  70                  75                  80

Gly Leu Gln Arg Arg Asn Ser Ser Glu Ala Ser Ser Gly Asp Phe Leu
                 85                  90                  95

Asp Leu Lys Gly Glu Gly Asp Ile His Glu Asn Val Asp Thr Asp Leu
            100                 105                 110

Pro Gly Ser Leu Gly Gln Ser Glu Glu Lys Pro Val Pro Ala Ala Pro
            115                 120                 125

Val Pro Ser Pro Val Ala Pro Ala Pro Val Pro Ser Arg Arg Asn Pro
130                 135                 140

Pro Gly Gly Lys Ser Ser Leu Val Leu Gly
145                 150

<210> SEQ ID NO 42
<211> LENGTH: 50
<212> TYPE: DNA
<213> ORGANISM: Homo sapiens

<400> SEQUENCE: 42
tgaaaaccct ataaaggcgt cgatcggccg gacaggcggc agcggcggct              50

<210> SEQ ID NO 43
<211> LENGTH: 28
<212> TYPE: DNA
<213> ORGANISM: Homo sapiens

<400> SEQUENCE: 43
catgaccaca accaccacct tcaaggga                                      28

<210> SEQ ID NO 44
<211> LENGTH: 28
<212> TYPE: DNA
<213> ORGANISM: Homo sapiens

<400> SEQUENCE: 44
tgccattatt tgcagagttt tgcggcct                                      28

<210> SEQ ID NO 45
<211> LENGTH: 28
<212> TYPE: DNA
<213> ORGANISM: Homo sapiens

<400> SEQUENCE: 45
aaatcaagct tcttgggcca agtcagca                                      28

<210> SEQ ID NO 46
<211> LENGTH: 28
<212> TYPE: DNA
<213> ORGANISM: Homo sapiens

<400> SEQUENCE: 46
tattttgatt tttaggtgcc aagtctag                                      28

<210> SEQ ID NO 47
<211> LENGTH: 28
```

<210> SEQ ID NO 48
<211> LENGTH: 22
<212> TYPE: DNA
<213> ORGANISM: Homo sapiens

<400> SEQUENCE: 48
tttttctttt tctagggaga ag    22

<210> SEQ ID NO 49
<211> LENGTH: 27
<212> TYPE: DNA
<213> ORGANISM: Homo sapiens

<400> SEQUENCE: 49
gtgatattca tggtaagtac ttctgaa    27

<210> SEQ ID NO 50
<211> LENGTH: 28
<212> TYPE: DNA
<213> ORGANISM: Homo sapiens

<400> SEQUENCE: 50 tccctgttttt catagaaaat gtggacac    28

<210> SEQ ID NO 51
<211> LENGTH: 3526
<212> TYPE: DNA
<213> ORGANISM: Homo sapiens

<400> SEQUENCE: 51

```
atgaccgacg cgctgttgcc cgcggccccc cagccgctgg agaaggagaa cgacggctac    60
tttcggaagg gctgtaatcc ccttgcacaa accggccgga gtaaattgca gaatcaaaga   120
gctgctttga atcagcagat cctgaaagcc gtgcggatga ggaccggagc ggaaaacctt   180
ctgaaagtgg ccacaaactc aaaggtgcgg gagcaagtgc ggctgagct gagcttcgtc   240
aactcagacc tgcagatgct caaggaagag ctggagggc tgaacatctc ggtgggcgtc   300
tatcagaaca cagaggaggc atttacgatt cccctgattc ctcttggcct gaaggaaacg   360
aaagacgtcg actttgcagt cgtcctcaag gatttttatcc tggaacatta cagtgaagat   420
ggctattat atgaagatga aattgcagat cttatggatc tgagacaagc ttgtcggacg   480
cctagccggg atgaggccgg ggtggaactg ctgatgacat acttcatcca gctgggcttt   540
gtcgagagtc gattcttccc gcccacacgg cagatgggac tctgttcac ctggtatgac   600
tctctcactg gggttccggt cagccagcag aacctgctgc tggagaaggc cagtgtcctg   660
ttcaacactg ggcccctcta cacccagatt gggaccccgg tcgatcggca gacgcaggct   720
gggctggaga gtgccataga tgcctttcag agagccgcag gggttttaaa ttacctgaaa   780
gacacattta cccatactcc aagttacgac atgagccctg ccatgctcag cgtgctcgtc   840
aaaatgatgc ttgcacaagc ccaagaaagc gtgtttgaga aaatcagcct tcctgggatc   900
cggaatgaat tcttcatgct ggtgaaggtg gctcaggagg ctgctaaggt ggggagagtc   960
taccaacagc tacacgcagc catgagccag gcgccggtga aagagaacat ccctactcc  1020
```

```
tgggccagct tagcctgcgt gaaggcccac cactacgcgg ccctggccca ctacttcact    1080
gccatcctcc tcatcgacca ccaggtgaag ccaggcacgg atctggacca ccaggagaag    1140
tgcctgtccc agctctacga ccacatgcca gaggggctga cacccttggc cacactgaag    1200
aatgatcagc agcgccgaca gctggggaag tcccacttgc gcagagccat ggctcatcac    1260
gaggagtcgg tgcgggaggc gagcctctgc aagaagctgc ggagcattga ggtgctacag    1320
aaggtgctgt gtgccgcaca ggaacgctcc cggctcacgt acgcccagca ccaggaggag    1380
gatgacctgc tgaacctgat cgacgccccc agtgttgttg ctaaaactga gcaagaggtt    1440
gacattatat tgccccagtt ctccaagctg acagtcacgg acttcttcca gaagctgggc    1500
cccttatctg tgttttcggc taacaagcgg tggacgcctc ctcgaagcat ccgcttcact    1560
gcagaagaag gggacttggg gttcaccttg agagggaacg cccccgttca ggttcacttc    1620
ctggatcctt actgctctgc ctcggtggca ggagcccggg aaggagatta tattgtctcc    1680
attcagcttg tggattgtaa gtggctgacg ctgagtgagg ttatgaagct gctgaagagc    1740
tttggcgagg acgagatcga gatgaaagtc gtgagcctcc tggactccac atcatccatg    1800
cataataaga gtgccacata ctccgtggga atgcagaaaa cgtactccat gatctgctta    1860
gccattgatg atgacgacaa aactgataaa accaagaaaa tctccaagaa gctttccttc    1920
ctgagttggg gcaccaacaa gaacagacag aagtcagcca gcaccttgtg cctcccatcg    1980
gtcggggctg cacggcctca ggtcaagaag aagctgccct cccctttcag ccttctcaac    2040
tcagacagtt cttggtacta atgtgaggaa acaaacatgt tcaggccccg aacatttccg    2100
gtgctgactc ggccttaaac gtttgtgcca taatggaaaa tatctatcta tctgttctca    2160
aatcctgttt ttctcatagt gtaaactcac atttgatgtg tttttatgaa ggaaagtaac    2220
caagaaacct ctaggaatta gtgaaaaaag aactttttg aggtgtgtta ctatactgct    2280
gtaagttatt tattatataa agtattgtaa atagaatagt gttgaagata tgaaatatgg    2340
ctattttaa tggtgacaat tatgactttt agtcactatt aaattggggt tacctatatc    2400
agtacaattt gtagttgttt ccaggtttgg ctaataatca ttccttaacc tagaattcag    2460
atgatcctgg aattaaggca ggtcagagga ctgtaatgat agaattaaat tagtgtcact    2520
aaaaactgtc ccaaagtgct gcttcctaat aggaattcat taacctaaaa caagatgtta    2580
ctattatatc gatagactat gaatgctatt tctagaaaaa gtctagtgcc aaatttgtct    2640
tattaaataa aaacaatgta ggagcagctt ttcttctagt ttgatgtcat ttaagaatta    2700
ctaacacagt ggcagtgtta gatgaagatg ctgtctacaa ggtagataat atactgtttg    2760
atactcaaaa cattttttcat tttgtttaaa gtagaagtta cataattcta tattttaagt    2820
cttgggtaaa aaagtagttt tacattttat aaagtaaaga tgtaaatgat tcaggtttaa    2880
agctctattt gacttccttt ttttgtttga gatagcgtct tgctgtgttg cccaggctgg    2940
agtgcagtgg tgtgatctca gctcagtgca acctccgccc cctgggatca gcgattctc    3000
ctacctcagc ctcccaaata gctgggacta caaggtgccc tccagcatgc ctggctgatt    3060
tttgtatttt tagttgaggt gaggtttcac catgttggcc aggcgggttt cgaaatcctg    3120
acctcaaatg atccacccac ctcagcctcc caaagtgctg ggattacagg catgagccac    3180
cacaaccgtc ccactatttt actttttaaa atgacattcc tactgattga ttttttatctt    3240
gctataagtt cgatgacacc gtgaatctaa taaggttcac tgttgacaca gtacaagtta    3300
catagctaaa atacatagca ttgaagacta attttaagga ttgacaagag tttatttct    3360
attgtgcaat atcttaaagg aagcaaccac ctttgggaaa gtgtatctgc tgctcctagg    3420
```

```
gccatgcttg tatacatatt taaataaaca tattcattta cccgaaaaaa aaaaaaaaaa      3480
aaaaaaaaaa aaaaaaaaaa aaaaaaaaaa aaaaaaaaaa aaaaaa                    3526

<210> SEQ ID NO 52
<211> LENGTH: 2100
<212> TYPE: DNA
<213> ORGANISM: Homo sapiens

<400> SEQUENCE: 52
atgaccgacg cgctgttgcc cgcggccccc cagccgctgg agaaggagaa cgacggctac       60
tttcggaagg gctgtaatcc ccttgcacaa accggccgga gtaaattgca gaatcaaaga      120
gctgctttga atcagcagat cctgaaagcc gtgcggatga ggaccggagc ggaaaacctt      180
ctgaaagtgg ccacaaactc aaaggtgcgg agcaagtgc ggctggagct gagcttcgtc       240
aactcagacc tgcagatgct caaggaagag ctggagggc tgaacatctc ggtgggcgtc       300
tatcagaaca cagaggaggc atttacgatt ccctgattc ctcttggcct gaaggaaacg       360
aaagacgtcg actttgcagt cgtcctcaag gattttatcc tggaacatta cagtgaagat      420
ggctatttat atgaagatga aattgcagat cttatggatc tgagacaagc ttgtcggacg      480
cctagccggg atgaggccgg ggtggaactg ctgatgacat acttcatcca gctgggcttt      540
gtcgagagtc gattcttccc gcccacacgg cagatggac tcctgttcac ctggtatgac       600
tctctcactg gggttccggt cagccagcag aacctgctgc tggagaaggc cagtgtcctg      660
ttcaacactg gggccctcta cacccagatt gggacccgt gcgatcggca gacgcaggct       720
gggctggaga gtgccataga tgcctttcag agagccgcag gggttttaaa ttacctgaaa      780
gacacattta cccatactcc aagttacgac atgagccctg ccatgctcag cgtgctcgtc      840
aaaatgatgc ttgcacaagc ccaagaaagc gtgtttgaga aaatcagcct tcctgggatc      900
cggaatgaat tcttcatgct ggtgaaggtg gctcaggagg ctgctaaggt gggagaggtc      960
taccaacagc tacacgcagc catgagccag gcgccggtga agagaacat cccctactcc      1020 tgggccagct tagcctgcgt gaaggccac cactacgcgg ccctggccca ctacttcact      1080
gccatcctcc tcatcgacca ccaggtgaag ccaggcacgg atctggacca ccaggagaag      1140
tgcctgtccc agctctacga ccacatgcca gaggggctga cacccttggc cacactgaag      1200
aatgatcagc agcgccgaca gctggggaag tcccacttgc gcagagccat ggctcatcac      1260
gaggagtcgg tgcgggaggc gagcctctgc aagaagctgc ggagcattga ggtgctacag      1320
aaggtgctgt gtgccgcaca ggaacgctcc cggctcacgt acgcccagca ccaggaggag      1380
gatgacctgc tgaacctgat cgacgccccc agtgttgttg ctaaaactga gcaagaggtt      1440
gacattatat tgccccagtt ctccaagctg acagtcacgg acttcttcca gaagctgggc      1500
cccttatctg tgttttcggc taacaagcgg tggacgcctc ctcgaagcat ccgcttcact      1560
gcagaagaag gggacttggg gttcaccttg agagggaacg ccccgttca ggttcacttc      1620 ctggatcctt actgctctgc ctcggtggca ggagcccggg aaggagatta tattgtctcc      1680
attcagcttg tggattgtaa gtggctgacg ctgagtgagg ttatgaagct gctgaagagc      1740
tttggcgagg acgagatcga gatgaaagtc gtgagcctcc tggactccac atcatccatg      1800
cataataaga gtgccacata ctccgtggga atgcagaaaa cgtactccat gatctgctta      1860
gccattgatg atgacgacaa aactgataaa accaagaaaa tctccaagaa gctttccttc      1920
ctgagttggg gcaccaacaa gaacagacag aagtcagcca gcaccttgtg cctcccatcg      1980
```

```
gtcggggctg cacggcctca ggtcaagaag aagctgccct ccccttccag ccttctcaac    2040
tcagacagtt cttggtacta atgtgaggaa acaaacatgt tcaggccccg aacatttccg    2100
```

<210> SEQ ID NO 53
<211> LENGTH: 686
<212> TYPE: PRT
<213> ORGANISM: Homo sapiens

<400> SEQUENCE: 53

```
Met Thr Asp Ala Leu Leu Pro Ala Ala Pro Gln Pro Leu Glu Lys Glu
 1               5                  10                  15

Asn Asp Gly Tyr Phe Arg Lys Gly Cys Asn Pro Leu Ala Gln Thr Gly
                20                  25                  30

Arg Ser Lys Leu Gln Asn Gln Arg Ala Ala Leu Asn Gln Gln Ile Leu
            35                  40                  45

Lys Ala Val Arg Met Arg Thr Gly Ala Glu Asn Leu Leu Lys Val Ala
        50                  55                  60

Thr Asn Ser Lys Val Arg Glu Gln Val Arg Leu Glu Leu Ser Phe Val
65                  70                  75                  80

Asn Ser Asp Leu Gln Met Leu Lys Glu Glu Leu Glu Gly Leu Asn Ile
                85                  90                  95

Ser Val Gly Val Tyr Gln Asn Thr Glu Glu Ala Phe Thr Ile Pro Leu
            100                 105                 110

Ile Pro Leu Gly Leu Lys Glu Thr Lys Asp Val Asp Phe Ala Val Val
        115                 120                 125

Leu Lys Asp Phe Ile Leu Glu His Tyr Ser Glu Asp Gly Tyr Leu Tyr
    130                 135                 140

Glu Asp Glu Ile Ala Asp Leu Met Asp Leu Arg Gln Ala Cys Arg Thr
145                 150                 155                 160

Pro Ser Arg Asp Glu Ala Gly Val Glu Leu Leu Met Thr Tyr Phe Ile
                165                 170                 175

Gln Leu Gly Phe Val Glu Ser Arg Phe Phe Pro Thr Arg Gln Met
            180                 185                 190

Gly Leu Leu Phe Thr Trp Tyr Asp Ser Leu Thr Gly Val Pro Val Ser
        195                 200                 205

Gln Gln Asn Leu Leu Glu Lys Ala Ser Val Leu Phe Asn Thr Gly
    210                 215                 220

Ala Leu Tyr Thr Gln Ile Gly Thr Arg Cys Asp Arg Gln Thr Gln Ala
225                 230                 235                 240

Gly Leu Glu Ser Ala Ile Asp Ala Phe Gln Arg Ala Ala Gly Val Leu
                245                 250                 255

Asn Tyr Leu Lys Asp Thr Phe Thr His Thr Pro Ser Tyr Asp Met Ser
            260                 265                 270

Pro Ala Met Leu Ser Val Leu Val Lys Met Met Leu Ala Gln Ala Gln
        275                 280                 285

Glu Ser Val Phe Glu Lys Ile Ser Leu Pro Gly Ile Arg Asn Glu Phe
    290                 295                 300

Phe Met Leu Val Lys Val Ala Gln Glu Ala Lys Val Gly Glu Val
305                 310                 315                 320

Tyr Gln Gln Leu His Ala Ala Met Ser Gln Ala Pro Val Lys Glu Asn
                325                 330                 335

Ile Pro Tyr Ser Trp Ala Ser Leu Ala Cys Val Lys Ala His His Tyr
            340                 345                 350

Ala Ala Leu Ala His Tyr Phe Thr Ala Ile Leu Leu Ile Asp His Gln
```

```
              355                 360                 365
Val Lys Pro Gly Thr Asp Leu Asp His Gln Glu Lys Cys Leu Ser Gln
370                 375                 380

Leu Tyr Asp His Met Pro Glu Gly Leu Thr Pro Leu Ala Thr Leu Lys
385                 390                 395                 400

Asn Asp Gln Gln Arg Arg Gln Leu Gly Lys Ser His Leu Arg Arg Ala
                405                 410                 415

Met Ala His His Glu Glu Ser Val Arg Glu Ala Ser Leu Cys Lys Lys
            420                 425                 430

Leu Arg Ser Ile Glu Val Leu Gln Lys Val Leu Cys Ala Ala Gln Glu
        435                 440                 445

Arg Ser Arg Leu Thr Tyr Ala Gln His Gln Glu Glu Asp Asp Leu Leu
    450                 455                 460

Asn Leu Ile Asp Ala Pro Ser Val Val Ala Lys Thr Glu Gln Glu Val
465                 470                 475                 480

Asp Ile Ile Leu Pro Gln Phe Ser Lys Leu Thr Val Thr Asp Phe Phe
                485                 490                 495

Gln Lys Leu Gly Pro Leu Ser Val Phe Ser Ala Asn Lys Arg Trp Thr
                500                 505                 510

Pro Pro Arg Ser Ile Arg Phe Thr Ala Glu Glu Gly Asp Leu Gly Phe
            515                 520                 525

Thr Leu Arg Gly Asn Ala Pro Val Gln Val His Phe Leu Asp Pro Tyr
        530                 535                 540

Cys Ser Ala Ser Val Ala Gly Ala Arg Glu Gly Asp Tyr Ile Val Ser
545                 550                 555                 560

Ile Gln Leu Val Asp Cys Lys Trp Leu Thr Leu Ser Glu Val Met Lys
                565                 570                 575

Leu Leu Lys Ser Phe Gly Glu Asp Glu Ile Glu Met Lys Val Val Ser
                580                 585                 590

Leu Leu Asp Ser Thr Ser Ser Met His Asn Lys Ser Ala Thr Tyr Ser
            595                 600                 605

Val Gly Met Gln Lys Thr Tyr Ser Met Ile Cys Leu Ala Ile Asp Asp
        610                 615                 620

Asp Asp Lys Thr Asp Lys Thr Lys Ile Ser Lys Lys Leu Ser Phe
625                 630                 635                 640

Leu Ser Trp Gly Thr Asn Lys Asn Arg Gln Lys Ser Ala Ser Thr Leu
                645                 650                 655

Cys Leu Pro Ser Val Gly Ala Ala Arg Pro Gln Val Lys Lys Lys Leu
                660                 665                 670

Pro Ser Pro Phe Ser Leu Leu Asn Ser Asp Ser Ser Trp Tyr
            675                 680                 685

<210> SEQ ID NO 54
<211> LENGTH: 50
<212> TYPE: DNA
<213> ORGANISM: Homo sapiens

<400> SEQUENCE: 54
aaaaaaaata aataaaaagg ccgggcgcgt tggcccgcgc ctgcagcccc            50

<210> SEQ ID NO 55
<211> LENGTH: 869
<212> TYPE: DNA
<213> ORGANISM: Homo sapiens

<400> SEQUENCE: 55
```

```
tgctacttgg gaggctgagg ctggagcatc gcttgatcct gggaggtcga ggctgcaaag      60
agtcgagatc gcaacactgc tctccagcct gggcgacaga gcgaggtccc atctcttaaa     120
aaaaagaact gtgctcaagg acatctgccg tgtctgggc gcaaaacccc tcctggtccc     180
ctctctcagg gcagtccgcg agcccagcgg atcccactcg tctttgcagc gcggacaggg     240
aatcggctga gttgatccca tgccaacaag cccgagtagt ccgggcaagg cgctcggcgg     300
ggcagtcaac gctccctccg ccatgggctc ccctcttggg aaaagctttt ccaaaccgcc     360
gggcccaggg cccagagctc ccgccgcgcc ctcgacgtgg cgtcgagtct ggccccttcc     420
cccgcggcgc acgggcttca cccaggaggg acgcgcctgg atccacgcct tcctcactga     480
ctccccgggc tccagggcag ggtgcaggtc cacagccagg gcttcgctgc ggcccctgag     540
accccagtgc ctttcctgcg ctctcgcggc actcgcaaag ttgagtcagc cacgacgccc     600
acagacaacc ccgaggcgcc gcgcccaggg cgcagctctc cgggtgacga gcgcctcaag     660
gggcgcgggt tcggggcccg cgacggggcg gggcgcgtct ccagggctcc agtgctcggc     720
ctcaggcggg gctagaaggg ccgcgggacg gggtgggagt ggaggggcgg ggaagggcgg     780
ggacaggggc ggggccgcac gtcctctcgg gccagcctca gccgccgcgc ctcagtccgc     840
cgtccgccct ccgcgcccgc gccgctagc                                      869
```

<210> SEQ ID NO 56
<211> LENGTH: 69
<212> TYPE: DNA
<213> ORGANISM: Homo sapiens

<400> SEQUENCE: 56

```
atgaccgacg cgctgttgcc cgcggccccc cagccgctgg agaaggagaa cgacggctac      60
tttcggaag                                                              69
```

<210> SEQ ID NO 57
<211> LENGTH: 117
<212> TYPE: DNA
<213> ORGANISM: Homo sapiens

<400> SEQUENCE: 57

```
ggctgtaatc cccttgcaca aaccggccgg agtaaattgc agaatcaaag agctgctttg      60
aatcagcaga tcctgaaagc cgtgcggatg aggaccggag cggaaaacct tctgaaa        117
```

<210> SEQ ID NO 58
<211> LENGTH: 129
<212> TYPE: DNA
<213> ORGANISM: Homo sapiens

<400> SEQUENCE: 58

```
gtggccacaa actcaaaggt gcgggagcaa gtgcggctgg agctgagctt cgtcaactca      60
gacctgcaga tgctcaagga agagctggag gggctgaaca tctcggtggg cgtctatcag     120
aacacagag                                                             129
```

<210> SEQ ID NO 59
<211> LENGTH: 75
<212> TYPE: DNA
<213> ORGANISM: Homo sapiens

<400> SEQUENCE: 59

```
gaggcattta cgattcccct gattcctctt ggcctgaagg aaacgaaaga cgtcgacttt      60
```

```
gcagtcgtcc tcaag                                                    75

<210> SEQ ID NO 60
<211> LENGTH: 79
<212> TYPE: DNA
<213> ORGANISM: Homo sapiens

<400> SEQUENCE: 60
gattttatcc tggaacatta cagtgaagat ggctatttat atgaagatga aattgcagat    60
cttatggatc tgagacaag                                                79

<210> SEQ ID NO 61
<211> LENGTH: 124
<212> TYPE: DNA
<213> ORGANISM: Homo sapiens

<400> SEQUENCE: 61
cttgtcggac gcctagccgg gatgaggccg gggtggaact gctgatgaca tacttcatcc    60
agctgggctt tgtcgagagt cgattcttcc cgcccacacg gcagatggga ctcctgttca   120
cctg                                                               124

<210> SEQ ID NO 62
<211> LENGTH: 167
<212> TYPE: DNA
<213> ORGANISM: Homo sapiens

<400> SEQUENCE: 62
gtatgactct ctcactgggg ttccggtcag ccagcagaac ctgctgctgg agaaggccag    60
tgtcctgttc aacactgggg ccctctacac ccagattggg accggtgcg atcggcagac    120 gcaggctggg ctggagagtg ccatagatgc ctttcagaga gccgcag                167

<210> SEQ ID NO 63
<211> LENGTH: 188
<212> TYPE: DNA
<213> ORGANISM: Homo sapiens

<400> SEQUENCE: 63
gggttttaaa ttacctgaaa gacacattta cccatactcc aagttacgac atgagccctg    60
ccatgctcag cgtgctcgtc aaaatgatgc ttgcacaagc ccaagaaagc gtgtttgaga   120
aaatcagcct tcctgggatc cggaatgaat tcttcatgct ggtgaaggtg gctcaggagg   180
ctgctaag                                                           188

<210> SEQ ID NO 64
<211> LENGTH: 156
<212> TYPE: DNA
<213> ORGANISM: Homo sapiens

<400> SEQUENCE: 64
gtgggagagg tctaccaaca gctacacgca gccatgagcc aggcgccggt gaaagagaac    60
atcccctact cctgggccag cttagcctgc gtgaaggccc accactacgc ggccctggcc   120
cactacttca ctgccatcct cctcatcgac caccag                            156

<210> SEQ ID NO 65
<211> LENGTH: 120
<212> TYPE: DNA
<213> ORGANISM: Homo sapiens

<400> SEQUENCE: 65
```

```
gtgaagccag gcacggatct ggaccaccag gagaagtgcc tgtcccagct ctacgaccac      60
atgccagagg ggctgacacc cttggccaca ctgaagaatg atcagcagcg ccgacagctg     120

<210> SEQ ID NO 66
<211> LENGTH: 196
<212> TYPE: DNA
<213> ORGANISM: Homo sapiens

<400> SEQUENCE: 66
gggaagtccc acttgcgcag agccatggct catcacgagg agtcggtgcg ggaggcgagc      60
ctctgcaaga agctgcggag cattgaggtg ctacagaagg tgctgtgtgc cgcacaggaa     120
cgctcccggc tcacgtacgc ccagcaccag gaggaggatg acctgctgaa cctgatcgac     180
gcccccagtg ttgttg                                                    196

<210> SEQ ID NO 67
<211> LENGTH: 77
<212> TYPE: DNA
<213> ORGANISM: Homo sapiens

<400> SEQUENCE: 67
ctaaaactga gcaagaggtt gacattatat tgccccagtt ctccaagctg acagtcacgg      60
acttcttcca gaagctg                                                    77

<210> SEQ ID NO 68
<211> LENGTH: 147
<212> TYPE: DNA
<213> ORGANISM: Homo sapiens

<400> SEQUENCE: 68
ggccccttat ctgtgttttc ggctaacaag cggtggacgc ctcctcgaag catccgcttc      60
actgcagaag aaggggactt gggggttcacc ttgagaggga cgcccccgt tcaggttcac     120 ttcctggatc cttactgctc tgcctcg                                         147

<210> SEQ ID NO 69
<211> LENGTH: 156
<212> TYPE: DNA
<213> ORGANISM: Homo sapiens

<400> SEQUENCE: 69
gtggcaggag cccgggaagg agattatatt gtctccattc agcttgtgga ttgtaagtgg      60
ctgacgctga gtgaggttat gaagctgctg aagagctttg gcgaggacga gatcgagatg     120
aaagtcgtga gcctcctgga ctccacatca tccatg                               156

<210> SEQ ID NO 70
<211> LENGTH: 1726
<212> TYPE: DNA
<213> ORGANISM: Homo sapiens

<400> SEQUENCE: 70
cataataaga gtgccacata ctccgtggga atgcagaaaa cgtactccat gatctgctta      60
gccattgatg atgacgacaa aactgataaa accaagaaaa tctccaagaa gctttccttc     120
ctgagttggg gcaccaacaa gaacagacag aagtcagcca gcaccttgtg cctcccatcg     180
gtcggggctg cacggcctca ggtcaagaag aagctgccct cccctttcag ccttctcaac     240
tcagacagtt cttggtacta atgtgaggaa acaaacatgt tcaggcccg aacatttccg      300
```

```
gtgctgactc ggccttaaac gtttgtgcca taatggaaaa tatctatcta tctgttctca    360
aatcctgttt ttctcatagt gtaaactcac atttgatgtg ttttatgaa ggaaagtaac     420 caagaaacct ctaggaatta gtgaaaaaag aacttttttg aggtgtgtta ctatactgct    480
gtaagttatt tattatataa agtattgtaa atagaatagt gttgaagata tgaaatatgg    540
ctatttttaa tggtgacaat tatgactttt agtcactatt aaattggggt tacctatatc    600
agtacaattt gtagttgttt ccaggtttgg ctaataatca ttccttaacc tagaattcag    660
atgatcctgg aattaaggca ggtcagagga ctgtaatgat agaattaaat tagtgtcact    720
aaaaactgtc ccaaagtgct gcttcctaat aggaattcat taacctaaaa caagatgtta    780
ctattatatc gatagactat gaatgctatt tctagaaaaa gtctagtgcc aaatttgtct    840
tattaaataa aaacaatgta ggagcagctt ttcttctagt ttgatgtcat ttaagaatta    900
ctaacacagt ggcagtgtta gatgaagatg ctgtctacaa ggtagataat atactgtttg    960
atactcaaaa cattttcat tttgtttaaa gtagaagtta cataattcta tattttaagt    1020
cttgggtaaa aaagtagttt tacattttat aaagtaaaga tgtaaatgat tcaggtttaa    1080
agctctattt gacttccttt ttttgtttga gatagcgtct tgctgtgttg cccaggctgg    1140
agtgcagtgg tgtgatctca gctcagtgca acctccgccc cctgggatca agcgattctc    1200
ctacctcagc ctcccaaata gctgggacta caaggtgccc tccagcatgc ctggctgatt    1260
tttgtatttt tagttgaggt gaggtttcac catgttggcc aggcgggttt cgaaatcctg    1320
acctcaaatg atccacccac ctcagcctcc caaagtgctg ggattacagg catgagccac    1380
cacaaccgtc ccactatttt acttttaaa atgacattcc tactgattga tttttatctt    1440
gctataagtt cgatgacacc gtgaatctaa taaggttcac tgttgacaca gtacaagtta    1500
catagctaaa atacatagca ttgaagacta attttaagga ttgacaagag tttatttttct   1560 attgtgcaat atcttaaagg aagcaaccac ctttgggaaa gtgtatctgc tgctcctagg    1620
gccatgcttg tatacatatt taaataaaca tattcattta cccgaaaaaa aaaaaaaaa     1680 aaaaaaaaa aaaaaaaaa aaaaaaaaa aaaaaaaaa aaaaaa                      1726
```

<210> SEQ ID NO 71
<211> LENGTH: 643
<212> TYPE: PRT
<213> ORGANISM: Mus musculus

<400> SEQUENCE: 71

```
Met Ile Leu Glu Glu Arg Pro Asp Gly Gln Gly Thr Gly Glu Glu Ser
 1               5                  10                  15

Ser Arg Pro Gln Asp Asp Gly Ser Ile Arg Lys Gly Tyr Gly Ser Phe
            20                  25                  30

Val Gln Asn Gln Pro Gly Gln Leu Gln Ser His Arg Ala Arg Leu His
        35                  40                  45

Gln Gln Ile Ser Lys Glu Leu Arg Met Arg Thr Gly Ala Glu Asn Leu
    50                  55                  60

Tyr Arg Ala Thr Ser Asn Thr Trp Val Arg Glu Thr Val Ala Leu Glu
65                  70                  75                  80

Leu Ser Tyr Val Asn Ser Asn Leu Gln Leu Leu Lys Glu Glu Leu Ala
                85                  90                  95

Glu Leu Ser Thr Ser Val Asp Val Asp Gln Pro Glu Gly Glu Gly Ile
            100                 105                 110

Thr Ile Pro Met Ile Pro Leu Gly Leu Lys Glu Thr Lys Glu Leu Asp
        115                 120                 125
```

```
Trp Ala Thr Pro Leu Lys Glu Leu Ile Ser Glu His Phe Gly Glu Asp
    130                 135                 140
Gly Thr Ser Phe Glu Thr Glu Ile Gln Glu Leu Glu Asp Leu Arg Gln
145                 150                 155                 160
Ala Thr Arg Thr Pro Ser Arg Asp Glu Ala Gly Leu Asp Leu Leu Ala
                165                 170                 175
Ala Tyr Tyr Ser Gln Leu Cys Phe Leu Asp Ala Arg Phe Phe Ser Pro
            180                 185                 190
Ser Arg Ser Pro Gly Leu Leu Phe His Trp Tyr Asp Ser Leu Thr Gly
        195                 200                 205
Val Pro Ala Gln Gln Arg Ala Leu Ala Phe Glu Lys Gly Ser Val Leu
    210                 215                 220
Phe Asn Ile Gly Ala Leu His Thr Gln Ile Gly Ala Arg Gln Asp Cys
225                 230                 235                 240
Ser Cys Thr Glu Gly Thr Asn His Ala Ala Glu Ala Phe Gln Arg Ala
                245                 250                 255
Ala Gly Ala Phe Arg Leu Leu Arg Glu Asn Phe Ser His Ala Pro Ser
            260                 265                 270
Pro Asp Met Ser Ala Ala Ser Leu Ser Met Leu Glu Gln Leu Met Ile
        275                 280                 285
Ala Gln Ala Gln Glu Cys Ile Phe Lys Gly Leu Leu Pro Ala Ser
    290                 295                 300
Ala Thr Pro Asp Ile Cys Pro Asp Gln Leu Gln Leu Ala Gln Glu Ala
305                 310                 315                 320
Ala Gln Val Ala Thr Glu Tyr Gly Leu Val His Arg Ala Met Ala Gln
                325                 330                 335
Pro Pro Val Arg Asp Tyr Leu Pro Ala Ser Trp Thr Asn Leu Ala His
            340                 345                 350
Val Lys Ala Glu His Phe Cys Ala Leu Ala His Tyr His Ala Ala Met
        355                 360                 365
Ala Leu Cys Glu Ser His Pro Ala Lys Gly Glu Leu Ala Arg Gln Glu
    370                 375                 380
His Val Phe Gln Pro Ser Thr Pro His Glu Pro Leu Gly Pro Thr Leu
385                 390                 395                 400
Pro Gln His Pro Glu Asp Arg Arg Lys Leu Ala Lys Ala His Leu Lys
                405                 410                 415
Arg Ala Ile Leu Gly Gln Glu Glu Ala Leu Arg Leu His Thr Leu Cys
            420                 425                 430
Arg Val Leu Arg Lys Val Asp Leu Leu Gln Val Val Thr Gln Ala
    435                 440                 445
Leu Arg Arg Ser Leu Ala Lys Tyr Ser Gln Leu Glu Arg Glu Asp Asp
    450                 455                 460
Phe Phe Glu Ala Thr Glu Ala Pro Asp Ile Gln Pro Lys Thr His Gln
465                 470                 475                 480
Thr Pro Glu Gly Pro Leu Ser Val Phe Ser Thr Lys Asn Arg Trp Gln
                485                 490                 495
Leu Val Gly Pro Val His Met Thr Arg Gly Glu Gly Phe Gly Phe
            500                 505                 510
Thr Leu Arg Gly Asp Ser Pro Val Leu Ile Ala Ala Val Val Pro Gly
        515                 520                 525
Gly Gln Ala Glu Ser Ala Gly Leu Lys Glu Gly Asp Tyr Ile Val Ser
    530                 535                 540
```

```
Val Asn Gly Gln Pro Cys Lys Trp Trp Lys His Leu Glu Val Val Thr
545                 550                 555                 560

Gln Leu Arg Ser Met Gly Glu Gly Val Ser Leu Gln Val Val Ser
                565                 570                 575

Leu Leu Pro Ser Pro Glu Pro Arg Gly Thr Gly Pro Arg Arg Ala Ala
            580                 585                 590

Leu Leu Trp Asn Gln Arg Glu Cys Gly Phe Glu Thr Pro Met Pro Thr
            595                 600                 605

Arg Thr Arg Pro Trp Pro Ile Leu Gly Trp Ser Arg Lys Asn Lys Gln
            610                 615                 620

Gly Lys Thr Gly Ser His Pro Asp Pro Cys Thr Asn Arg Asn Cys Val
625                 630                 635                 640

Thr Cys Pro

<210> SEQ ID NO 72
<211> LENGTH: 718
<212> TYPE: PRT
<213> ORGANISM: Drosophila melanogaster

<400> SEQUENCE: 72

Met Asp Glu Lys Glu His Glu Leu Ser Thr Arg Val Val Lys Asn Glu
1               5                   10                  15

Glu Asn Glu Asp Asp Glu Lys Leu Asn Glu Leu Ser Phe Cys Phe Val
                20                  25                  30

Arg Gly Ser Asp Pro Arg Ala Ala Thr Cys Arg Ser Lys Leu Gln Asn
            35                  40                  45

Arg Arg Cys Lys Leu Asn Lys Glu Ile Asn Lys Glu Leu Arg Leu Arg
        50                  55                  60

Ala Gly Ala Glu Asn Leu Tyr Lys Ala Thr Ser Asn Arg Lys Leu Arg
65                  70                  75                  80

Asp Thr Val Ala Leu Glu Leu Ser Phe Val Asn Ser Asn Leu Gln Leu
                85                  90                  95

Leu Lys Glu Gln Leu Ala Glu Leu Asn Ser Ser Val Glu Ile Tyr Gln
                100                 105                 110

Ser Glu Ser His Asn Gly Ile Met Pro Met Ile Pro Leu Gly Leu Lys
            115                 120                 125

Glu Thr Lys Glu Ile Asn Phe Met Glu Pro Phe Ser Asp Phe Ile Leu
130                 135                 140

Glu His Tyr Ser Glu Glu Pro Ser Met Tyr Ile Asp Ala Ile Ala Asp
145                 150                 155                 160

Met Thr Asp Thr Arg Gln Ala Ser Lys Thr Pro Ser Arg Asp Ala Leu
                165                 170                 175

Gly Val Ala Leu Leu Phe Arg Tyr Tyr Asn Thr Leu Tyr Tyr Val Glu
            180                 185                 190

Arg Arg Phe Phe Pro Pro Asp Arg Asn Leu Gly Val Tyr Phe Glu Trp
        195                 200                 205

Tyr Asp Ser Leu Thr Gly Val Pro Ser Cys Gln Arg Thr Ile Ala Phe
210                 215                 220

Glu Lys Ala Cys Thr Leu Phe Asn Leu Gly Ile Tyr Thr Gln Ile
225                 230                 235                 240

Gly Ala Arg His Asp Arg Thr Thr Glu Arg Gly Leu Asp Leu Ala Val
                245                 250                 255

Asp Ser Phe Leu Arg Ala Ala Gly Val Phe Arg His Ile Tyr Asp Thr
            260                 265                 270

Phe Thr Asn Ala Pro Ser Met Asp Leu Lys Pro Gln Val Leu Asp Val
```

-continued

```
            275                 280                 285
Leu Val Ser Leu Met Leu Ser Gln Ala Arg Glu Cys Leu Phe Glu Lys
        290                 295                 300
Leu Gln Leu Gln Ile Glu Ala Met Ser His Asp Cys Gln Ala Phe Arg
305                 310                 315                 320
Asp Leu Ala Gly Glu Ala Ala Gln Ile Ser His Glu Tyr Asn Glu Met
                325                 330                 335
His Lys Asn Ile Gln Ala Asn Asp Thr His Thr Tyr Leu Pro Glu Cys
            340                 345                 350
Trp Ala Gly Leu Val Pro Val Lys Ala Glu Leu Tyr Lys Ala Phe Ala
            355                 360                 365
His Phe Tyr Lys Ala Arg Ser Ile Asp Ala Thr Asp Glu Leu Lys Ala
        370                 375                 380
Ser Lys Ser Ser Gln Lys Asn Gln Glu Ser Phe Ile Gly Asn Ser Gln
385                 390                 395                 400
Glu Val Glu Arg Ile Thr Thr Ala Asp Tyr Gly Ala Ser Asp Glu Ala
                405                 410                 415
Ser Thr Ser Ile Ala Asn Lys Leu Ala His Leu Lys Glu Ala Leu Ala
            420                 425                 430
Ser Ile Glu Glu Ala Gln Arg Leu Gln Arg Met Cys Arg Phe Leu Lys
        435                 440                 445
Asn Lys Ala Ser Leu Thr Glu Val Met Lys Glu Val His Ser Lys Ser
450                 455                 460
Gln Glu Glu Leu Glu Lys Phe Arg Leu Gln Ala Ser Ala Lys Asn Ile
465                 470                 475                 480
Glu Asp Gly Asp Leu Leu Glu Arg Ser Val Glu Ala Ser Ser Lys Phe
                485                 490                 495
Thr Leu Ser Leu Thr Gly Pro Asp Phe Thr Ser His Lys Val Lys Asp
            500                 505                 510
Pro Phe Lys Arg Leu Gly Pro Ile Ala Ile Phe Ser Ala Arg Arg His
            515                 520                 525
Trp Thr Ala Pro Arg Cys Val Arg Leu Gln Lys Gly Ser Ser Leu Tyr
        530                 535                 540
His Ser Val Pro Ser Asn Asp Asn Lys Cys Pro Leu Asp Asn Asp Asp
545                 550                 555                 560
Asp Glu Glu His Asp Gly Gly Tyr Asn Leu Tyr Lys Glu Glu Phe Glu
                565                 570                 575
Asn Phe Gly Phe His Val Arg Gly Asp Ala Pro Val Ile Ile Ala His
            580                 585                 590
Val Glu Ile Asn Ser Leu Ala Asp Leu Gly Gly Ile Lys Glu Gly Asp
            595                 600                 605
Phe Ile Val Glu Ile Ala Gly Val Asp Val Lys Trp Tyr Ser His Gln
        610                 615                 620
Gln Val Val Gln Leu Ile Gln Ser Cys Gly Ser Thr Leu Glu Leu Arg
625                 630                 635                 640
Val Ile Thr Pro Met Asp Arg Asn Tyr Leu Lys Pro Leu Ser Ser Lys
                645                 650                 655
Gly Ser Leu Ser Thr Leu Ser Ala Ala Ser Ser Gly Ile Ser Ser
            660                 665                 670
Gly Phe Pro Ser Pro Thr Ser Ile Ala Ala Lys Pro Lys Leu His Leu
        675                 680                 685
Lys Thr Ser Ser Ser Ser Arg Pro Ala Gly Ser Val Ser Ser Ser
        690                 695                 700
```

Trp Asn Pro Phe Arg Arg Thr Pro Ser Leu Ala Lys Ile Phe
705                 710             715

<210> SEQ ID NO 73
<211> LENGTH: 686
<212> TYPE: PRT
<213> ORGANISM: Mus musculus

<400> SEQUENCE: 73

Met Thr Asp Thr Leu Leu Pro Ala Ala Pro Gln Pro Leu Glu Lys Glu
1               5                   10                  15

Gly Asp Asp Tyr Phe Arg Lys Gly Cys Asn Pro Leu Ala Gln Thr Gly
                20                  25                  30

Arg Ser Lys Leu Gln Asn Gln Arg Ala Ala Leu Asn Gln Gln Ile Leu
        35                  40                  45

Lys Ala Val Arg Met Arg Thr Gly Ala Glu Asn Leu Leu Lys Val Ala
50                  55                  60

Thr Asn Gln Lys Val Arg Glu Gln Val Arg Leu Glu Leu Ser Phe Val
65                  70                  75                  80

Asn Ser Asp Leu Gln Met Leu Lys Glu Glu Leu Glu Gly Leu Asn Ile
                85                  90                  95

Ser Val Gly Val Tyr Gln Gly Thr Glu Glu Ala Phe Thr Ile Pro Leu
                100                 105                 110

Ile Pro Leu Gly Leu Lys Glu Thr Lys Glu Val Asp Phe Ser Ile Val
            115                 120                 125

Phe Lys Asp Phe Ile Leu Glu His Tyr Ser Glu Asp Ser Tyr Leu Tyr
        130                 135                 140

Glu Asp Asp Ile Ala Asp Leu Met Asp Leu Arg Gln Ala Cys Arg Thr
145                 150                 155                 160

Pro Ser Arg Asp Glu Ala Gly Val Glu Leu Leu Met Ser Tyr Phe Ile
                165                 170                 175

Gln Leu Gly Phe Val Glu Ser Arg Phe Phe Pro Thr Arg His Met
                180                 185                 190

Gly Leu Leu Phe Thr Trp Tyr Asp Ser Phe Thr Gly Val Pro Val Ser
            195                 200                 205

Gln Gln Thr Leu Leu Glu Lys Ala Ser Val Leu Phe Asn Ile Gly
        210                 215                 220

Ala Leu Tyr Thr Gln Ile Gly Thr Arg Cys Asn Arg Gln Thr Gln Ala
225                 230                 235                 240

Gly Leu Glu Ser Ala Val Asp Ala Phe Gln Arg Ala Ala Gly Val Leu
                245                 250                 255

Asn Tyr Leu Lys Glu Thr Phe Thr His Thr Pro Ser Tyr Asp Met Ser
                260                 265                 270

Pro Ala Met Leu Ser Val Leu Val Lys Met Met Leu Ala Gln Ala Gln
            275                 280                 285

Glu Ser Val Phe Glu Lys Val Cys Leu Pro Gly Ile Gln Asn Glu Phe
        290                 295                 300

Phe Val Leu Val Lys Val Ala Gln Glu Ala Ala Lys Val Ala Glu Ala
305                 310                 315                 320

Tyr Arg Gln Leu His Ala Ala Met Ser Gln Glu Pro Val Lys Glu Asn
                325                 330                 335

Ile Pro Tyr Ser Trp Ala Ser Val Ala Tyr Val Lys Ala Tyr His Tyr
            340                 345                 350

Gly Ala Leu Ala His Tyr Phe Ala Ala Thr Leu Leu Ile Asp His Gln

```
                355                 360                 365
Leu Lys Pro Gly Ala Asp Glu Asp His Gln Glu Lys Cys Leu Ser Gln
            370                 375                 380
Leu Tyr Asp Arg Met Pro Glu Gly Met Thr Pro Leu Ala Thr Leu Lys
385                 390                 395                 400
Asn Ala Gly Gln Arg Val Leu Leu Gly Lys Gly His Leu His Arg Ala
                405                 410                 415
Ile Gly Phe His Glu Glu Ser Leu Arg Glu Ala Asn Leu Cys Lys Lys
            420                 425                 430
Leu Arg Asp Ile Gln Val Leu Arg Asp Val Leu Ser Ala Ala His Gln
        435                 440                 445
Arg Thr Gln Leu Lys His Thr Gln His Arg Glu Asp Asp Leu Leu
450                 455                 460
Asn Leu Ile Asp Ala Pro Asp Val Leu Pro Lys Thr Glu Arg Glu Val
465                 470                 475                 480
Lys Ile Thr Phe Pro Asp Phe Ser Lys Val Thr Val Thr Asp Phe Phe
                485                 490                 495
Gln Lys Leu Gly Pro Leu Ser Val Phe Ser Ala Ser Lys Arg Trp Ser
            500                 505                 510
Pro Pro Arg Gly Ile His Phe Thr Val Glu Glu Gly Asp Leu Gly Phe
        515                 520                 525
Thr Leu Arg Gly Asn Thr Pro Val Gln Val His Phe Leu Asp Pro His
        530                 535                 540
Cys Ser Ala Ser Leu Ala Gly Ala Lys Glu Gly Asp Tyr Ile Val Ser
545                 550                 555                 560
Ile Gln Gly Val Asp Cys Lys Trp Leu Thr Val Ser Glu Val Met Lys
                565                 570                 575
Leu Leu Lys Ser Phe Gly Gly Glu Val Glu Met Lys Val Val Ser
            580                 585                 590
Leu Leu Asp Ser Thr Ser Ser Met His Asn Lys Cys Ala Thr Tyr Ser
        595                 600                 605
Val Gly Met Gln Lys Thr Tyr Ser Met Ile Cys Leu Ser Met Asp Asp
    610                 615                 620
Asp Asp Lys Ala Asp Lys Thr Lys Lys Ile Ser Lys Lys Leu Ser Phe
625                 630                 635                 640
Leu Ser Trp Gly Thr Ser Lys Asn Arg Gln Lys Ser Ala Ser Thr Leu
                645                 650                 655
Cys Leu Pro Glu Val Gly Leu Ala Arg Ser Gln Asn Lys Lys Lys Leu
            660                 665                 670
Pro Thr Pro Phe Ser Leu Leu Asn Ser Asp Ser Ser Leu Tyr
        675                 680                 685

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
tgcaagtcgg caggtgtttg                                              20

<210> SEQ ID NO 75
<211> LENGTH: 20
<212> TYPE: DNA
<213> ORGANISM: Artificial Sequence
```

-continued

```
<220> FEATURE:
<223> OTHER INFORMATION: primer

<400> SEQUENCE: 75
gcaaagcatc cagtggtcaa                                              20

<210> SEQ ID NO 76
<211> LENGTH: 25
<212> TYPE: DNA
<213> ORGANISM: Artificial Sequence
<220> FEATURE:
<223> OTHER INFORMATION: primer

<400> SEQUENCE: 76
cagtgattat aggctttcgc tctaa                                        25

<210> SEQ ID NO 77
<211> LENGTH: 23
<212> TYPE: DNA
<213> ORGANISM: Artificial Sequence
<220> FEATURE:
<223> OTHER INFORMATION: primer

<400> SEQUENCE: 77
cagggctatt ggttgaatga gta                                          23
```